(12) United States Patent
Kawabe et al.

(10) Patent No.: US 12,174,204 B2
(45) Date of Patent: Dec. 24, 2024

(54) ANALYSIS METHOD, ANALYSIS APPARATUS, AND ANALYSIS PROGRAM

(71) Applicant: SEKISUI MEDICAL CO., LTD., Chuo-ku (JP)

(72) Inventors: Toshiki Kawabe, Chuo-ku (JP); Yukio Oda, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 810 days.

(21) Appl. No.: 17/294,151

(22) PCT Filed: Nov. 15, 2019

(86) PCT No.: PCT/JP2019/044943
§ 371 (c)(1),
(2) Date: May 14, 2021

(87) PCT Pub. No.: WO2020/101025
PCT Pub. Date: May 22, 2020

(65) Prior Publication Data
US 2021/0333295 A1    Oct. 28, 2021

(30) Foreign Application Priority Data

Nov. 15, 2018  (JP) .................. 2018-214949
Nov. 15, 2018  (JP) .................. 2018-214961
Apr. 25, 2019  (JP) .................. 2019-084727

(51) Int. Cl.
*G01N 33/86*    (2006.01)
(52) U.S. Cl.
CPC .................. *G01N 33/86* (2013.01)

(58) Field of Classification Search
CPC .................................................. G01N 33/86
See application file for complete search history.

(56) References Cited

U.S. PATENT DOCUMENTS 5,967,994  A   10/1999  Wang
6,524,861  B1    2/2003  Anderson
(Continued)

FOREIGN PATENT DOCUMENTS

EP      3 287 791 A1   2/2018
JP      2016-118442 A  6/2016
(Continued)

OTHER PUBLICATIONS

Extended European Search Report issued Jul. 11, 2022 in European Patent Application No. 19883974.8, 8 pages.
(Continued)

*Primary Examiner* — Brian R Gordon
*Assistant Examiner* — Dwan A Gerido
(74) *Attorney, Agent, or Firm* — Oblon, McClelland, Maier & Neustadt, L.L.P.

(57) ABSTRACT

Excellent analysis of a coagulation characteristic of a blood sample is implemented. A method for analyzing a coagulation characteristic of a blood specimen according to the present invention includes: acquiring data for a coagulation reaction curve indicating a coagulation reaction amount of a mixed solution containing a blood sample and a reagent with respect to reaction time; calculating data for a differential curve obtained by differentiating the coagulation reaction curve; calculating information related to a center-of-gravity point of the differential curve; and evaluating the coagulation characteristic of the blood sample using the information related to the center-of-gravity point.

21 Claims, 127 Drawing Sheets

(56) References Cited

U.S. PATENT DOCUMENTS

2016/0291042 A1  10/2016  Kumano et al.
2018/0031539 A1   2/2018  Shima et al.
2018/0045709 A1   2/2018  Shima et al.
2018/0306820 A1  10/2018  Suzuki et al.

FOREIGN PATENT DOCUMENTS

| JP | 2016-194426 A | | 11/2016 |
| JP | 2017-106925 A | | 6/2017 |
| JP | 2019-86518 A | | 6/2019 |
| JP | 2019086518 | * | 6/2019 |
| JP | 7220055 B2 | | 2/2023 |
| WO | WO 2016/170944 A1 | | 10/2016 |

OTHER PUBLICATIONS

Japanese Office Action issued Apr. 4, 2023 in Japanese Patent Application No. 2020-556195 (with unedited computer- generated English Translation), 8 pages.

International Search Report issued on Feb. 18, 2020 in PCT/JP2019/044943 filed on Nov. 15, 2019, 3 pages.

Wada, H., "APTT waveform," Japanese Journal of Thrombosis and Hemostasis, vol. 29, No. 4, 2018, pp. 413-420, 9 total pages.

Matsumoto, T., "Usage and perspective of clot waveform analysis," Medical Technology, vol. 46, No. 1, 2018, pp. 66-71, 7 total pages.

Sevenet, P.-O et al., "Clot waveform analysis: Where do we stand in 2017?" International Journal of Laboratory Hematology, vol. 39, No. 6, 2017, pp. 561-568.

Shimonishi, S. et al., "Diagnosis of hemophilia A using barycentric parameters of APTT clot waveform and development for assay method of factor VIII," Japanese Journal of Thrombosis and Hemostasis, vol. 30, No. 2, 2019, p. 411, 3 total pages.

Ogiwara, K. et al., "Development of a diagnostic algorithm for hemophilia A by template matching of APTT clot waveform," Japanese Journal of Thrombosis and Hemostasis, vol. 30, No. 2, 2019, p. 411, 3 total pages.

Shimonishi, S. et al., "Rapid quantification of APTT cross-mixing test using barycentric parameters of APTT clot waveform analysis," Japanese Journal of Thrombosis and Hemostasis, vol. 30, No. 2, 2019, p. 440, 3 total pages.

* cited by examiner

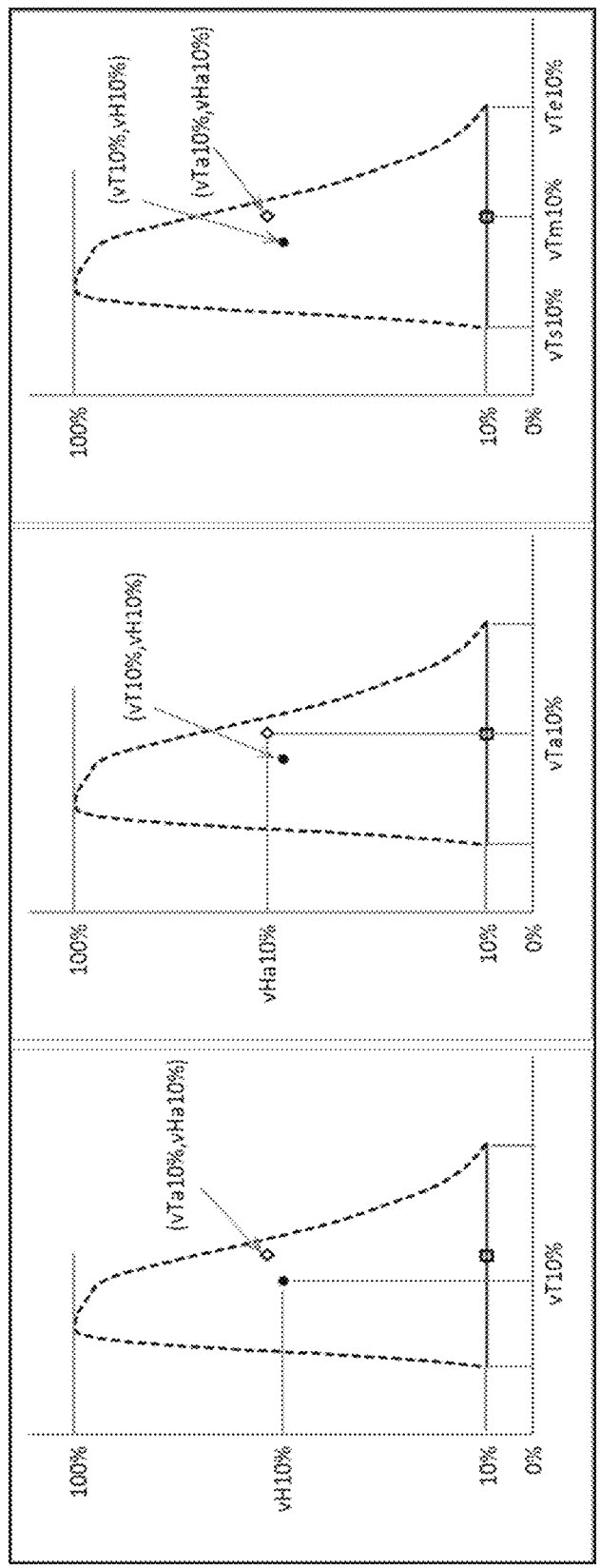

Fig. 29

| | vTB 5% | vTB 10% | vTB20% | vTB 30% | vTB 40% | vTB 50% | vTB60% | vTB70% | vTB80% | vTB90% | vTB95% |
|---|---|---|---|---|---|---|---|---|---|---|---|
| | vT5%/vB5% | vT10%/vB10% | vT20%/vB20% | vT30%/vB30% | vT40%/vB40% | vT50%/vB50% | vT60%/vB60% | vT70%/vB70% | vT80%/vB80% | vT90%/vB90% | vT95%/vB95% |
| FVIII(0%) | -0.2 | -0.2 | -0.1 | -0.1 | 0.0 | 0.0 | 0.0 | 0.1 | 0.3 | 1.0 | 1.2 |
| FVIII(0.25%) | -0.1 | -0.1 | 0.0 | 0.0 | 0.1 | 0.1 | 0.1 | 0.2 | 0.3 | 0.5 | 0.7 |
| FVIII(0.5%) | -0.1 | 0.0 | 0.0 | 0.1 | 0.1 | 0.1 | 0.2 | 0.2 | 0.4 | 0.7 | 0.9 |
| FVIII(0.75%) | -0.1 | 0.0 | 0.1 | 0.1 | 0.1 | 0.2 | 0.2 | 0.3 | 0.3 | 0.6 | 0.9 |
| FVIII(1%) | 0.0 | 0.0 | 0.1 | 0.1 | 0.2 | 0.2 | 0.2 | 0.3 | 0.4 | 0.7 | 0.9 |
| FVIII(2.5%) | 0.0 | 0.1 | 0.2 | 0.2 | 0.2 | 0.3 | 0.3 | 0.3 | 0.4 | 0.7 | 0.9 |
| FVIII(5%) | 0.1 | 0.1 | 0.2 | 0.3 | 0.3 | 0.3 | 0.4 | 0.4 | 0.5 | 0.6 | 0.8 |
| FVIII(10%) | 0.1 | 0.2 | 0.2 | 0.3 | 0.3 | 0.4 | 0.4 | 0.4 | 0.5 | 0.6 | 1.0 |
| FVIII(25%) | 0.1 | 0.2 | 0.3 | 0.3 | 0.4 | 0.4 | 0.5 | 0.5 | 0.6 | 0.7 | 0.7 |
| FVIII(50%) | 0.2 | 0.2 | 0.3 | 0.4 | 0.4 | 0.5 | 0.5 | 0.6 | 0.6 | 0.7 | 0.8 |

Fig. 30

|  | vTB 5% | vTB 10% | vTB20% | vTB 30% | vTB 40% | vTB 50% | vTB60% | vTB70% | vTB80% | vTB90% | vTB95% |
|---|---|---|---|---|---|---|---|---|---|---|---|
| FVIII(0%) | 1 | 1 | 1 | 1 | 1 | 1 | 1 | 1 | 3 | 67 | 67 |
| FVIII(0.25%) | 2 | 2 | 2 | 2 | 2 | 2 | 2 | 2 | 1 | 1 | 2 |
| FVIII(0.5%) | 3 | 3 | 3 | 3 | 3 | 3 | 3 | 3 | 5 | 6 | 20 |
| FVIII(0.75%) | 4 | 4 | 4 | 4 | 4 | 4 | 4 | 4 | 2 | 2 | 10 |
| FVIII(1%) | 5 | 5 | 5 | 5 | 5 | 5 | 5 | 5 | 4 | 7 | 19 |
| FVIII(2.5%) | 6 | 6 | 6 | 6 | 7 | 7 | 7 | 7 | 6 | 9 | 25 |
| FVIII(5%) | 8 | 10 | 10 | 10 | 10 | 10 | 10 | 10 | 7 | 4 | 8 |
| FVIII(10%) | 11 | 11 | 12 | 13 | 13 | 13 | 13 | 12 | 8 | 3 | 32 |
| FVIII(25%) | 21 | 24 | 28 | 29 | 31 | 32 | 30 | 25 | 16 | 5 | 1 |
| FVIII(50%) | 32 | 34 | 37 | 37 | 38 | 38 | 40 | 36 | 27 | 11 | 4 |

Fig. 31

|  | vTB 5% | vTB 10% | vTB20% | vTB 30% | vTB 40% | vTB 50% | vTB60% | vTB70% | vTB80% | vTB90% | vTB95% |
|---|---|---|---|---|---|---|---|---|---|---|---|
| CORRELATION COEFFICIENT | 0.987 | 0.991 | 0.993 | 0.996 | 0.996 | 0.997 | 0.997 | 0.998 | 0.948 | −0.299 | −0.481 |
| SLOPE | 0.135 | 0.141 | 0.152 | 0.157 | 0.165 | 0.168 | 0.175 | 0.177 | 0.124 | −0.049 | −0.075 |
| INTERCEPT | −0.051 | 0.011 | 0.073 | 0.119 | 0.156 | 0.195 | 0.233 | 0.276 | 0.385 | 0.687 | 0.913 |

Fig. 38

| | vAB5% | vAB10% | vAB20% | vAB30% | vAB40% | vAB50% | vAB60% | vAB70% | vAB80% | vAB90% | vAB95% | Vmax(vH100%) |
|---|---|---|---|---|---|---|---|---|---|---|---|---|
| F VIII(0%) | 0.2 | 0.3 | 0.3 | 0.4 | 0.5 | 0.6 | 0.7 | 0.9 | 1.7 | 15.8 | 22.3 | 0.9 |
| F VIII(0.25%) | 0.6 | 0.7 | 1.0 | 1.3 | 1.5 | 1.8 | 2.0 | 2.4 | 3.2 | 5.6 | 9.2 | 1.5 |
| F VIII(0.5%) | 0.8 | 1.1 | 1.5 | 1.9 | 2.2 | 2.6 | 3.1 | 3.5 | 5.3 | 10.1 | 18.8 | 1.8 |
| F VIII(0.75%) | 1.2 | 1.7 | 2.2 | 2.7 | 3.2 | 3.8 | 4.4 | 5.1 | 6.0 | 11.4 | 22.0 | 2.1 |
| F VIII(1%) | 1.4 | 1.9 | 2.6 | 3.2 | 3.8 | 4.4 | 5.1 | 6.0 | 7.6 | 15.2 | 27.1 | 2.3 |
| F VIII(2.5%) | 2.3 | 3.3 | 4.5 | 5.6 | 6.8 | 7.9 | 9.2 | 10.6 | 12.7 | 25.4 | 45.8 | 3.0 |
| F VIII(5%) | 4.0 | 5.6 | 7.7 | 9.4 | 11.4 | 13.3 | 15.5 | 17.8 | 21.1 | 31.9 | 54.0 | 3.9 |
| F VIII(10%) | 6.1 | 8.4 | 12.0 | 14.9 | 18.1 | 21.2 | 24.8 | 28.4 | 33.9 | 41.0 | 103.3 | 4.8 |
| F VIII(25%) | 10.7 | 15.6 | 22.5 | 28.7 | 34.8 | 41.2 | 48.0 | 56.4 | 65.9 | 81.1 | 95.0 | 6.6 |
| F VIII(50%) | 16.0 | 23.2 | 34.3 | 44.6 | 54.7 | 65.1 | 78.1 | 93.3 | 109.3 | 136.7 | 166.3 | 8.3 |

Fig. 39

| | vAB5% | vAB10% | vAB20% | vAB30% | vAB40% | vAB50% | vAB60% | vAB70% | vAB80% | vAB90% | vAB95% | Vmax |
|---|---|---|---|---|---|---|---|---|---|---|---|---|
| CORRELATION COEFFICIENT | 0.994 | 0.995 | 0.996 | 0.997 | 0.997 | 0.997 | 0.998 | 0.998 | 0.999 | 0.913 | 0.929 | 0.998 |
| SLOPE | 0.690 | 0.694 | 0.708 | 0.709 | 0.716 | 0.715 | 0.720 | 0.717 | 0.661 | 0.443 | 0.415 | 0.339 |
| INTERCEPT | 0.090 | 0.237 | 0.375 | 0.474 | 0.549 | 0.621 | 0.685 | 0.754 | 0.884 | 1.235 | 1.465 | 0.348 |

Fig. 40

| | vAB5% | vAB10% | vAB20% | vAB30% | vAB40% | vAB50% | vAB60% | vAB70% | vAB80% | vAB90% | vAB95% | Vmax |
|---|---|---|---|---|---|---|---|---|---|---|---|---|
| F VIII(0%) | 59.0 | 63.0 | 64.1 | 68.3 | 70.3 | 71.6 | 72.3 | 75.8 | 100.5 | 825.3 | 524.1 | 76.1 |
| F VIII(0.25%) | 127.6 | 116.7 | 122.6 | 123.5 | 123.4 | 121.4 | 120.3 | 123.1 | 107.5 | 31.6 | 24.8 | 114.2 |
| F VIII(0.5%) | 103.1 | 109.7 | 108.7 | 107.6 | 101.2 | 104.5 | 105.4 | 101.7 | 114.6 | 60.3 | 69.0 | 104.3 |
| F VIII(0.75%) | 126.6 | 125.8 | 119.4 | 117.0 | 116.7 | 117.4 | 117.5 | 113.8 | 93.4 | 53.1 | 67.5 | 115.1 |
| F VIII(1%) | 117.2 | 113.8 | 113.5 | 109.0 | 110.7 | 107.6 | 106.9 | 107.8 | 98.1 | 76.1 | 83.8 | 107.9 |
| F VIII(2.5%) | 99.8 | 101.7 | 100.1 | 97.7 | 99.0 | 97.2 | 97.6 | 95.0 | 85.7 | 96.8 | 118.4 | 98.5 |
| F VIII(5%) | 112.3 | 107.9 | 104.7 | 101.9 | 102.7 | 101.5 | 100.3 | 98.4 | 93.0 | 80.7 | 98.0 | 100.6 |
| F VIII(10%) | 102.0 | 98.0 | 98.8 | 97.5 | 97.5 | 96.9 | 96.5 | 94.5 | 95.1 | 70.9 | 209.4 | 97.9 |
| F VIII(25%) | 92.1 | 95.6 | 96.1 | 97.6 | 97.2 | 98.0 | 96.7 | 98.1 | 104.0 | 132.4 | 68.5 | 96.6 |
| F VIII(50%) | 92.5 | 84.3 | 86.9 | 91.2 | 91.5 | 93.0 | 95.1 | 99.1 | 111.8 | 214.9 | 131.8 | 94.8 |

[Fig. 43J]
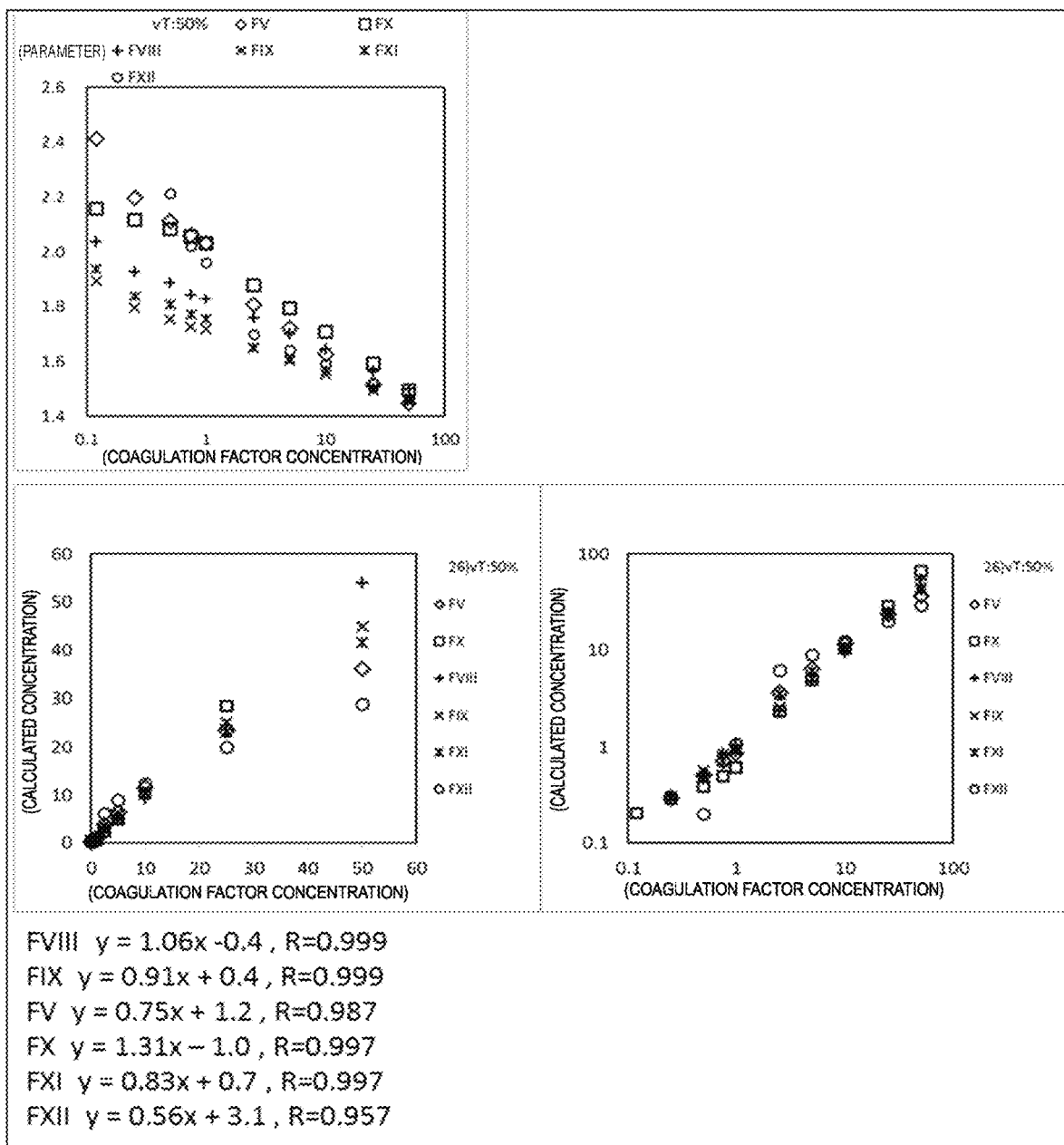

FVIII  y = 0.83x + 1.2 , R=0.979
FIX  y = 0.37x + 3.4 , R=0.784
FV  y = 0.38x + 3.2 , R=0.846
FX  y = 1.08x + 0.2 , R=0.992
FXI  y = 0.77x + 0.9 , R=0.996
FXII  y = 0.40x + 4.9 , R=0.838

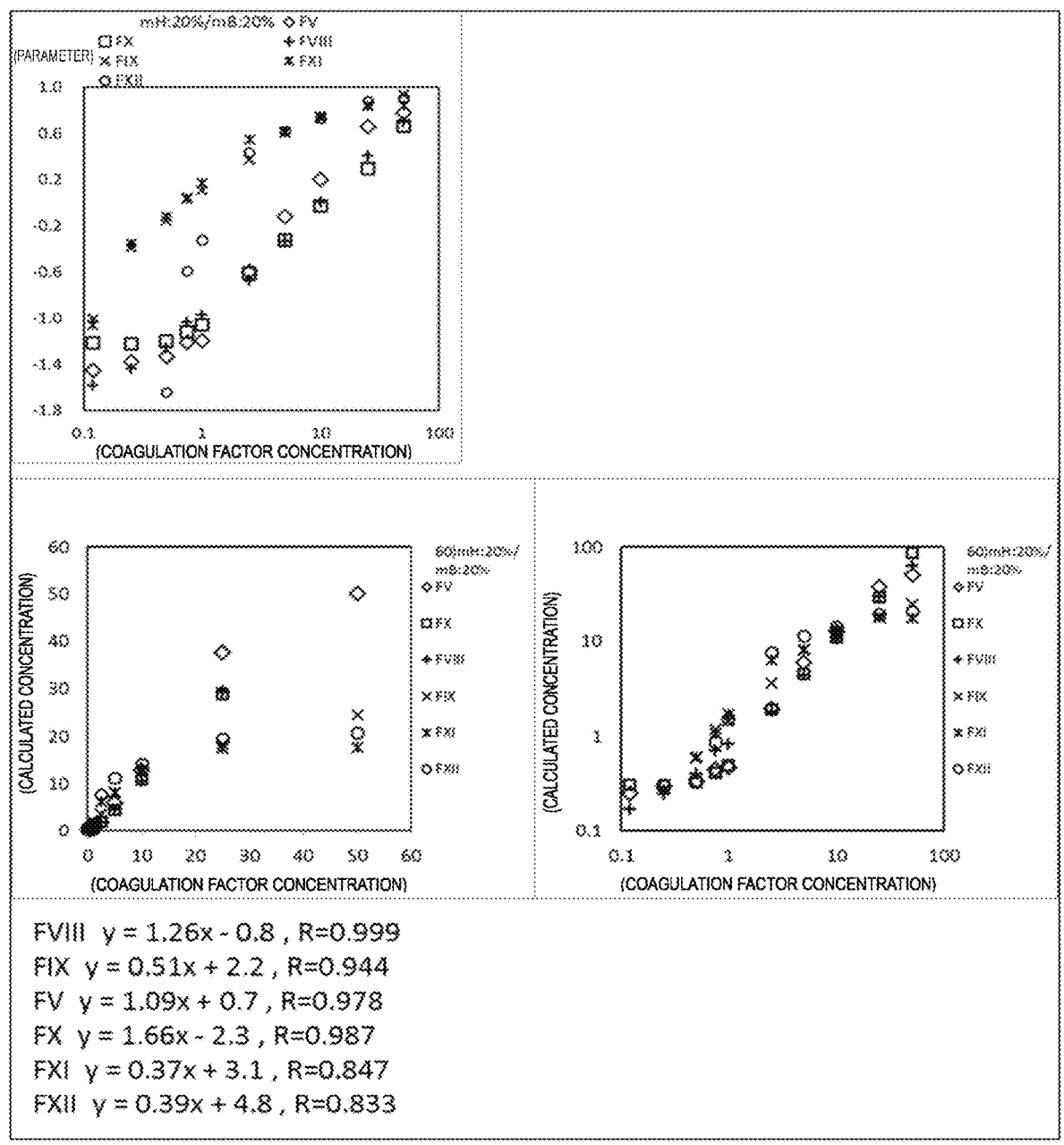

Fig. 48

| SPECIMEN | AFTER HEATING TREATMENT FOR 10 MINUTES (Pb) | | | | WITHOUT HEATING TREATMENT (Pa) | | | | RATIO (Pb/Pa) | | | |
|---|---|---|---|---|---|---|---|---|---|---|---|---|
| | NP 10min | LA 10min | LA.M 10min | IN 10min | IN.M 10min | NP 0min | LA 0min | LA.M 0min | IN 0min | IN.M 0min | NP | LA | LA.M | IN | IN.M |
| COAGULATION TIME (sec) | | | | | | | | | | | | | | | |
| VmaxT | 26.1 | 65.9 | 50.8 | 120.2 | 77.9 | 26.0 | 61.8 | 51.2 | 137.1 | 46.8 | 1.004 | 1.066 | 0.993 | 0.950 | 1.596 |
| Vmax | 23.6 | 63.5 | 49.6 | 81.2 | 75.3 | 23.6 | 58.1 | 49.7 | 120.6 | 47.4 | 1.000 | 1.093 | 0.998 | 0.673 | 1.589 |
| AmaxT | 1.1146 | 0.7639 | 0.2901 | 0.0826 | 0.1682 | 1.1430 | 0.2875 | 0.2847 | 0.0677 | 0.4929 | 0.975 | 0.935 | 1.059 | 1.220 | 0.435 |
| Amax | 21.8 | 46.6 | 37.7 | 74.0 | 55.0 | 21.8 | 43.3 | 37.2 | 73.3 | 37.7 | 1.000 | 1.076 | 1.013 | 1.010 | 1.387 |
| vG10% | 0.05113 | 0.00848 | 0.01215 | 0.00398 | 0.00398 | 0.05226 | 0.00513 | 0.00647 | 0.00094 | 0.01151 | 0.978 | 1.264 | 1.435 | 1.450 | 0.289 |
| vAG10% | 14.7 | 57.9 | 39.1 | 217.6 | 80.9 | 14.6 | 55.2 | 40.8 | 241.1 | 35.6 | 1.007 | 1.049 | 0.958 | 0.903 | 2.270 |
| vT65% | 4.080 | 0.360 | 0.573 | 0.080 | 0.191 | 4.100 | 0.260 | 0.528 | 0.080 | 0.697 | 0.988 | 0.914 | 1.097 | 1.229 | 0.191 |
| vT85% | 1.5 | 1.0 | 1.1 | 0.6 | 0.9 | 1.5 | 1.0 | 1.1 | 0.6 | 1.2 | 1.004 | 1.017 | 1.019 | 1.062 | 0.718 |
| vT95% | 25.2 | 50.3 | 48.6 | 125.1 | 75.0 | 25.1 | 59.3 | 49.2 | 137.2 | 47.1 | 1.006 | 1.066 | 0.988 | 0.912 | 1.592 |
| vH95% | 0.97092 | 0.22552 | 0.24127 | 0.06349 | 0.16201 | 0.98594 | 0.22893 | 0.22244 | 0.05705 | 0.57953 | 0.985 | 0.942 | 1.052 | 1.113 | 0.427 |

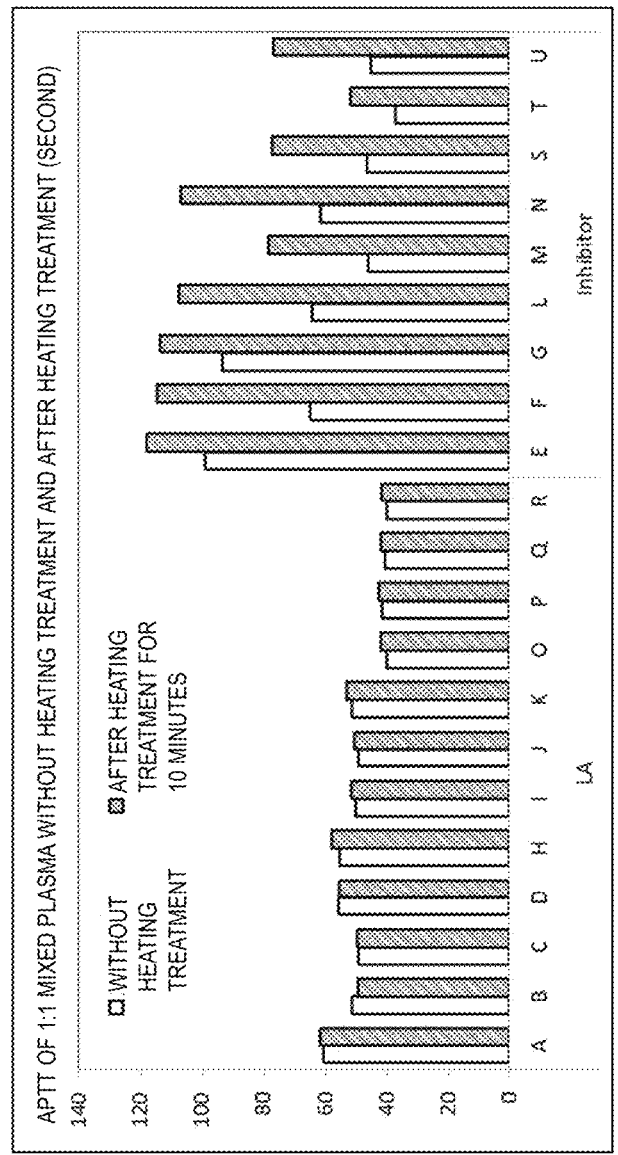

Fig. 62

| SPECIMEN | AFTER HEATING TREATMENT FOR 2 MINUTES (Pb) | | | | | WITHOUT HEATING TREATMENT (Pa) | | | | | RATIO (Pb/Pa) | | | | |
|---|---|---|---|---|---|---|---|---|---|---|---|---|---|---|---|
| | NP 2min | LA 2min | LA M 2min | IN 2min | IN M 2min | NP 0min | LA 0min | LA M 0min | IN 0min | IN M 0min | NP | LA | LA M | IN | IN M |
| COAGULATION TIME (sec) | 26.6 | 80.5 | 70.3 | 88.0 | 78.0 | 26.7 | 78.2 | 67.3 | 87.5 | 72.1 | 0.996 | 1.029 | 1.045 | 1.006 | 1.082 |
| VmaxT | 24.6 | 81.4 | 71.1 | 75.1 | 88.8 | 24.7 | 78.3 | 69.7 | 74.6 | 75.1 | 0.996 | 1.040 | 1.020 | 1.007 | 1.182 |
| Vmax | 1.1432 | 0.2486 | 0.2534 | 0.0811 | 0.1259 | 1.1484 | 0.2606 | 0.2659 | 0.0820 | 0.1724 | 0.995 | 0.954 | 0.953 | 0.990 | 0.731 |
| AmaxT | 22.7 | 66.8 | 54.6 | 70.0 | 56.3 | 22.7 | 64.9 | 52.6 | 68.3 | 52.8 | 1.000 | 1.029 | 1.038 | 1.025 | 1.066 |
| Amax | 0.05253 | 0.00584 | 0.00621 | 0.00118 | 0.00227 | 0.05255 | 0.00641 | 0.00726 | 0.00152 | 0.00311 | 1.000 | 0.911 | 0.869 | 0.775 | 0.728 |
| vS10% | 14.1 | 68.6 | 62.2 | 207.3 | 126.9 | 14.0 | 66.1 | 57.8 | 205.6 | 90.3 | 1.007 | 1.038 | 1.076 | 1.008 | 1.405 |
| vAB10% | 4.410 | 0.174 | 0.224 | 0.019 | 0.051 | 4.482 | 0.188 | 0.259 | 0.019 | 0.103 | 0.984 | 0.930 | 0.864 | 0.986 | 0.490 |
| vTf85% | 1.6 | 1.0 | 1.1 | 0.6 | 0.7 | 1.6 | 1.0 | 1.1 | 0.6 | 0.8 | 0.998 | 1.015 | 0.975 | 1.015 | 0.840 |
| vTf80% | 26.1 | 61.2 | 71.2 | 120.6 | 88.3 | 26.1 | 78.7 | 68.2 | 120.5 | 77.0 | 0.999 | 1.032 | 1.044 | 1.001 | 1.145 |
| vHf50% | 1.00553 | 0.21513 | 0.02166 | 0.06517 | 0.10819 | 1.01002 | 0.225 | 0.22866 | 0.06539 | 0.14674 | 0.996 | 0.956 | 0.947 | 0.997 | 0.737 |

ANALYSIS METHOD, ANALYSIS APPARATUS, AND ANALYSIS PROGRAM

RELATED APPLICATIONS

This application is a national stage application of PCT/JP2019/044943, filed on Nov. 15, 2019, which is based on and claims priority to Japanese applications 2018-214949 and 2018-214961, both filed on Nov. 15, 2018, and Japanese application 2019-084727, filed on Apr. 25, 2019, the entire contents of all applications are incorporated herein by reference.

FIELD OF THE INVENTION

The present invention relates to an analysis method, an analysis apparatus, and analysis program.

BACKGROUND OF THE INVENTION

A blood coagulation test is performed in order to diagnose a blood coagulation function of a patient. In the blood coagulation test, a predetermined reagent is added to a blood specimen of a patient, and a blood coagulation function such as coagulation time is examined. The blood coagulation test can determine a state of hemostatic or fibrinolytic capacity of a patient. Examples of a cause of prolongation of blood coagulation time include an effect of a coagulation inhibitor, a decrease in a coagulation-related component, congenital deficiency in blood coagulation factors, and presence of an acquired autoantibody that inhibits a coagulation reaction.

For example, the clinical severity of a bleeding symptom in hemophilia A is determined by using 1% as a boundary when coagulation factor VIII activity (hereinafter, for example, coagulation factor VIII is referred to as factor VIII) of a normal person is assumed to be 100%. As a method for measuring the factor VIII activity, a method for adding a predetermined reagent to a blood specimen of a patient and performing measurement based on a coagulation reaction curve obtained from a coagulation reaction amount with respect to reaction time at this time is known.

Patent Literatures 1 to 3 disclose the following techniques. A maximum coagulation rate is determined based on a coagulation rate curve obtained from first order differentiation of a coagulation reaction curve indicating a coagulation reaction amount with respect to reaction time. A maximum coagulation acceleration and a maximum coagulation deceleration are determined based on a coagulation acceleration curve obtained from second differentiation of the coagulation reaction curve. Times required for reaching respective states from start of coagulation reaction are determined as a maximum coagulation rate time, a maximum coagulation acceleration time, and a maximum coagulation deceleration time. These values are called coagulation waveform parameters obtained from the coagulation reaction curve, the coagulation rate curve, or the coagulation acceleration curve, and for example, presence or absence of coagulation factor abnormality is determined based on these values.

Patent Literature 2 discloses a method for distinguishing between congenital coagulopathy and acquired coagulopathy by performing a test (cross-mixing test) for measuring coagulation time of a sample obtained by mixing a normal plasma with a test plasma exhibiting a prolongation of coagulation time. In general, when an extension of activated partial thromboplastin time (APTT) is observed in measurement of APTT, a cross-mixing test is performed to identify a cause of extending APTT. In the cross-mixing test, the following two tests are performed on each of a test plasma, a normal plasma, and a mixed plasma of the test plasma and the normal plasma.

Immediate type test in which each of the plasmas is measured without heating treatment to examine an immediate reaction Delayed type test in which each of the plasmas is subjected to heating treatment (incubation) at 37° C. for two hours and then measured to examine a delayed reaction Based on the result of the cross-mixing test, it is determined by which of a coagulation factor inhibitor (inhibitor), a lupus anticoagulant (LA), and a coagulation factor deficiency such as hemophilia, APTT is extended. The result of the cross-mixing test is expressed by a graph in which the vertical axis indicates an APTT measurement value (second) and the horizontal axis indicates a volume mixing ratio between the test plasma and the normal plasma. Graphs created indicate the following patterns when causes of coagulation delay are as follows.

Coagulation factor inhibitor (hereinafter, referred to as inhibitor): In an immediate reaction, various patterns such as a "convex downward curve" pattern, a "straight line" pattern, and a "convex upward curve" pattern are obtained. In a delayed reaction, a "straight line" pattern or an apparent "convex upward curve" pattern is obtained.

Lupus anticoagulant (hereinafter, referred to as LA): In both an immediate reaction and a delayed reaction, a "convex upward curve" pattern or a "straight line" pattern is obtained.

Coagulation factor deficiency such as hemophilia (hereinafter, referred to as factor deficiency): In both an immediate reaction and a delayed reaction, a "convex downward curve" pattern is obtained.

Therefore, a cause of coagulation delay is determined by the following method based on the result of the cross-mixing test on a test plasma in which a cause of coagulation delay is unknown. When a "convex downward curve" result is obtained in the immediate type test, a cause of coagulation delay is inhibitor or factor deficiency. However, it is not possible to distinguish between inhibitor and factor deficiency. In this case, when a "convex downward curve" result is obtained in the delayed type test, a cause of coagulation delay can be determined to be factor deficiency, and when a "straight line" result or a "convex upward curve" result is obtained, a cause of coagulation delay can be determined to be inhibitor. When a "convex upward curve" result is obtained in the immediate type test, a cause of coagulation delay is inhibitor or LA. However, it is not possible to distinguish between inhibitor and LA. In this case, when a "convex upward curve" result is obtained more clearly in the delayed type test than in the immediate type test, a cause of coagulation delay can be determined to be inhibitor.

As described above, since the conventional cross-mixing test is determined by a qualitative graph pattern, a graph pattern that makes determination difficult may be obtained depending on a test plasma. In addition, since it is required to measure APTT after subjecting the mixed plasma to heating treatment (incubation) at 37° C. for two hours, it takes a lot of time of about 2.5 hours for the test when heating time and measurement time are taken into consideration.

CITATION LIST

Patent Literature

Patent Literature 1: JP 2016-194426 A
Patent Literature 2: JP 2016-118442 A
Patent Literature 3: JP 2017-106925 A

SUMMARY OF THE INVENTION

The present invention provides:
[1] A method for analyzing a coagulation characteristic of a blood specimen, the method including:
  (1) acquiring data for a coagulation reaction curve indicating a coagulation reaction amount of a mixed solution containing a blood sample and a reagent with respect to reaction time;
  (2) calculating data for a differential curve obtained by differentiating the coagulation reaction curve;
  (3) calculating information related to a center-of-gravity point of the differential curve; and
  (4) evaluating the coagulation characteristic of the blood sample using the information related to the center-of-gravity point.
[2] The method according to [1], in which the differential curve is at least one selected from the group consisting of a first order differential curve related to the coagulation reaction curve and a second order differential curve related to the coagulation reaction curve.
[3] The analysis method according to [2], in which the center-of-gravity point of the differential curve is a center-of-gravity point of the first order differential curve represented by coordinates (VT, vii) defined by center-of-gravity time vT and center-of-gravity height and the vT and the vH are represented by the following formulas when the first order differential curve is represented by F(t) (t: time) and time when F(t) is a predetermined value x is represented by t1 or t2 (t1<t2).

[Numerical Formula 1]

$$vT = \frac{M}{\sum_{i=t1}^{t2} F(i)} \quad (6)$$

$$vH = \frac{M}{\sum_{i=t1}^{t2} i} \quad (7)$$

in which $$M = \sum_{i=t1}^{t2} (i \times F(i)) \quad (5)$$

[4] The analysis method according to [3], in which
the information related to the center-of-gravity point includes one or more parameters selected from the group consisting of the VT, the vH, peak width vB, center-of-gravity peak width vW, B flattening ratio vAB, B time ratio vTB, W flattening ratio vAW, W time ratio vTW, average time vTa, average height vita, vTm, vABa, and vAWa,
the peak width vB is a length of time where F(t)≥x within a period from the t1 to the t2,
the center-of-gravity peak width vW is a length of time where F(t)≥vH within a period from the t1 to the t2,
the vAB represents a ratio between the vH and the vB,
the vTB represents a ratio between the vT and the vB,
the vAW represents a ratio between the vH and the vW,
the vTW represents a ratio between the vT and the vW,
the vTa, the vHa, and the vTm are represented by the following formulas, respectively, when F(t), t1, and t2 have the same definitions as those described above, and the number of data points from F(t1) to F(t2) is n,

[Numerical Formula 2]

$$vTa = \frac{\sum_{i=t1}^{t2} i}{n} \quad (10)$$

$$vHa = \frac{\sum_{i=t1}^{t2} F(i)}{n} \quad (11)$$

$$vTm = \frac{t1 + t2}{2} \quad (12)$$

the vABa represents a ratio between the vHa and the vB, and
the vAWa represents a ratio between the vHa and the vW.
[5] The analysis method according to [2], in which the center-of-gravity point of the differential curve is a center-of-gravity point of a positive peak of the second order differential curve represented by coordinates (pT, pH) defined by center-of-gravity time pT and center-of-gravity height pH, and the pT and the pH are represented by the following formulas when the second order differential curve is represented by F'(t) (t: time) and time when F"(t) is a predetermined value x is represented by t1 or t2 (t1<t2).

[Numerical Formula 3]

$$pT = \frac{M}{\sum_{i=t1}^{t2} F'(i)} \quad (6)'$$

$$pH = \frac{M}{\sum_{i=t1}^{t2} i} \quad (7)'$$

in which $$M = \sum_{i=t1}^{t2} (i \times F'(i)) \quad (5)'$$

[6] The analysis method according to [5], in which
the information related to the center-of-gravity point includes one or more parameters selected from the group consisting of the pT, the pH, peak width pB, center-of-gravity peak width pW, B flattening ratio pAB, B time ratio pTB, W flattening ratio pAW, and W time ratio pTW,
the peak width pB is a length of time where F'(t)≥x within a period from the t1 to the t2,
the center-of-gravity peak width pW is a length of time where F'(t)≥pH within a period from the t1 to the t2,
the pAB represents a ratio between the pH and the pB,
the pTB represents a ratio between the pT and the pB, the pAW represents a ratio between the pH and the pW, and the pTW represents a ratio between the pT and the pW.

[7] The analysis method according to [2], in which the center-of-gravity point of the differential curve is a center-of-gravity point of a negative peak of the second order differential curve represented by coordinates (mT, mH) defined by center-of-gravity time mT and center-of-gravity height mH, and the mT and the mH are represented by the following formulas when the second order differential curve is represented by F'(t) (t: time) and time when F'(t) is a predetermined value x is represented by t1 or t2 (t1<t2).

[NumericalFormula 4]

$$mT = \frac{M}{\sum_{i=t1}^{t2} F'(i)} \quad (6)''$$

$$mH = \frac{M}{\sum_{i=t1}^{t2} i} \quad (7)''$$

in which $$M = \sum_{i=t1}^{t2} (i \times F'(i)) \quad (5)''$$

[8] The analysis method according to [7], in which the information related to the center-of-gravity point includes one or more parameters selected from the group consisting of the mT, the mH, peak width mB, center-of-gravity peak width mW, B flattening ratio mAB, B time ratio mTB, W flattening ratio mAW, and W time ratio mTW, the peak width mB is a length of time where F'(t)≤x within a period from the t1 to the t2, the center-of-gravity peak width mW is a length of time where F'(t)≤mH within a period from the t1 to the t2, the mAB represents a ratio between the and the mB, the mTB represents a ratio between the mT and the mB, the mAW represents a ratio between the and the mat, and the mTW represents a ratio between the mT and the mW.

[9] The analysis method according to any one of [3] to [8], in which the predetermined value x is a value that is 0.5% to 99% of a maximum value of the first order differential curve F(t).

[10] The analysis method according to [4], [6], or [8], in which the coagulation characteristic is a coagulation factor concentration, and the coagulation factor is at least one selected from the group consisting of coagulation factor V, coagulation factor VIII, coagulation factor IX, coagulation factor X, coagulation factor XI, and coagulation factor XII.

[11] The analysis method according to [4], [6], or [8], in which the above step (4) includes qualifying an analysis target component and quantifying the concentration of the analysis target component based on a relationship between the concentration of the analysis target component and the flattening ratio, and the obtained flattening ratio.

[12] The analysis method according to [4], [6], or [8], in which the above step (4) includes an analysis using a ratio (time ratio) between the center-of-gravity time and the peak width.

[13] The analysis method according to [12], in which the above step (4) includes determining whether or not a cause of prolongation of coagulation time is coagulation factor VIII based on the time ratio.

[14] The analysis method according to [12] or [13], in which the above step (4) includes qualifying an analysis target component and quantifying the concentration of the analysis target component based on a relationship between the concentration of the analysis target component and the time ratio, and the obtained time ratio.

[15] The analysis method according to any one of [1] to [14], in which the data of the coagulation reaction curve is obtained by measuring activated partial thromboplastin time.

[16] The analysis method according to any one of [1] to [15], in which the above step (2) further includes performing a correction process based on a maximum value of the acquired data of the coagulation reaction curve to calculate corrected data of the coagulation reaction curve, and in the above step (2), the corrected data of the coagulation reaction curve is used for calculating the data of the differential curve.

[17] The analysis method according to any one of [1] to [16], in which the above step (1) includes:

preparing a mixed plasma obtained by mixing a test plasma and a normal plasma;

measuring coagulation time of the mixed plasma without heating treatment; and measuring coagulation time of the mixed plasma after heating treatment, the above step (3) includes:

calculating a first parameter related to a coagulation reaction state based on the coagulation time measurement data of the mixed plasma without heating treatment; and calculating a second parameter related to a coagulation reaction state based on the coagulation time measurement data of the mixed plasma after heating treatment, and the above step (4) includes identifying a cause of prolongation of coagulation time based on a ratio or a difference between the first parameter and the second parameter.

[18] The analysis method according to [17], in which the measurement of coagulation time is at least one of measurement of prothrombin time, measurement of activated partial thromboplastin time, measurement of diluted prothrombin time, measurement of diluted partial thromboplastin time, measurement of kaolin clotting time, and measurement of diluted Russell's viper venom time.

[19] The analysis method according to [17] or [18], in which the identification includes determining whether the cause of prolongation of coagulation time is an effect of a coagulation factor inhibitor or an effect of a lupus anticoagulant.

[20] The analysis method according to any one of [17] to [19], in which heating time of the mixed plasma is 2 minutes or longer and 30 minutes or shorter.

The analysis method according to any one of [17] to [20], in which the first parameter and the second parameter each include at least one selected from the group consisting of a maximum value of the first order differential curve, center-of-gravity height vH, center-of-gravity time vT, peak width vB, center-of-gravity peak width vW, B flattening ratio vAB, B time ratio vTB, W flattening ratio vAW, W time ratio vTW, average time vTa, average height vHa, vTm, vABa, and vAWa.

The analysis method according to any one of [17] to [20].

[22] The analysis method according to any one of [17] to [21], in which the identification includes determining that a cause of prolongation of coagulation time is an effect of a coagulation factor inhibitor when a ratio between the first parameter and the second parameter does not fall within a predetermined range including 1.

[23] The analysis method according to any one of [17] to [21], in which the identification includes determining that a cause of prolongation of coagulation time is an effect of a lupus anticoagulant when a ratio between the first parameter and the second parameter falls within a predetermined range including 1.

[24] The analysis method according to any one of [17] to [21], in which the identification includes determining that a cause of prolongation of coagulation time is an effect of a coagulation factor inhibitor when a difference between the first parameter and the second parameter does not fall within a predetermined range including 0.

[25] The analysis method according to any one of [17] to [21], in which the identification includes determining that a cause of prolongation of coagulation time is an effect of a lupus anticoagulant when a difference between the first parameter and the second parameter falls within a predetermined range including 0.

[26] The analysis method according to any one of [17] to [25], in which a mixing ratio between the test plasma and the normal plasma is 1:1.

[27] The analysis method according to any one of [17] to [26], in which heating treatment temperature of the mixed plasma is 35° C. or higher and 39° C. or lower.

[28] An analysis apparatus for executing the analysis method according to any one of [1] to [27].

BRIEF DESCRIPTION OF THE DRAWINGS

FIG. 10D is a conceptual diagram illustrating vTa, vHa, and vTm. The dotted line indicates a 10% calculation target area of a first order curve.

FIG. 26C is a diagram illustrating an example of a relationship between a logarithm of each of the concentrations of various coagulation factors and a logarithm of time ratio vTB20%.

FIG. 29 illustrates an example of a relationship between a factor VIII concentration and time ratio vTB for each calculation target area value.

FIG. 30 illustrates an example of the order of time ratios obtained for factors VIII having respective concentrations among time ratios obtained for the concentrations of various coagulation factors.

FIG. 31 illustrates an example of a correlation between a logarithm of a factor VIII concentration and a logarithm of a time ratio.

FIG. 38 illustrates an example of a relationship between a factor VIII concentration and each of flattening ratio vAB for each calculation target area value and maximum first order differential value Vmax.

FIG. 39 illustrates an example of a correlation between a logarithm of a factor VIII concentration and each of a logarithm of a flattening ratio and a logarithm of maximum first order differential value Vmax.

FIG. 40 illustrates an example of a ratio (recovery ratio) between the known concentration of factor VIII and a calculated concentration determined from a calibration curve using the values illustrated in FIG. 39.

Figure 43A:
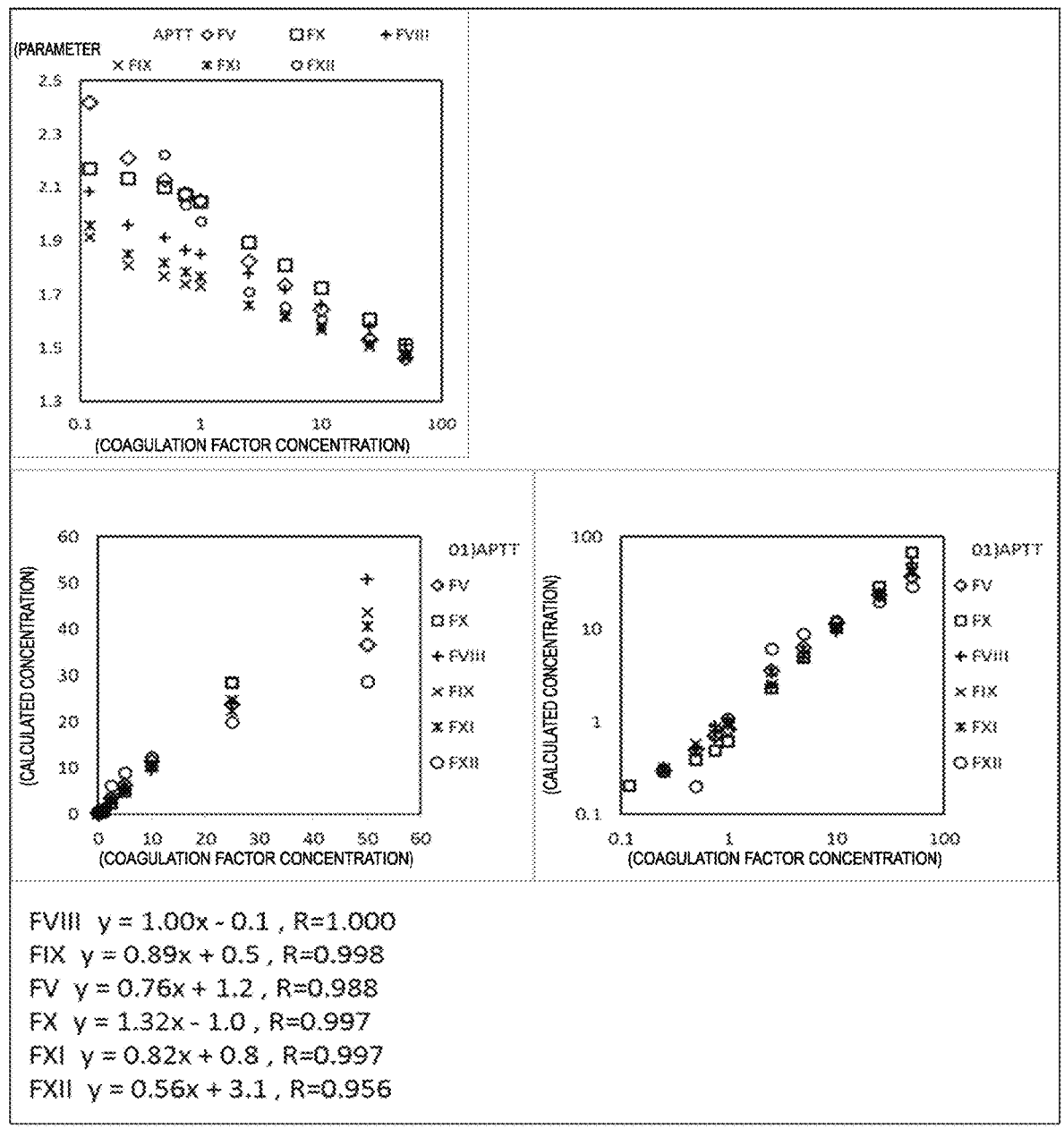

The top diagram of FIG. 43A is a diagram illustrating an example of a relationship between a logarithm of each of the concentrations of various coagulation factors and a logarithm of APTT. The middle left diagram of FIG. 43A illustrates plots of a calculated concentration based on a calibration curve with respect to the measured concentration of a coagulation factor. The middle right diagram of FIG. 43A illustrates logarithmic plots between a measured concentration and a calculated concentration.

Figure 43B:
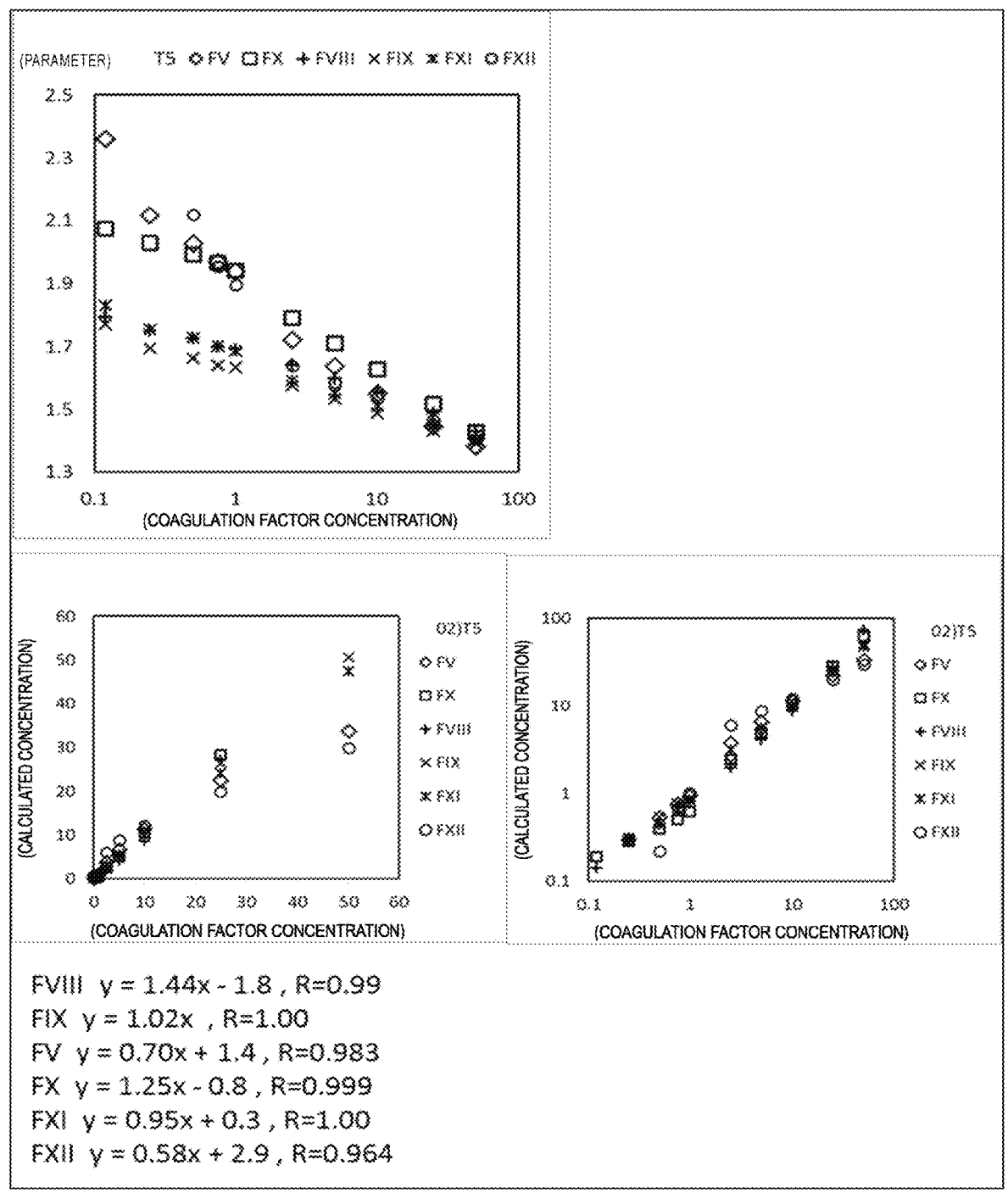

The top diagram of FIG. 43B is a diagram illustrating an example of a relationship between a logarithm of each of the concentrations of various coagulation factors and a logarithm of T5. The middle left diagram of FIG. 43B illustrates plots of a calculated concentration based on a calibration curve with respect to the measured concentration of a coagulation factor. The middle right diagram of FIG. 43B illustrates logarithmic plots between a measured concentration and a calculated concentration.

Figure 43C:
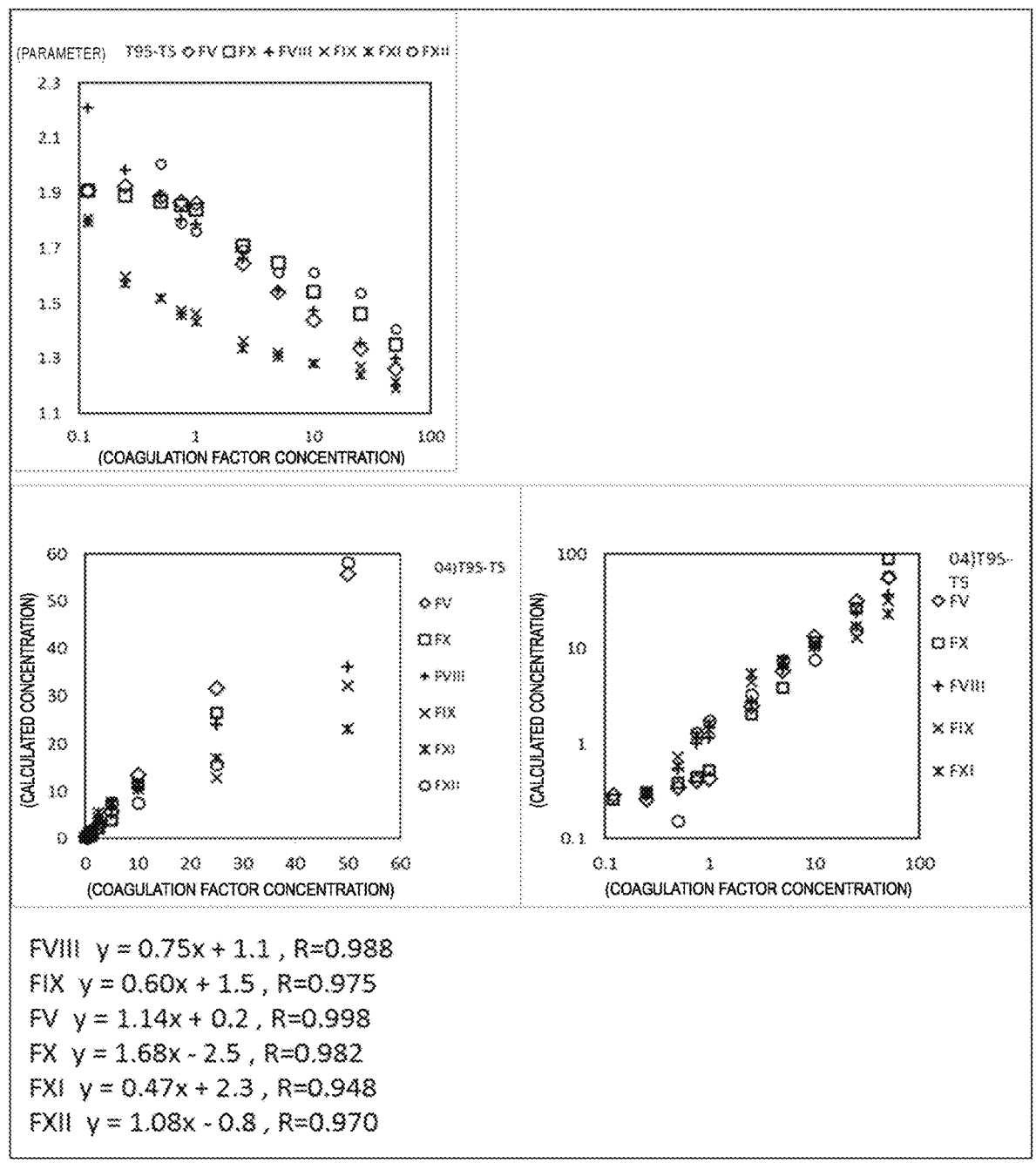

The top diagram of FIG. 43C is a diagram illustrating an example of a relationship between a logarithm of each of the concentrations of various coagulation factors and a logarithm of T95-T5. The middle left diagram of FIG. 43C illustrates plots of a calculated concentration based on a calibration curve with respect to the measured concentration of a coagulation factor. The middle right diagram of FIG. 43C illustrates logarithmic plots between a measured concentration and a calculated concentration.

Figure 43D:
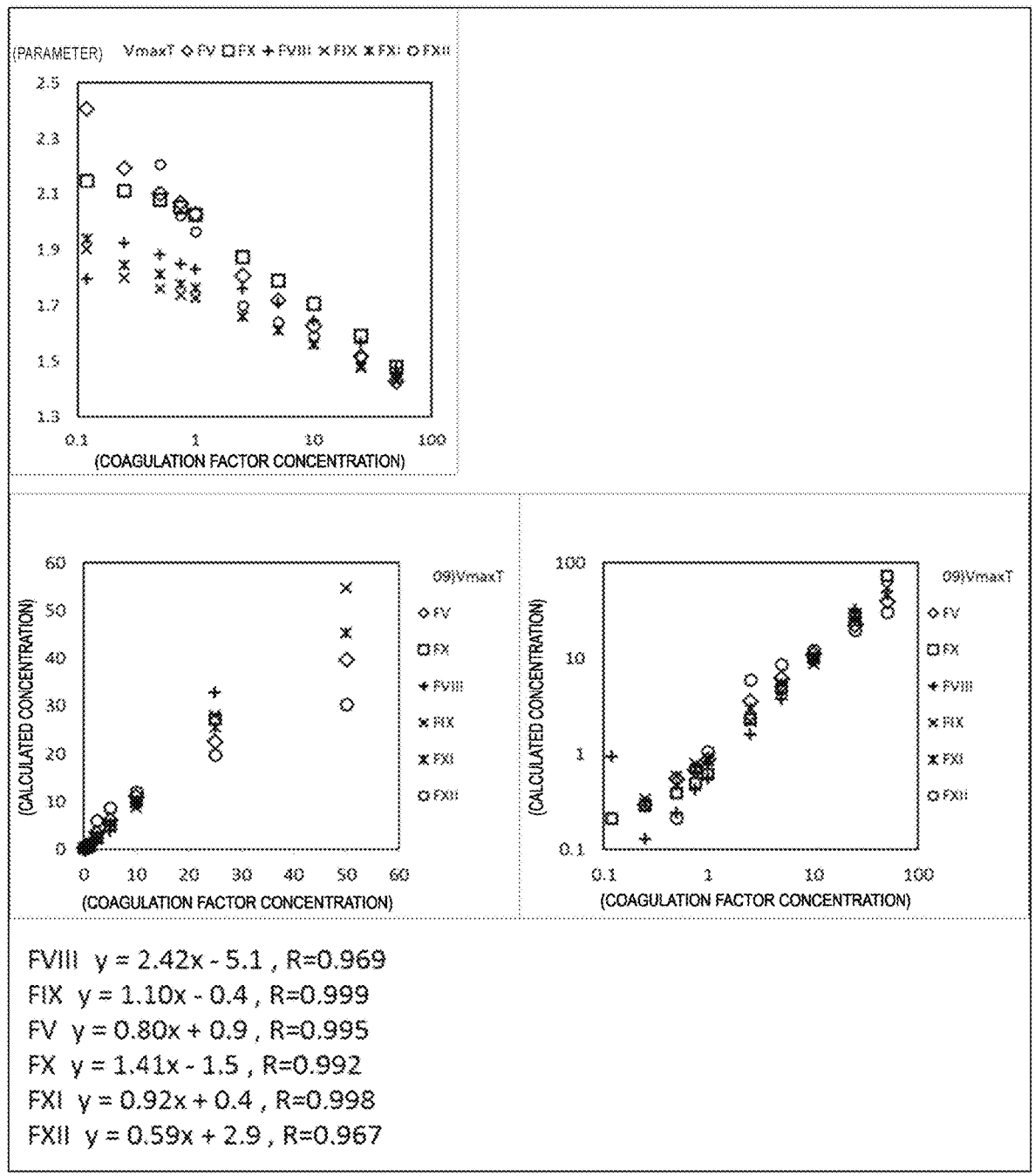

The top diagram of FIG. 43D is a diagram illustrating an example of a relationship between a logarithm of each of the concentrations of various coagulation factors and a logarithm of VmaxT. The middle left diagram of FIG. 43D illustrates plots of a calculated concentration based on a calibration curve with respect to the measured concentration of a coagulation factor. The middle right diagram of FIG. 43D illustrates logarithmic plots between a measured concentration and a calculated concentration.

Figure 43E:
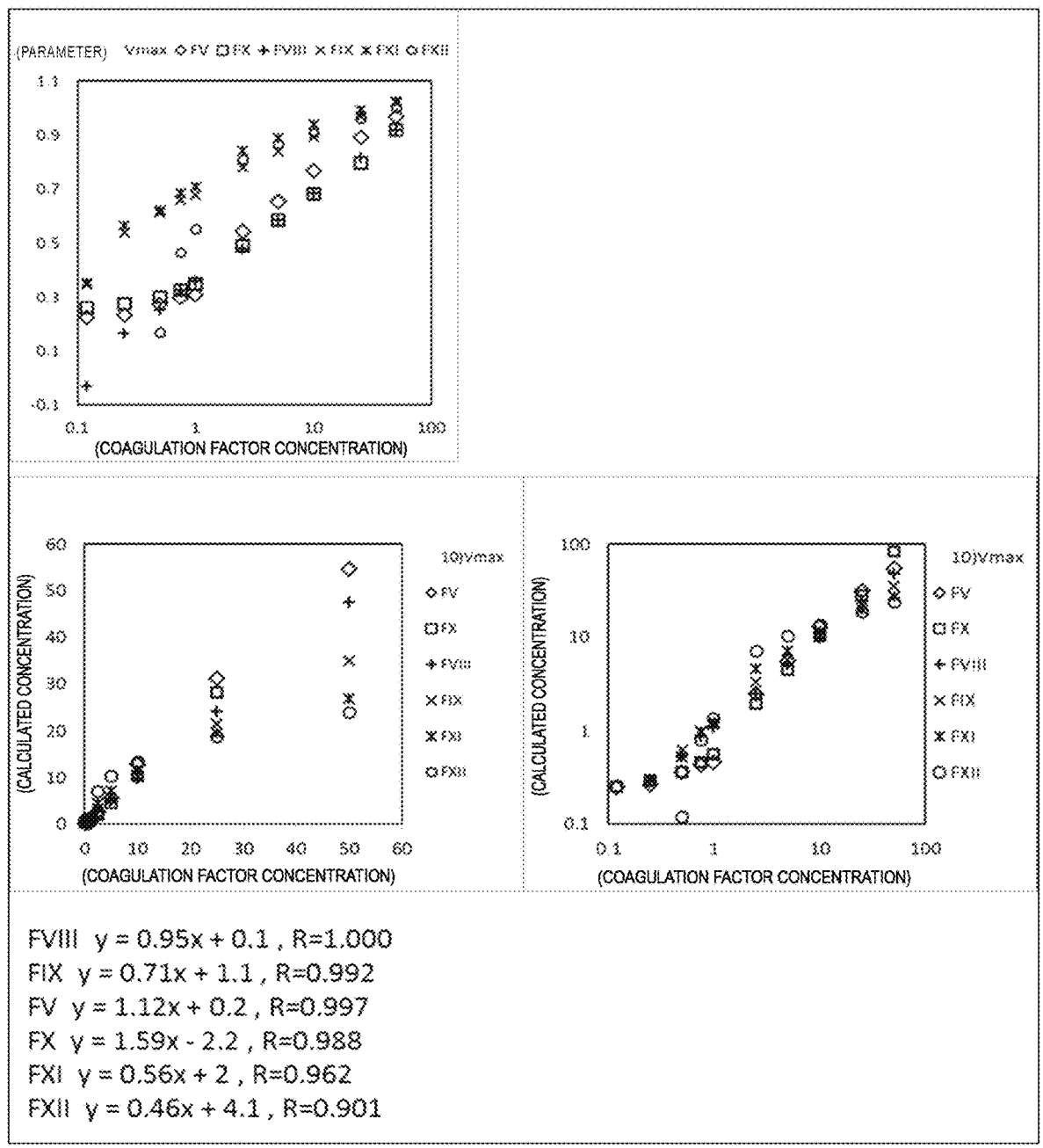

The top diagram of FIG. 43E is a diagram illustrating an example of a relationship between a logarithm of each of the concentrations of various coagulation factors and a logarithm of Vmax. The middle left diagram of FIG. 43E illustrates plots of a calculated concentration based on a calibration curve with respect to the measured concentration of a coagulation factor. The middle right diagram of FIG. 43E illustrates logarithmic plots between a measured concentration and a calculated concentration.

Figure 43F:
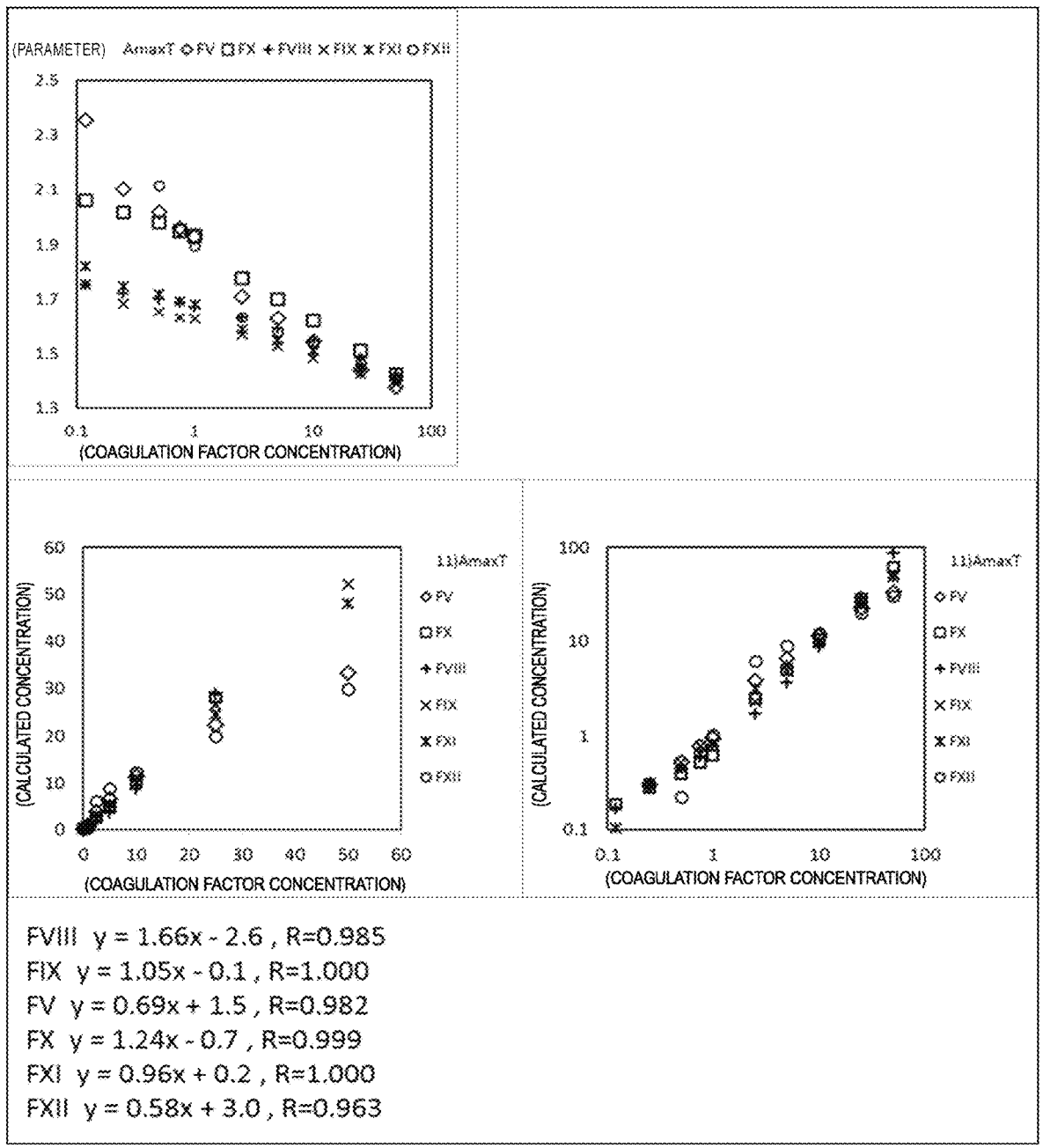

The top diagram of FIG. 43F is a diagram illustrating an example of a relationship between a logarithm of each of the concentrations of various coagulation factors and a logarithm of AmaxT. The middle left diagram of FIG. 43F illustrates plots of a calculated concentration based on a calibration curve with respect to the measured concentration of a coagulation factor. The middle right diagram of FIG. 43F illustrates logarithmic plots between a measured concentration and a calculated concentration.

Figure 43G:
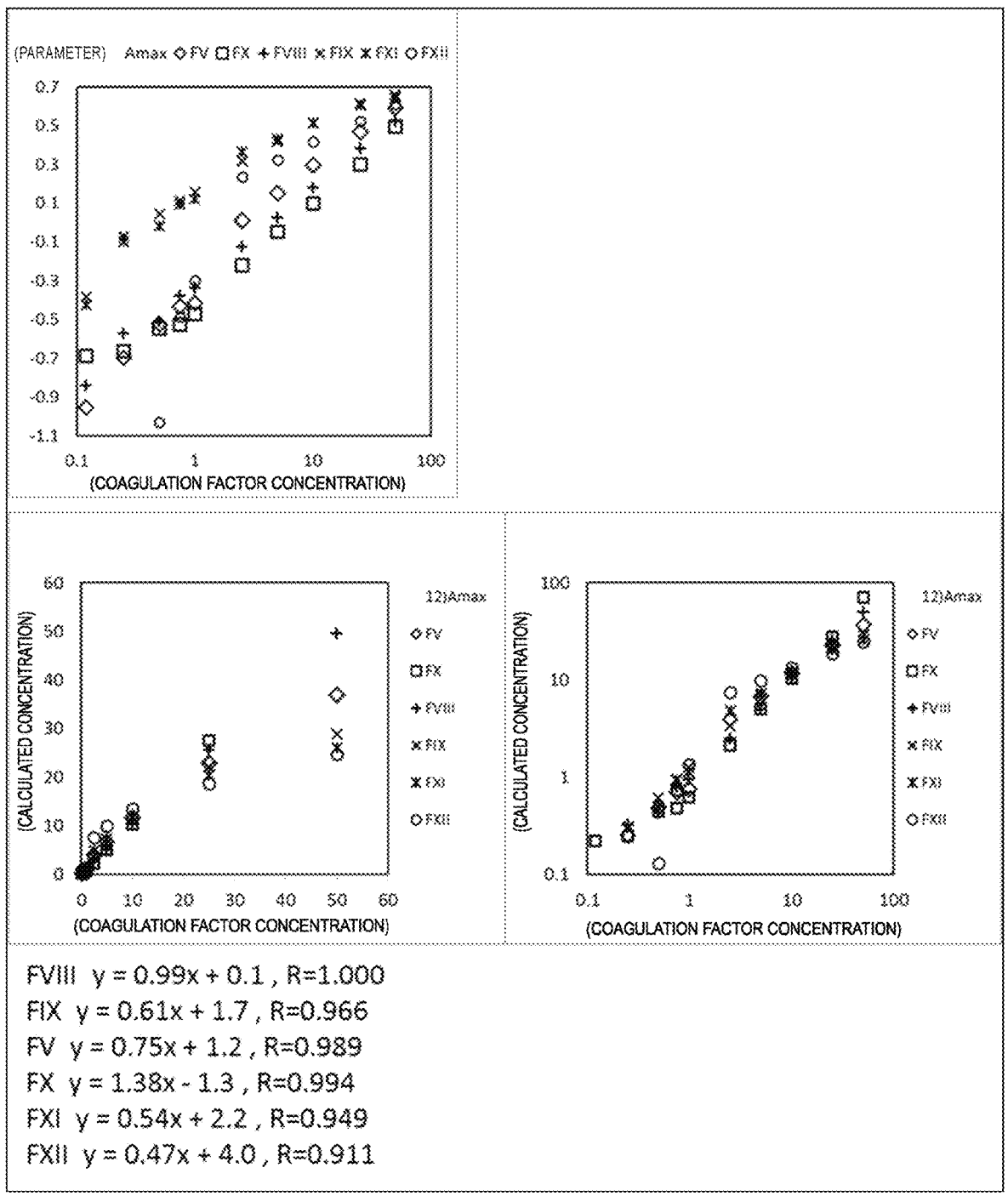

The top diagram of FIG. 43G is a diagram illustrating an example of a relationship between a logarithm of each of the concentrations of various coagulation factors and a logarithm of Amax. The middle left diagram of FIG. 43G illustrates plots of a calculated concentration based on a calibration curve with respect to the measured concentration of a coagulation factor. The middle right diagram of FIG. 43G illustrates logarithmic plots between a measured concentration and a calculated concentration.

Figure 43H:
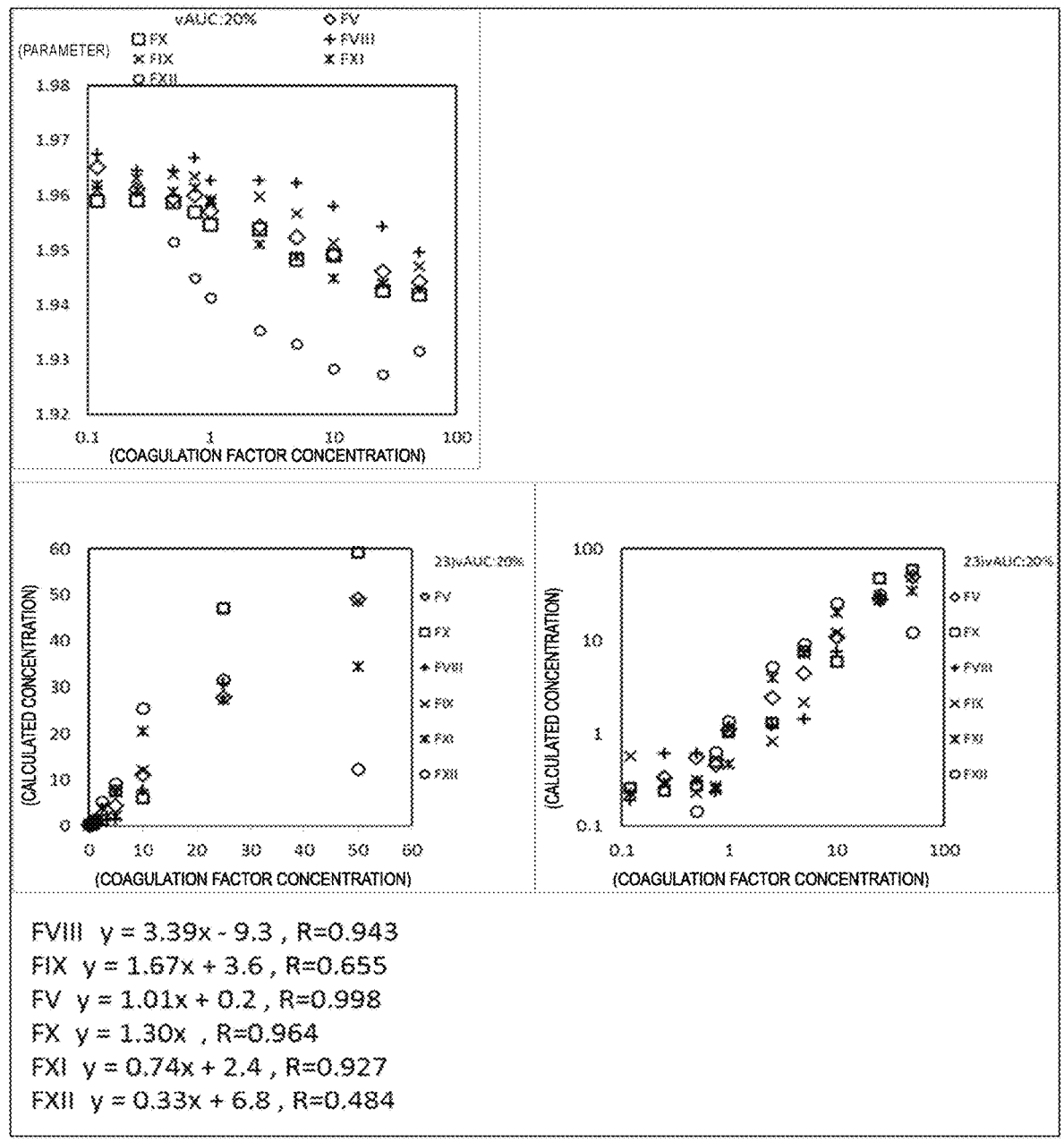

The top diagram of FIG. 43H is a diagram illustrating an example of a relationship between a logarithm of each of the concentrations of various coagulation factors and a logarithm of vAUC20%. The middle left diagram of FIG. 43H illustrates plots of a calculated concentration based on a calibration curve with respect to the measured concentration of a coagulation factor. The middle right diagram of FIG. 43H illustrates logarithmic plots between a measured concentration and a calculated concentration.

Figure 43I:
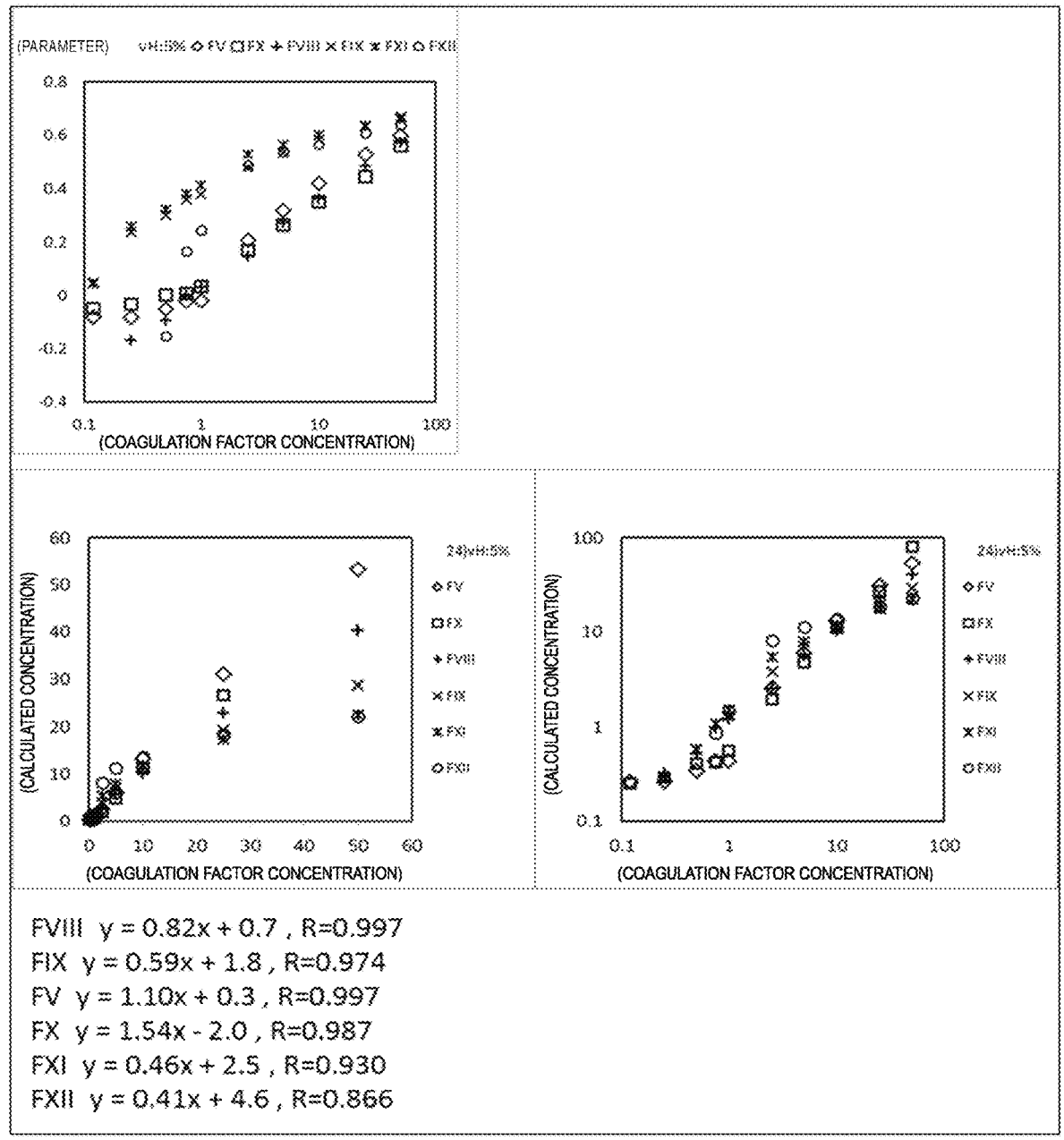

The top diagram of FIG. 43I is a diagram illustrating an example of a relationship between a logarithm of each of the concentrations of various coagulation factors and a logarithm of vH5%. The middle left diagram of FIG. 43I illustrates plots of a calculated concentration based on a calibration curve with respect to the measured concentration of a coagulation factor. The middle right diagram of FIG. 43I illustrates logarithmic plots between a measured concentration and a calculated concentration.

The top diagram of FIG. 43J is a diagram illustrating an example of a relationship between a logarithm of each of the concentrations of various coagulation factors and a logarithm of vT50%. The middle left diagram of FIG. 43J illustrates plots of a calculated concentration based on a calibration curve with respect to the measured concentration of a coagulation factor. The middle right diagram of FIG. 43J illustrates logarithmic plots between a measured concentration and a calculated concentration.

Figure 43K:
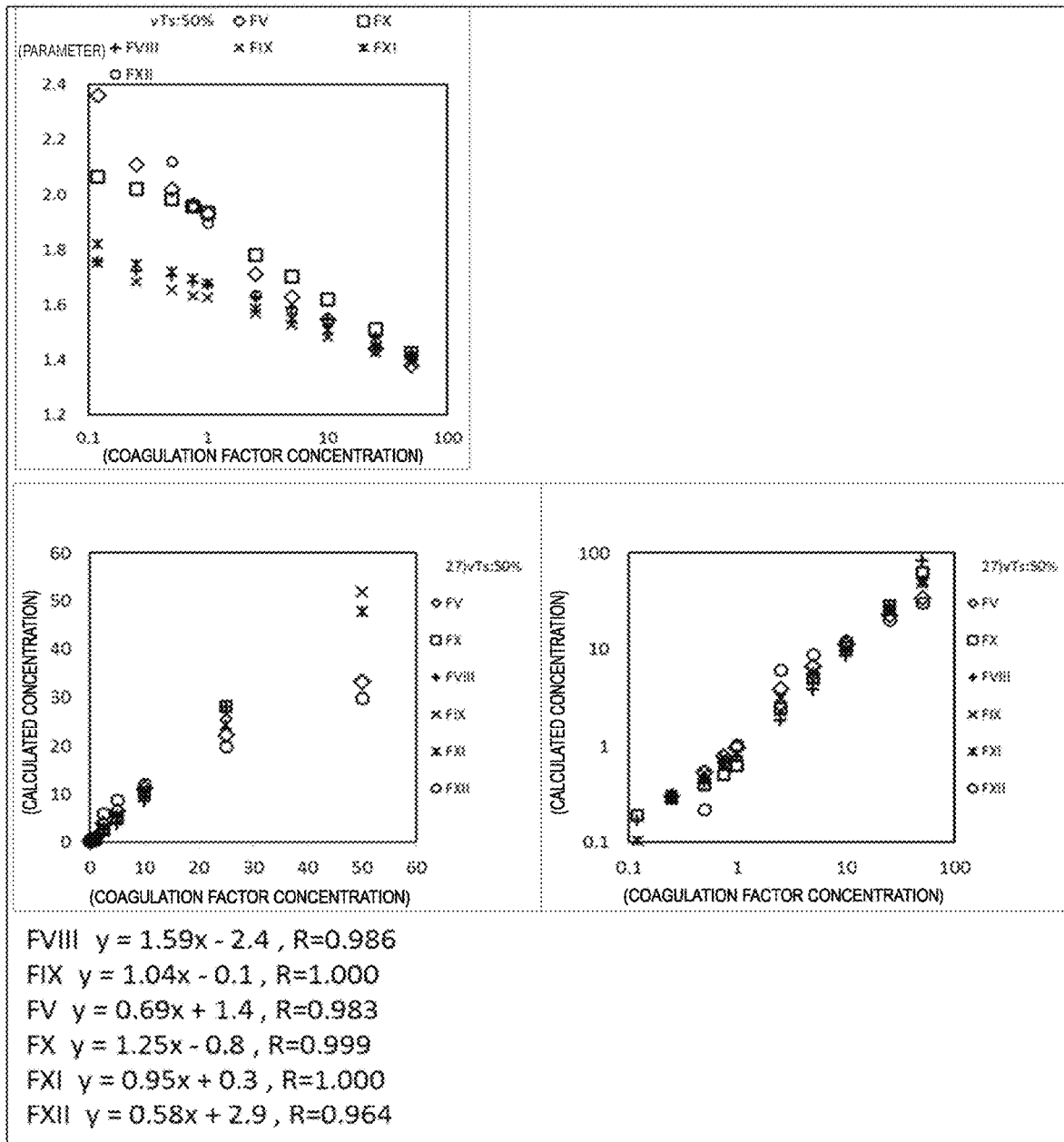

The top diagram of FIG. 43K is a diagram illustrating an example of a relationship between a logarithm of each of the concentrations of various coagulation factors and a logarithm of vTs50%. The middle left diagram of FIG. 43K illustrates plots of a calculated concentration based on a calibration curve with respect to the measured concentration of a coagulation factor. The middle right diagram of FIG. 43K illustrates logarithmic plots between a measured concentration and a calculated concentration.

Figure 43L:
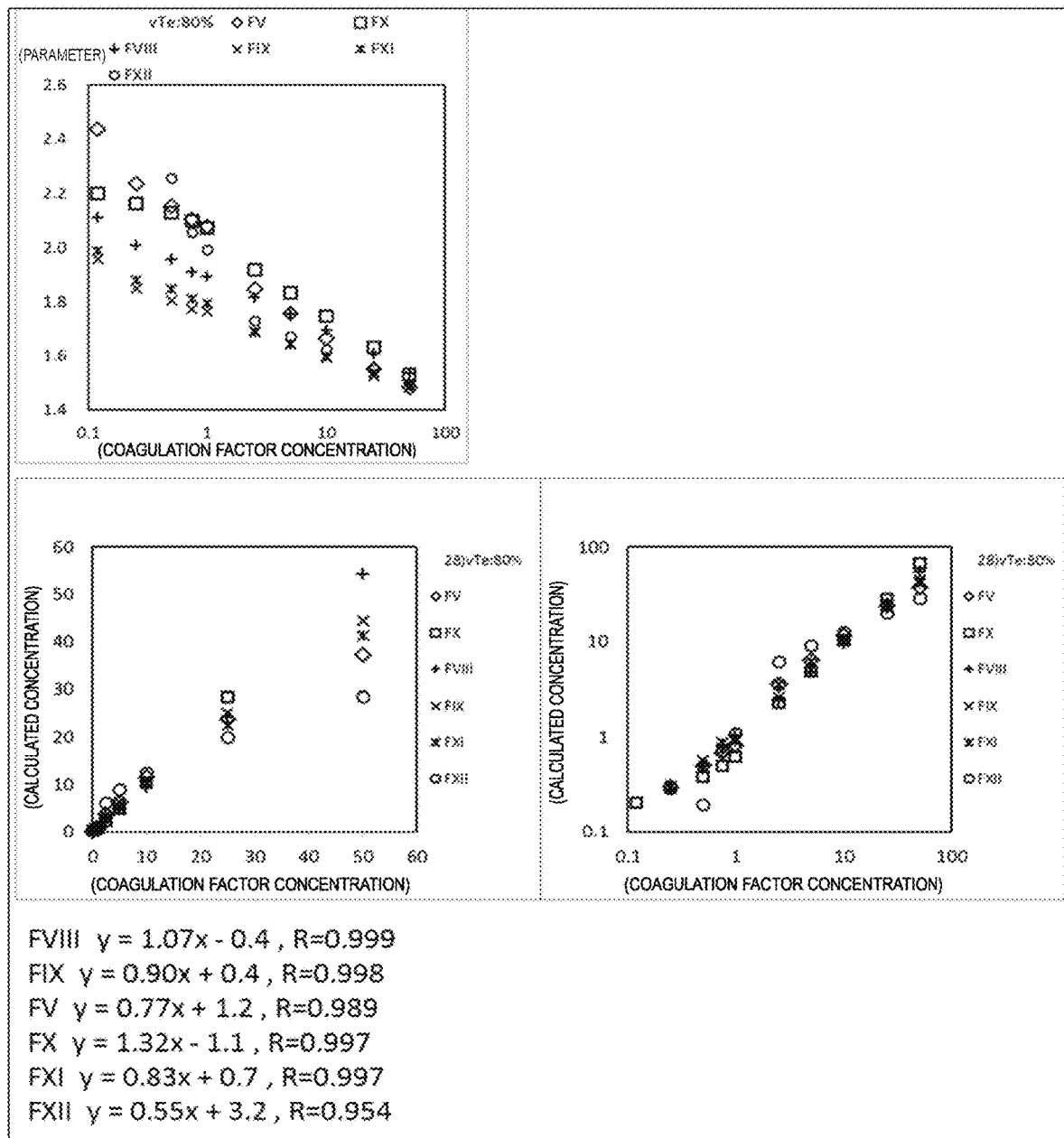

The top diagram of FIG. 43L is a diagram illustrating an example of a relationship between a logarithm of each of the concentrations of various coagulation factors and a logarithm of vTe80%. The middle left diagram of FIG. 43L illustrates plots of a calculated concentration based on a calibration curve with respect to the measured concentration of a coagulation factor. The middle right diagram of FIG. 43L illustrates logarithmic plots between a measured concentration and a calculated concentration.

Figure 43M:
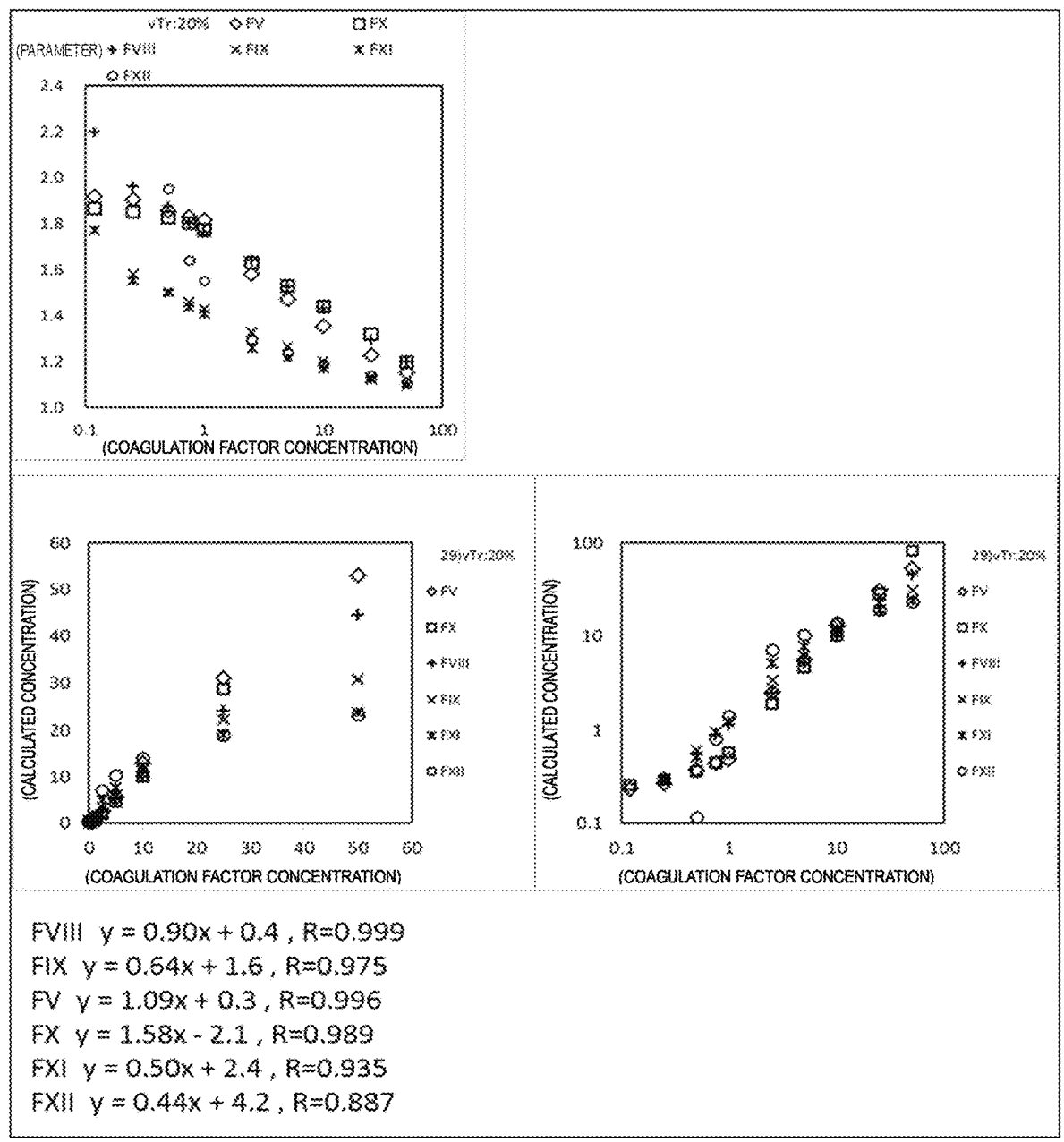

The top diagram of FIG. 43M is a diagram illustrating an example of a relationship between a logarithm of each of the concentrations of various coagulation factors and a logarithm of vTr20%. The middle left diagram of FIG. 43M illustrates plots of a calculated concentration based on a calibration curve with respect to the measured concentration of a coagulation factor. The middle right diagram of FIG. 43M illustrates logarithmic plots between a measured concentration and a calculated concentration.

Figure 43N:
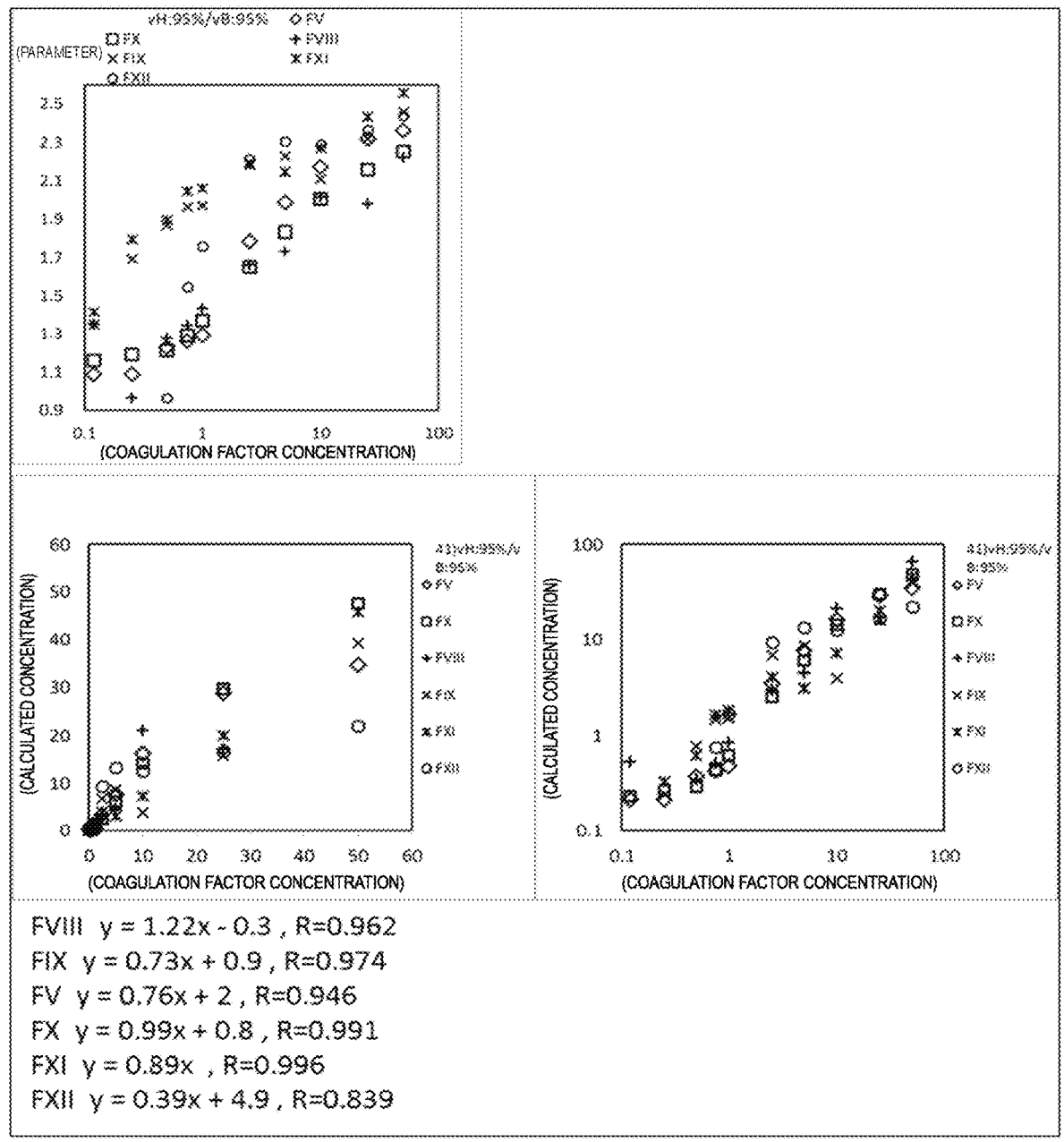
Figure 430:
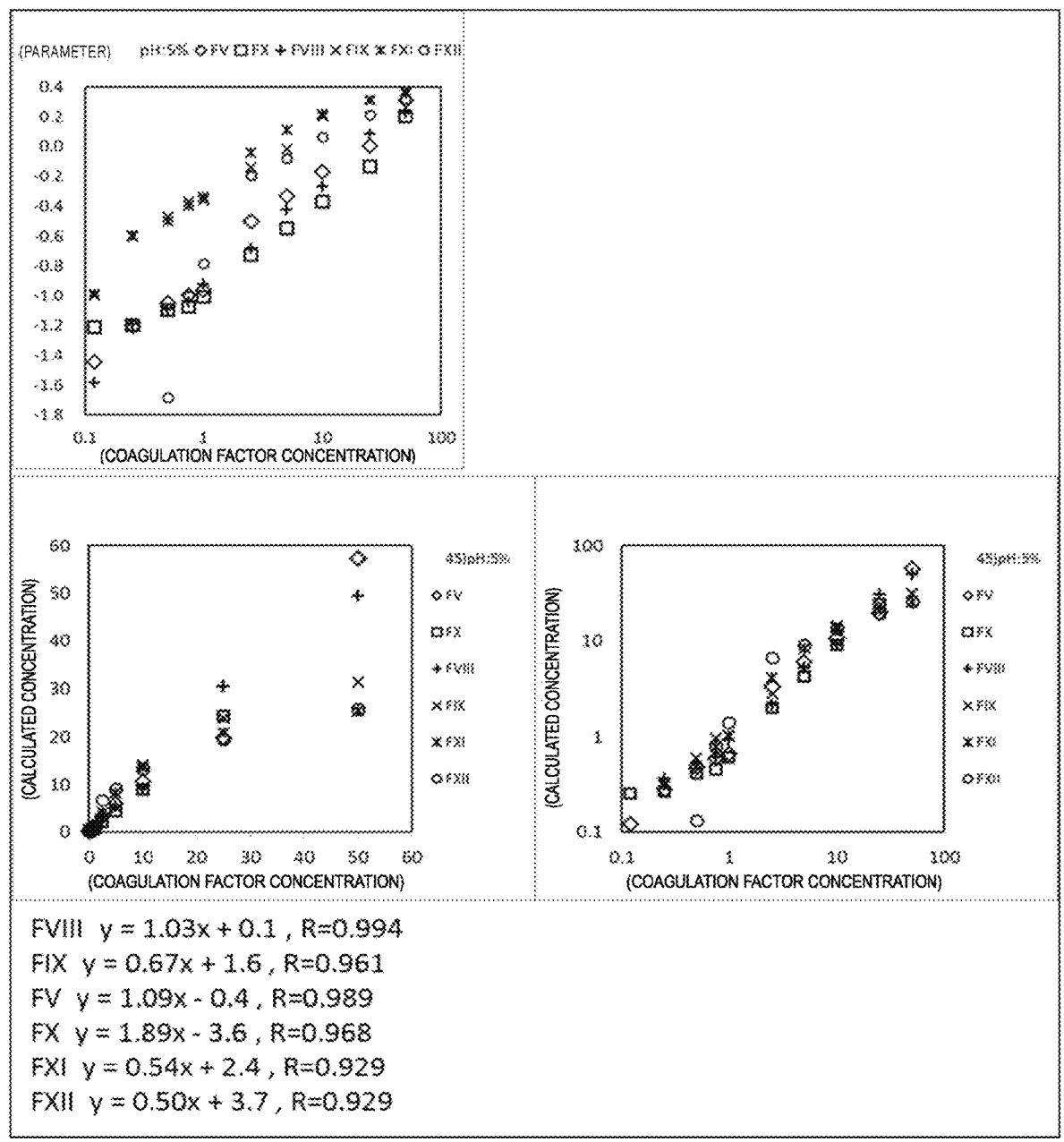

The top diagram of FIG. 43N is a diagram illustrating an example of a relationship between a logarithm of each of the concentrations of various coagulation factors and a logarithm of vH95%/vB95%. The middle left diagram of FIG. 43N illustrates plots of a calculated concentration based on a calibration curve with respect to the measured concentration of a coagulation factor. The middle right diagram of FIG. 43N illustrates logarithmic plots between a measured concentration and a calculated concentration.

The top diagram of FIG. 43O is a diagram illustrating an example of a relationship between a logarithm of each of the concentrations of various coagulation factors and a logarithm of pH5%. The middle left diagram of FIG. 43O illustrates plots of a calculated concentration based on a calibration curve with respect to the measured concentration of a coagulation factor. The middle right diagram of FIG. 43O illustrates logarithmic plots between a measured concentration and a calculated concentration.

Figure 43P:
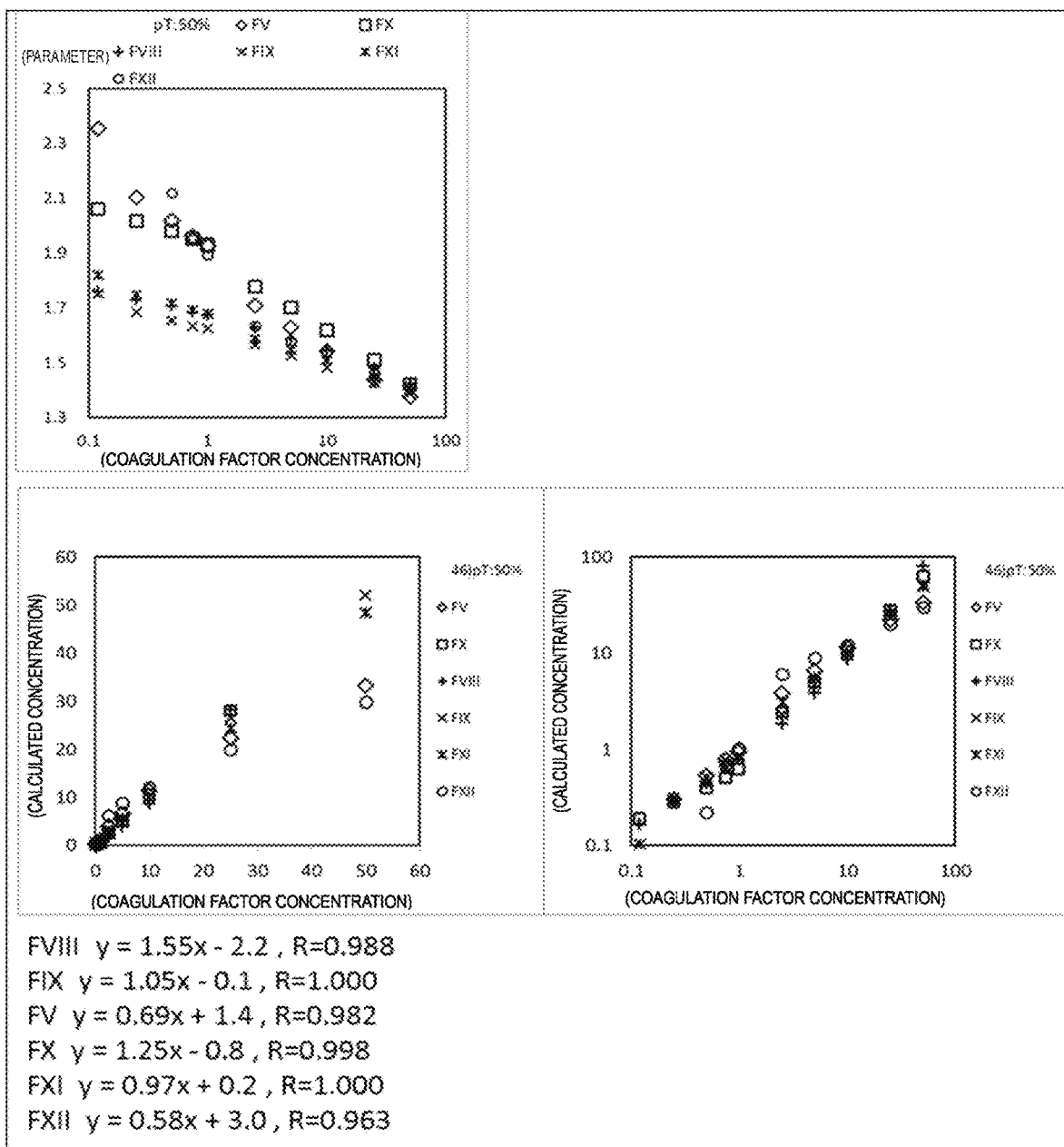

The top diagram of FIG. 43P is a diagram illustrating an example of a relationship between a logarithm of each of the concentrations of various coagulation factors and a logarithm of pT50%. The middle left diagram of FIG. 43P illustrates plots of a calculated concentration based on a calibration curve with respect to the measured concentration of a coagulation factor. The middle right diagram of FIG. 43P illustrates logarithmic plots between a measured concentration and a calculated concentration.

Figure 43Q:
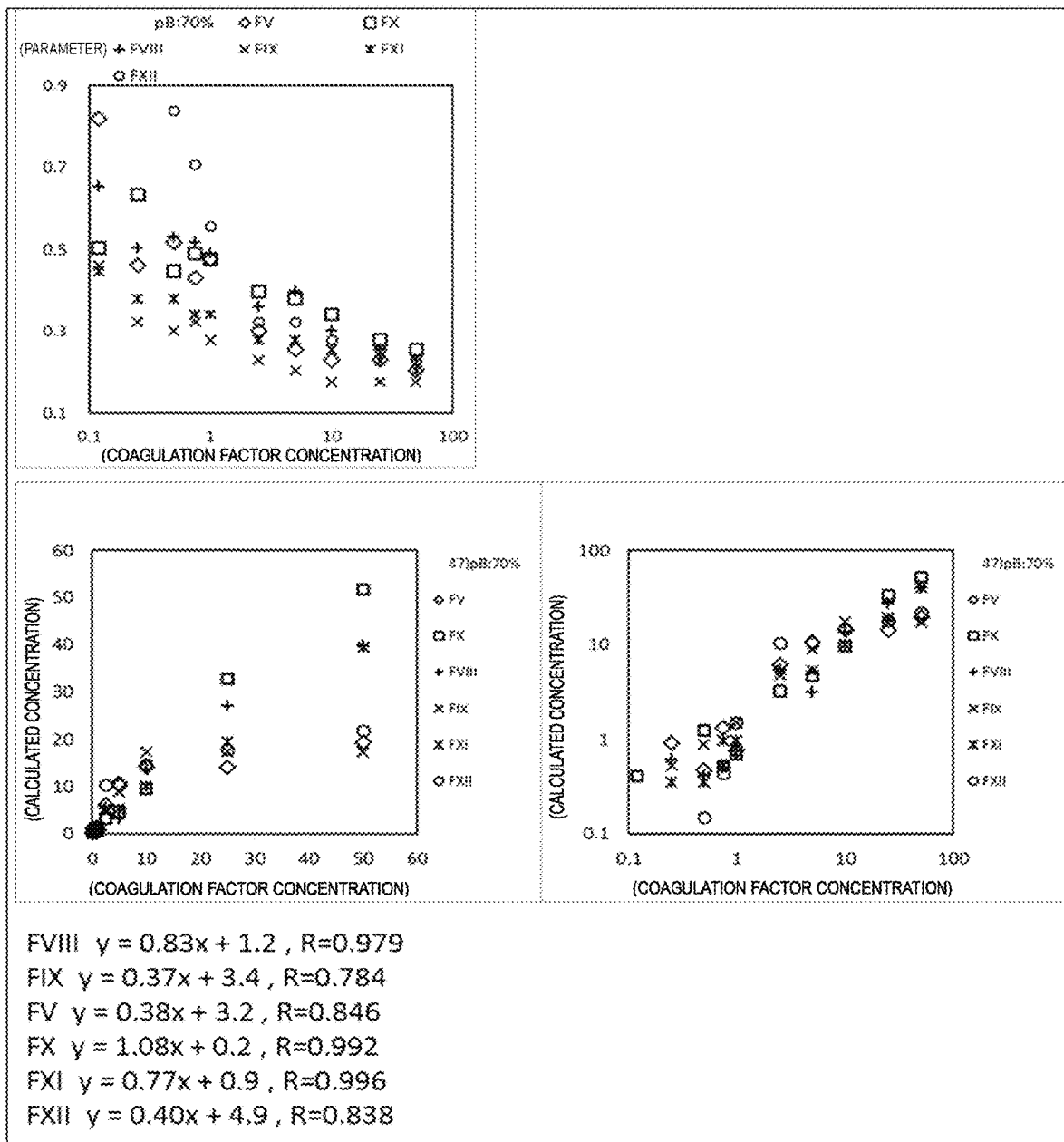

The top diagram of FIG. 43Q is a diagram illustrating an example of a relationship between a logarithm of each of the concentrations of various coagulation factors and a logarithm of pB70%. The middle left diagram of FIG. 43Q illustrates plots of a calculated concentration based on a calibration curve with respect to the measured concentration of a coagulation factor. The middle right diagram of FIG. 43Q illustrates logarithmic plots between a measured concentration and a calculated concentration.

Figure 43R:
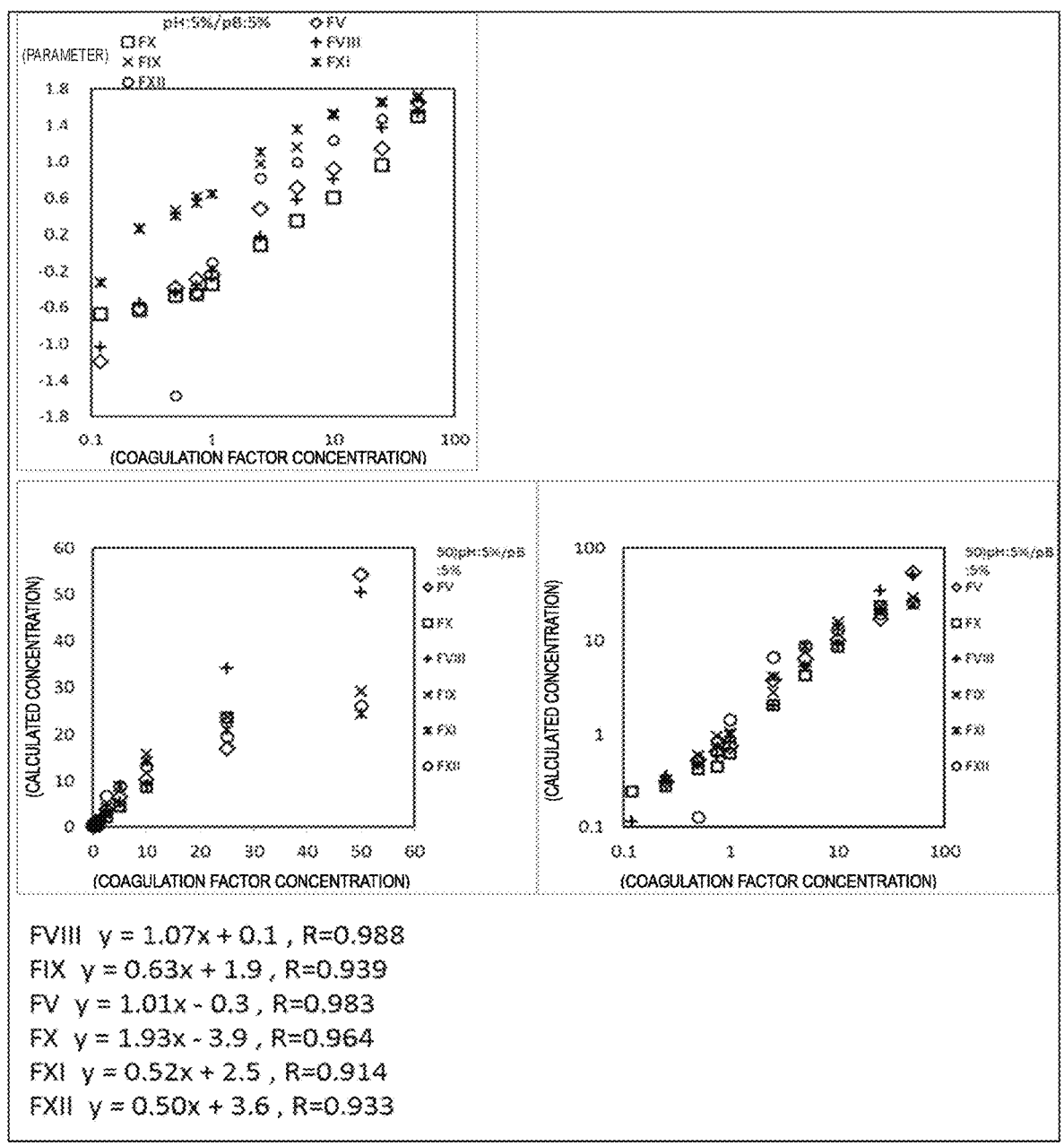

The top diagram of FIG. 43R is a diagram illustrating an example of a relationship between a logarithm of each of the concentrations of various coagulation factors and a logarithm of pH5%/pB5%. The middle left diagram of FIG. 43R illustrates plots of a calculated concentration based on a calibration curve with respect to the measured concentration of a coagulation factor. The middle right diagram of FIG. 43R illustrates logarithmic plots between a measured concentration and a calculated concentration.

Figure 43S:
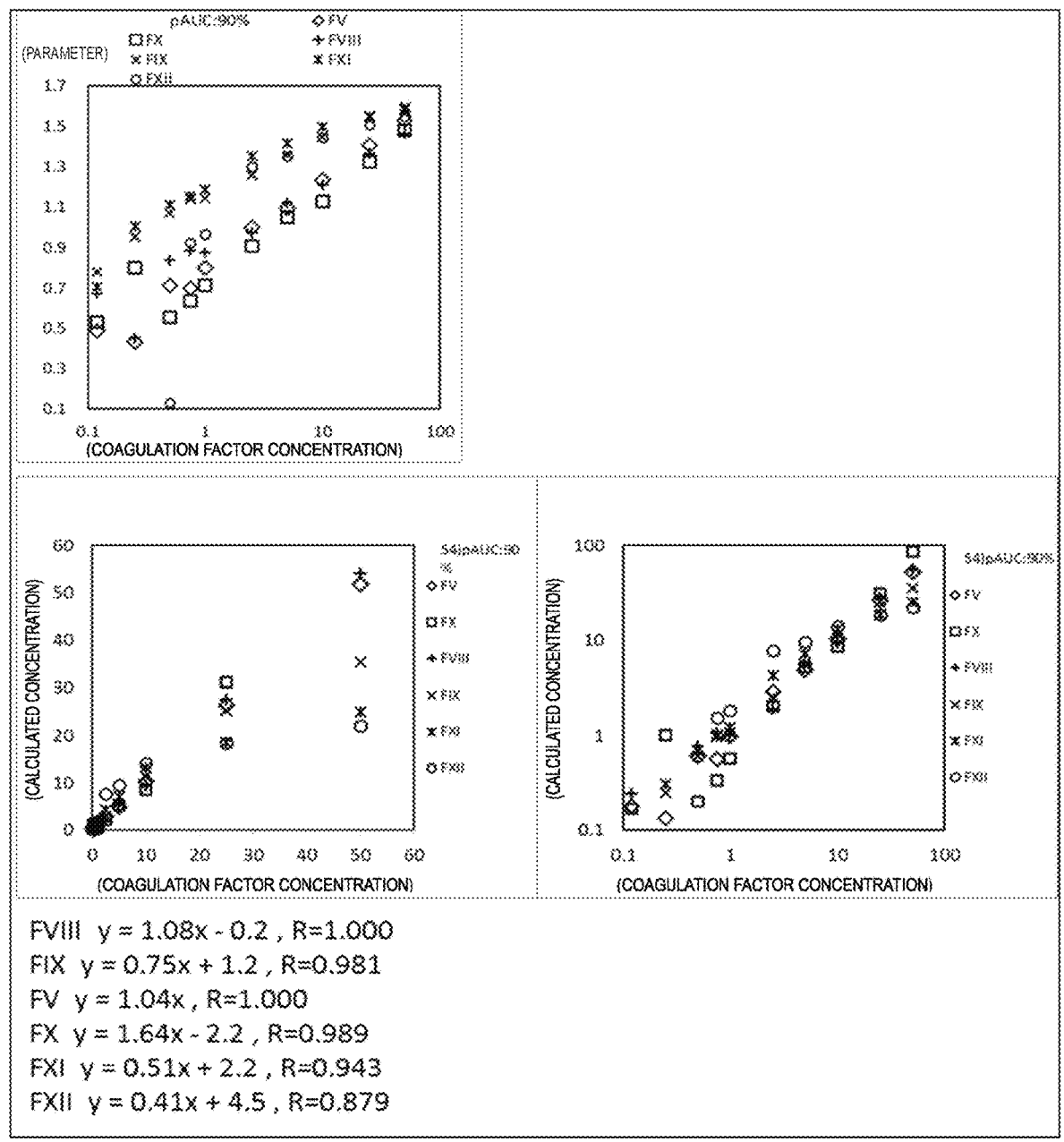

The top diagram of FIG. 43S is a diagram illustrating an example of a relationship between a logarithm of each of the concentrations of various coagulation factors and a logarithm of pAUC90%. The middle left diagram of FIG. 43S illustrates plots of a calculated concentration based on a calibration curve with respect to the measured concentration of a coagulation factor. The middle right diagram of FIG. 43S illustrates logarithmic plots between a measured concentration and a calculated concentration.

Figure 43T:
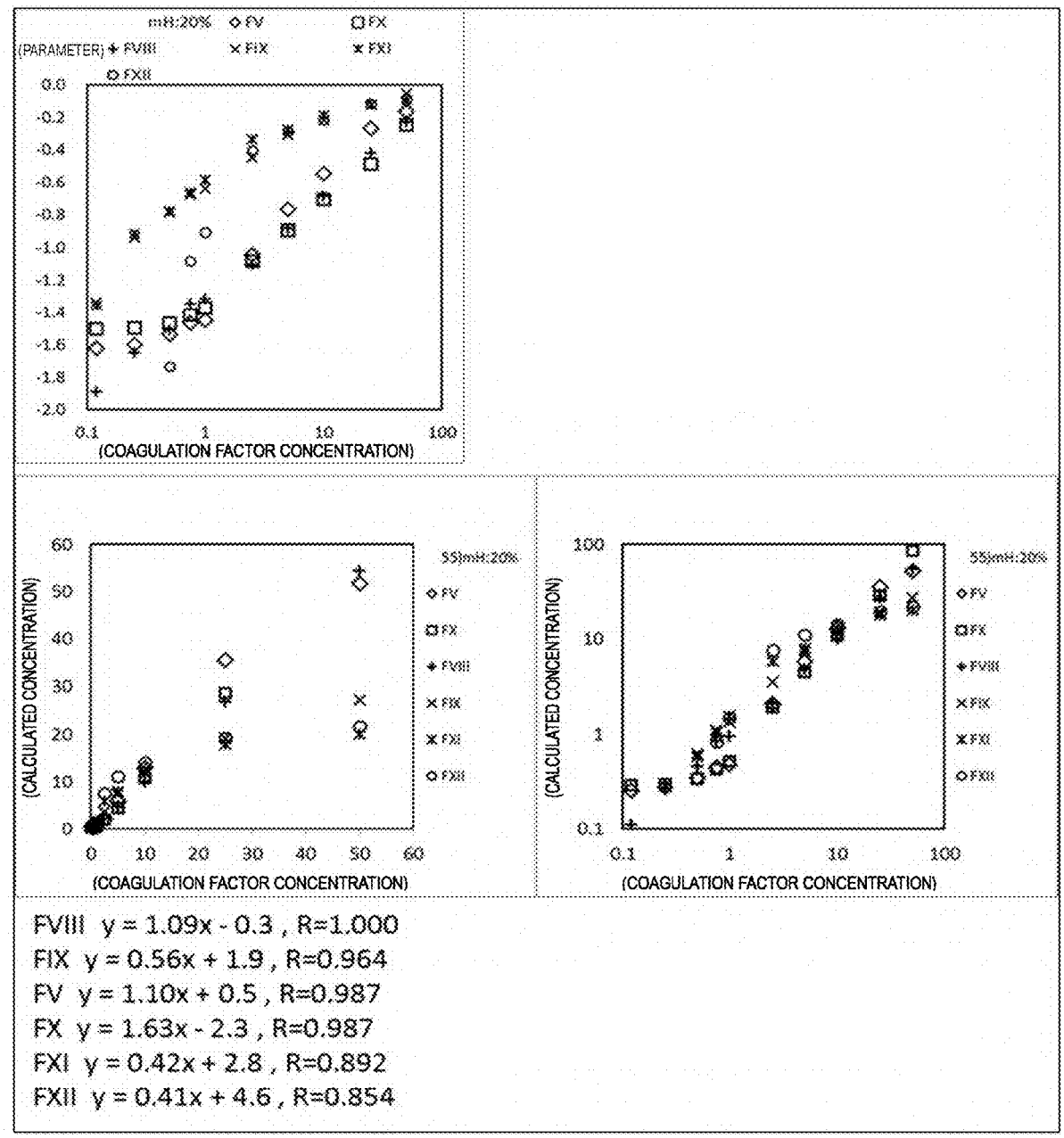

The top diagram of FIG. 43T is a diagram illustrating an example of a relationship between a logarithm of each of the concentrations of various coagulation factors and a logarithm of mH20%. The middle left diagram of FIG. 43T illustrates plots of a calculated concentration based on a calibration curve with respect to the measured concentration of a coagulation factor. The middle right diagram of FIG. 43T illustrates logarithmic plots between a measured concentration and a calculated concentration.

The top diagram of FIG. 43U is a diagram illustrating an example of a relationship between a logarithm of each of the concentrations of various coagulation factors and a logarithm of mH20%/mB20%. The middle left diagram of FIG. 43U illustrates plots of a calculated concentration based on a calibration curve with respect to the measured concentration of a coagulation factor. The middle right diagram of FIG. 43U illustrates logarithmic plots between a measured concentration and a calculated concentration.

Figure 43V:
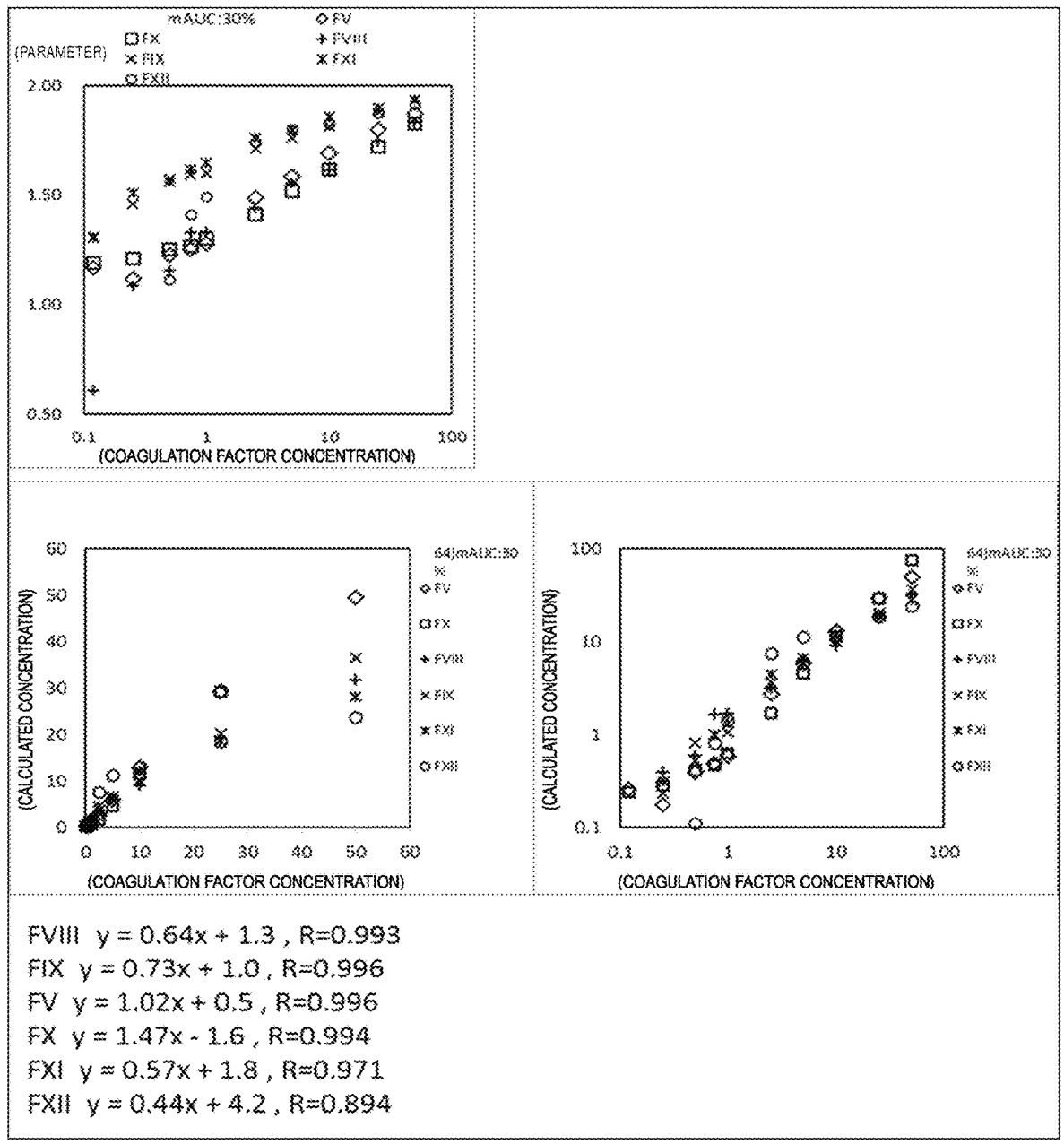
Figure 45W:
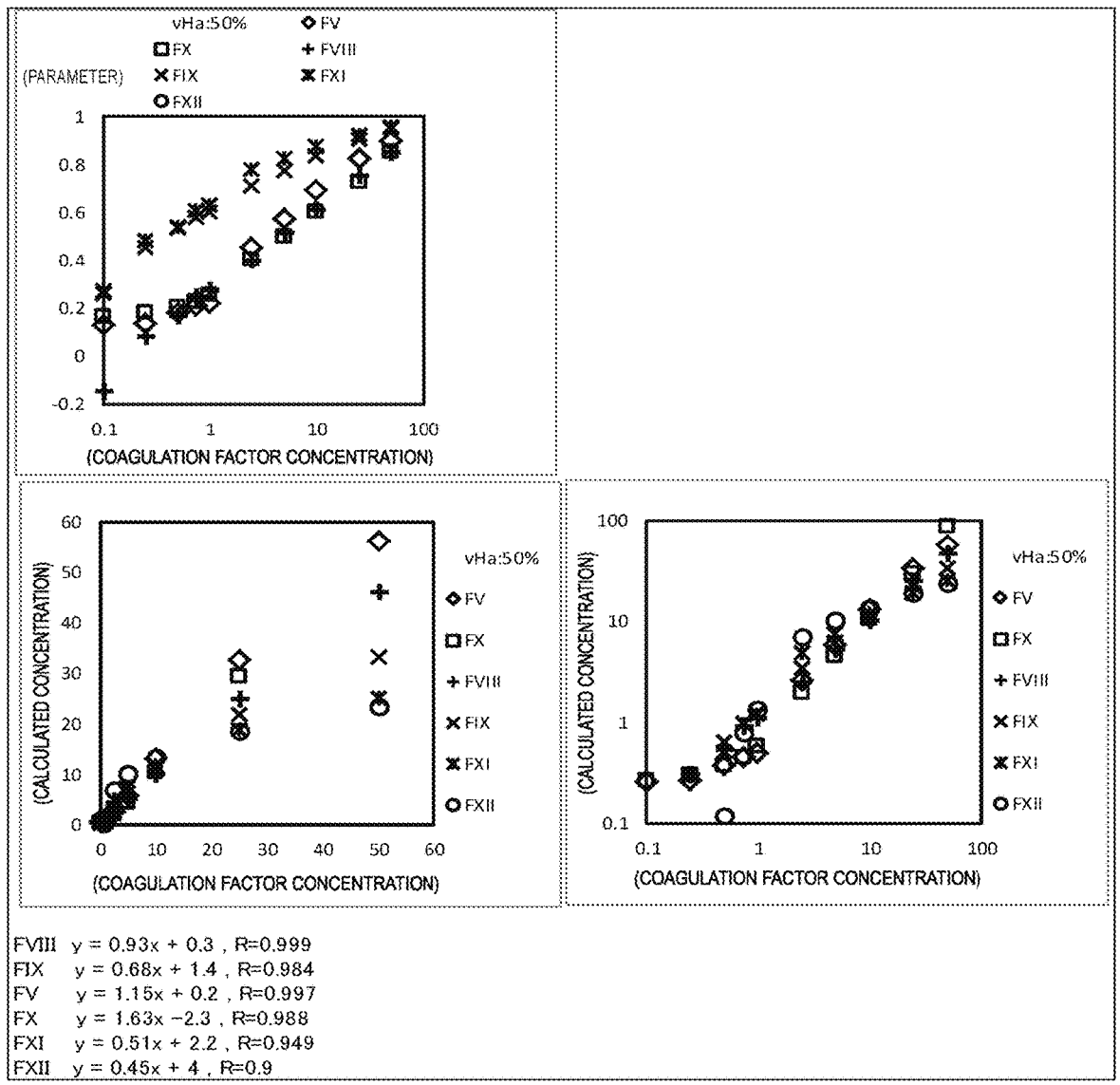

The top diagram of FIG. 43V is a diagram illustrating an example of a relationship between a logarithm of each of the concentrations of various coagulation factors and a logarithm of mAUC30%. The middle left diagram of FIG. 43V illustrates plots of a calculated concentration based on a calibration curve with respect to the measured concentration of a coagulation factor. The middle right diagram of FIG. 43V illustrates logarithmic plots between a measured concentration and a calculated concentration.

The top diagram of FIG. 43W is a diagram illustrating an example of a relationship between a logarithm of each of the concentrations of various coagulation factors and a logarithm of vHa50%. The middle left diagram of FIG. 43W illustrates plots of a calculated concentration based on a calibration curve with respect to the measured concentration of a coagulation factor. The middle right diagram of FIG. 43W illustrates logarithmic plots between a measured concentration and a calculated concentration.

Figure 43X:
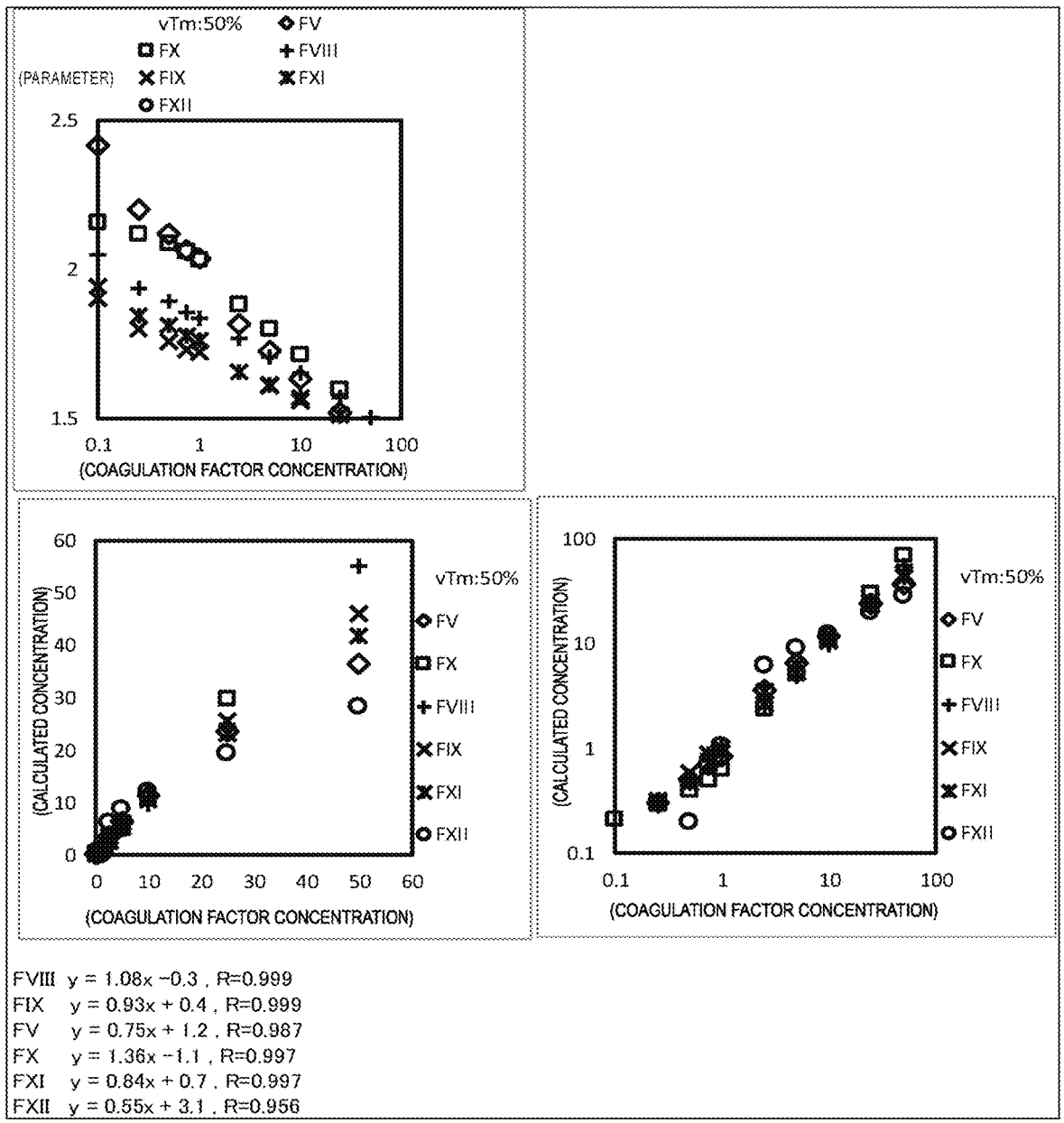

The top diagram of FIG. 43X is a diagram illustrating an example of a relationship between a logarithm of each of the concentrations of various coagulation factors and a logarithm of vTm50%. The middle left diagram of FIG. 43X illustrates plots of a calculated concentration based on a calibration curve with respect to the measured concentration of a coagulation factor. The middle right diagram of FIG. 43X illustrates logarithmic plots between a measured concentration and a calculated concentration.

Figure 43Y:
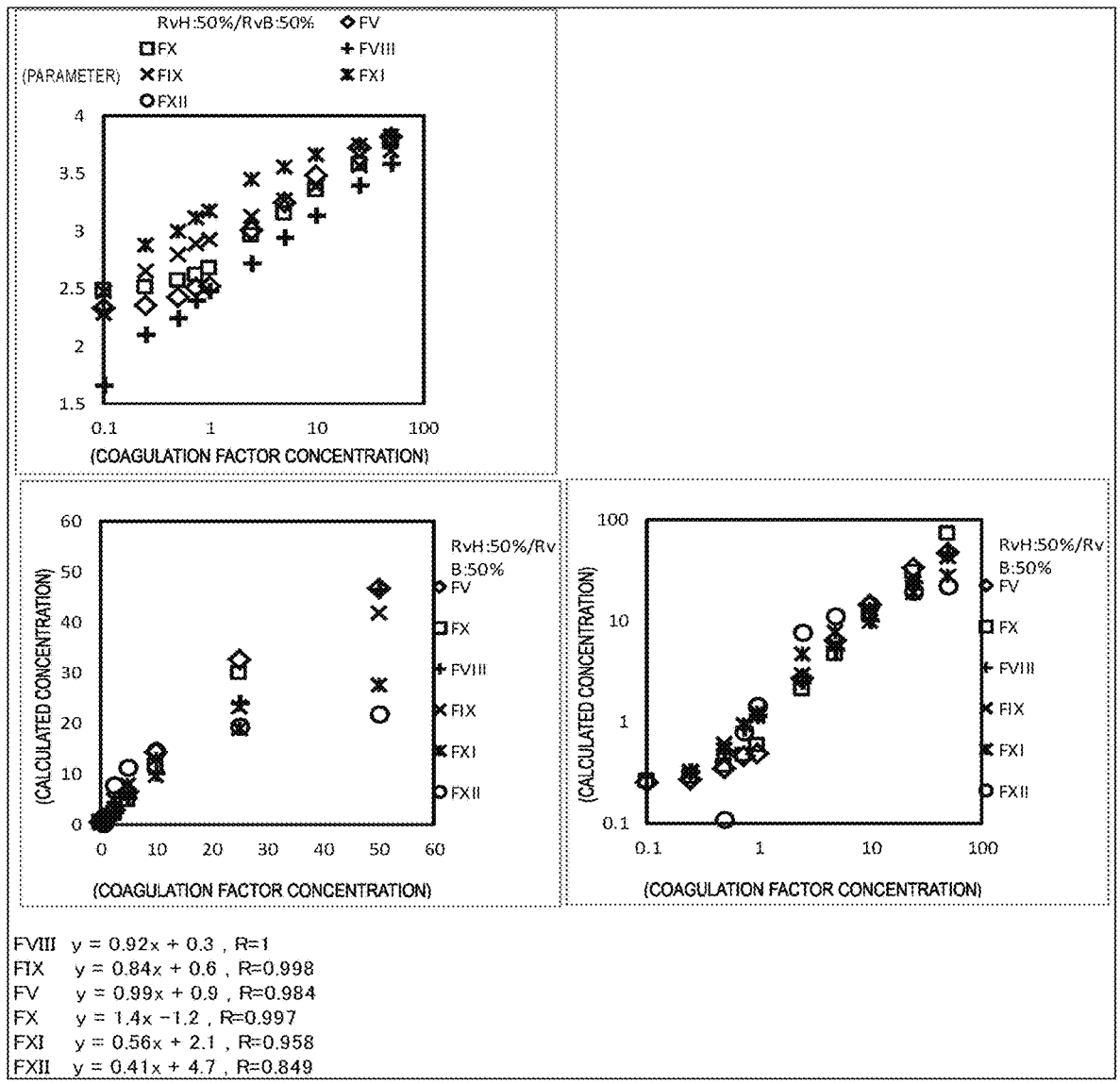

The top diagram of FIG. 43Y is a diagram illustrating an example of a relationship between a logarithm of each of the concentrations of various coagulation factors and a logarithm of RvH50%/RvB50%. The middle left diagram of FIG. 43Y illustrates plots of a calculated concentration based on a calibration curve with respect to the measured concentration of a coagulation factor. The middle right diagram of FIG. 43Y illustrates logarithmic plots between a measured concentration and a calculated concentration.

Figure 44A:
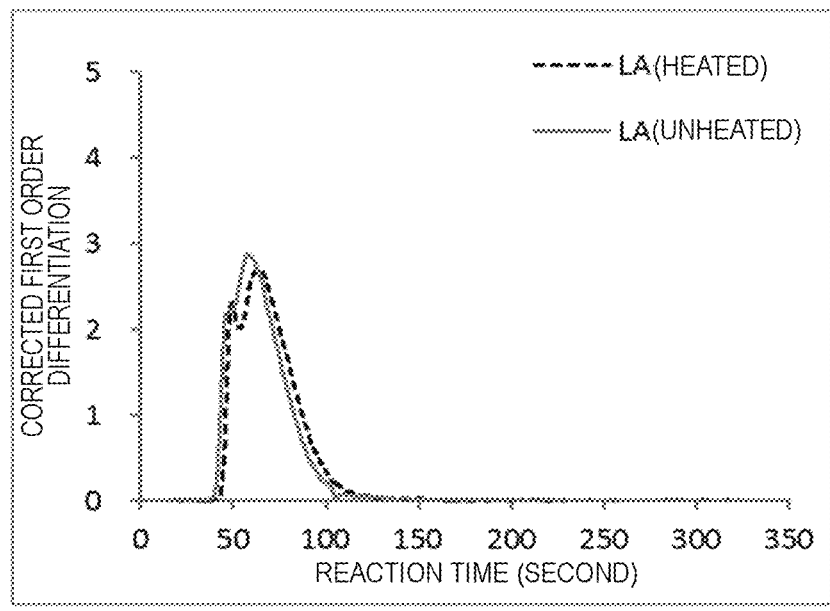

FIG. 44A is a diagram illustrating corrected first order curves of a LA plasma with and without heating.

Figure 44B:
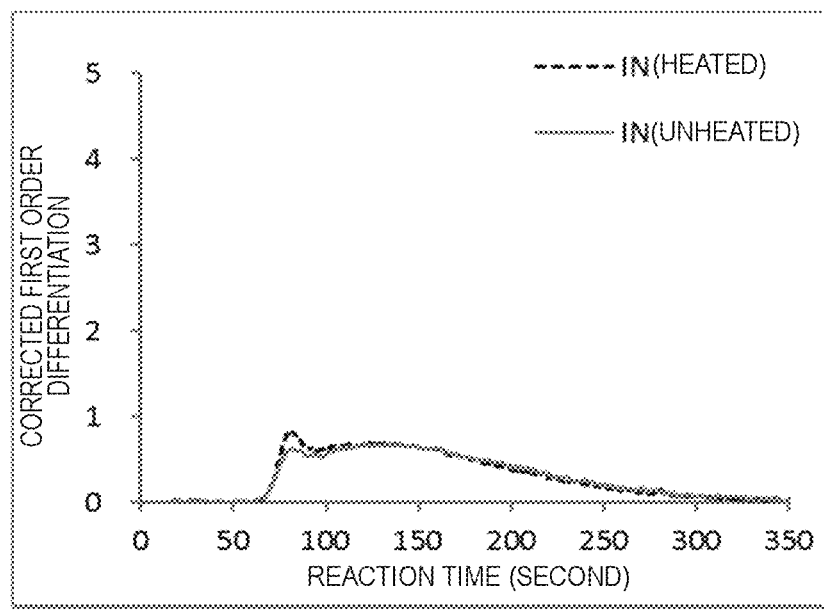

FIG. 44B illustrates corrected first order curves of a factor VIII inhibitor-positive plasma with and without heating.

Figure 45A:
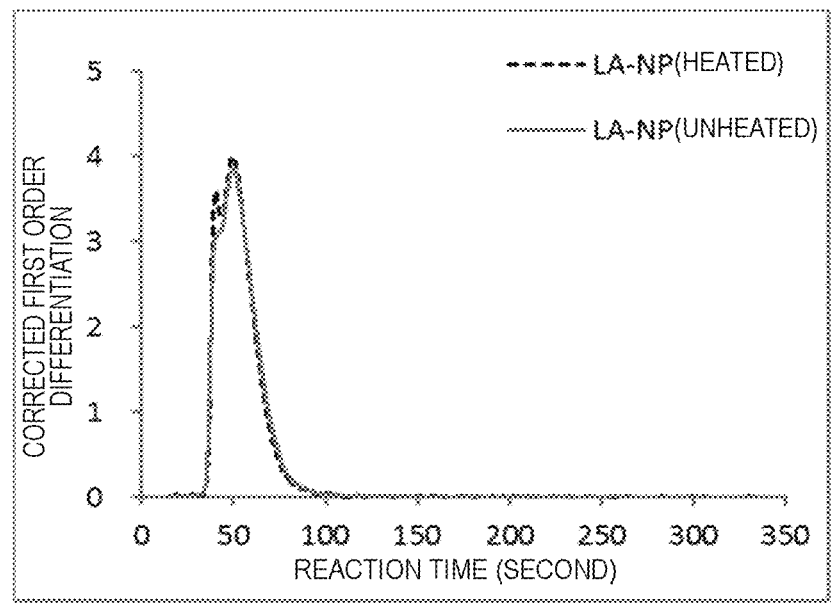

FIG. 45A is a diagram illustrating corrected first order curves of a mixed plasma (LA-NP) of a LA plasma and a normal plasma without and with heating.

Figure 45B:
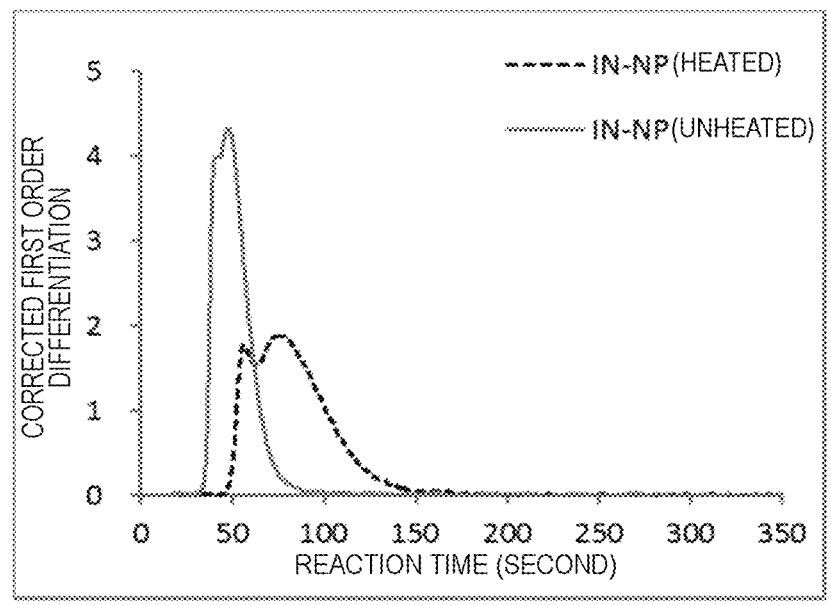

FIG. 45B is a diagram illustrating corrected first order curves of a mixed plasma (IN-NP) of a factor VIII inhibitor-positive plasma and a normal plasma without and with heating.

Figure 46A:
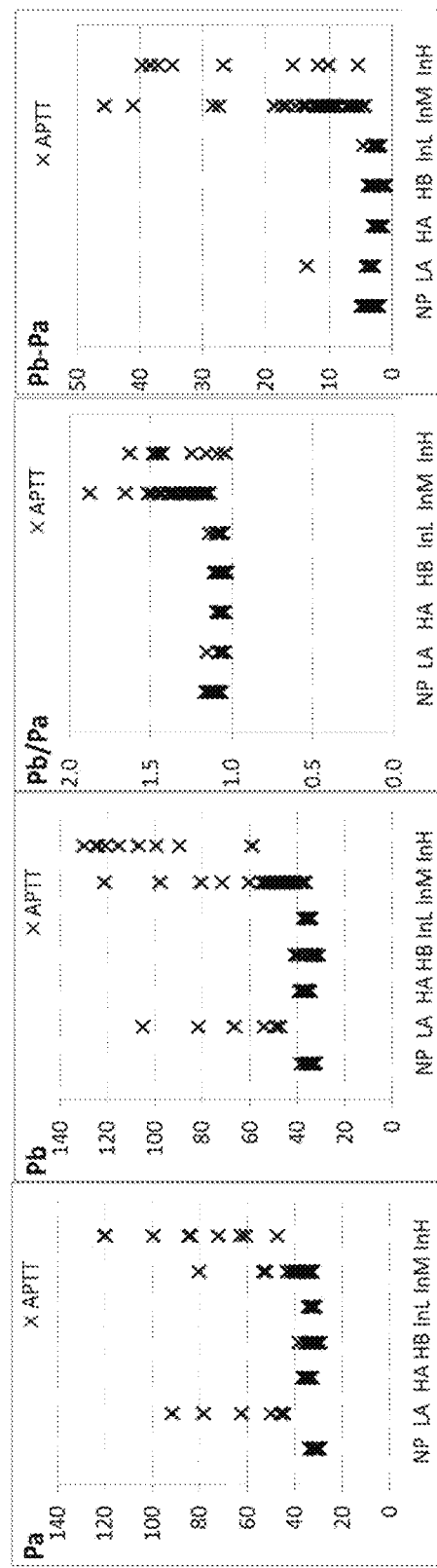

FIG. 46A is a diagram illustrating a value Pa in an unheated plasma, a value Pb in a heated plasma, a ratio therebetween Pa/Pb, and a difference therebetween Pb−Pa for APTT of each of various plasmas.

Figure 46B:
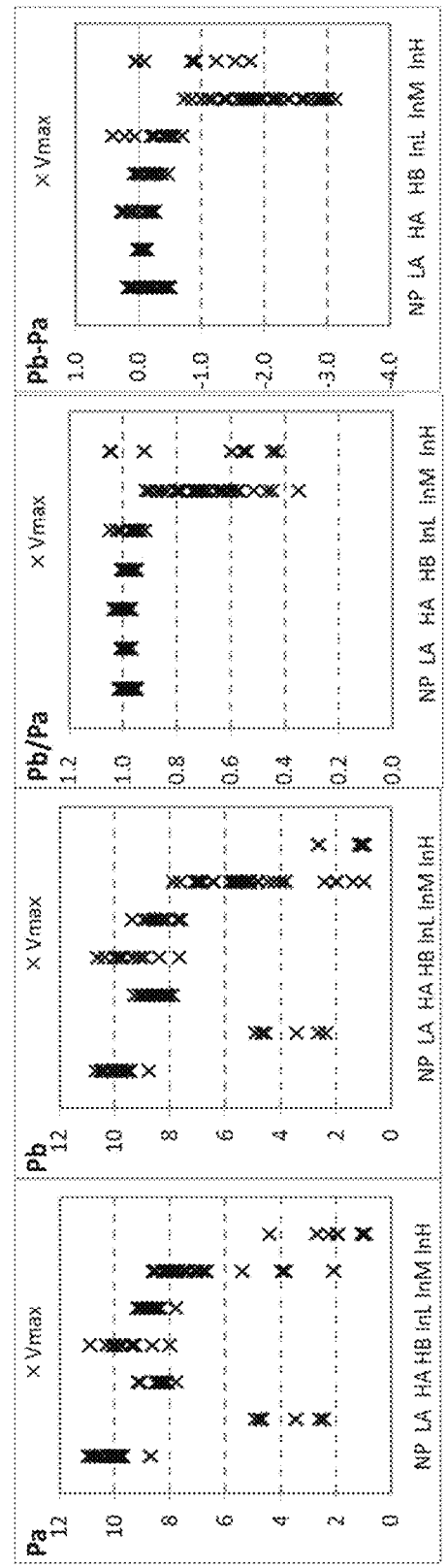

FIG. 46B is a diagram illustrating a value Pa in an unheated plasma, a value Pb in a heated plasma, a ratio therebetween Pa/Pb, and a difference therebetween Pb−Pa for Vmax of each of various plasmas.

Figure 46C:
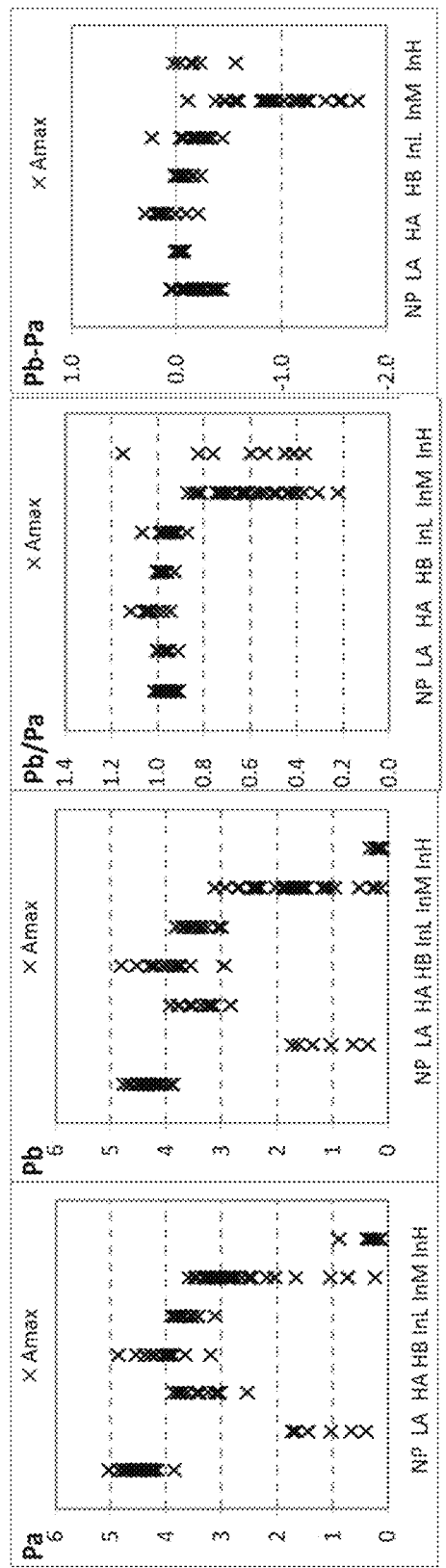

FIG. 46C is a diagram illustrating a value Pa in an unheated plasma, a value Pb in a heated plasma, a ratio therebetween Pa/Pb, and a difference therebetween Pb−Pa for Amax of each of various plasmas.

Figure 46D:
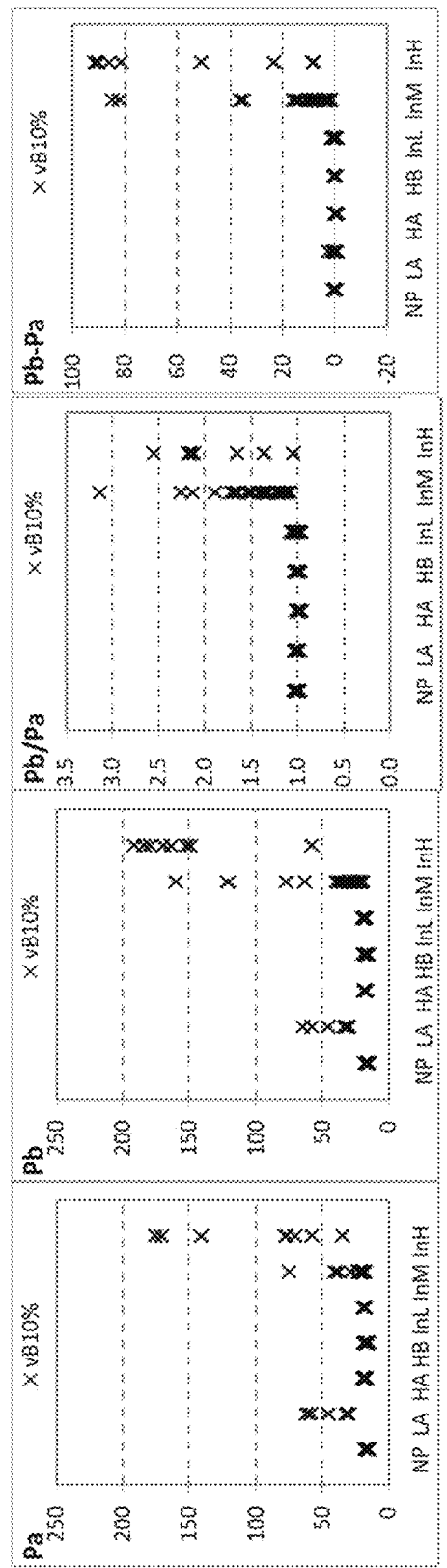

FIG. 46D is a diagram illustrating a value Pa in an unheated plasma, a value Pb in a heated plasma, a ratio therebetween Pa/Pb, and a difference therebetween Pb−Pa for vB10% of each of various plasmas.

Figure 46E:
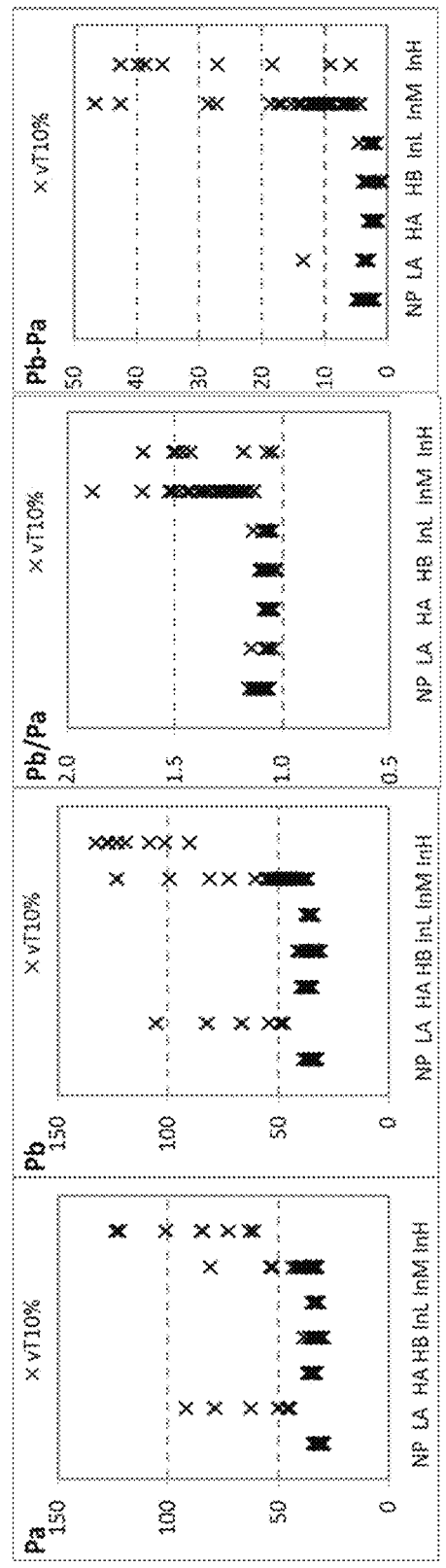

FIG. 46E is a diagram illustrating a value Pa in an unheated plasma, a value Pb in a heated plasma, a ratio therebetween Pa/Pb, and a difference therebetween Pb−Pa for vT10% of each of various plasmas.

Figure 46F:
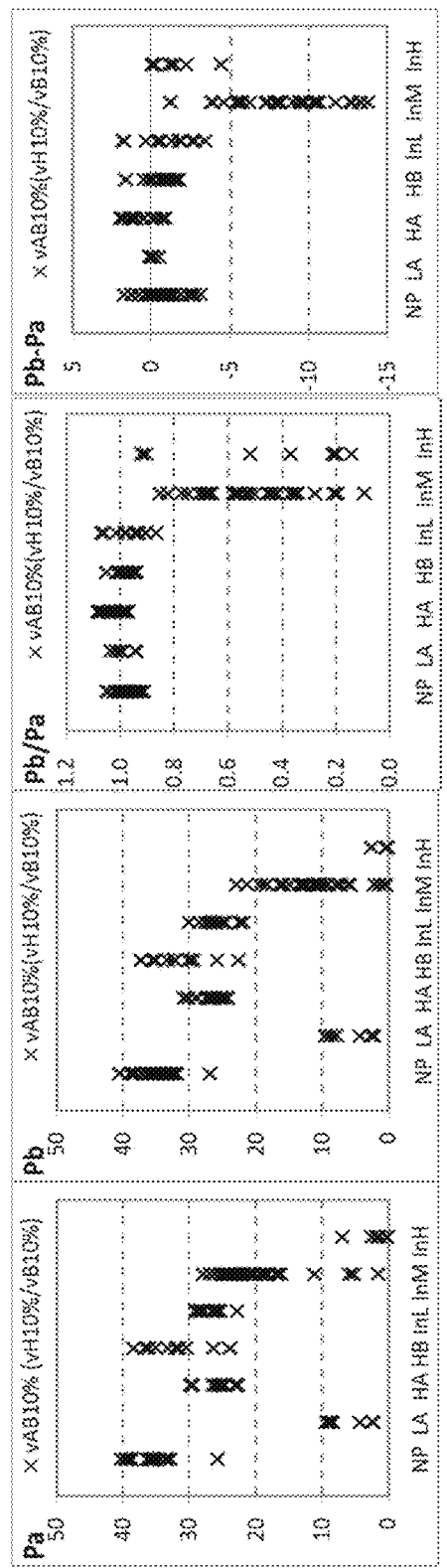

FIG. 46F is a diagram illustrating a value Pa in an unheated plasma, a value Pb in a heated plasma, a ratio therebetween Pa/Pb, and a difference therebetween Pb−Pa for vAB10% of each of various plasmas.

Figure 46G:
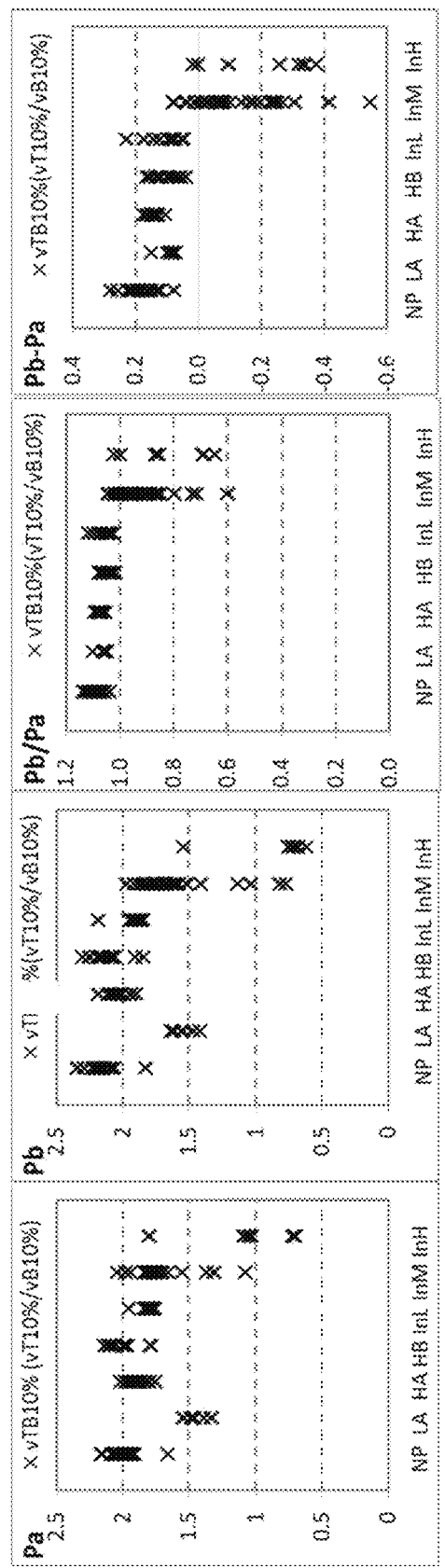

FIG. 46G is a diagram illustrating a value Pa in an unheated plasma, a value Pb in a heated plasma, a ratio therebetween Pa/Pb, and a difference therebetween Pb−Pa for vTB10% of each of various plasmas.

Figure 47A:
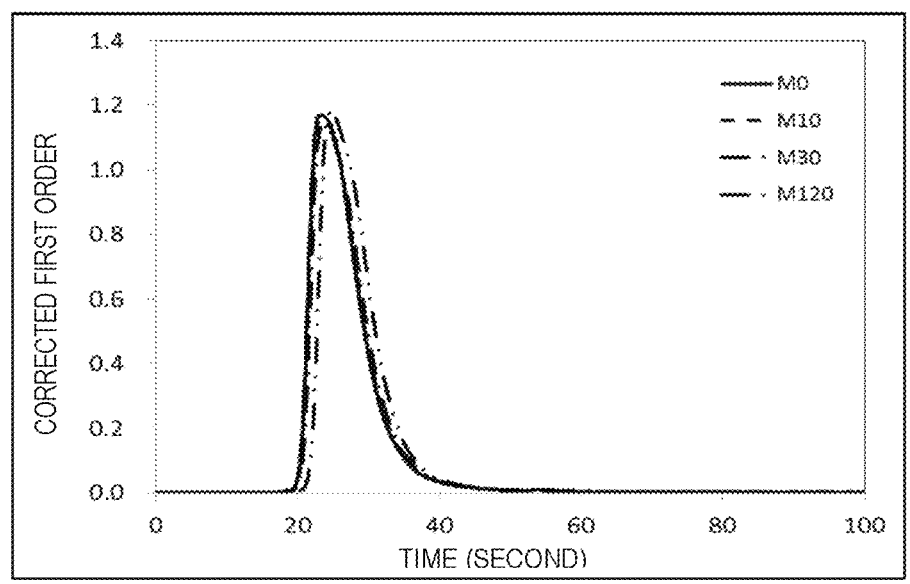

FIG. 47A is a diagram illustrating corrected first order curves of "normal plasma" when heating time is set to 0 minutes, 10 minutes, 30 minutes, and 120 minutes.

Figure 47B:
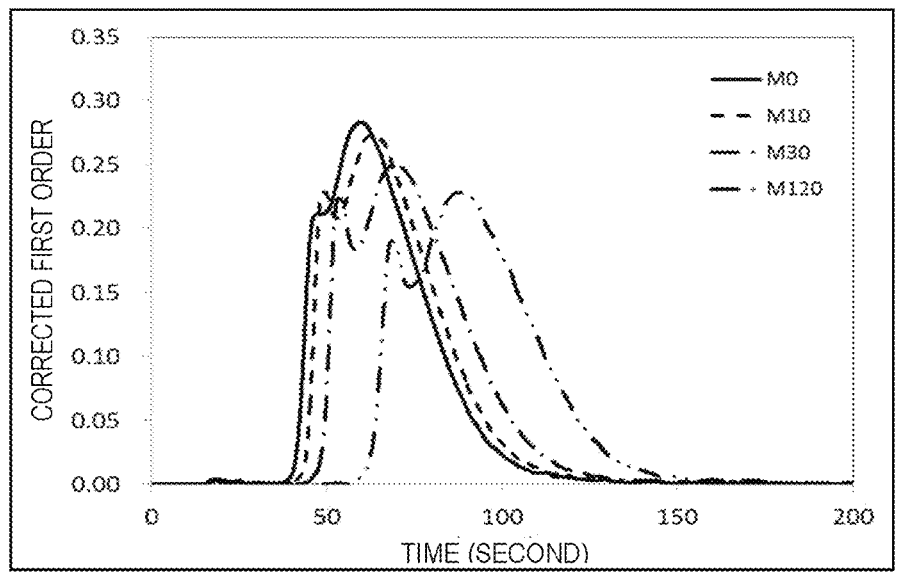

FIG. 47B is a diagram illustrating corrected first order curves of "LA-positive plasma" when heating time is set to 0 minutes, 10 minutes, 30 minutes, and 120 minutes.

Figure 47C:
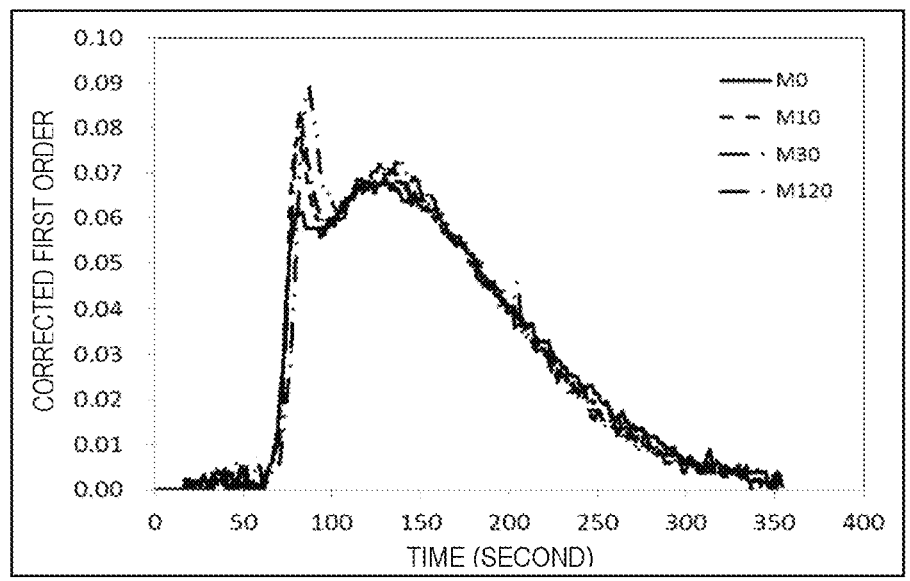

FIG. 47C is a diagram illustrating corrected first order curves of "factor VIII inhibitor-positive plasma" when heating time is set to 0 minutes, 10 minutes, 30 minutes, and 120 minutes.

Figure 47D:
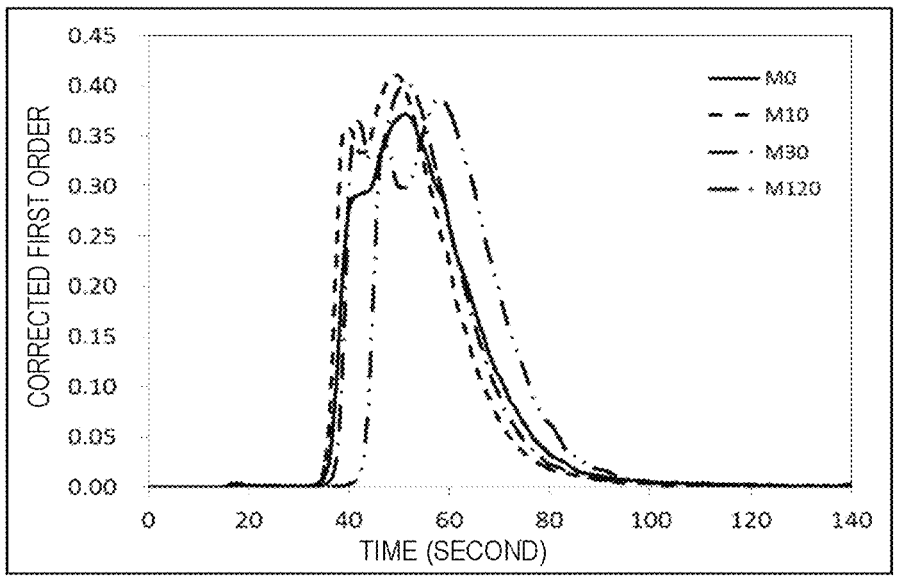

FIG. 47D is a diagram illustrating corrected first order curves of "equal volume mixed plasma of a LA-positive plasma and a normal plasma" when heating time is set to 0 minutes, 10 minutes, 30 minutes, and 120 minutes.

Figure 47E:
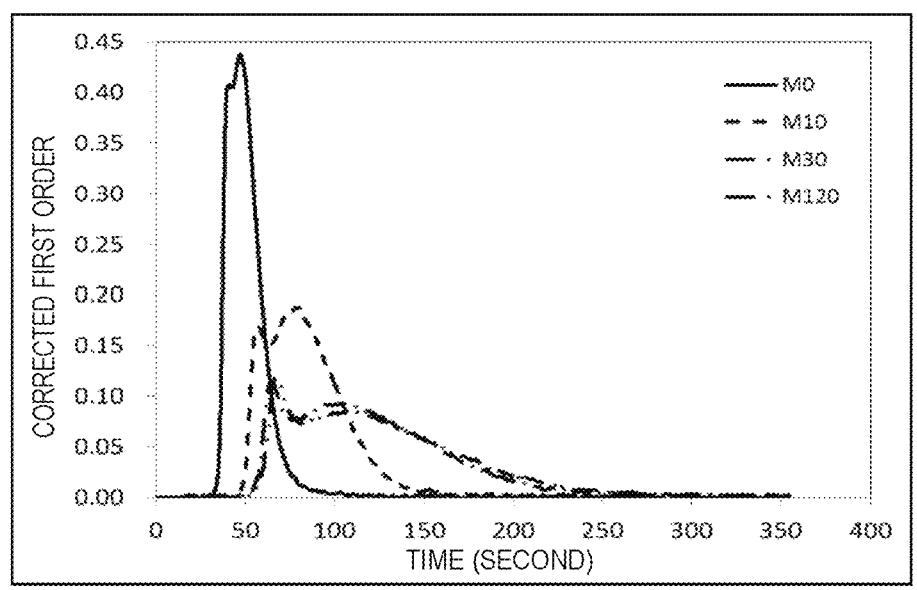

FIG. 47E is a diagram illustrating corrected first order curves of "equal volume mixed plasma of a factor VIII inhibitor-positive plasma and a normal plasma" when heating time is set to 0 minutes, 10 minutes, 30 minutes, and 120 minutes.

FIG. 48 is a diagram illustrating an example of a table illustrating various evaluation parameters obtained from APTT measurement data of each of five types of samples after heating treatment for 10 minutes, various evaluation parameters obtained from APTT measurement data of each of the five samples without heating treatment, and results of calculating ratios between both the various evaluation parameters.

Figure 49A:
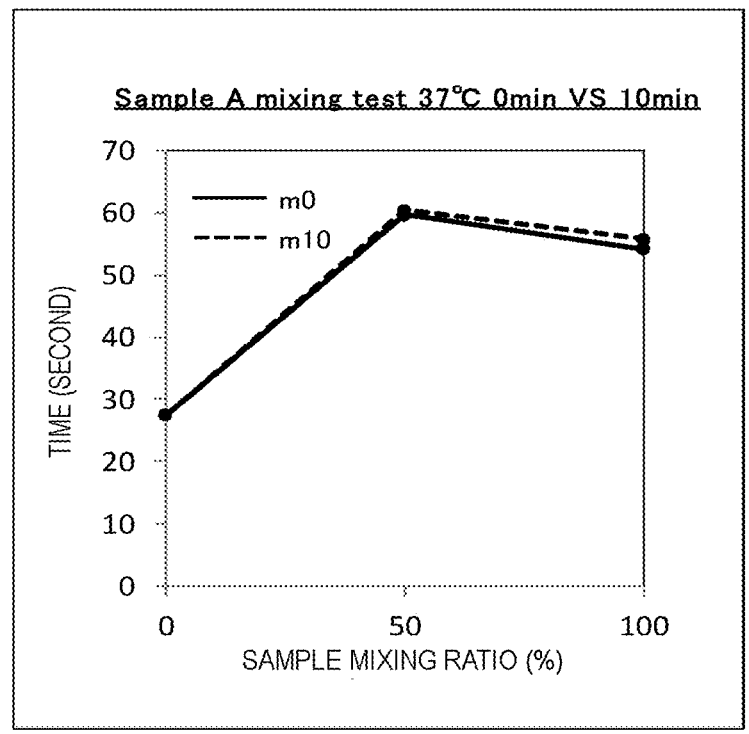

FIG. 49A is a diagram illustrating results of a cross-mixing test related to sample A of a LA-positive plasma without heating treatment and after heating treatment at 37° C. for 10 minutes.

Figure 49B:
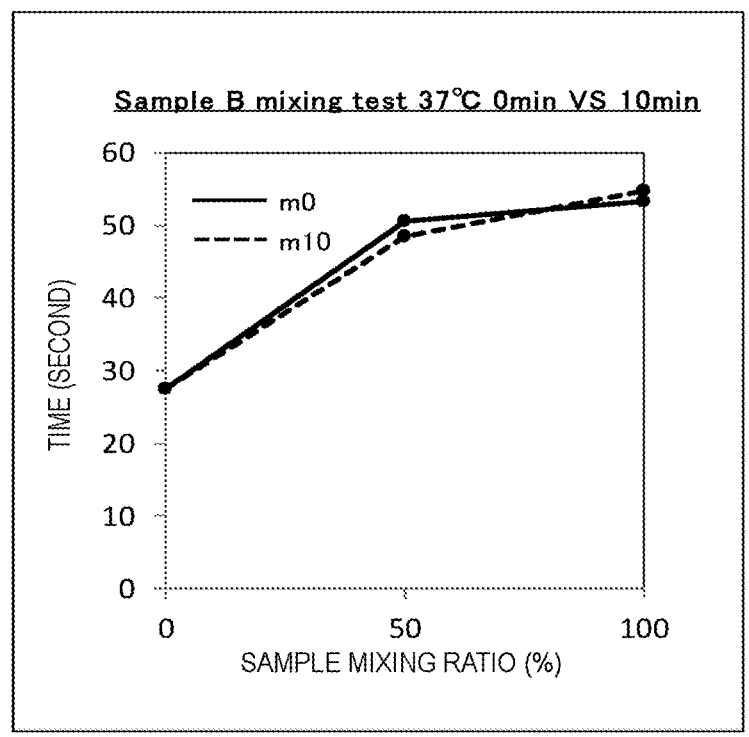

FIG. 49B is a diagram illustrating results of a cross-mixing test related to sample B of a LA-positive plasma without heating treatment and after heating treatment at 37° C. for 10 minutes.

Figure 49C:
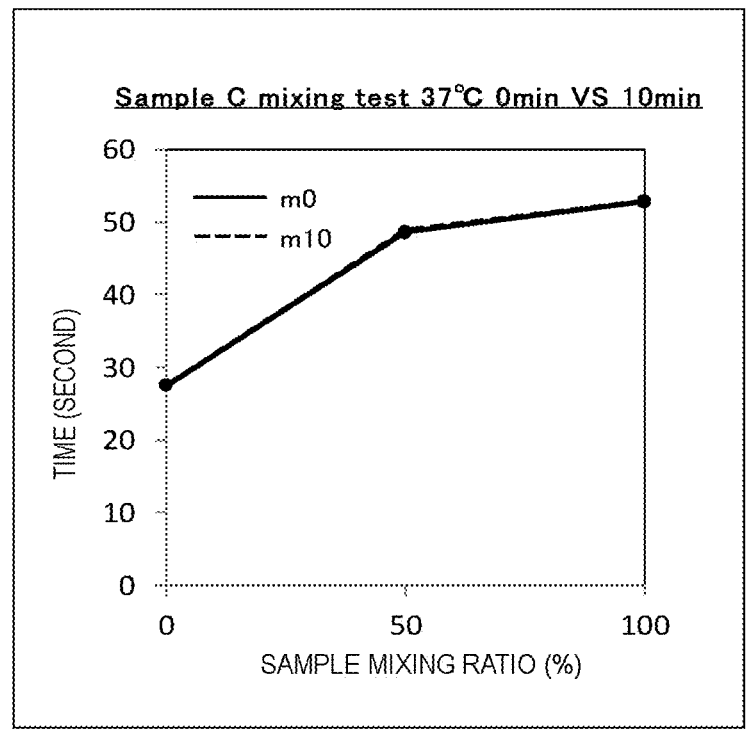

FIG. 49C is a diagram illustrating results of a cross-mixing test related to sample C of a LA-positive plasma without heating treatment and after heating treatment at 37° C. for 10 minutes.

Figure 49D:
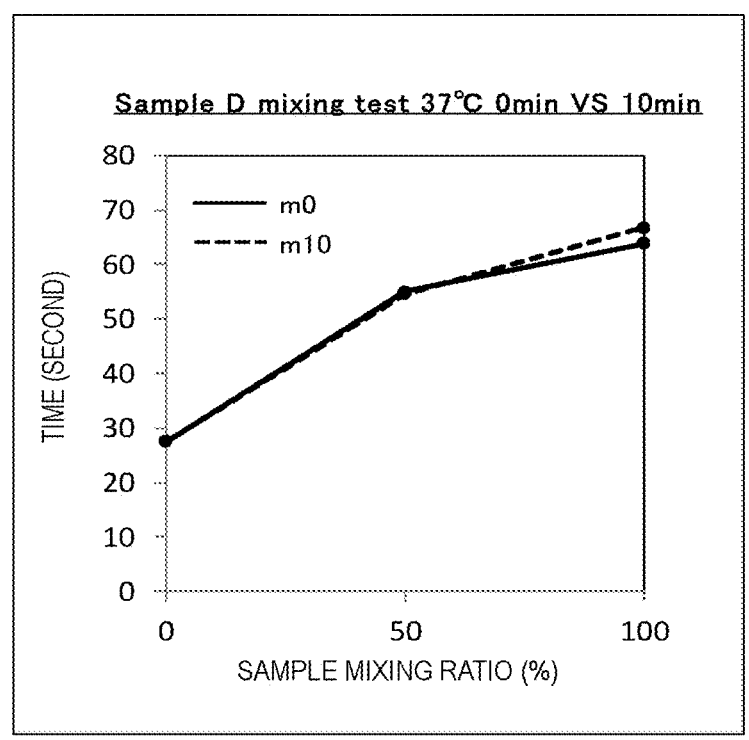

FIG. 49D is a diagram illustrating results of a cross-mixing test related to sample D of a LA-positive plasma without heating treatment and after heating treatment at 37° C. for 10 minutes.

Figure 49E:
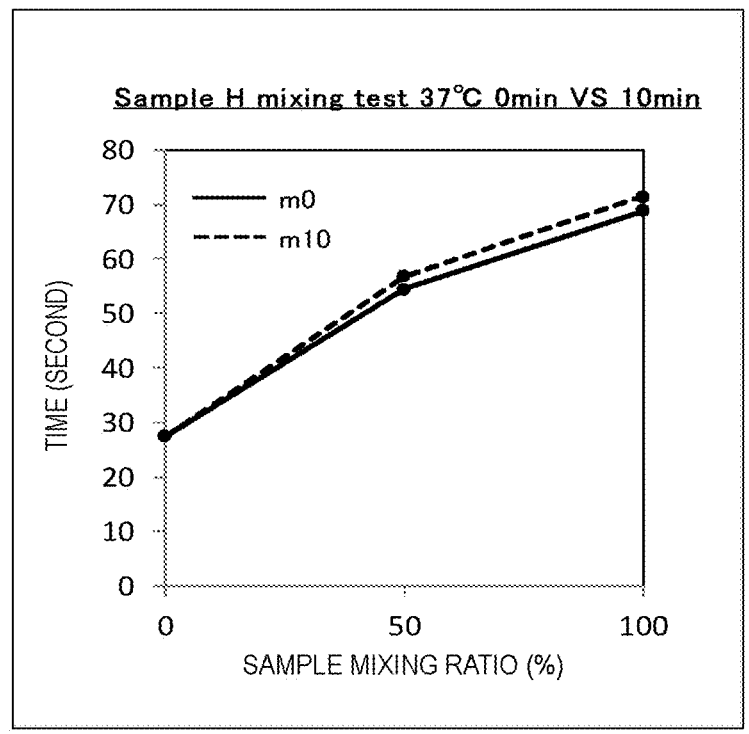

FIG. 49E is a diagram illustrating results of a cross-mixing test related to sample H of a LA-positive plasma without heating treatment and after heating treatment at 37° C. for 10 minutes.

Figure 49F:
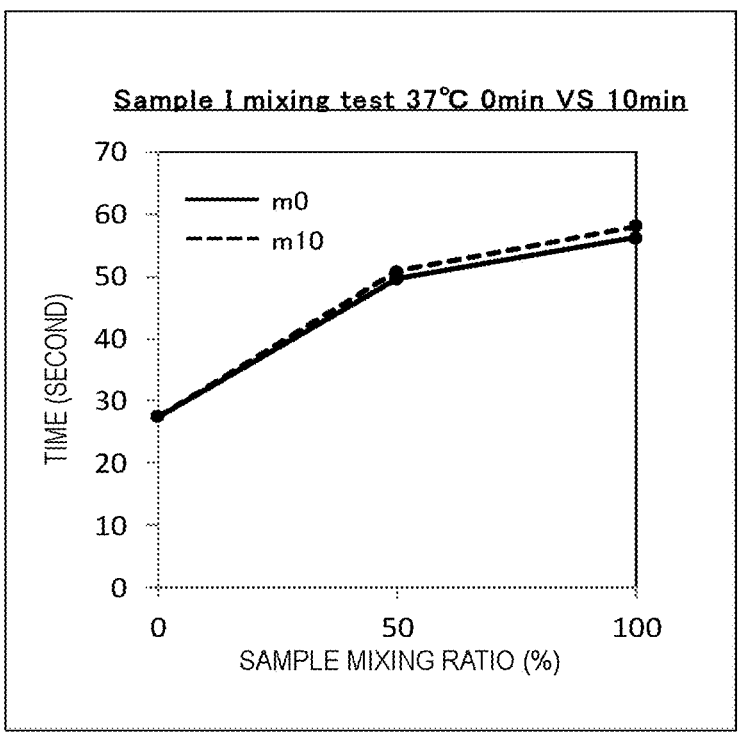

FIG. 49F is a diagram illustrating results of a cross-mixing test related to sample I of a LA-positive plasma without heating treatment and after heating treatment at 37° C. for 10 minutes.

Figure 49G:
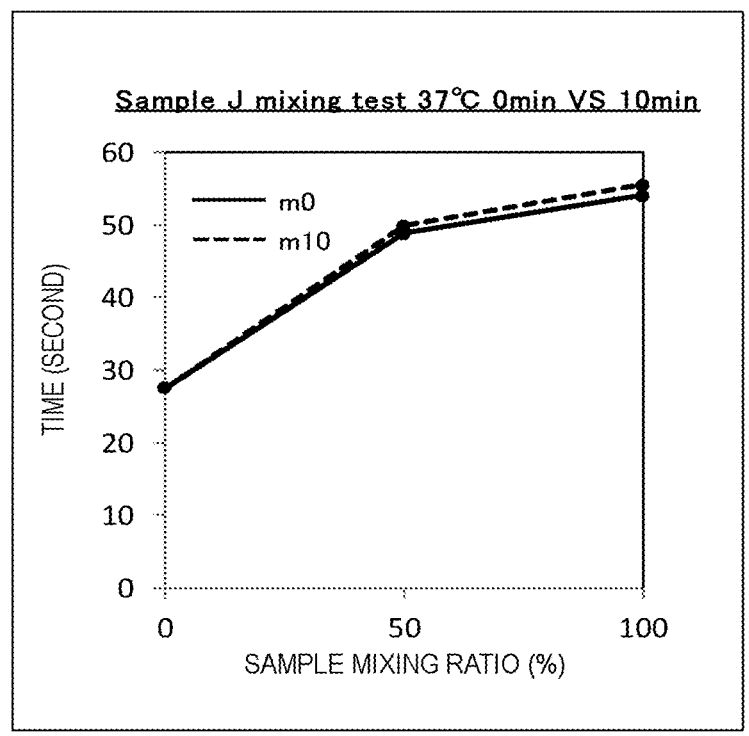

FIG. 49G is a diagram illustrating results of a cross-mixing test related to sample J of a LA-positive plasma without heating treatment and after heating treatment at 37° C. for 10 minutes.

Figure 49H:
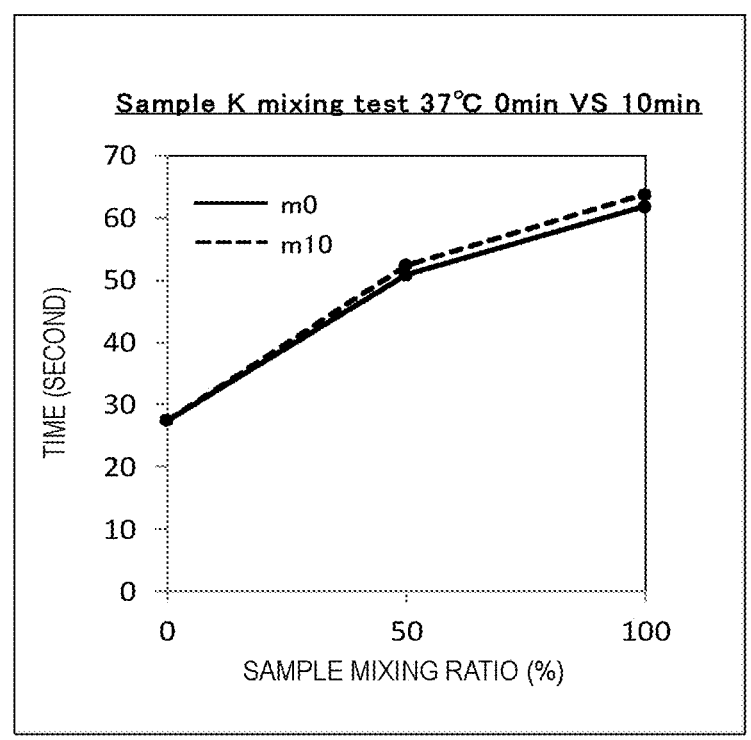

FIG. 49H is a diagram illustrating results of a cross-mixing test related to sample K of a LA-positive plasma without heating treatment and after heating treatment at 37° C. for 10 minutes.

Figure 49I:
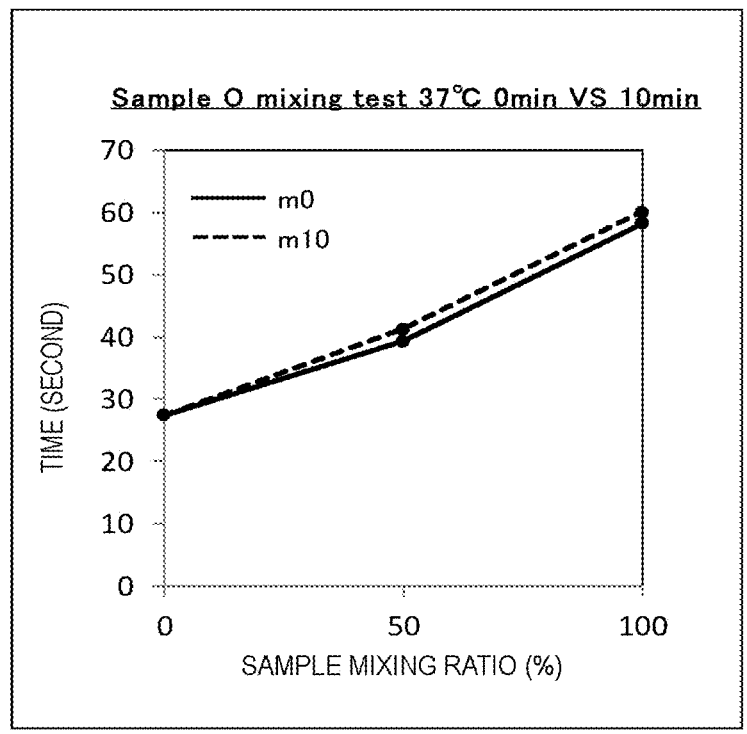

FIG. 49I is a diagram illustrating results of a cross-mixing test related to sample O of a LA-positive plasma without heating treatment and after heating treatment at 37° C. for 10 minutes.

Figure 49J:
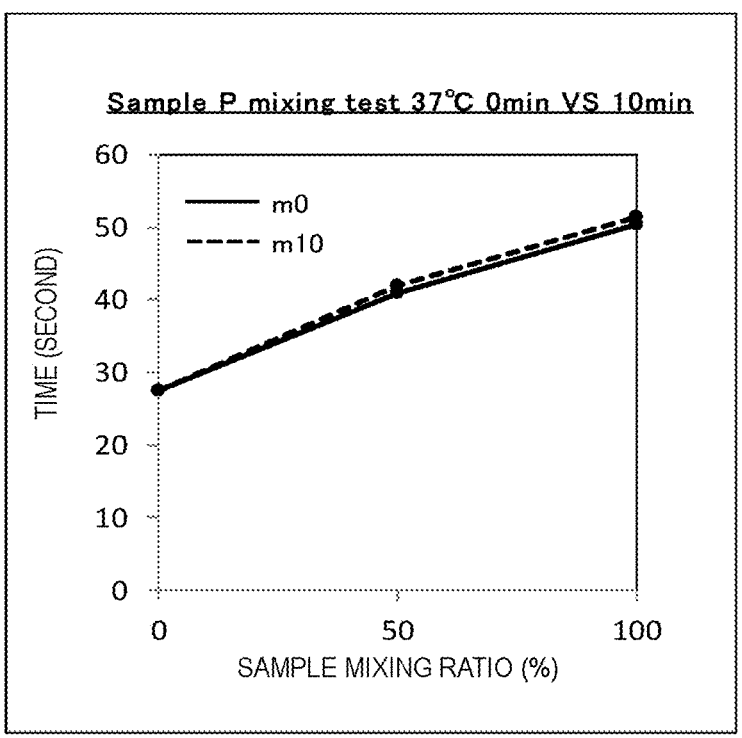

FIG. 49J is a diagram illustrating results of a cross-mixing test related to sample P of a LA-positive plasma without heating treatment and after heating treatment at 37° C. for 10 minutes.

Figure 49K:
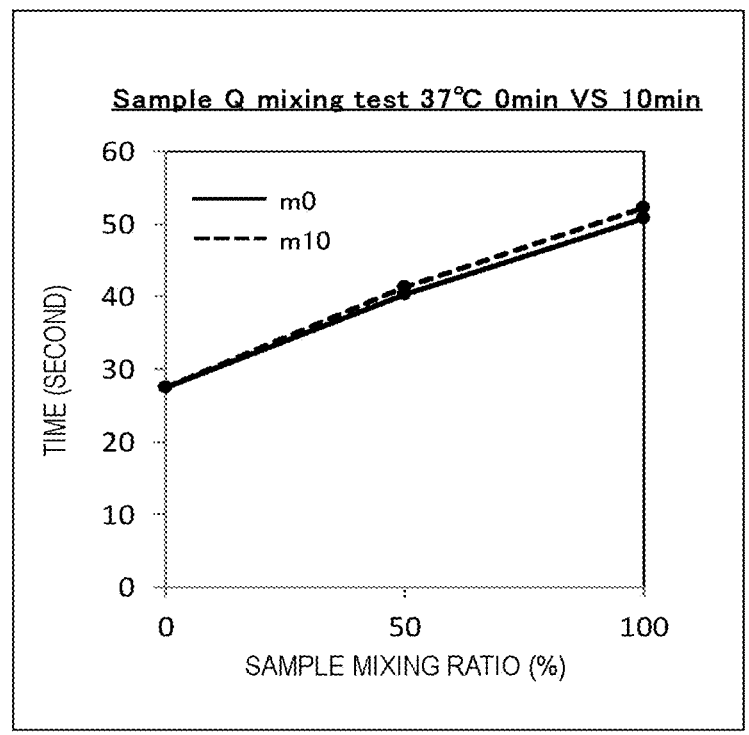

FIG. 49K is a diagram illustrating results of a cross-mixing test related to sample Q of a LA-positive plasma without heating treatment and after heating treatment at 37° C. for 10 minutes.

Figure 49L:
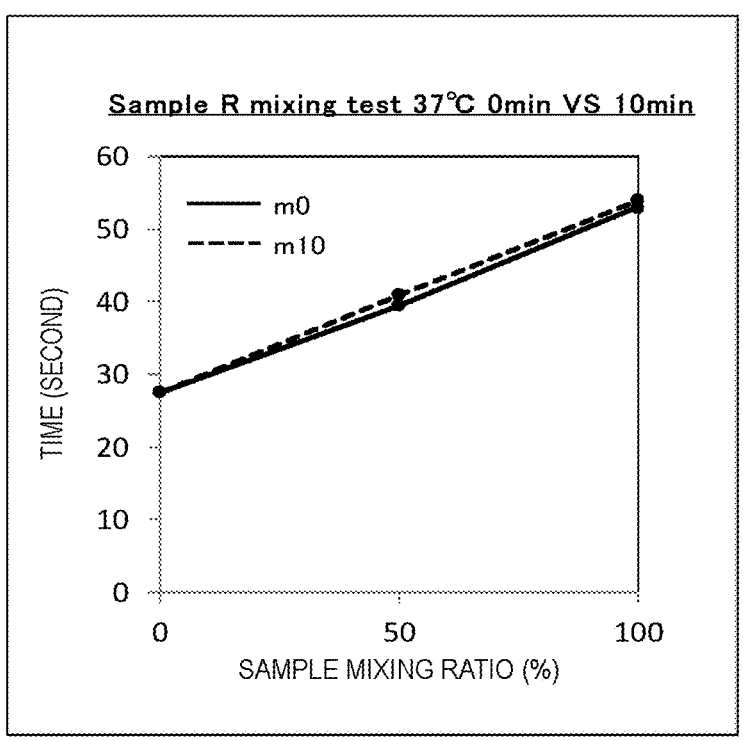

FIG. 49L is a diagram illustrating results of a cross-mixing test related to sample R of a LA-positive plasma without heating treatment and after heating treatment at 37° C. for 10 minutes.

Figure 50A:
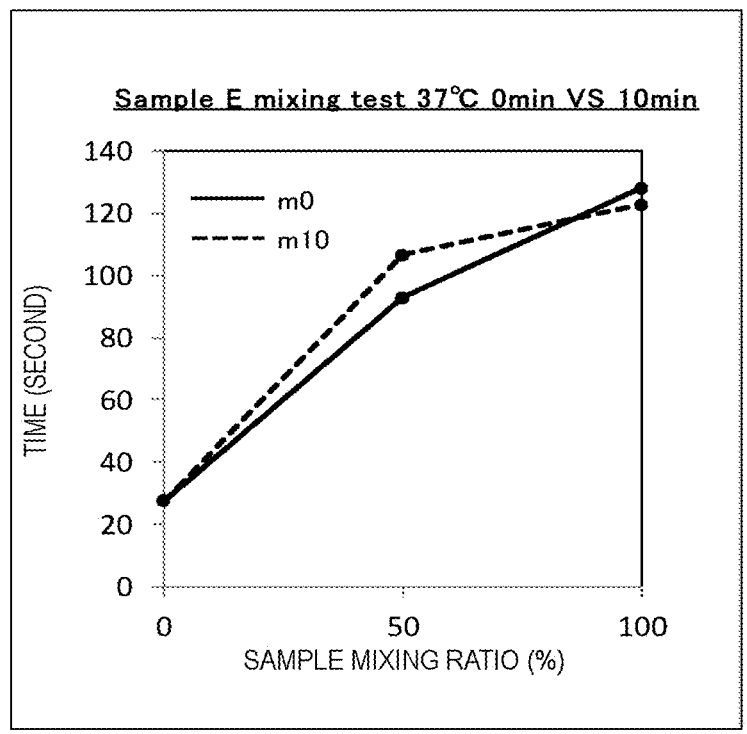

FIG. 50A is a diagram illustrating results of a cross-mixing test related to sample E of a factor VIII inhibitor-positive plasma without heating treatment and after heating treatment at 37° C. for 10 minutes.

Figure 50B:
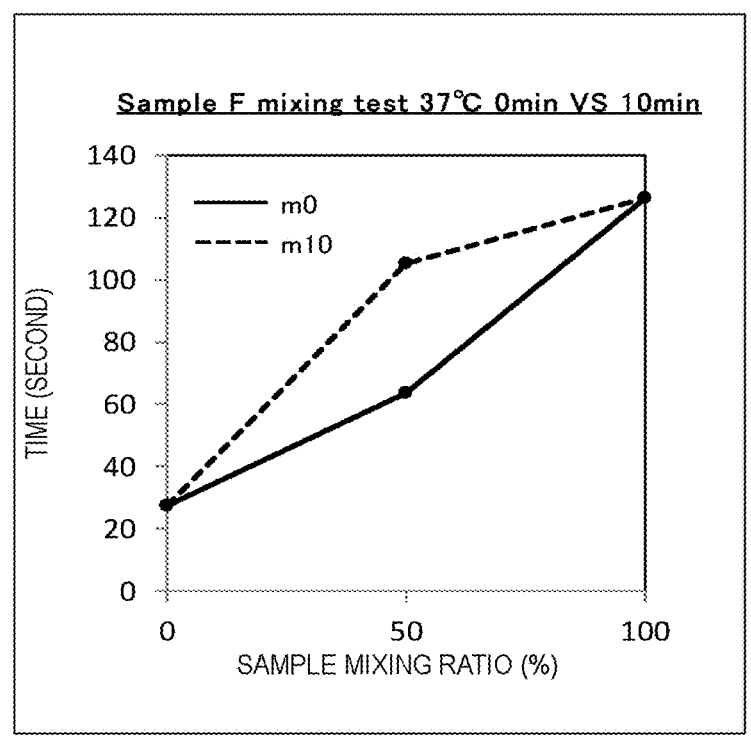

FIG. 50B is a diagram illustrating results of a cross-mixing test related to sample F of a factor VIII inhibitor-positive plasma without heating treatment and after heating treatment at 37° C. for 10 minutes.

Figure 50C:
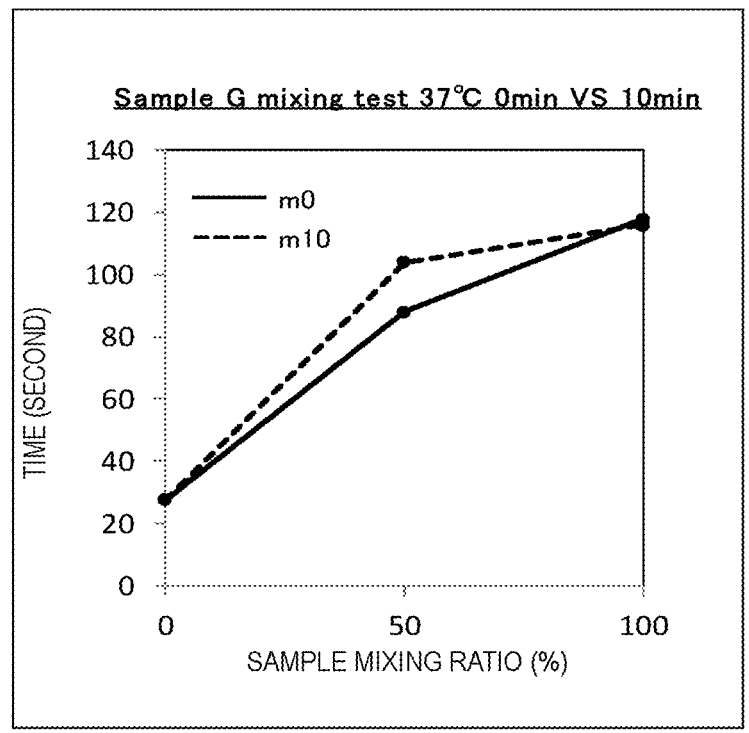

FIG. 50C is a diagram illustrating results of a cross-mixing test related to sample G of a factor VIII inhibitor-positive plasma without heating treatment and after heating treatment at 37° C. for 10 minutes.

Figure 50D:
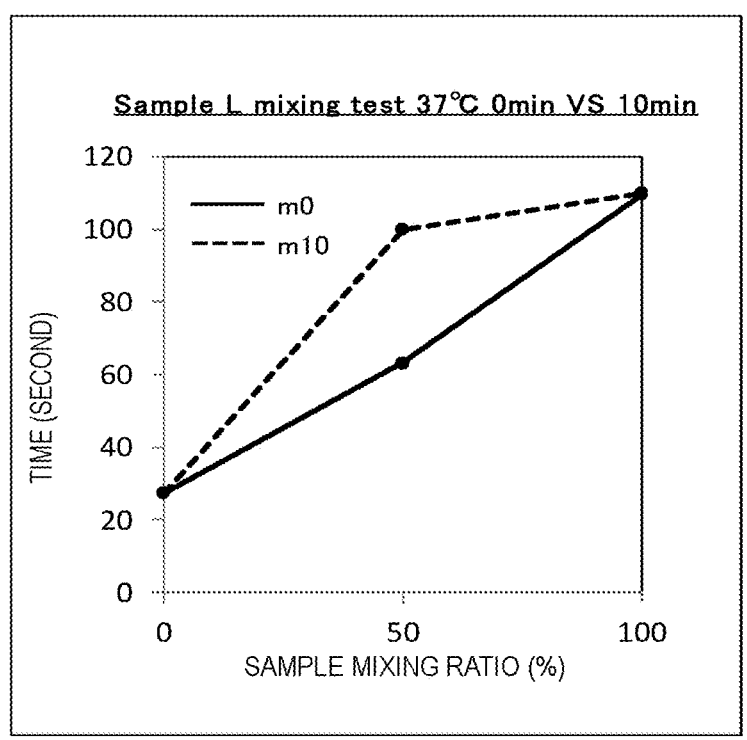

FIG. 50D is a diagram illustrating results of a cross-mixing test related to sample L of a factor VIII inhibitor-positive plasma without heating treatment and after heating treatment at 37° C. for 10 minutes.

Figure 50E:
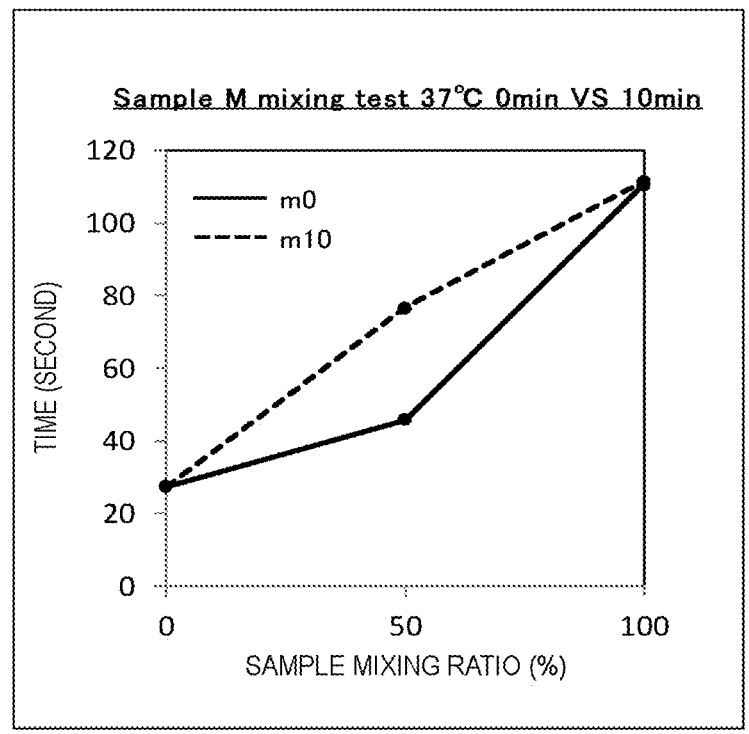

FIG. 50E is a diagram illustrating results of a cross-mixing test related to sample M of a factor VIII inhibitor-positive plasma without heating treatment and after heating treatment at 37° C. for 10 minutes.

Figure 50F:
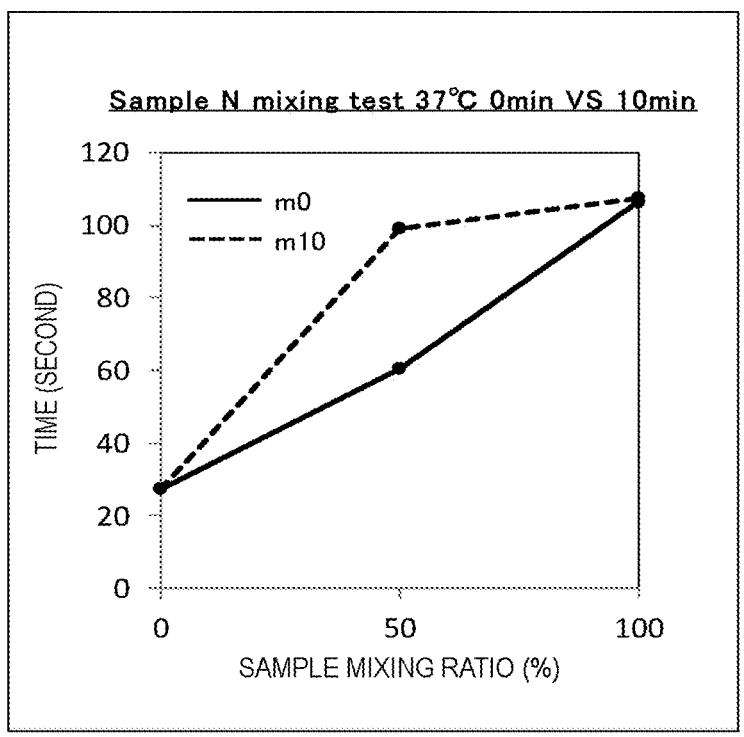

FIG. 50F is a diagram illustrating results of a cross-mixing test related to sample N of a factor VIII inhibitor-positive plasma without heating treatment and after heating treatment at 37° C. for 10 minutes.

Figure 50G:
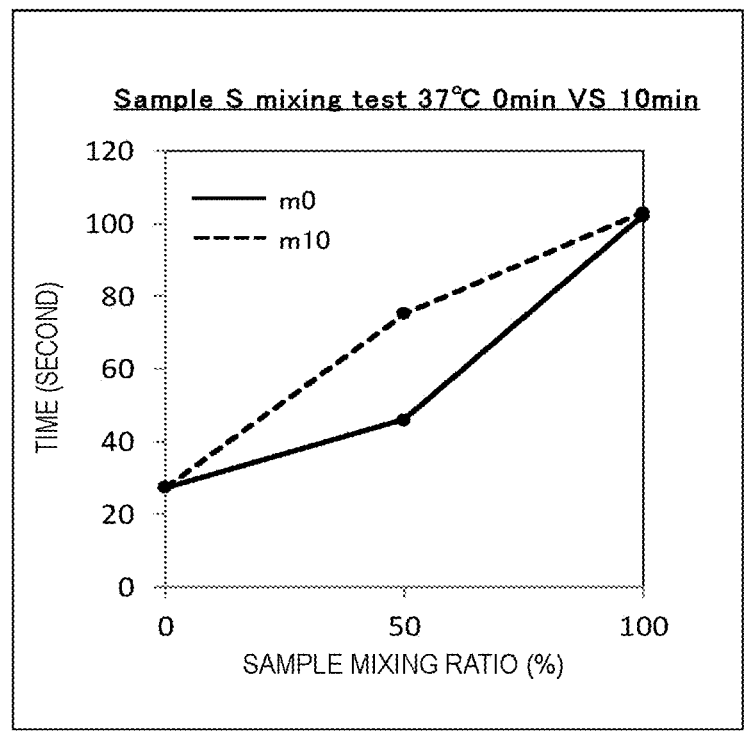

FIG. 50G is a diagram illustrating results of a cross-mixing test related to sample S of a factor VIII inhibitor-positive plasma without heating treatment and after heating treatment at 37° C. for 10 minutes.

Figure 50H:
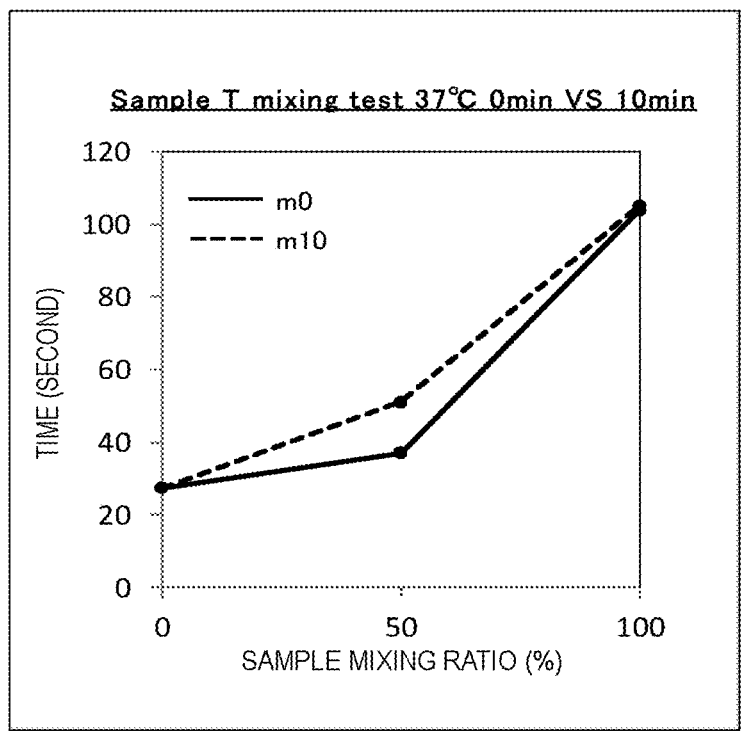

FIG. 50H is a diagram illustrating results of a cross-mixing test related to sample T of a factor VIII inhibitor-positive plasma without heating treatment and after heating treatment at 37° C. for 10 minutes.

Figure 50I:
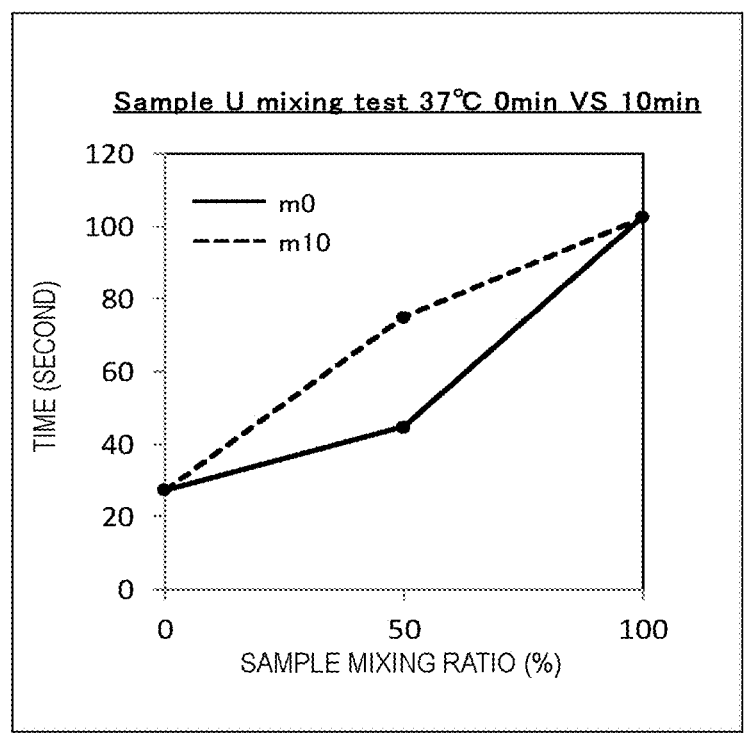

FIG. 50I is a diagram illustrating results of a cross-mixing test related to sample U of a factor VIII inhibitor-positive plasma without heating treatment and after heating treatment at 37° C. for 10 minutes.

Figure 51A:
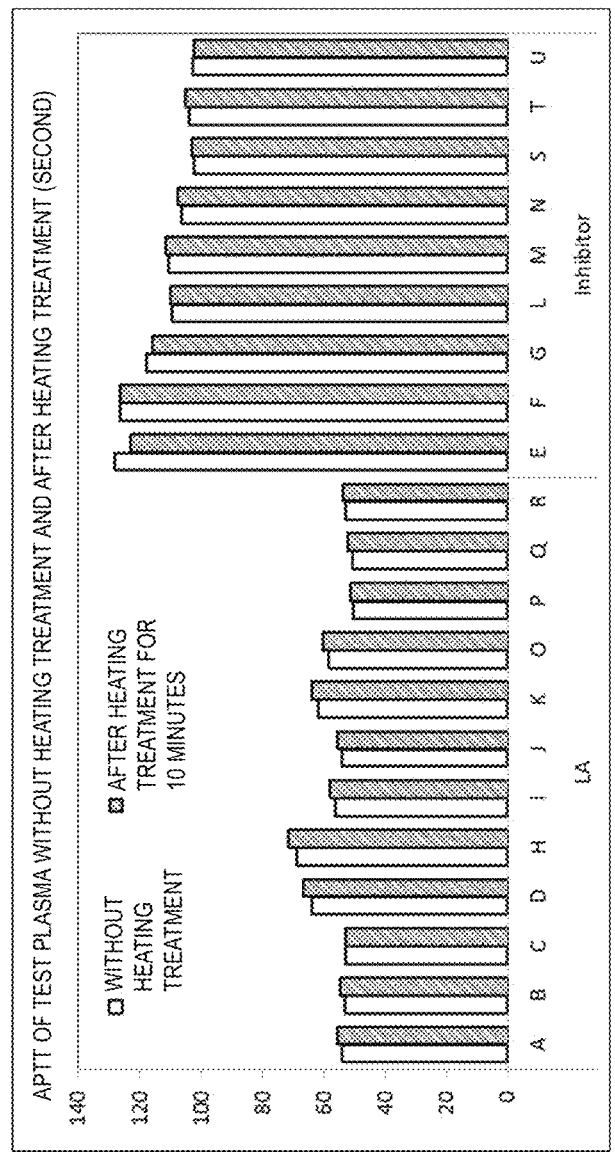

FIG. 51A is a diagram illustrating examples of APTT of each sample of a test plasma (single substance) without heating treatment and after heating treatment at 37° C. for 10 minutes.

FIG. 51B is a diagram illustrating examples of APTT of a mixed plasma of each sample of a test plasma and a normal plasma without heating treatment and after heating treatment at 37° C. for 10 minutes.

Figure 52A:
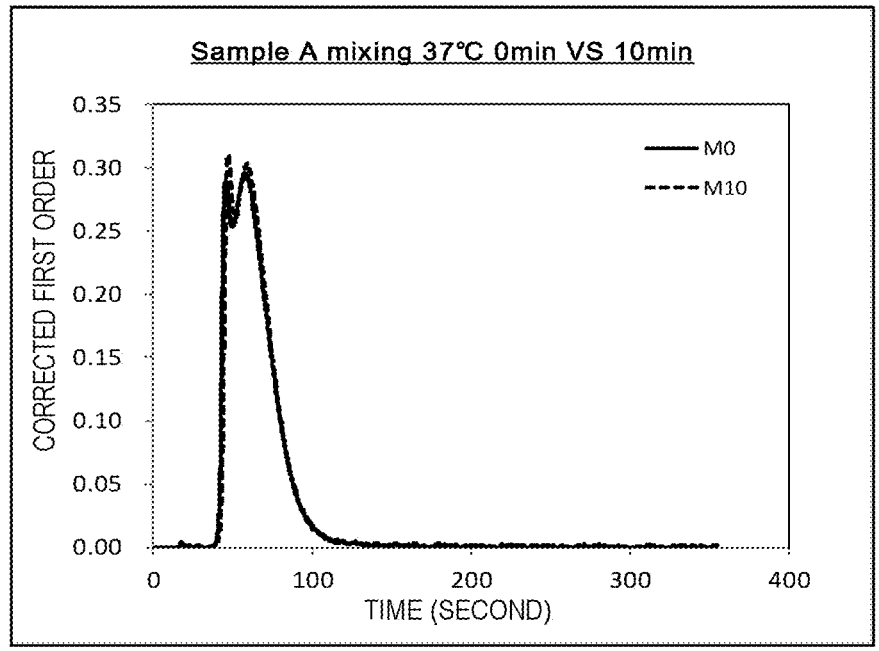

FIG. 52A is a diagram illustrating examples of corrected first order curves of an equal volume mixed plasma of sample A of a LA-positive plasma and a normal plasma without heating treatment and after heating treatment at 37° C. for 10 minutes.

Figure 52B:
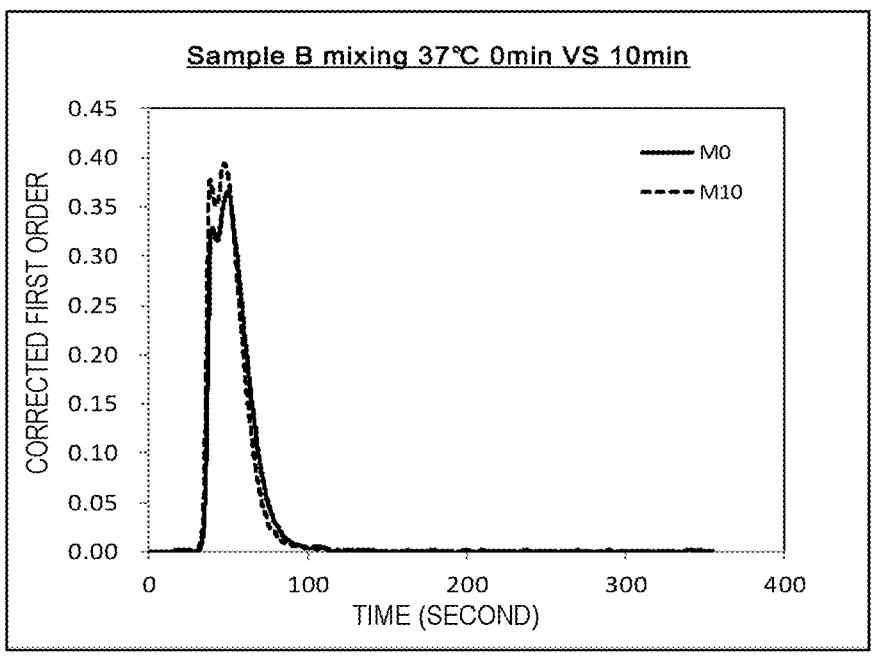

FIG. 52B is a diagram illustrating examples of a corrected first order curve of an equal volume mixed plasma of sample B of a LA-positive plasma and a normal plasma without heating treatment and after heating treatment at 37° C. for 10 minutes.

Figure 52C:
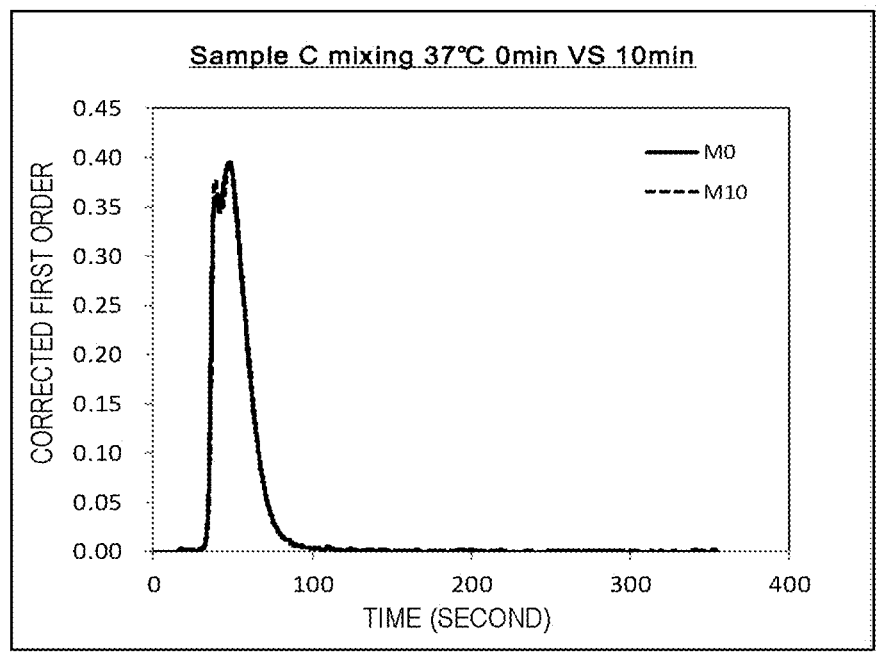

FIG. 52C is a diagram illustrating examples of a corrected first order curve of an equal volume mixed plasma of sample C of a LA-positive plasma and a normal plasma without heating treatment and after heating treatment at 37° C. for 10 minutes.

Figure 52D:
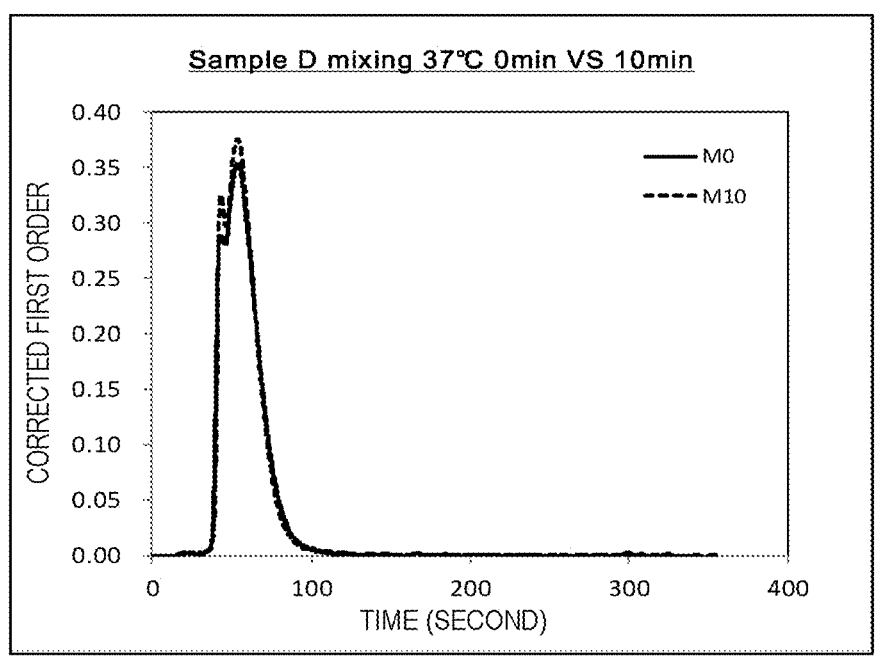

FIG. 52D is a diagram illustrating examples of a corrected first order curve of an equal volume mixed plasma of sample D of a LA-positive plasma and a normal plasma without heating treatment and after heating treatment at 37° C. for 10 minutes.

Figure 52E:
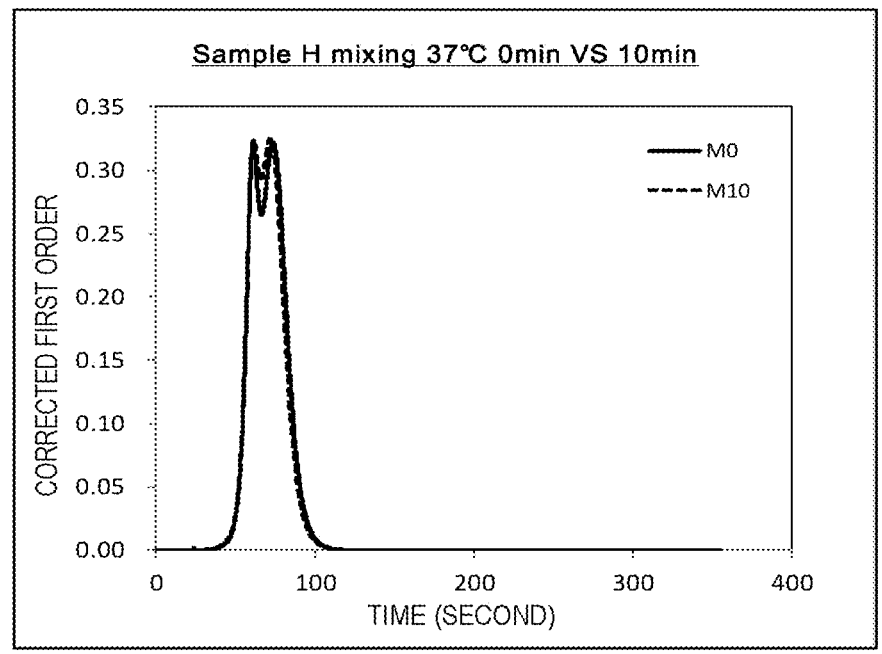

FIG. 52E is a diagram illustrating examples of a corrected first order curve of an equal volume mixed plasma of sample H of a LA-positive plasma and a normal plasma without heating treatment and after heating treatment at 37° C. for 10 minutes.

Figure 52F:
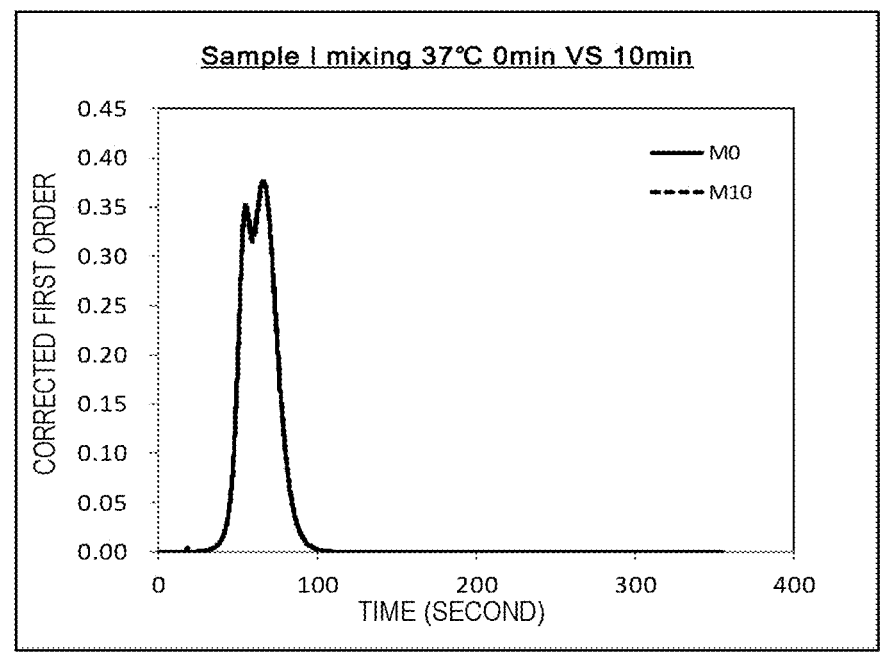

FIG. 52F is a diagram illustrating examples of a corrected first order curve of an equal volume mixed plasma of sample I of a LA-positive plasma and a normal plasma without heating treatment and after heating treatment at 37° C. for 10 minutes.

Figure 52G:
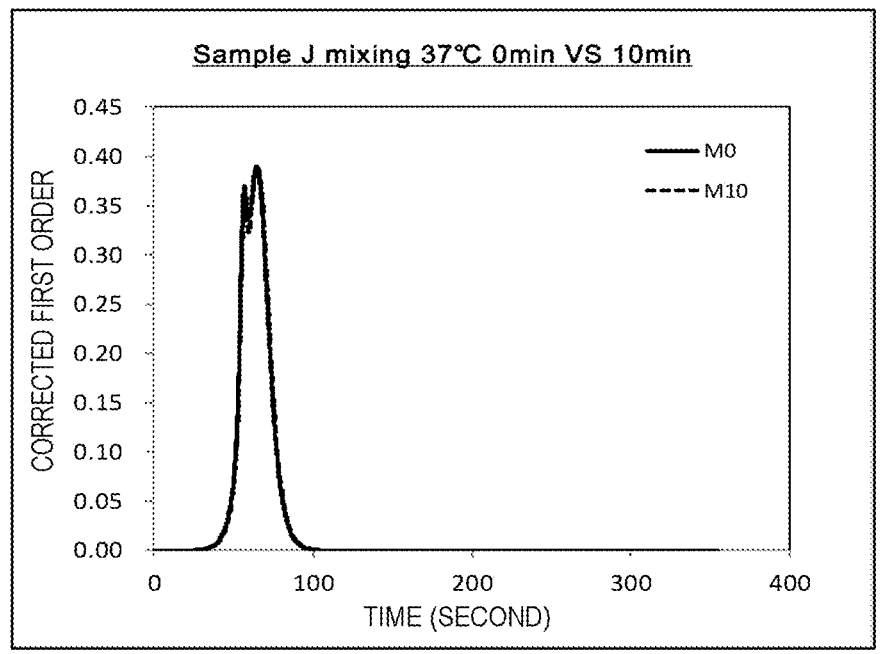

FIG. 52G is a diagram illustrating examples of a corrected first order curve of an equal volume mixed plasma of sample J of a LA-positive plasma and a normal plasma without heating treatment and after heating treatment at 37° C. for 10 minutes.

Figure 52H:
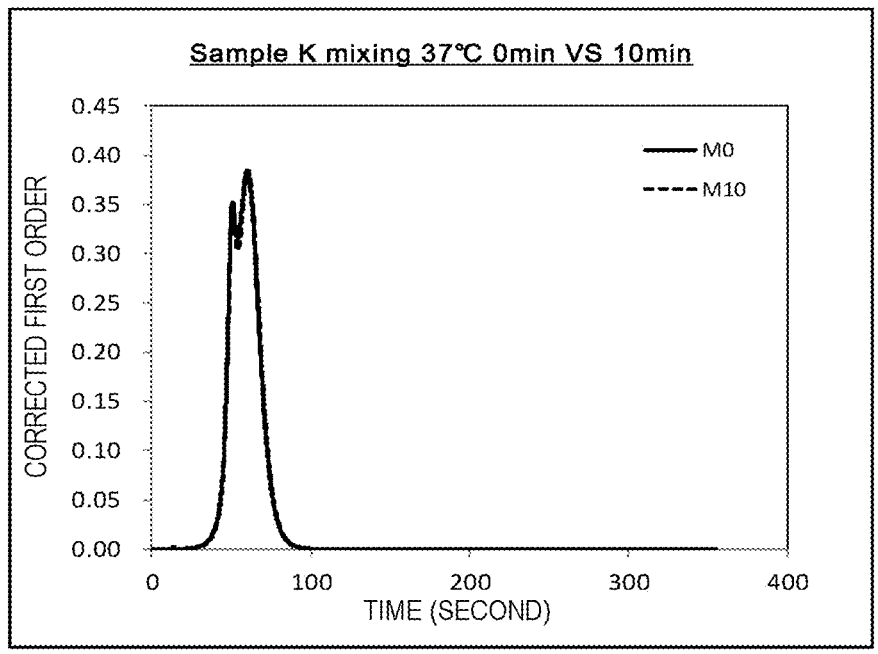

FIG. 52H is a diagram illustrating examples of a corrected first order curve of an equal volume mixed plasma of sample K of a LA-positive plasma and a normal plasma without heating treatment and after heating treatment at 37° C. for 10 minutes.

Figure 52I:
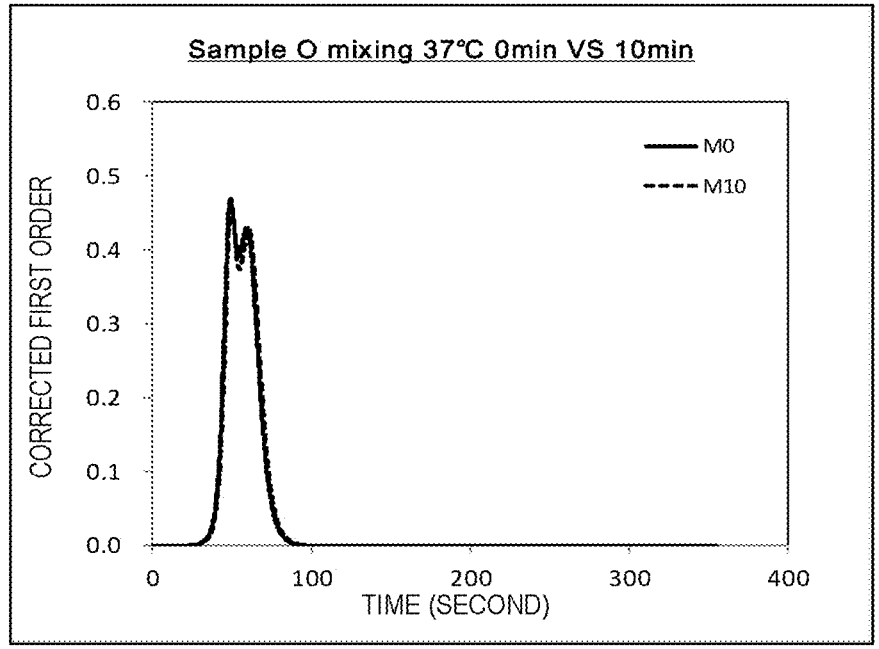

FIG. 52I is a diagram illustrating examples of a corrected first order curve of an equal volume mixed plasma of sample O of a LA-positive plasma and a normal plasma without heating treatment and after heating treatment at 37° C. for 10 minutes.

Figure 52J:
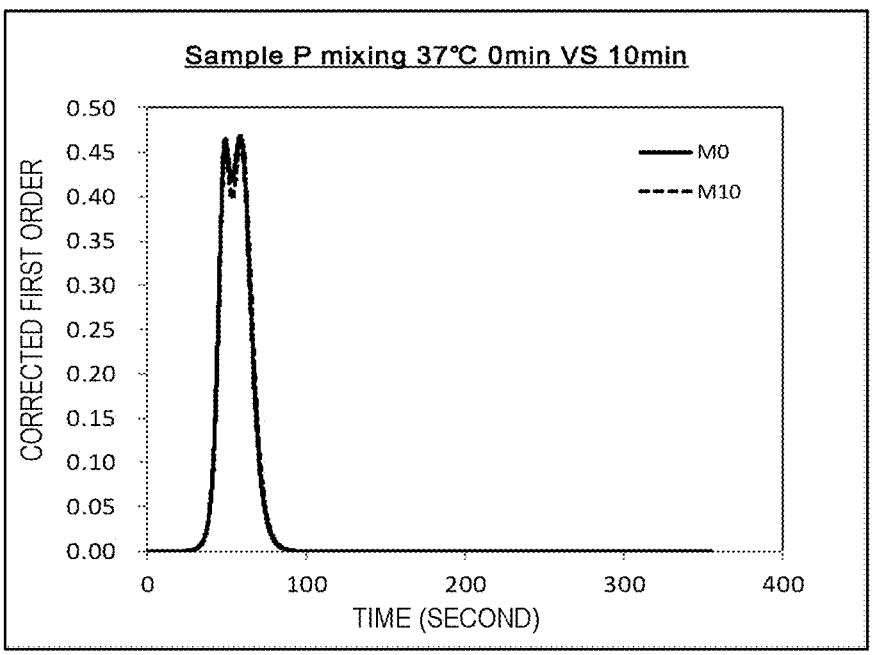

FIG. 52J is a diagram illustrating examples of a corrected first order curve of an equal volume mixed plasma of sample P of a LA-positive plasma and a normal plasma without heating treatment and after heating treatment at 37° C. for 10 minutes.

Figure 52K:
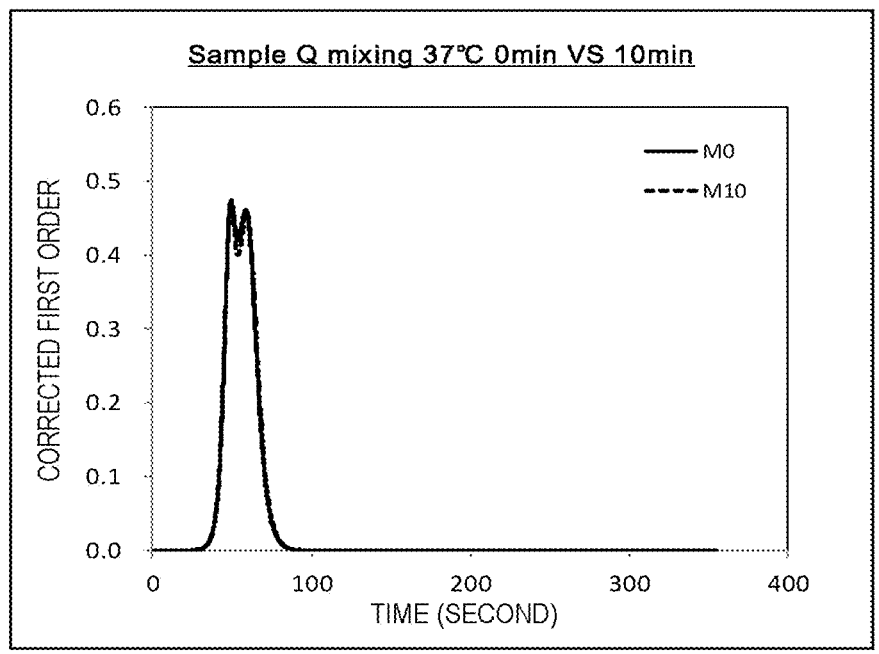

FIG. 52K is a diagram illustrating examples of a corrected first order curve of an equal volume mixed plasma of sample Q of a LA-positive plasma and a normal plasma without heating treatment and after heating treatment at 37° C. for 10 minutes.

Figure 52L:
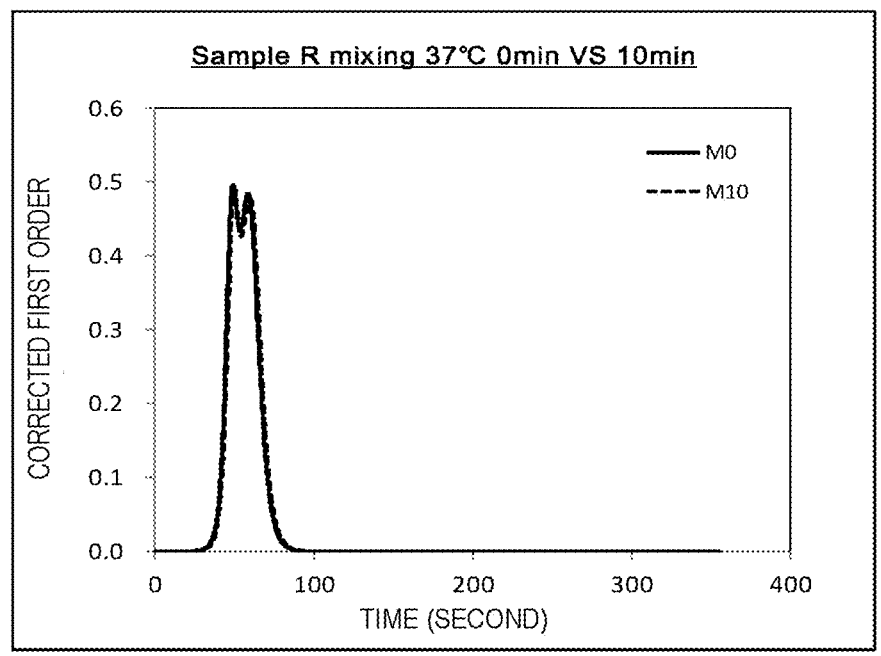

FIG. 52L is a diagram illustrating examples of a corrected first order curve of an equal volume mixed plasma of sample R of a LA-positive plasma and a normal plasma without heating treatment and after heating treatment at 37° C. for 10 minutes.

Figure 53A:
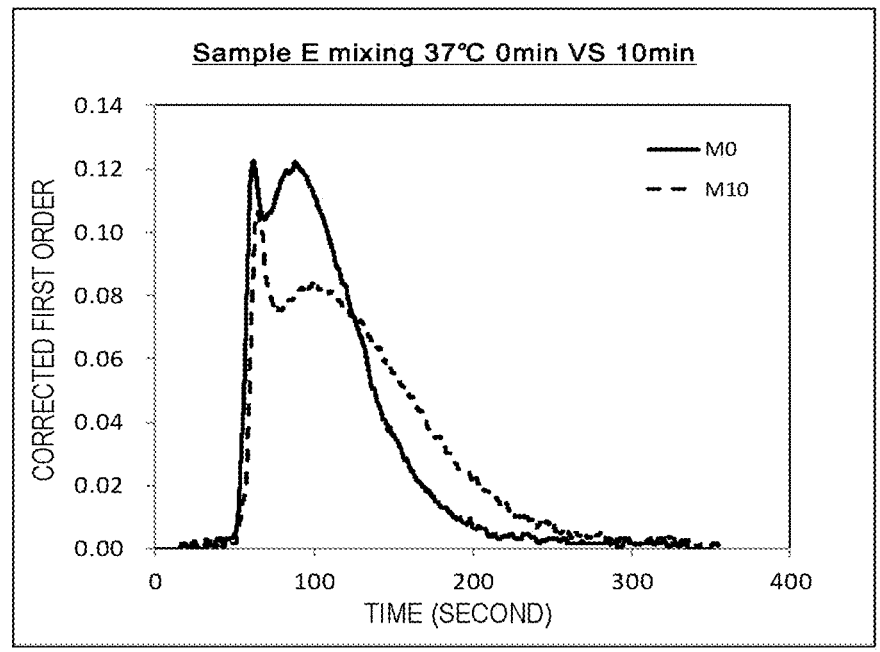

FIG. 53A is a diagram illustrating examples of a corrected first order curve of an equal volume mixed plasma of sample E of a factor VIII inhibitor-positive plasma and a normal plasma without heating treatment and after heating treatment at 37° C. for 10 minutes.

Figure 53B:
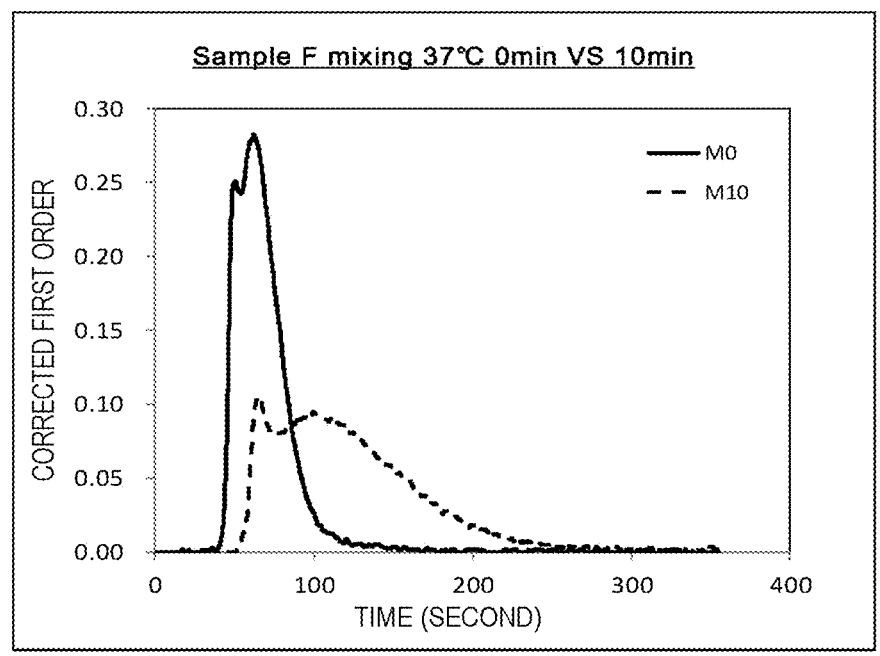

FIG. 53B is a diagram illustrating examples of a corrected first order curve of an equal volume mixed plasma of sample F of a factor VIII inhibitor-positive plasma and a normal plasma without heating treatment and after heating treatment at 37° C. for 10 minutes.

Figure 53C:
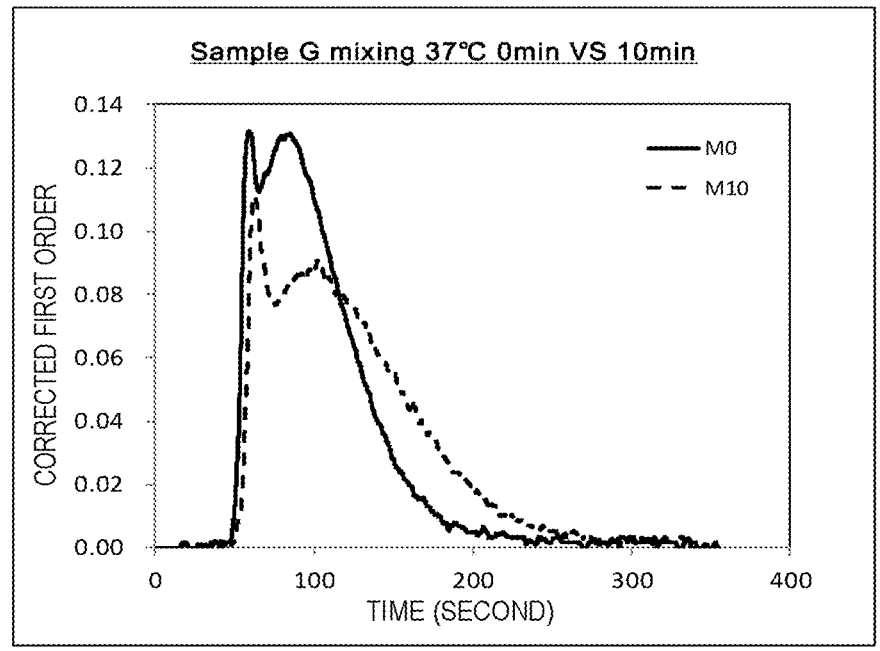

FIG. 53C is a diagram illustrating examples of a corrected first order curve of an equal volume mixed plasma of sample G of a factor VIII inhibitor-positive plasma and a normal plasma without heating treatment and after heating treatment at 37° C. for 10 minutes.

Figure 53D:
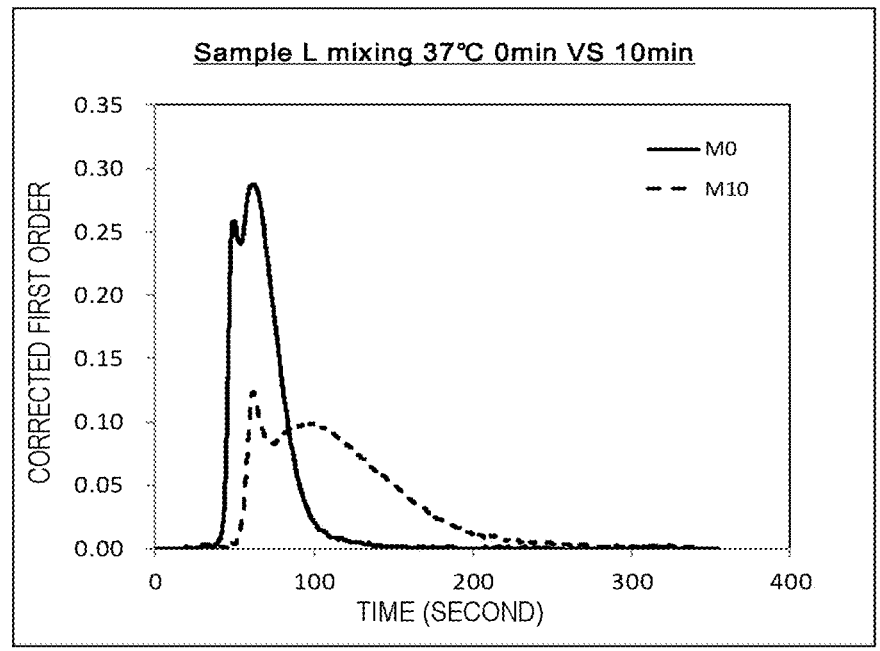

FIG. 53D is a diagram illustrating examples of a corrected first order curve of an equal volume mixed plasma of sample L of a factor VIII inhibitor-positive plasma and a normal plasma without heating treatment and after heating treatment at 37° C. for 10 minutes.

Figure 53E:
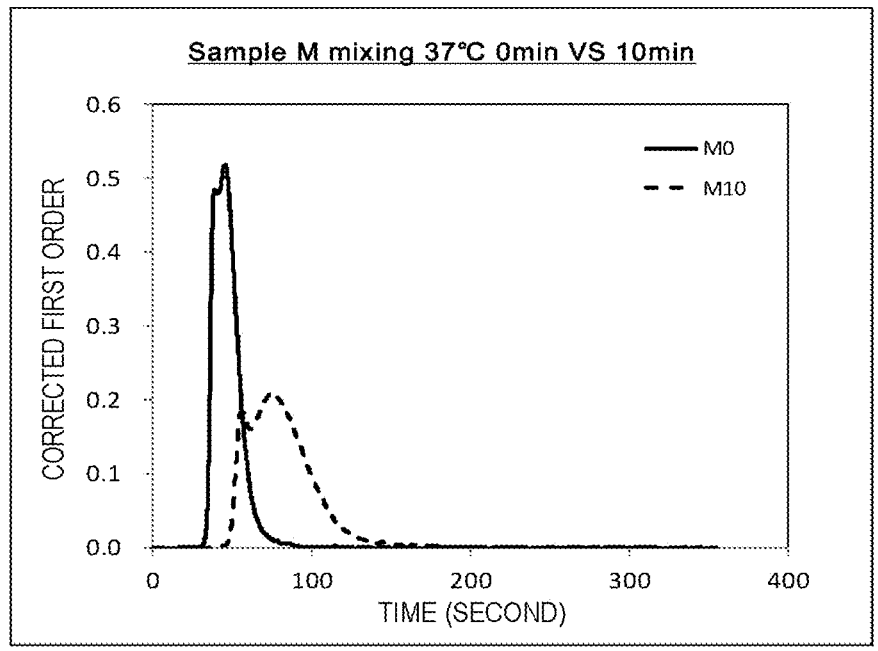

FIG. 53E is a diagram illustrating examples of a corrected first order curve of an equal volume mixed plasma of sample M of a factor VIII inhibitor-positive plasma and a normal plasma without heating treatment and after heating treatment at 37° C. for 10 minutes.

Figure 53F:
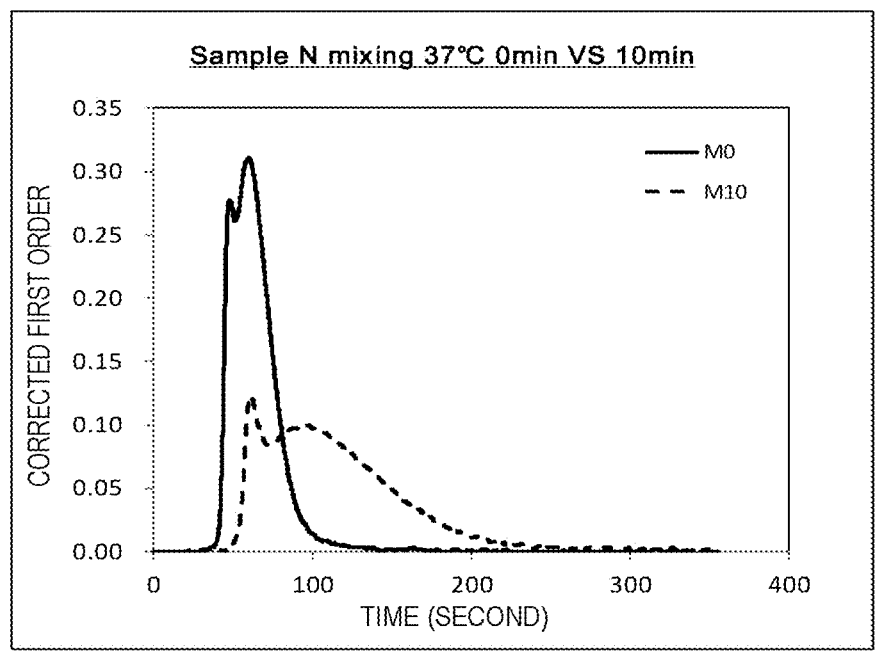

FIG. 53F is a diagram illustrating examples of a corrected first order curve of an equal volume mixed plasma of sample N of a factor VIII inhibitor-positive plasma and a normal plasma without heating treatment and after heating treatment at 37° C. for 10 minutes.

Figure 53G:
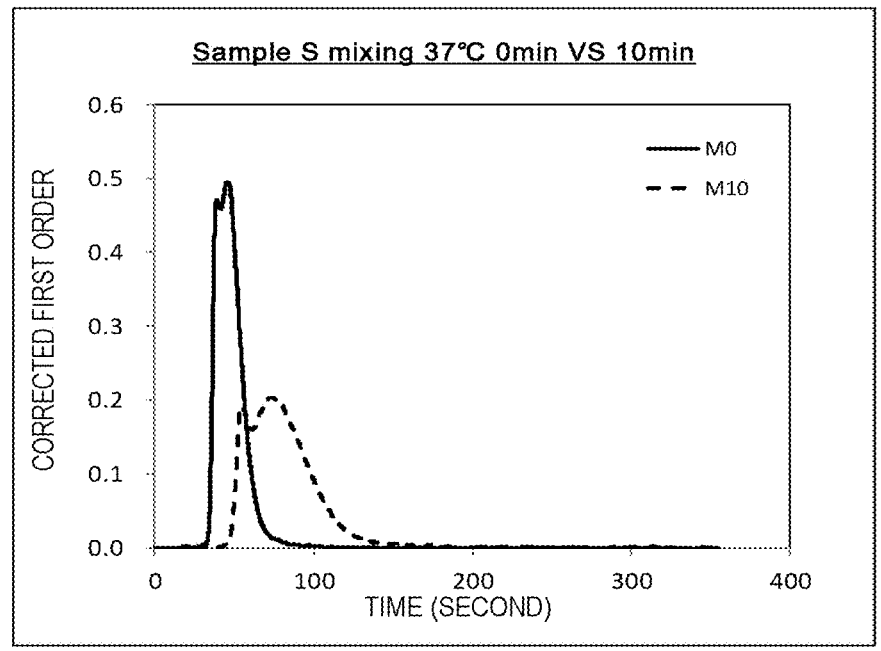

FIG. 53G is a diagram illustrating examples of a corrected first order curve of an equal volume mixed plasma of sample S of a factor VIII inhibitor-positive plasma and a normal plasma without heating treatment and after heating treatment at 37° C. for 10 minutes.

Figure 53H:
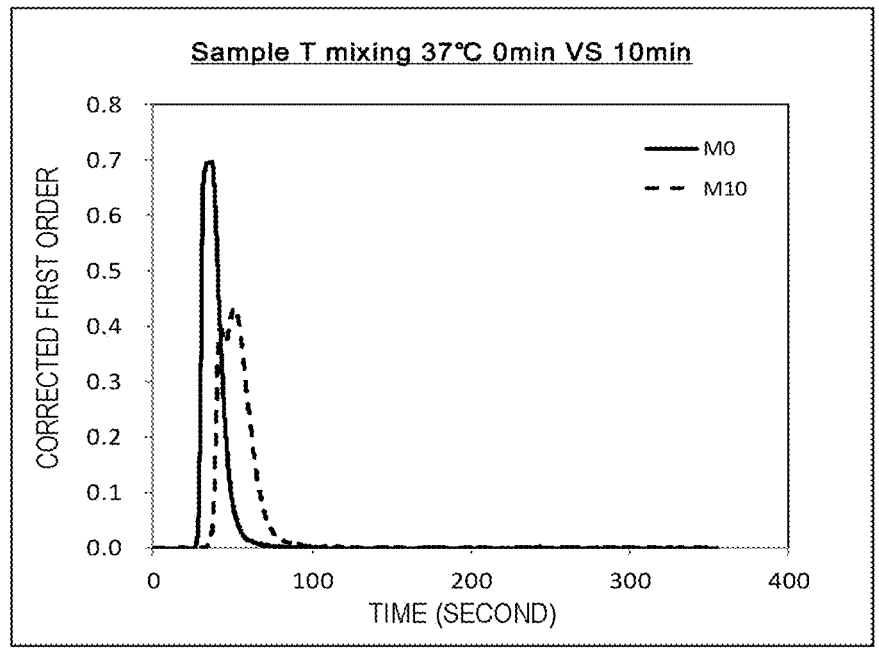

FIG. 53H is a diagram illustrating examples of a corrected first order curve of an equal volume mixed plasma of sample T of a factor VIII inhibitor-positive plasma and a normal plasma without heating treatment and after heating treatment at 37° C. for 10 minutes.

Figure 53I:
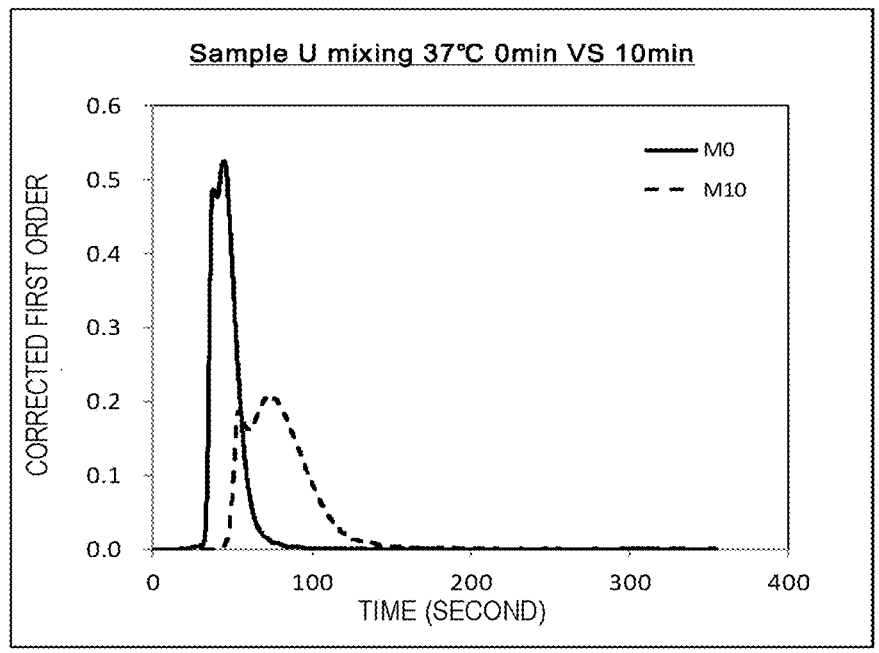

FIG. 53I is a diagram illustrating examples of a corrected first order curve of an equal volume mixed plasma of sample U of a factor VIII inhibitor-positive plasma and a normal plasma without heating treatment and after heating treatment at 37° C. for 10 minutes.

Figure 54A:
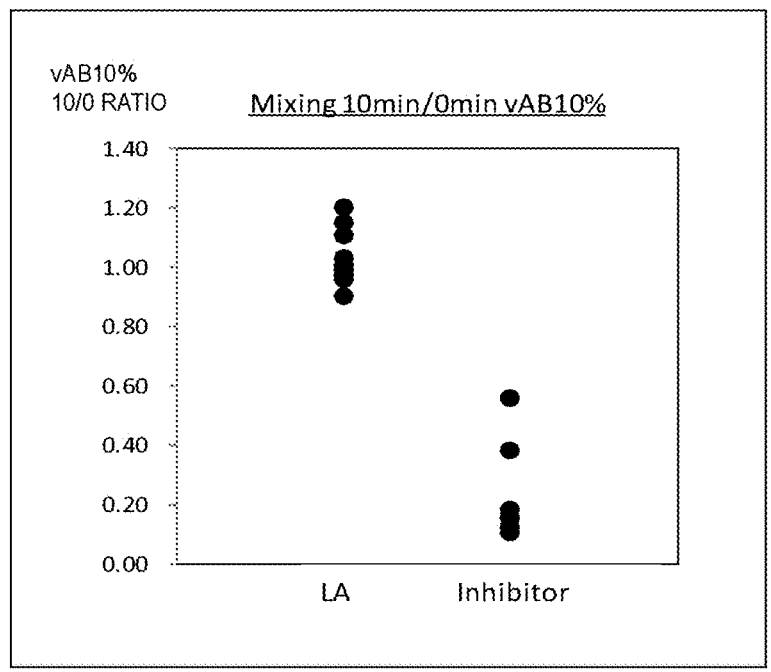

FIG. 54A is a diagram illustrating a ratio between a value without heating treatment and a value after heating treatment for 10 minutes (vAB10% 10/0 ratio) for "flattening ratio when calculation target area value S is set to 10%" related to an equal volume mixed plasma of each of samples of a LA-positive plasma and a normal plasma, and a ratio between a value without heating treatment and a value after heating treatment for 10 minutes (vAB10% 10/0 ratio) for "flattening ratio when calculation target area value S is set to 10%" related to an equal volume mixed plasma of each of samples of a factor VIII inhibitor-positive plasma and a normal plasma.

Figure 54B:
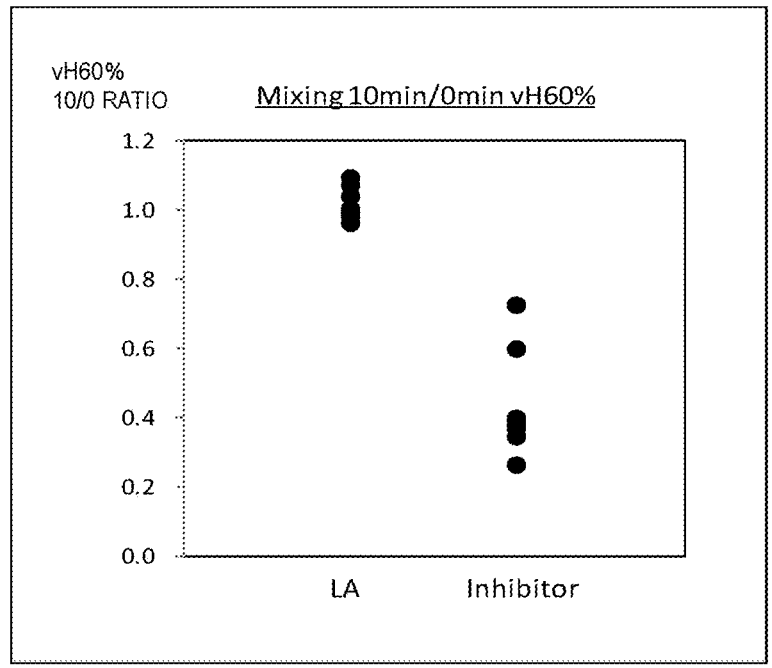

FIG. 54B is a diagram illustrating a ratio between a value without heating treatment and a value after heating treatment for 10 minutes (vH60% 10/0 ratio) for "center-of-gravity height when calculation target area value S is set to 60%" related to an equal volume mixed plasma of each of samples of a LA-positive plasma and a normal plasma, and a ratio between a value without heating treatment and a value after heating treatment for 10 minutes (vH60% 10/0 ratio) for "center-of-gravity height when calculation target area value S is set to 60%" related to an equal volume mixed plasma of each of samples of a factor VIII inhibitor-positive plasma and a normal plasma.

Figure 55A:
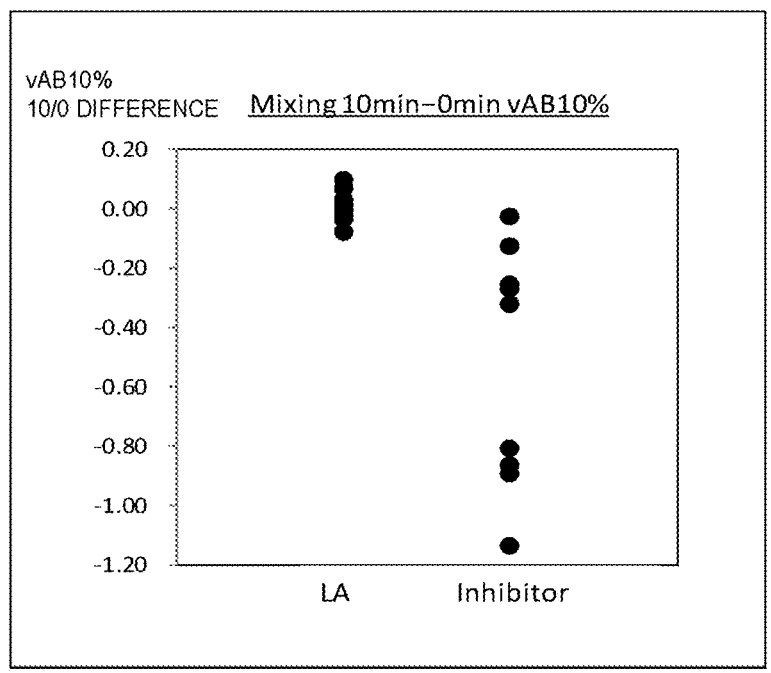

FIG. 55A is a diagram illustrating a difference between a value without heating treatment and a value after heating treatment for 10 minutes (vAB10% 10/0 difference) for "flattening ratio when calculation target area value S is set to 10%" related to an equal volume mixed plasma of each of samples of a LA-positive plasma and a normal plasma, and a difference between a value without heating treatment and a value after heating treatment for 10 minutes (vAB10% 10/0 difference) for "flattening ratio when calculation target area value S is set to 10%" related to an equal volume mixed plasma of each of samples of a factor VIII inhibitor-positive plasma and a normal plasma.

Figure 55B:
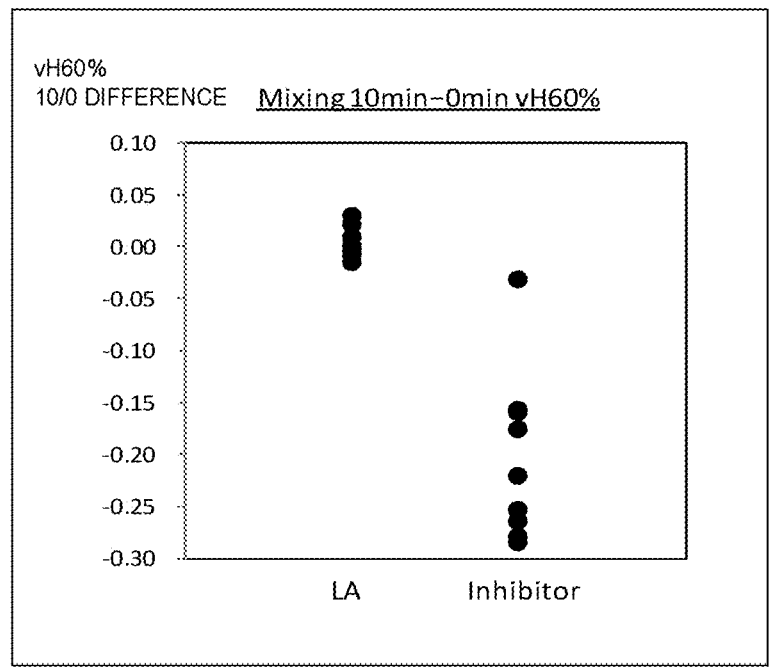

FIG. 55B is a diagram illustrating a difference between a value without heating treatment and a value after heating treatment for 10 minutes (vH60% 10/0 difference) for "center-of-gravity height when calculation target area value S is set to 60%" related to an equal volume mixed plasma of each of samples of a LA-positive plasma and a normal plasma, and a difference between a value without heating treatment and a value after heating treatment for 10 minutes (vH60% 10/0 difference) for "center-of-gravity height when calculation target area value S is set to 60%" related to an equal volume mixed plasma of each of samples of a factor VIII inhibitor-positive plasma and a normal plasma.

Figure 55C:
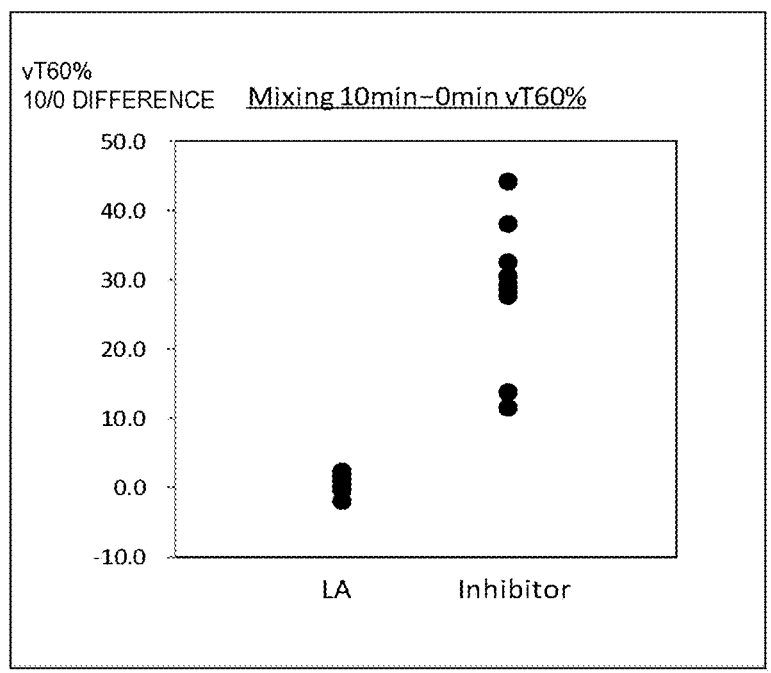

FIG. 55C is a diagram illustrating a difference between a value without heating treatment and a value after heating treatment for 10 minutes (vT60% 10/0 difference) for "center-of-gravity time when calculation target area value S is set to 60%" related to an equal volume mixed plasma of each of samples of a LA-positive plasma and a normal plasma, and a difference between a value without heating treatment and a value after heating treatment for 10 minutes (vT60% 10/0 difference) for "center-of-gravity time when calculation target area value S is set to 60%" related to an equal volume mixed plasma of each of samples of a factor VIII inhibitor-positive plasma and a normal plasma.

Figure 56:
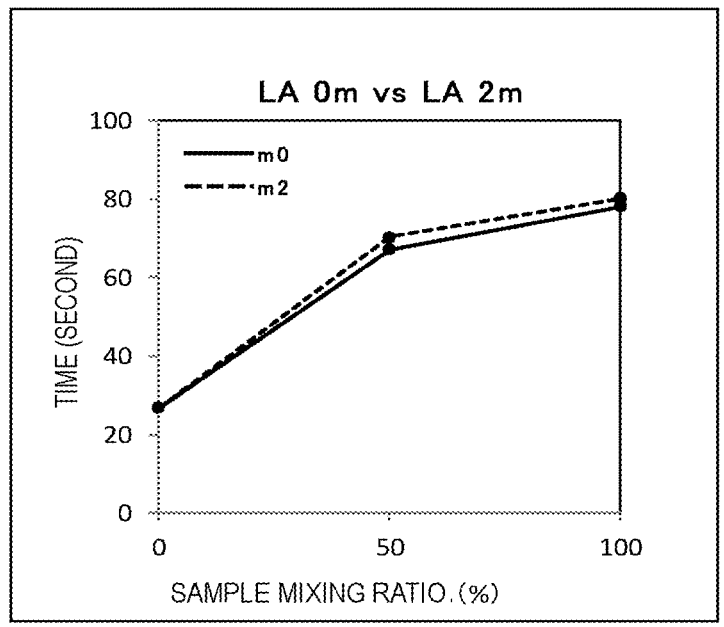

FIG. 56 is a diagram illustrating results of a cross-mixing test related to a sample of a LA-positive plasma without heating treatment and after heating treatment at 37° C. for 2 minutes.

Figure 57:
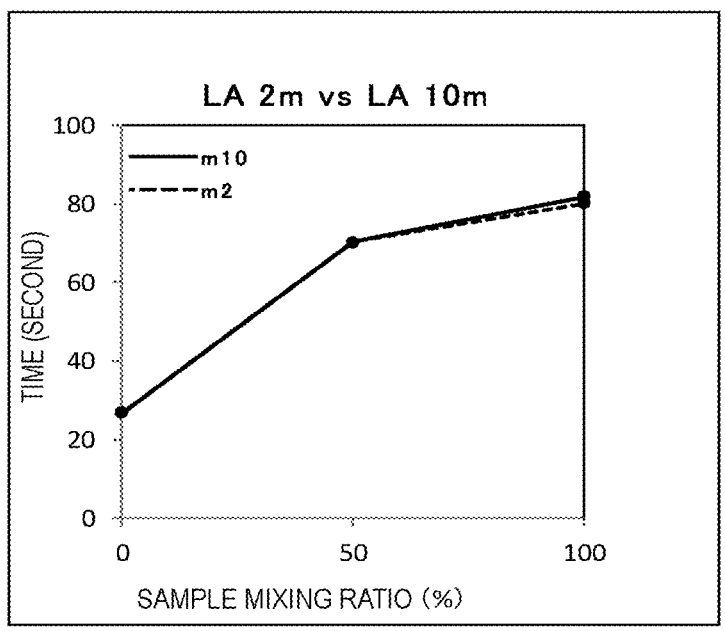

FIG. 57 is a diagram illustrating results of a cross-mixing test related to a sample of a LA-positive plasma after heating treatment at 37° C. for 2 minutes and after heating treatment at 37° C. for 10 minutes.

Figure 58:
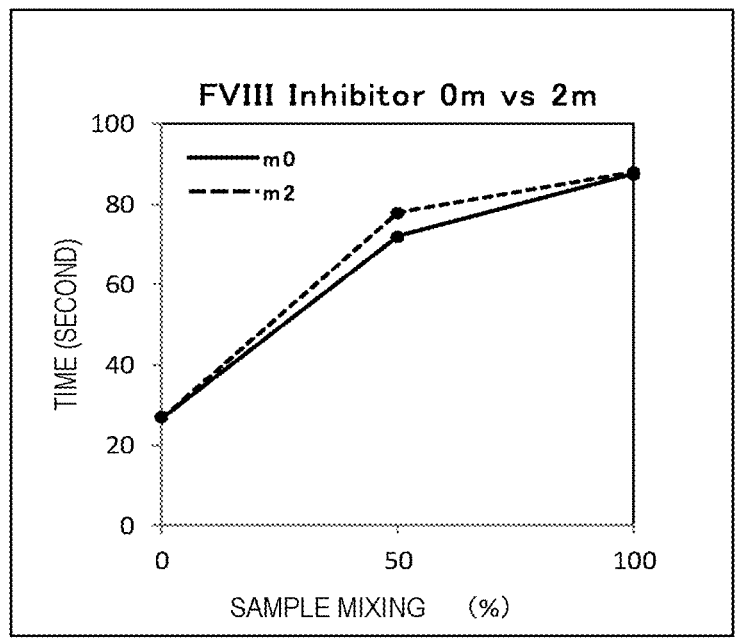

FIG. 58 is a diagram illustrating results of a cross-mixing test related to a sample of a factor VIII inhibitor-positive plasma without heating treatment and after heating treatment at 37° C. for 2 minutes.

Figure 59:
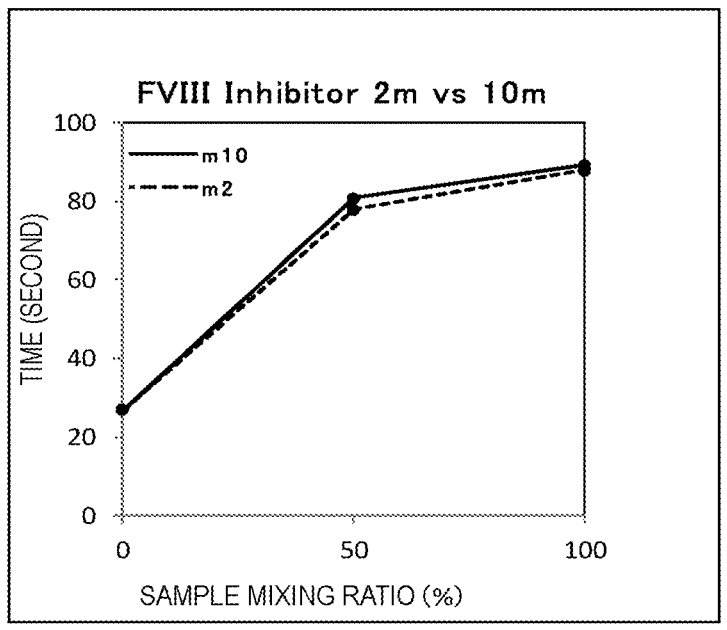

FIG. 59 is a diagram illustrating results of a cross-mixing test related to a sample of a factor VIII inhibitor-positive plasma after heating treatment at 37° C. for 2 minutes and after heating treatment at 37° C. for 10 minutes.

Figure 60:
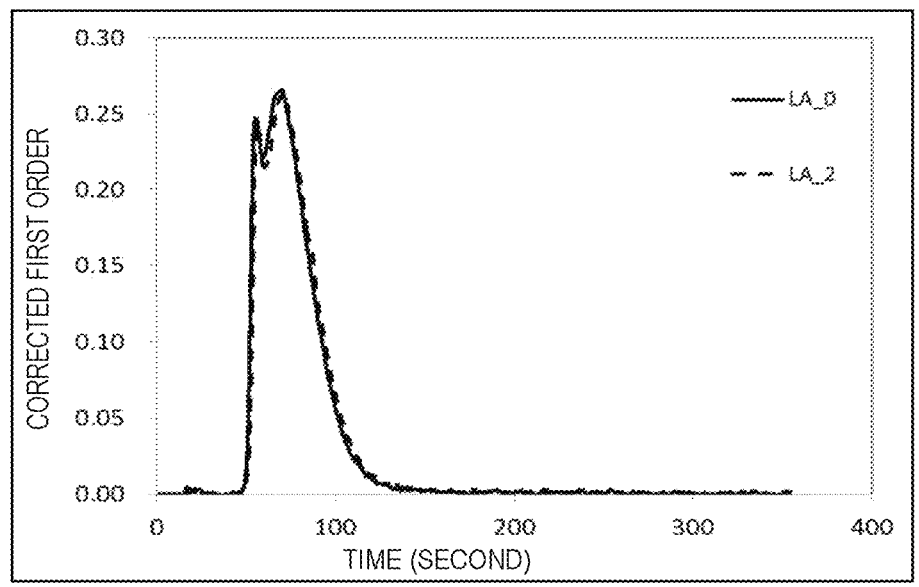

FIG. 60 is a diagram illustrating examples of corrected first order curves of an equal volume mixed plasma of a sample of a LA-positive plasma and a normal plasma without heating treatment and after heating treatment at 37° C. for 2 minutes.

Figure 61:
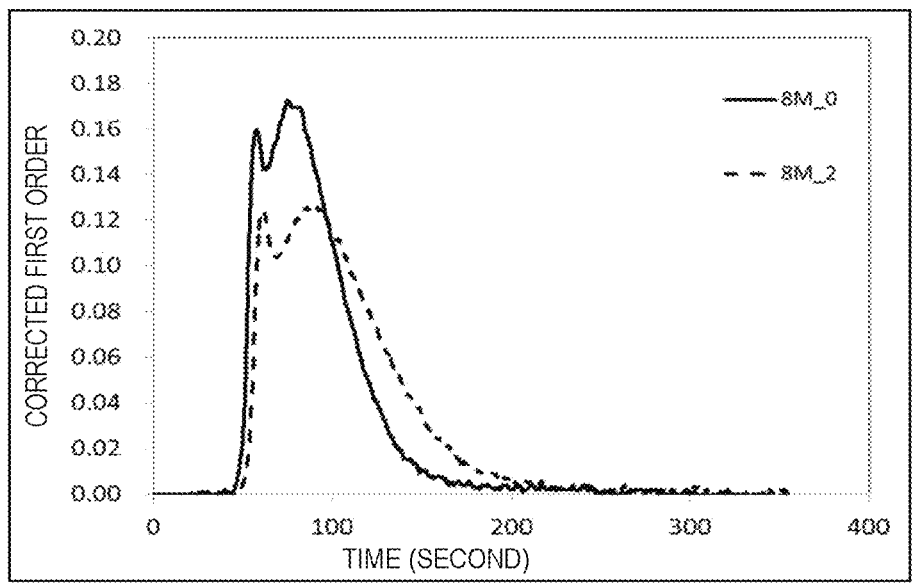

FIG. 61 is a diagram illustrating examples of corrected first order curves of an equal volume mixed plasma of a sample of a factor VIII inhibitor-positive plasma and a normal plasma without heating treatment and after heating treatment at 37° C. for 2 minutes.

FIG. 62 is a diagram illustrating an example of a table illustrating various evaluation parameters obtained from APTT measurement data of each of five types of samples after heating treatment for 2 minutes, various evaluation parameters obtained from APTT measurement data of each of the five samples without heating treatment, and results of calculating ratios between both the various evaluation parameters.

Figure 63A:
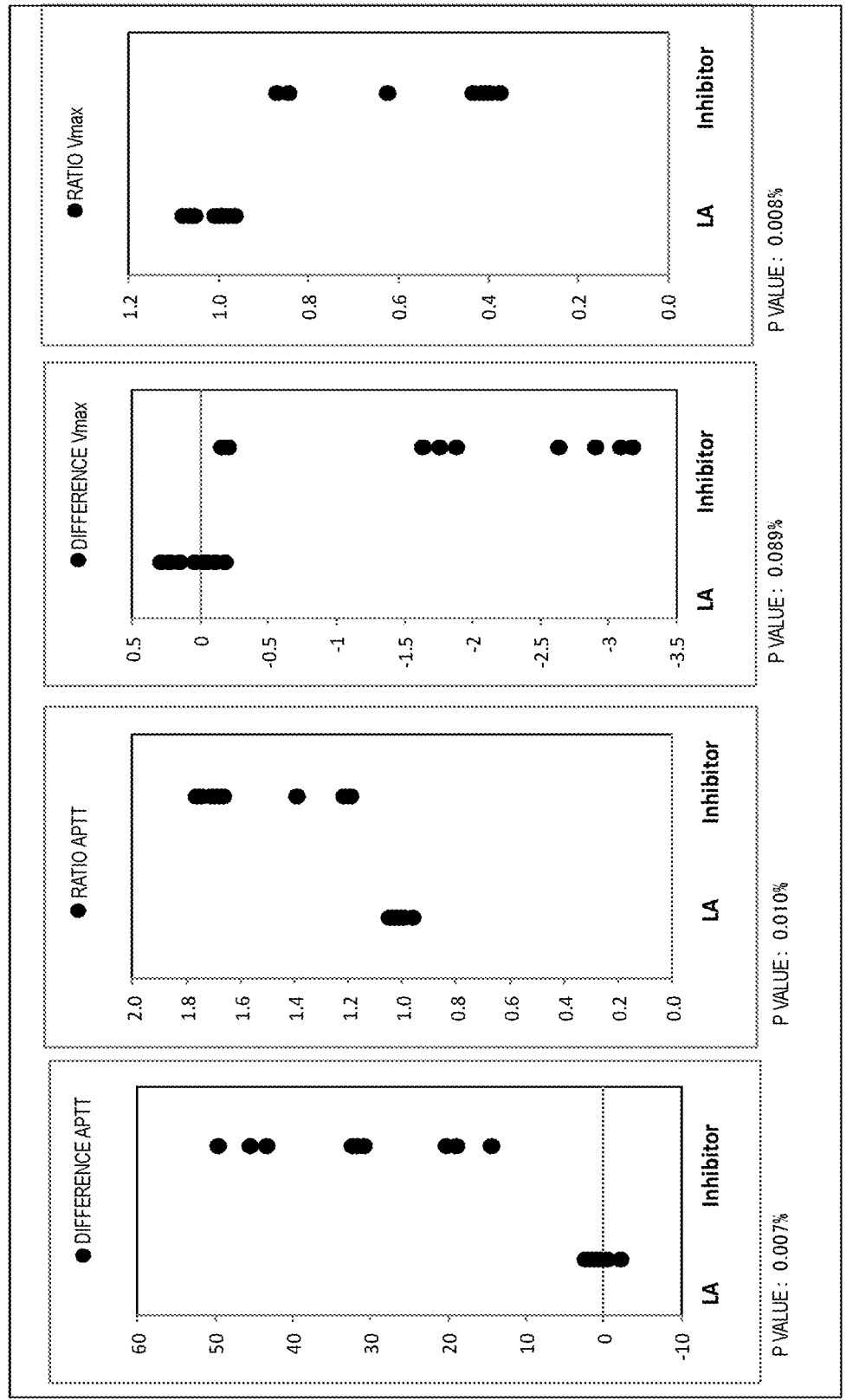

FIG. 63A is a diagram illustrating a difference (Pb−Pa) and a ratio (Pb/Pa) between an unheated plasma and a heated plasma for APTT time (T50) and Vmax of a mixed plasma. LA: Mixed plasma of LA-positive plasma and normal plasma, Inhibitor: Mixed plasma of factor VIII inhibitor-positive plasma and normal plasma.

Figure 63B:
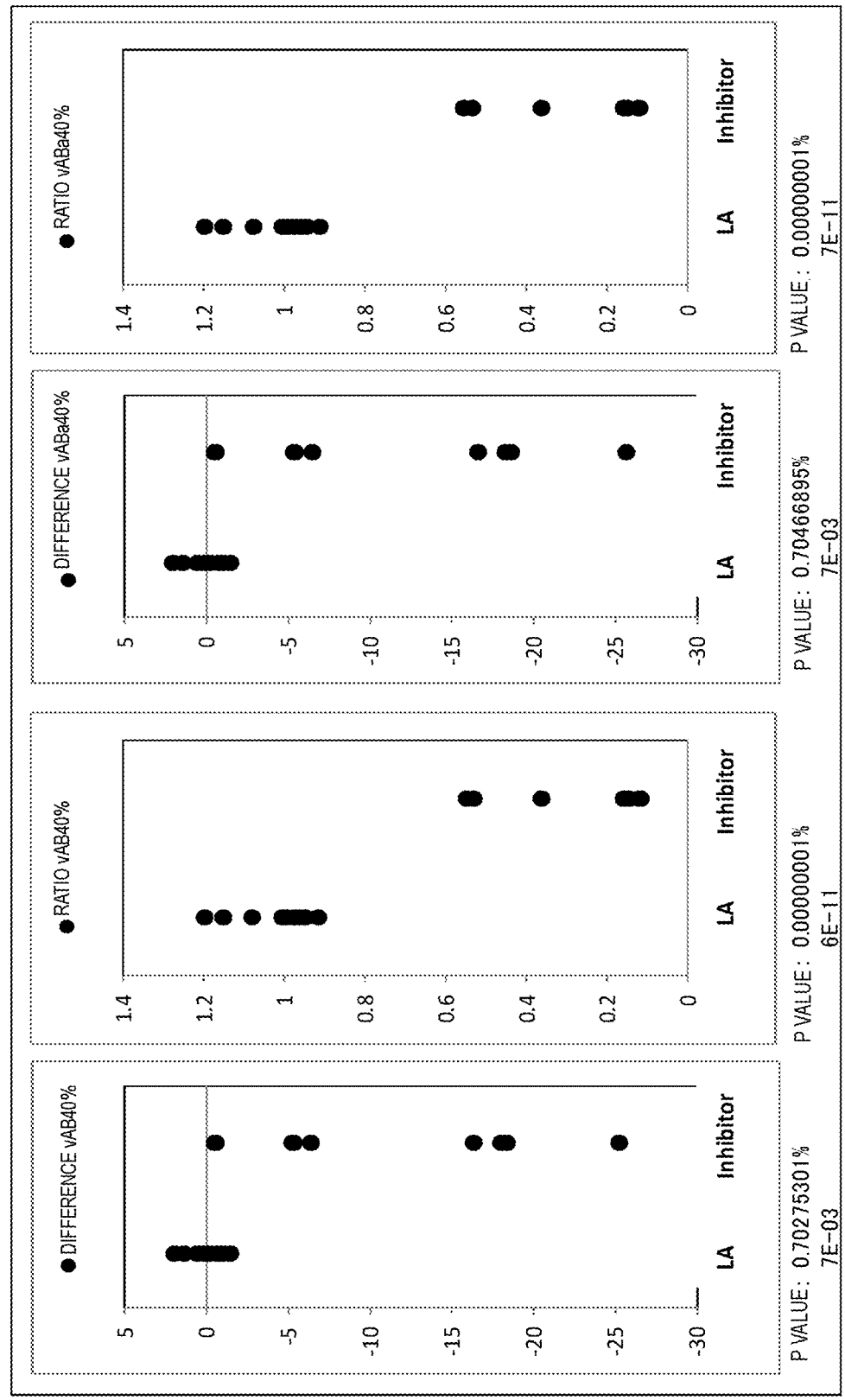

FIG. 63B is a diagram illustrating a difference (Pb−Pa) and a ratio (Pb/Pa) between an unheated plasma and a heated plasma for vAB40% and vABa40% of a mixed plasma (LA and Inhibitor).

Figure 63C:
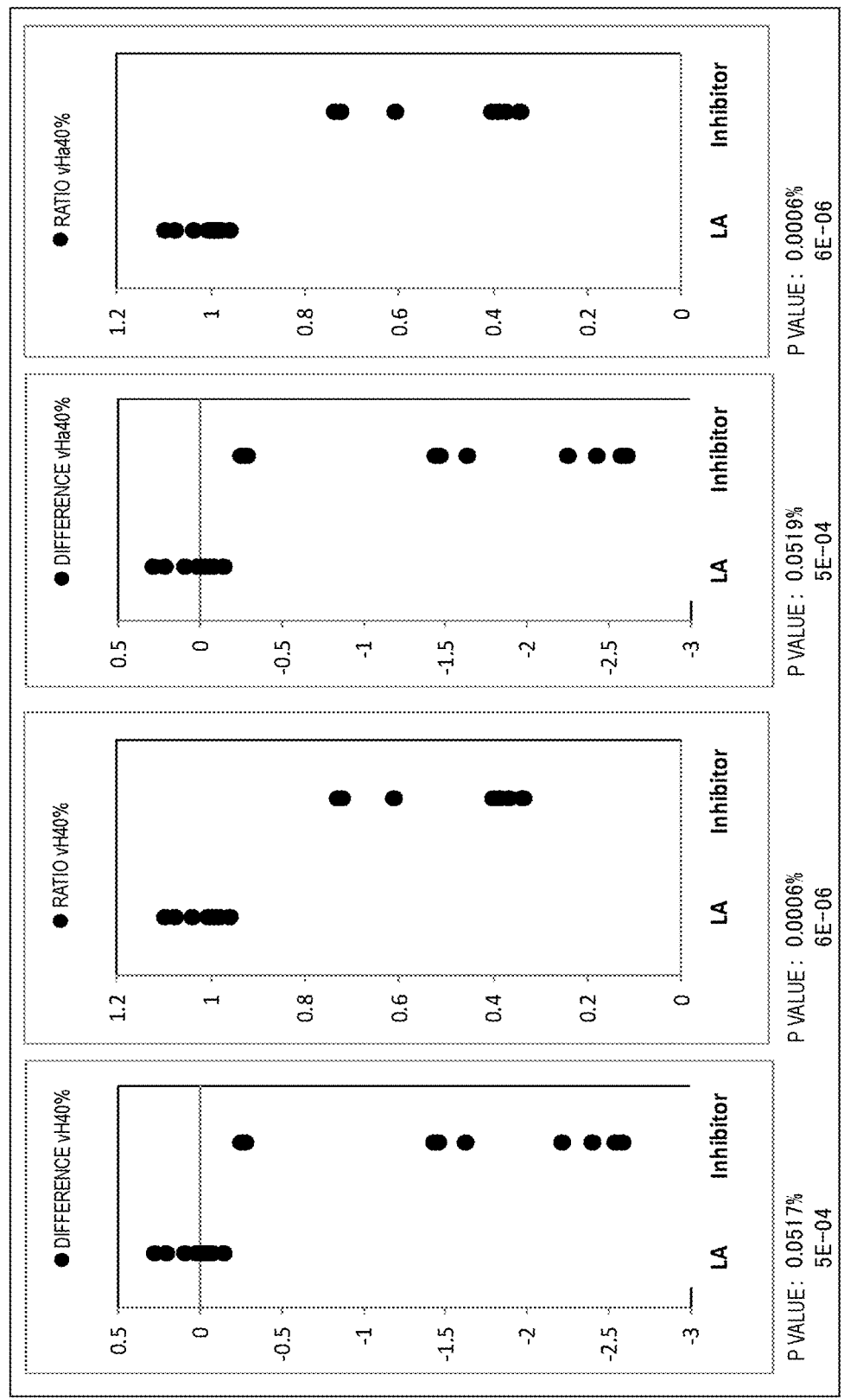

FIG. 63C is a diagram illustrating a difference (Pb−Pa) and a ratio (Pb/Pa) between an unheated plasma and a heated plasma for vH40% and vHa40% of a mixed plasma (LA and Inhibitor).

Figure 63D:
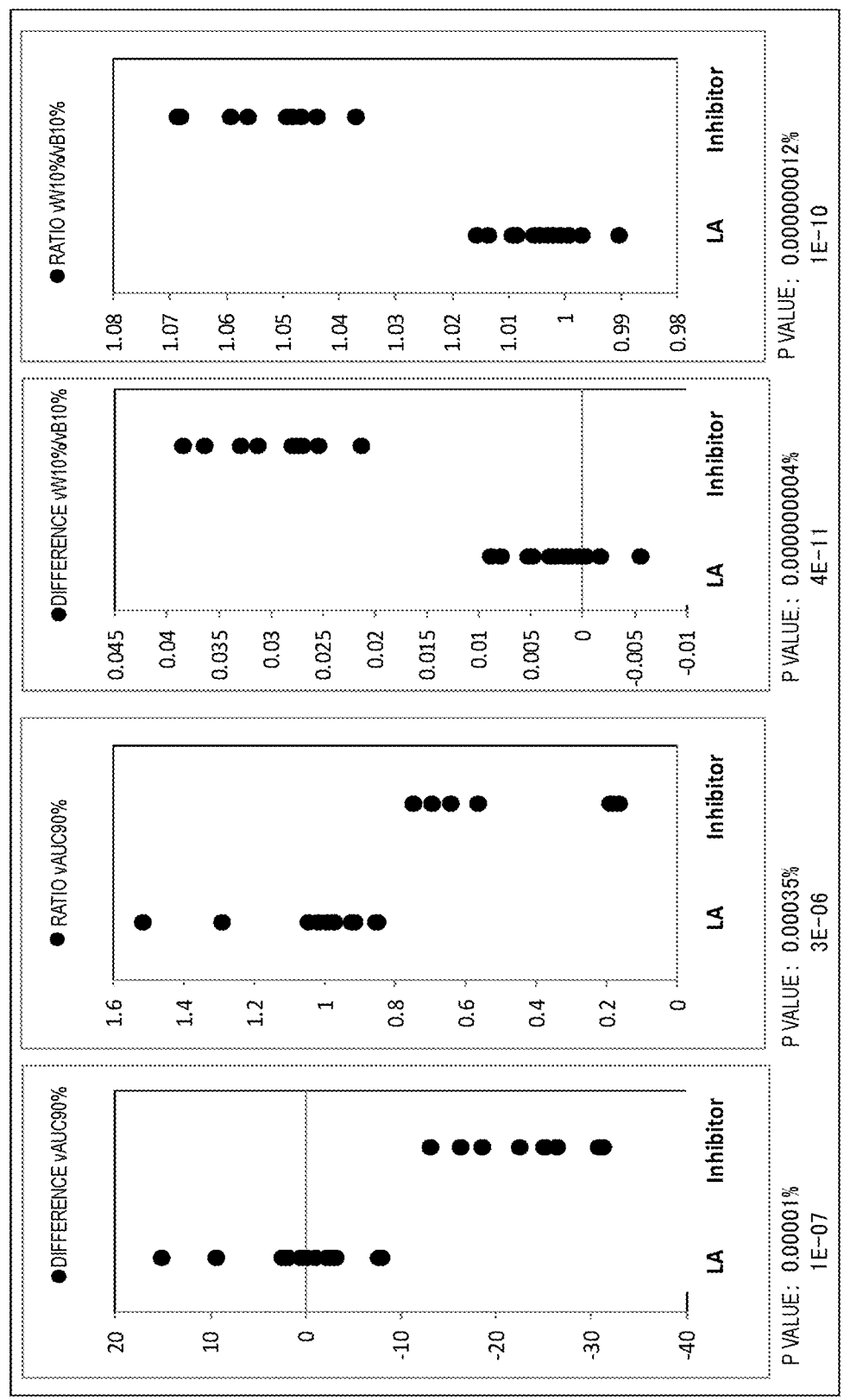

FIG. 63D is a diagram illustrating a difference (Pb−Pa) and a ratio (Pb/Pa) between an unheated plasma and a heated plasma for vAUC90% and vW10%/vB10% of a mixed plasma (LA and Inhibitor).

Figure 63E:
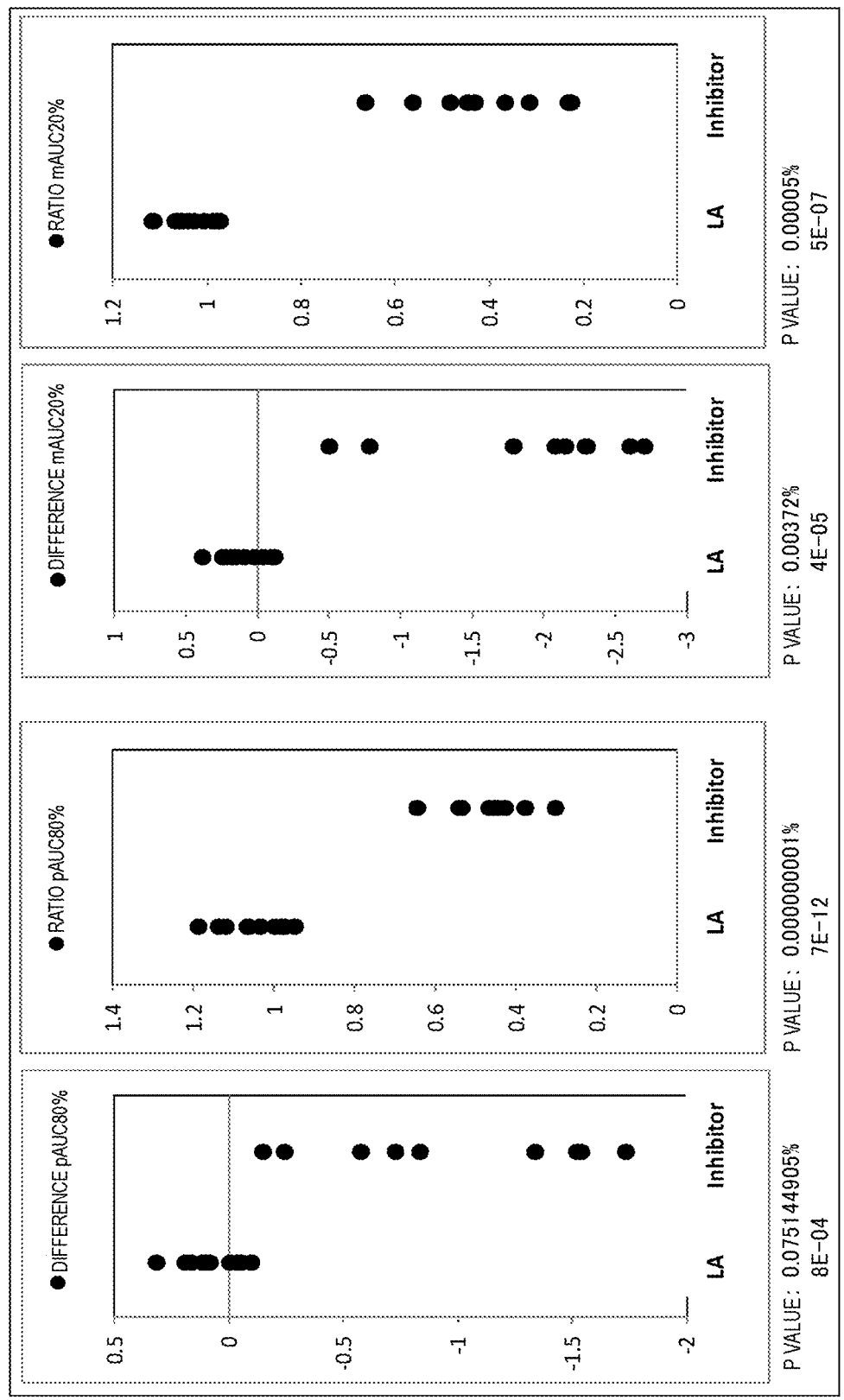

FIG. 63E is a diagram illustrating a difference (Pb−Pa) and a ratio (Pb/Pa) between an unheated plasma and a heated plasma for pAUC80% and mAUC20% of a mixed plasma (LA and Inhibitor).

DETAILED DESCRIPTION OF THE INVENTION

The present invention relates to a method for analyzing a coagulation characteristic of a blood sample to which waveform analysis is applied. In addition, the present invention relates to shortening test time of a blood coagulation test.

According to the present invention, excellent analysis of a coagulation characteristic of a blood sample can be implemented. According to the present invention, for example, a deficiency status of a coagulation factor in a patient specimen, the concentration of the coagulation factor, and effects of various coagulation factors can be estimated. In addition, according to the present invention, test time of a cross-mixing test can be shortened. For example, in identifying presence or absence of a coagulation factor inhibitor, heating time can be set to, for example, 10 minutes, which is shorter than two hours. Furthermore, in identifying presence or absence of a coagulation factor inhibitor, a quantitative determination can be made by determining a ratio or a difference between parameters.

An embodiment of the present invention will be described with reference to the drawings. The present embodiment relates to analyzing characteristics of a specimen related to blood coagulation. In particular, activated partial thromboplastin time (APTT) measurement used for an endogenous coagulation function test is performed, and the data obtained is analyzed. This can also be similarly applied to analysis of data obtained by measuring other test items using a coagulation reaction curve including prothrombin time (PT) used for an extrinsic coagulation function test.

1. Analysis Method 1.1. Outline of Analysis Method

Figure 1:
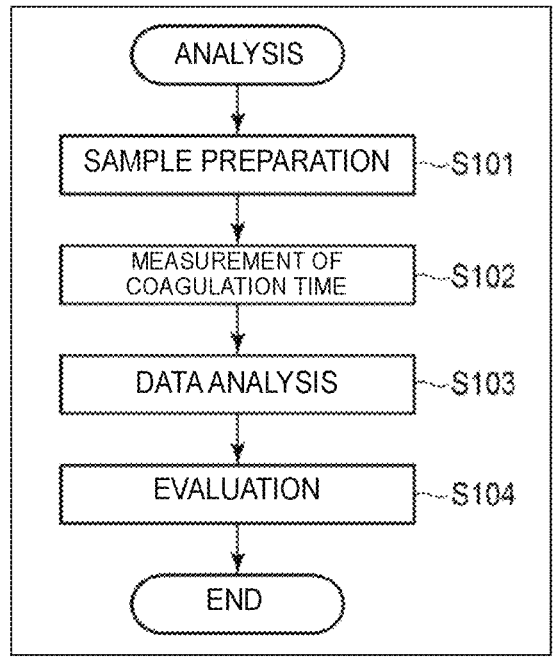
FIG. 1 is a flowchart illustrating an outline of an example of an analysis method related to blood coagulation according to an embodiment.

An outline of an analysis method according to the present embodiment will be described with reference to the flowchart illustrated in FIG. 1. First, for a specimen, a sample used for a test is prepared (step S101). Measurement of coagulation time is executed on the prepared sample (step S102). Examples of the measurement of coagulation time include measurement of APTT and PT. A predetermined analysis is performed on the data obtained by the measurement of coagulation time (step S103). Based on the analysis results, the specimen is evaluated for a blood coagulation function (step S104).

1.2. Sample Preparation and Measurement of Coagulation Time

The sample preparation performed in step S101 and the measurement of coagulation time performed in step S102 will be described. Here, as the measurement of coagulation time, measurement of APTT will be described as an example.

A specimen to be examined is, for example, a blood specimen derived from a subject who is required to be examined for abnormalities caused by a coagulation factor. More specifically, plasma of the subject is used as the blood specimen. A well-known anticoagulant commonly used in a coagulation test can be added to the blood specimen. For example, blood is collected using a blood collection tube containing sodium citrate, and plasma can be rapidly centrifuged.

A contact factor-based activator and a phospholipid are added to the test plasma. As the activator, for example, ellagic acid, celite, kaolin, silica, or a polyphenol compound can be used. As the phospholipid, animal-derived, plant-derived, and synthetic-derived phospholipids are used. Examples of the animal-derived phospholipid include those derived from rabbit brain, chicken, and pig. Examples of the plant-derived phospholipid include those derived from soybean. In addition, a buffer solution such as Tris-hydrochloric acid may be added appropriately.

In order to measure APTT, for example, a commercially available APTT measuring reagent or a reagent kit can be used. As an example, Coagpia APTT-N (manufactured by Sekisui Medical Co., Ltd.) is used.

A sample obtained by adding the activator and the phospholipid to the above-described test plasma is heated, and a contact factor in the plasma is activated. A temperature condition is, for example, 30° C. or higher and 40° C. or lower, and preferably 35° C. or higher and 39° C. or lower.

Thereafter, a calcium chloride solution (calcium ion) is added to the sample, and a coagulation reaction is started. A coagulation reaction of the mixed solution after addition of the calcium chloride solution can be measured. For the measurement, for example, an optical method for measuring the scattered light amount or transmittance (may be absorbance) of light or a mechanical method for measuring the viscosity of plasma can be used. Measurement time is, for example, about several tens of seconds to five minutes when the timing of adding a final reagent is used as a start time point. During this period, for example, the measurement is repeated periodically. For example, when an optical method is used, photometry may be performed at a cycle of 0.1 seconds. For example, the time point when the calcium chloride solution is added can be set as a reaction start time. Another timing may be defined as the reaction start time. A temperature condition during the measurement is, for example, 30° C. or higher and 40° C. or lower, and preferably 35° C. or higher and 39° C. or lower.

The above-described measurement may be performed using a device capable of automatically performing a series of measurements. Examples of such a device include a blood coagulation automatic analysis apparatus CP3000 (manufactured by Sekisui Medical Co., Ltd.). In addition, some operations may be performed by a manual method. For example, a sample may be prepared by a manual method and may be measured with an optical analysis apparatus. Various conditions can be appropriately set according to a mixing method and a measuring method.

1.3. Data Analysis 1.3.1. Outline of Data Analysis

Figure 2:
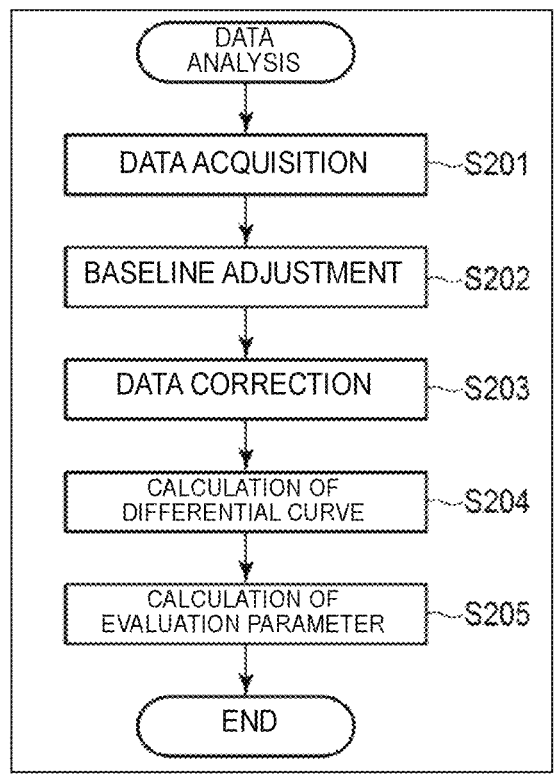
FIG. 2 is a flowchart illustrating an outline of an example of a data analysis method related to blood coagulation according to an embodiment.

The data analysis performed in step S103 will be described. FIG. 2 is a flowchart illustrating an outline of the data analysis.

In step S201, data to be analyzed is acquired. This data is obtained by blood coagulation measurement, and for example, reflects a coagulation reaction process obtained by the above-described measurement of APTT. For example, a calcium chloride solution is added to a sample obtained by adding an activator and a phospholipid to a test plasma, and data indicating a time change of the amount of scattered light thereafter is acquired. The data may be analyzed immediately after the measurement, or data measured in advance and stored may be analyzed later.

Figure 3:
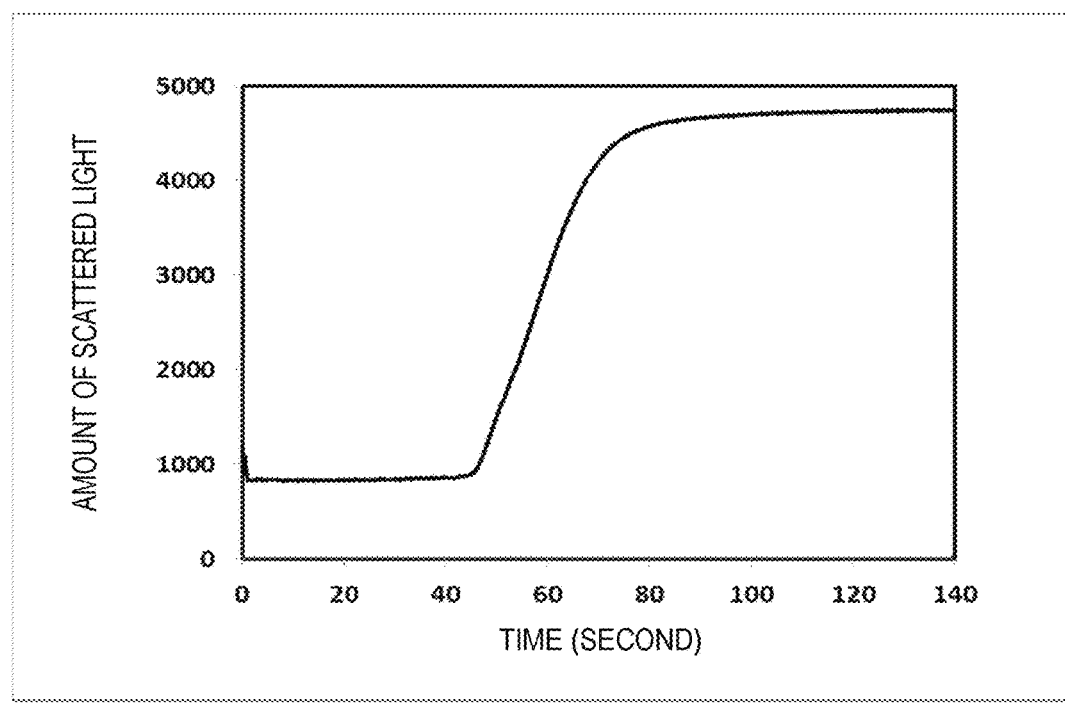
FIG. 3 is a diagram illustrating an example of a coagulation reaction curve.

FIG. 3 illustrates an example of the acquired data. In this drawing, the horizontal axis indicates elapsed time after the calcium chloride solution is added, and the vertical axis indicates the amount of scattered light. Since a coagulation reaction of the mixed solution progresses with an elapse of time, the amount of scattered light increases. In the present embodiment, the curve indicating a time change of the measured amount of light is referred to as a coagulation reaction curve.

The example illustrated in FIG. 3 is a measurement result of the amount of scattered light, and illustrates a sigmoid-shaped coagulation reaction curve. However, when the amount of transmitted light is measured, an inverse sigmoid-shaped coagulation reaction curve is obtained. In the following description, a case where the amount of scattered light is measured will be described as an example. However, a similar process can be performed also when the amount of transmitted light and absorbance are measured. Data indicating a coagulation reaction amount obtained by a method for obtaining a coagulation reaction curve by a change in the viscosity of the mixed solution and other methods may be analyzed.

Figure 4:
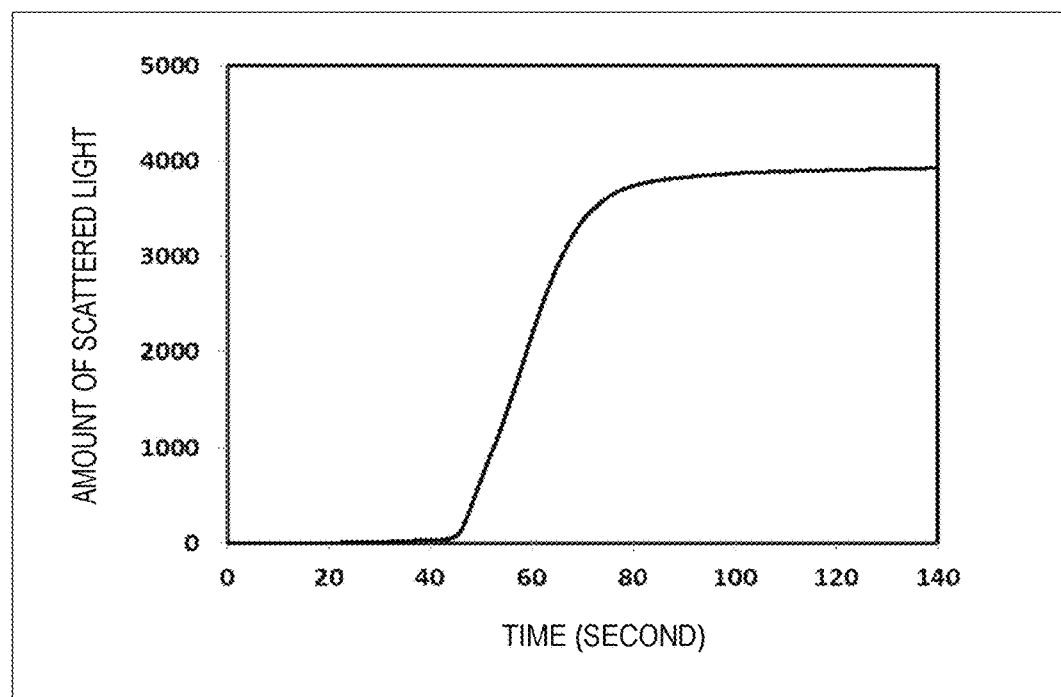
FIG. 4 is a diagram illustrating an example of a coagulation reaction curve after baseline adjustment.
Figure 5A:
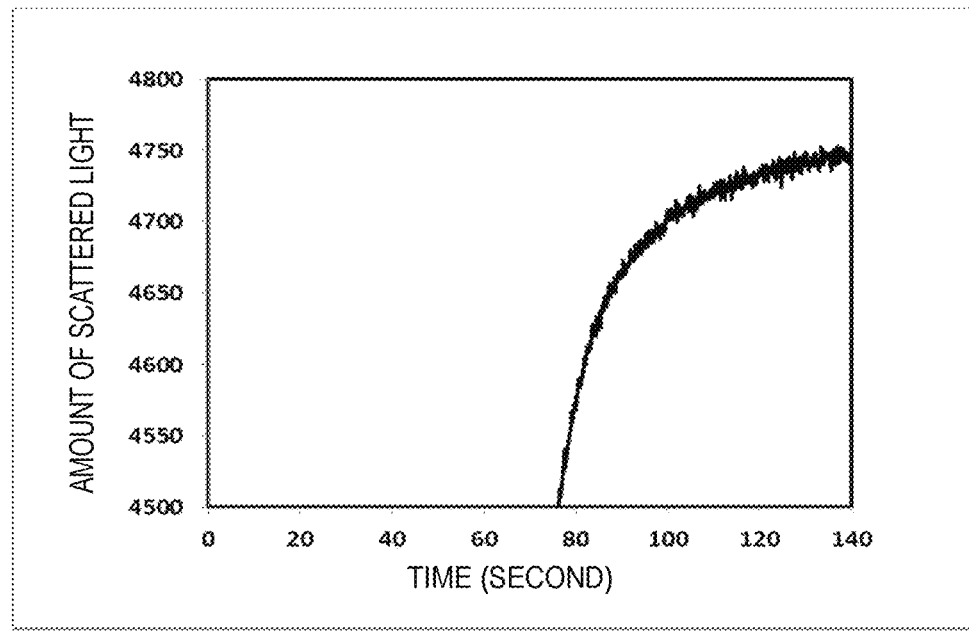
FIG. 5A is an enlarged diagram of a part of an example of a coagulation reaction curve.
Figure 5B:
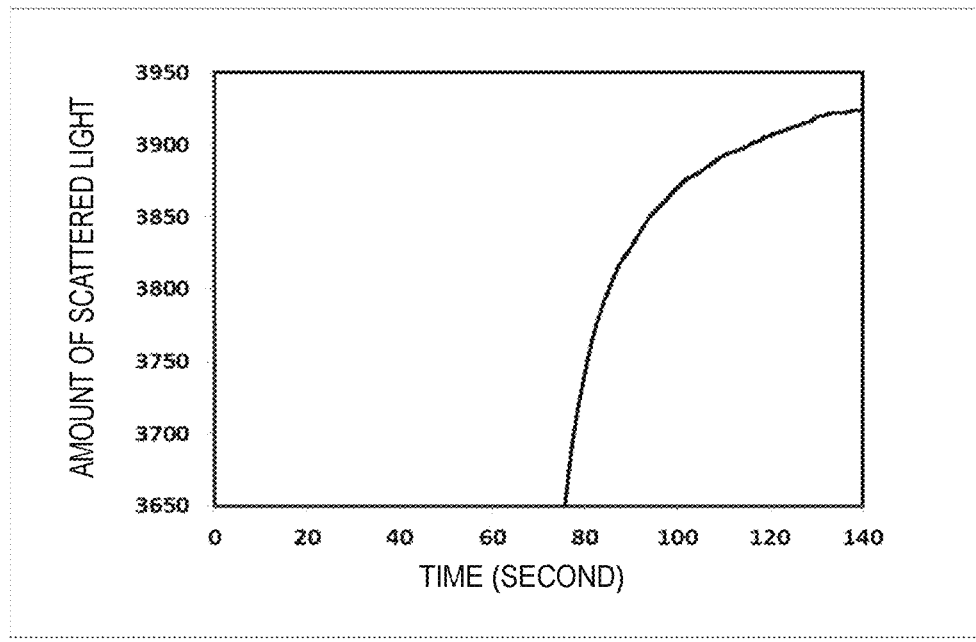
FIG. 5B is an enlarged diagram of a part of an example of a coagulation reaction curve after baseline adjustment.

In step S202, baseline adjustment is performed. Baseline adjustment includes a smoothing process and zero point adjustment. FIG. 4 illustrates an example of data after baseline adjustment is performed on the data illustrated in FIG. 3. FIG. 5A illustrates an enlarged diagram of the data before baseline adjustment illustrated in FIG. 3. FIG. 5B illustrates an enlarged diagram of the data after baseline adjustment illustrated in FIG. 4. As can be seen by comparing FIG. 5A with FIG. 5B, in the baseline adjustment, a smoothing process including noise removal is performed. For the smoothing process, any of various known methods related to noise removal can be used. As illustrated in FIG. 3, the amount of scattered light at a measurement start time point is more than 0. This is because the mixed solution containing the test plasma originally scatters light. In the baseline adjustment, the amount of scattered light at the measurement start time point is adjusted to 0 as illustrated in FIG. 4.

Figure 6:
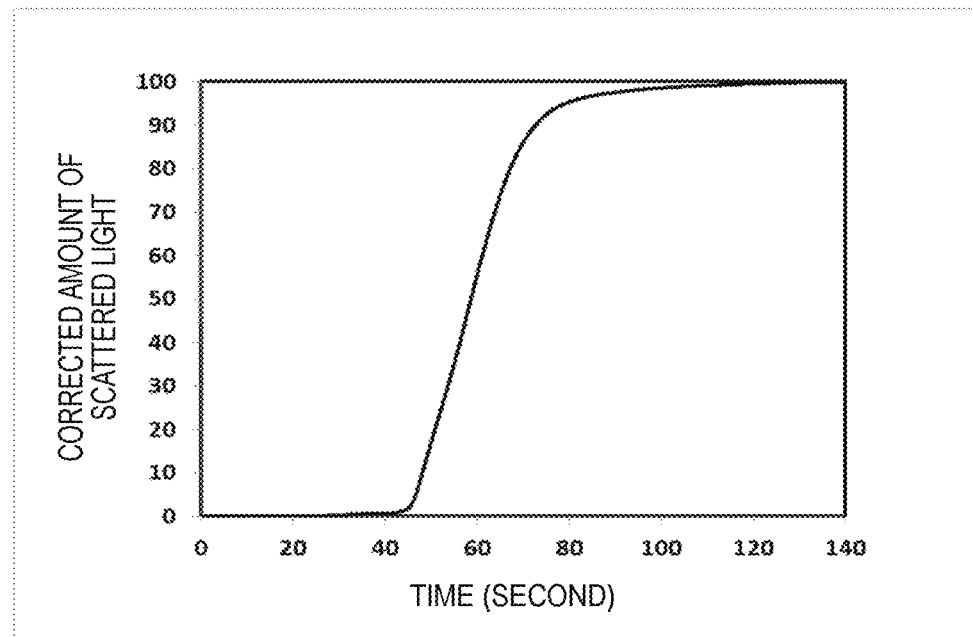
FIG. 6 is a diagram illustrating an example of a corrected coagulation reaction curve.

In step S203, a correction process is performed on the data after the baseline adjustment. In the present embodiment, correction is performed such that a maximum value of the coagulation reaction curve after the baseline adjustment is 100. FIG. 6 illustrates a result of performing a correction process on the data illustrated in FIG. 4.

Specifically, the following process is performed in the correction process. The coagulation reaction curve after the baseline adjustment is referred to as $D(t)$. A maximum value of $D(t)$ is referred to as $Dmax$, and a minimum value of $D(t)$ is referred to as $Dmin$. A change width of $D(t)$, that is, $Dmax-Dmin$ is referred to as $Drange$. When a corrected value is referred to as $P(t)$, $P(t)$ is expressed by the following formula (1).

$$P(t)=[D(t)-Dmin)/Drange]\times 100 \quad (1)$$

A coagulation reaction curve obtained from the corrected data is referred to as a corrected coagulation reaction curve. A purpose of this correction process is as follows. The height of the coagulation reaction curve after the baseline adjustment depends on the fibrinogen concentration of a specimen. The fibrinogen concentration varies from person to person and can vary from specimen to specimen. With this correction, it is possible to determine, for example, a coagulation waveform parameter that does not depend on the fibrinogen concentration. That is, this correction makes it possible to quantitatively compare a difference in the shape of the coagulation reaction curve after the baseline adjustment between specimens. Note that here, correction is performed such that a corrected value is from 0 to 100. However, the corrected value may be another value. This correction process does not necessarily have to be performed.

Figure 7:
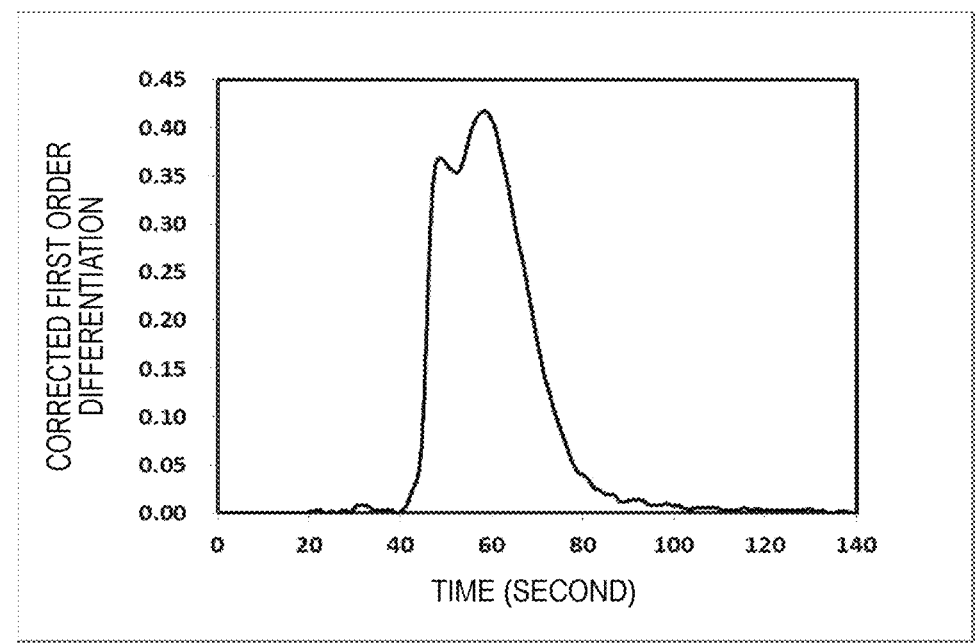
FIG. 7 is a diagram illustrating an example of a corrected first order curve.

In step S204, a differential curve obtained by differentiating the coagulation reaction curve is calculated. FIG. 7 illustrates a first order differential curve obtained by performing a process corresponding to first order differentiation on the corrected coagulation reaction curve illustrated in FIG. 6. A method for calculating the first order differential curve will be described in detail later. The first order differentiation (corrected first order differentiation) for the corrected coagulation reaction curve is a change width per time when a total reaction change width is 100, and therefore can be said to be a coagulation reaction progress rate (coagulation progress rate). Integration of the coagulation progress rate over the entire area gives 100. Meanwhile, the first order differentiation for the uncorrected coagulation reaction curve indicates a value of a measured reaction change width per time, and indicates a coagulation rate.

Figure 8:
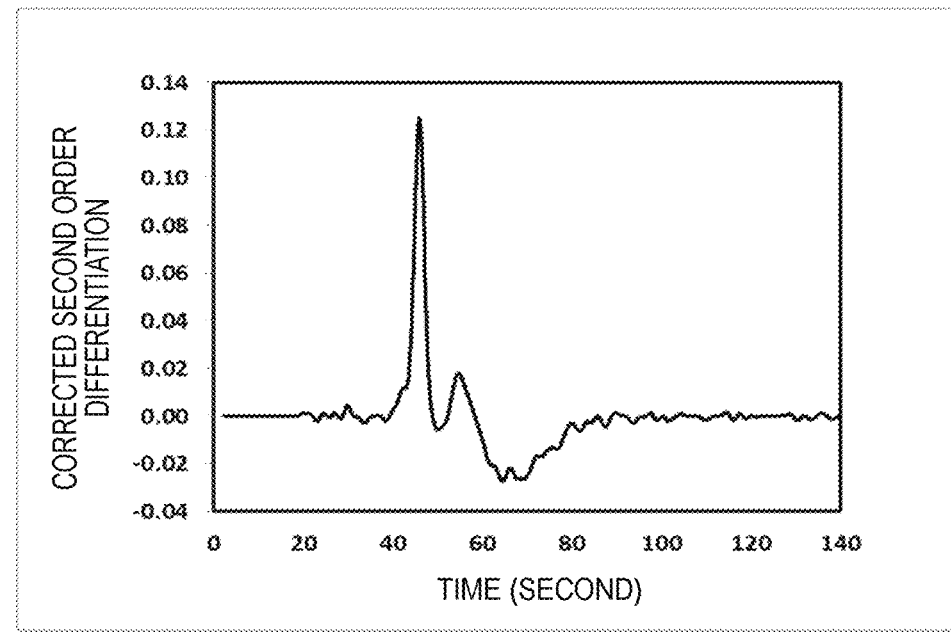
FIG. 8 is a diagram illustrating an example of a corrected second order curve.

The first order differential curve of the corrected coagulation reaction curve illustrated in FIG. 7 may be further differentiated to acquire a second order differential curve as illustrated in FIG. 8. The first order differential curve of the uncorrected coagulation reaction curve may be further differentiated to acquire a second order differential curve indicating a coagulation acceleration.

Note that here, the corrected coagulation reaction curve and the uncorrected coagulation reaction curve are also referred to as a corrected 0th order curve and an uncorrected 0th order curve, respectively, and these are also collectively referred to as "0th order curve". Here, the first order differential curves of the corrected 0th order curve and the uncorrected 0th order curve are also referred to as a corrected first order curve and an uncorrected first order curve, respectively, and these are also collectively referred to as "first order curve". Here, the second order differential curves of the corrected 0th order curve and the uncorrected 0th order curve, or the first order differential curves of the corrected first order curve and the uncorrected first order curve are also referred to as a corrected second order curve and an uncorrected second order curve, respectively, and these are also collectively referred to as "second order curve".

Here, the coagulation progress rate, the coagulation rate, and other values indicating progress of coagulation are collectively referred to as a first order differential value. Matters described by exemplifying the coagulation progress rate or the coagulation rate can be similarly applied to the first order differential value in general. Here, the coagulation acceleration and other values indicating a change ratio of the first order differential value are collectively referred to as a second order differential value.

In step S205, various evaluation parameters are calculated. The evaluation parameters indicate a blood coagulation characteristic of a specimen. The evaluation parameters will be described in detail later.

1.3.2. Calculation of Differential Curve

An example of calculating a differential curve of a coagulation reaction curve (0th order curve) performed in step S204 will be described. As a differential process for obtaining a first order curve $B(n)$ from a coagulation reaction curve $A(n)$, a difference method using the following formula (2) can be used.

$$B(n)=A(n)-A(n-1) \quad (2)$$

However, a coagulation reaction curve of an abnormal coagulation specimen in which coagulation time is significantly delayed has a gentler slope at the time of increase than that of a normal specimen, and the coagulation reaction curve at a reaction end stage also has a gentle plateau shape. In such a case, since a difference between $A(n)$ and $A(n-1)$ is small, a value of $B(n)$ is small even around a maximum value of the first order curve. In such a state, an S/N ratio deteriorates and is easily affected by noise in numerical calculation, and information caused by a coagulation reaction is easily buried in noise.

Depending on the amount of change and the timing of measurement, a calculation result of first order differentiation using the above formula (2) can be a discrete value. For example, for a blood coagulation reaction curve obtained by photometry performed every 0.1 seconds, it is considered to determine a first order differential value for the nth value as a difference between the nth value and the n−1th value. When the height of the coagulation reaction curve is low, the obtained first order differential curve may have discrete values. For example, when a fibrinogen concentration is low, the height of the coagulation reaction curve is low. In blood analysis as in the present embodiment, such a phenomenon can occur frequently. As one solution, it is conceivable to shorten a measurement time interval to increase measurement sensitivity. However, shortening the measurement time interval may be unpreferable because it increases cost of a device.

Therefore, the first order curve may be obtained as follows. An average slope value is determined for each measurement point N on an uncorrected coagulation reaction curve or a corrected coagulation reaction curve. Measurement data within a certain period of time can be used to calculate the average slope value. That is, a constant number of pieces of measurement data before and after each measurement point N, for example, 2K+1 pieces of measurement data from N−K to N+K can be used. For example, measurement data at five points of N−2, N−1, N, N+1, and N+2 can be used. The average slope value means a slope value when these plurality of measurement points are linearly approximated. A well-known method such as a least squares method can be used for the linear approximation calculation method. The average slope value of these pieces of measurement data can be regarded as a first order differential value at a measurement point N.

An example of the linear approximation calculation method is described below. x represents photometric time and y represents the height of a coagulation reaction curve. For example, when a measurement point is (xi, yi), in which i=N−K, . . . , N+K), partial differentiation of the following formula (3) is considered.

[Numerical Formula 5]

$$L = \Sigma(y_i - ax_i - b)^2 \quad (3)$$

An intra-section average slope a is represented by the following formula (4).

[Numerical Formula 6]

$$a = \frac{(2K+1)\sum_{i=N-K}^{N+K} x_i y_i - \sum_{i=N-K}^{N+K} x_i \sum_{i=N-K}^{N+K} y_i}{(2K+1)\sum_{i=N-K}^{N+K} x_i^2 - \left(\sum_{i=N-K}^{N+K} x_i\right)^2} \quad (4)$$

By substituting data related to each time point N into the above formula (4), the intra-section average slope a can be calculated.

By using a series of intra-section average slopes a obtained from the coagulation reaction curve as a first order curve, more detailed information can be obtained than in a case of using the first order curve calculated using the above formula (2). The same applies when a second order curve is determined from a first order curve.

1.3.3. Evaluation Parameter

In the present embodiment, various evaluation parameters are calculated based on the above 0th order curve, first order curve, and second order curve. These parameters will be described.

1.3.3.1. Coagulation Time

Figure 9:
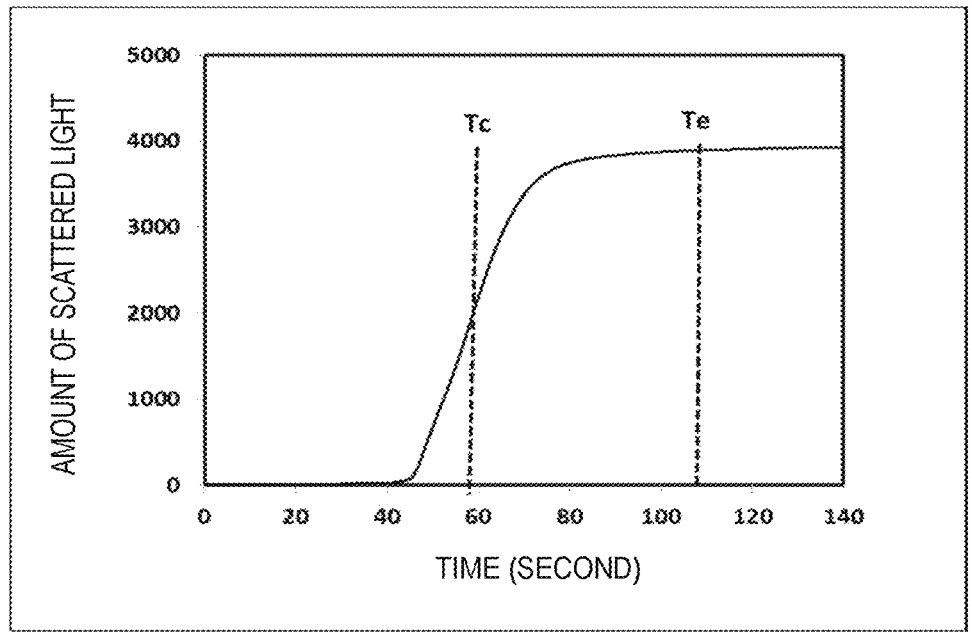
FIG. 9 is a diagram for explaining coagulation time, and is a diagram illustrating an example of a coagulation reaction curve after baseline adjustment.

Coagulation time, which is one of the evaluation parameters in the present embodiment, will be described with reference to the coagulation reaction curve after baseline adjustment illustrated in FIG. 9. A time point at which the amount of change in the amount of scattered light on the coagulation reaction curve after baseline adjustment satisfies a predetermined condition is defined as a coagulation end determination point Te. For example, a time point when the amount of change in the amount of scattered light per unit time reaches a value equal to or less than a predetermined value is defined as the coagulation end determination point Te. When the amount of scattered light at the coagulation end determination point Te is 100%, reaction elapsed time corresponding to the amount of scattered light of c % is defined as coagulation time Tc. For example, reaction elapsed time corresponding to the amount of scattered light of 50% is defined as coagulation time T50. By defining coagulation time Tc in this way, when coagulation end determination point Te (=T100) in which the coagulation reaction curve after baseline adjustment satisfies a predetermined condition is detected during measurement of APTT, coagulation time Tc can be immediately determined. Note that the method for determining coagulation time Tc is not limited to this method. The coagulation time may be defined by another method. For example, time at which the coagulation rate is a maximum value may be defined as the coagulation time, or reaction elapsed time T50 at which the corrected amount of scattered light is 50% as illustrated in FIG. 6 may be defined as coagulation time Tc.

1.3.3.2. Calculation Target Area Value

Figure 10A:
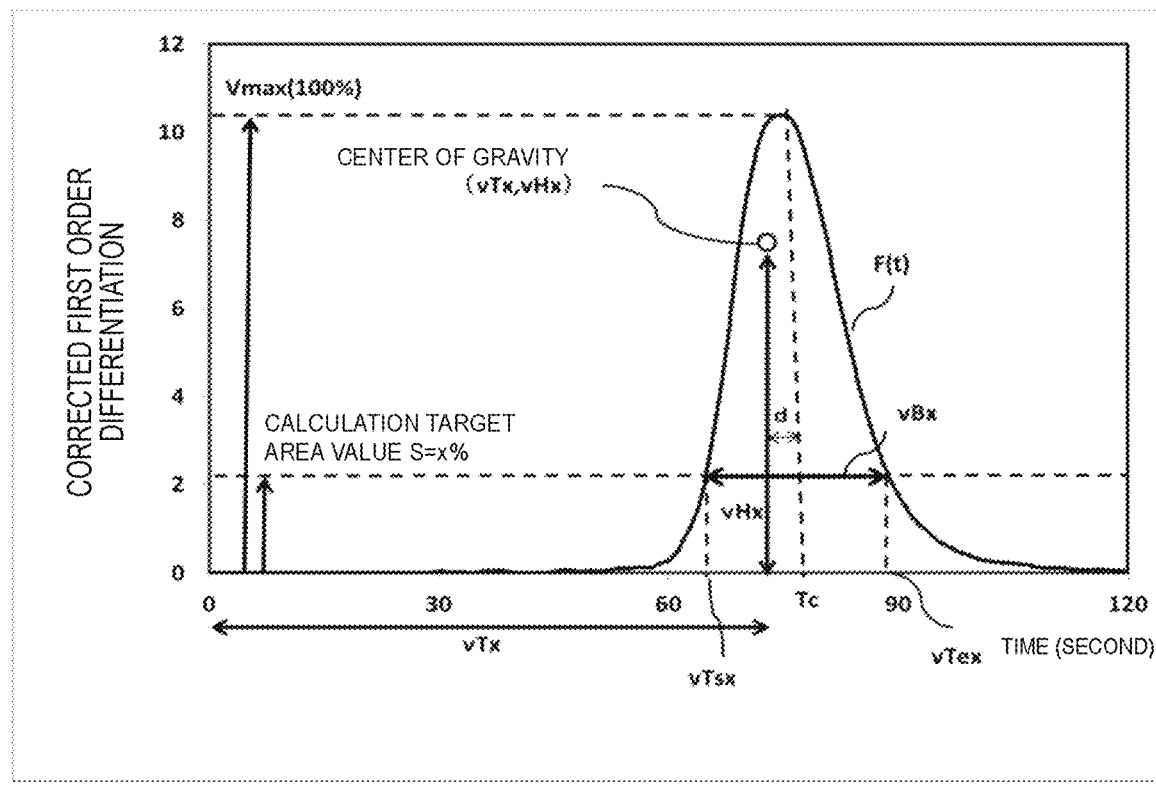
FIG. 10A is a diagram for explaining an evaluation parameter, and is a diagram illustrating an example of a coagulation rate curve.

A calculation target area value will be described with reference to FIG. 10A. FIG. 10A illustrates an example of a corrected first order curve. Maximum value Vmax of corrected first order differentiation (coagulation progress rate) can also be an evaluation parameter. Here, the corrected first order curve is exemplified. However, the same applies to an uncorrected first order curve. A maximum coagulation rate can also be an evaluation parameter.

In the present embodiment, when maximum value Vmax of the first order differential value is set to 100% and data whose first order differential value is S % or more is to be analyzed later, the value of S is referred to as calculation target area value S (%). Calculation target area value S can be set in order to limit a peak range reflecting characteristics of a peak shape of the first order curve. In order to limit the peak shape relatively widely, calculation target area value S can be set to 5% to 20%. When calculation target area value S is increased, an influence of the shape of an upper part of the peak is reflected in an analysis result relatively largely. In order to analyze the shape of an upper part of the peak, calculation target area value S can be set to 20% to 95%. Calculation target area value S can be similarly applied to a coagulation rate curve. Calculation target area value S can also be applied to a second order curve. As illustrated in FIG. 8, the second order curve has peaks in both positive and negative directions. Calculation target area value S can be set for each of the positive peak and the negative peak of the second order curve.

1.3.3.3. Center-of-Gravity Point

A center-of-gravity point on the first order curve will be described with reference to FIG. 10A. In FIG. 10A, a corrected first order curve is indicated by F(t). At this time, for F(t), a position corresponding to "weighted average value" using values for which calculation target area value S is equal to or more than x % as data to be calculated is defined as a center-of-gravity point (vTx, vHx).

In the first order curve, time indicating the center-of-gravity point is defined as center-of-gravity time VT. That is, center-of-gravity time vT of the first order curve is time from reaction start time to the center-of-gravity point, and is the x coordinate of the center-of-gravity point in the graph as illustrated in FIG. 10A. In the first order curve, a first order differential value indicating the center-of-gravity point is defined as center-of-gravity height vH. That is, center-of-gravity height vH of the first order curve is the y coordinate of the center-of-gravity point in the graph as illustrated in FIG. 10A.

More specifically, center-of-gravity time vT and center-of-gravity height vH are determined as follows. A maximum value of $V=F(t)$ is represented by Vmax. A data group of time t satisfying $F(t) \geq Vmax \times S \times 0.01$ is represented by $t[t1, \ldots t2]$ using calculation target area value S (%). That is, as illustrated in FIG. 10A, when $t1 < t2$, $F(t1) = Vmax \times S \times 0.01$, and $F(t2) = Vmax \times S \times 0.01$ are satisfied, a data group from time t1 to time t2 is represented by $t[t1, \ldots t2]$. At this time, integrated value M is represented by the following formula (5).

[Numerical Formula 7]

$$M = \sum_{i=t1}^{t2}(i \times F(i)) \quad (5)$$

At this time, center-of-gravity time vT and center-of-gravity height vH are calculated by the following formulas (6) and (7), respectively.

[Numerical Formula 8]

$$vT = \frac{M}{\sum_{i=t1}^{t2} F(i)} \quad (6)$$

$$vH = \frac{M}{\sum_{i=t1}^{t2} i} \quad (7)$$

In the above description, the case of the corrected first order curve has been described with reference to FIG. 10A. However, in a case of an uncorrected first order curve, the center-of-gravity point, center-of-gravity time VT, and center-of-gravity height vH can be similarly defined. That is, the center-of-gravity point, center-of-gravity time VT, and center-of-gravity height vH can be defined for a first order differential value including a coagulation rate and corrected first order differentiation. Center-of-gravity time vT and center-of-gravity height vH described above can be evaluation parameters. Note that t1 and t2 (t1<t2) satisfying the above $F(t1) = Vmax \times S \times 0.01$ and $F(t2) = Vmax \times S \times 0.01$ can also be evaluation parameters, and hereinafter, t1 and t2 related to the first order curve may be referred to as area start time vTs and area end time vTe (vTs<vTe), respectively (FIG. 10A).

Figure 11:
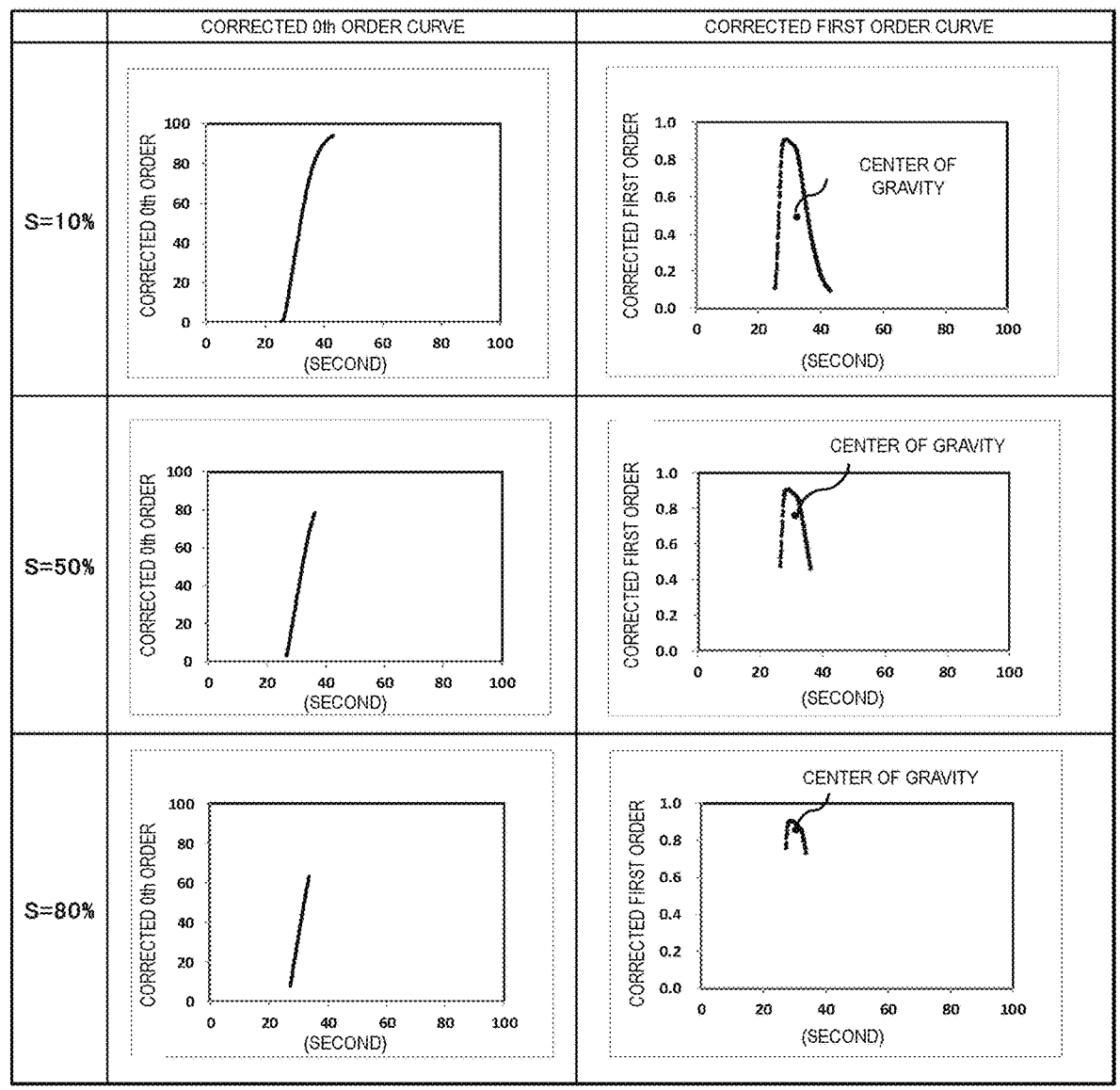
FIG. 11 is a diagram for explaining a calculation target area value, ranges of a corrected 0th order curve and a corrected first order curve to be analyzed, and a center-of-gravity point.

FIG. 11 illustrates, for a certain piece of data, a relationship among calculation target area value S, ranges of a corrected 0th order curve and a corrected first order curve to be analyzed at this time, and a center-of-gravity point obtained. In FIG. 11, the upper, middle, and lower rows illustrate the cases where calculation target area values S are 10%, 50%, and 80%, respectively. The left column illustrates a corrected 0th order curve, and the right column illustrates a corrected first order curve and a center-of-gravity point. The position of the center-of-gravity point changes as calculation target area value S changes as illustrated in FIG. 11.

Similarly, for a second order curve, a center-of-gravity point, a center-of-gravity time, and a center-of-gravity height can be defined. The second order curve has peaks in both positive and negative directions of a second order differential value as illustrated in FIG. 8. Therefore, a center-of-gravity point of the second order curve can be calculated for both the positive and negative peaks. For example, for the positive peak, when a maximum value of second order curve $A=F'(t)$ is Amax and a calculation target area value is S (%), time $t[t1, \ldots, t2]$ (t1<t2) satisfying $F'(t) \geq Amax \times S \times 0.01$ is determined, and center-of-gravity time pT and center-of-gravity height pH of the positive peak are calculated according to the above formulas (5) to (7). For the negative peak, when a minimum value of a second order curve $A=F'(t)$ is Amin and a calculation target area value is S (%), time $t[t1, \ldots, t2]$ (t1<t2) satisfying $F'(t) \leq Amin \times S \times 0.01$ is determined, and center-of-gravity time mT and center-of-gravity height mH of the negative peak are calculated according to the above formulas (5) to (7). The position of the center-of-gravity point changes as calculation target area value S changes.

1.3.3.4. Peak Width, Average Point, Flattening Ratio, and Time Ratio

Out of a period from a minimum reaction time at which a first order differential value is equal to or more than calculation target area value S in an area where reaction time is shorter than center-of-gravity time vT to a maximum reaction time at which the first order differential value is equal to or more than calculation target area value S in an area where reaction time is longer than center-of-gravity time vT, a time length satisfying $F(t) \geq S$ (value obtained by subtracting 1 from the number of data points satisfying $F(t) \geq S$ and multiplying the obtained value by a photometric time interval) is defined as peak width vB of a first order curve. In the example illustrated in FIG. 10A, peak width vB is from time vTs to time vTe. Similarly, out of a period from pTs to pTe in which pTs and pTe represent a minimum reaction time and a maximum reaction time at which a second order differential value in a positive peak of a second order curve is equal to or more than calculation target area value S, respectively, a time length satisfying $F'(t) \geq S$ (value obtained by subtracting 1 from the number of data points satisfying $F'(t) \geq S$ and multiplying the obtained value by a photometric time interval) is defined as peak width pB of the positive peak of the second order curve. Similarly, out of a period from mTs to mTe in which mTs and mTe represent a minimum reaction time and a maximum reaction time at which a second order differential value in a negative peak of a second order curve is equal to or less than calculation target area value S, respectively, a time length satisfying $F'(t) \leq S$ (value obtained by subtracting 1 from the number of data points satisfying $F'(t) \leq S$ and multiplying the obtained value by a photometric time interval) is defined as peak width mB of the negative peak of the second order curve.

Figure 10B:
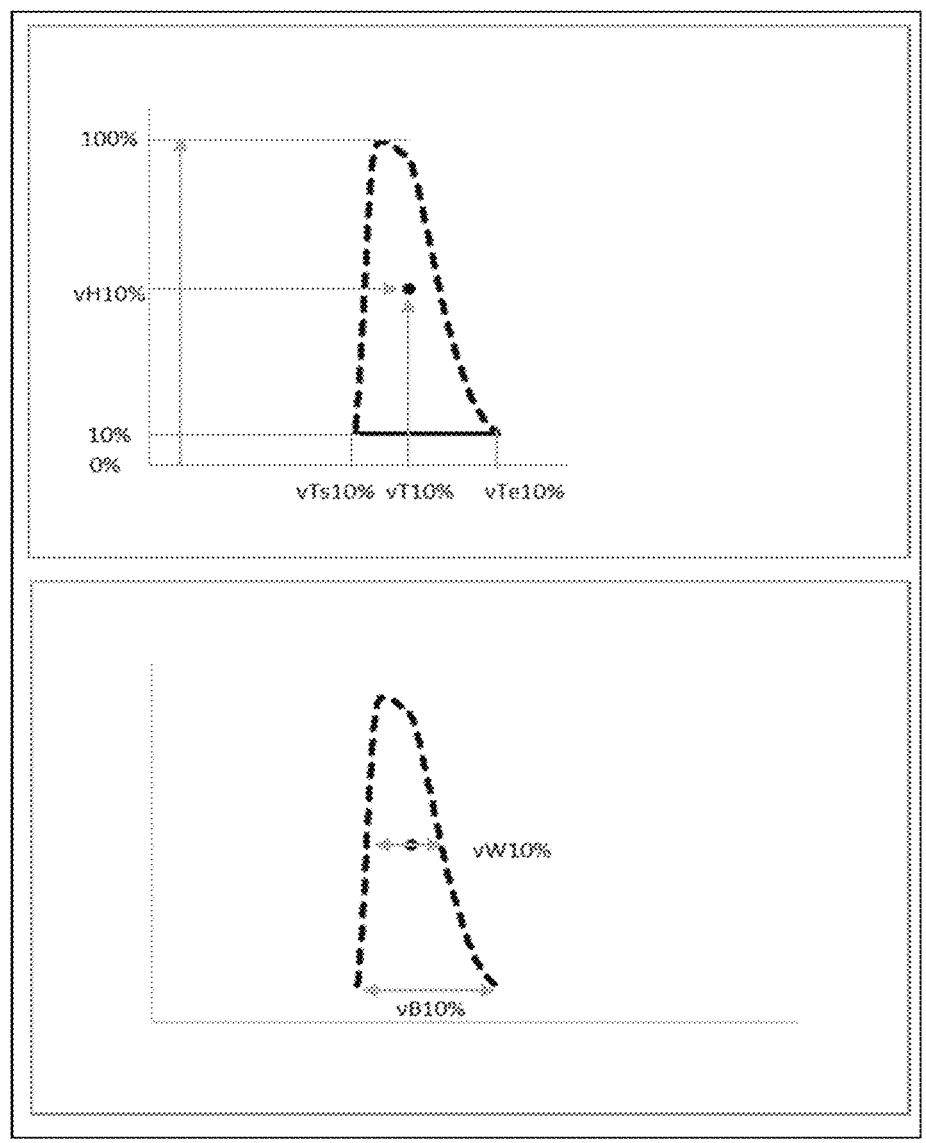
FIG. 10B is a conceptual diagram illustrating a center-of-gravity point, vTs, vTe, vB, and vW. The dotted line indicates a 10% calculation target area of a first order curve.
Figure 10C:
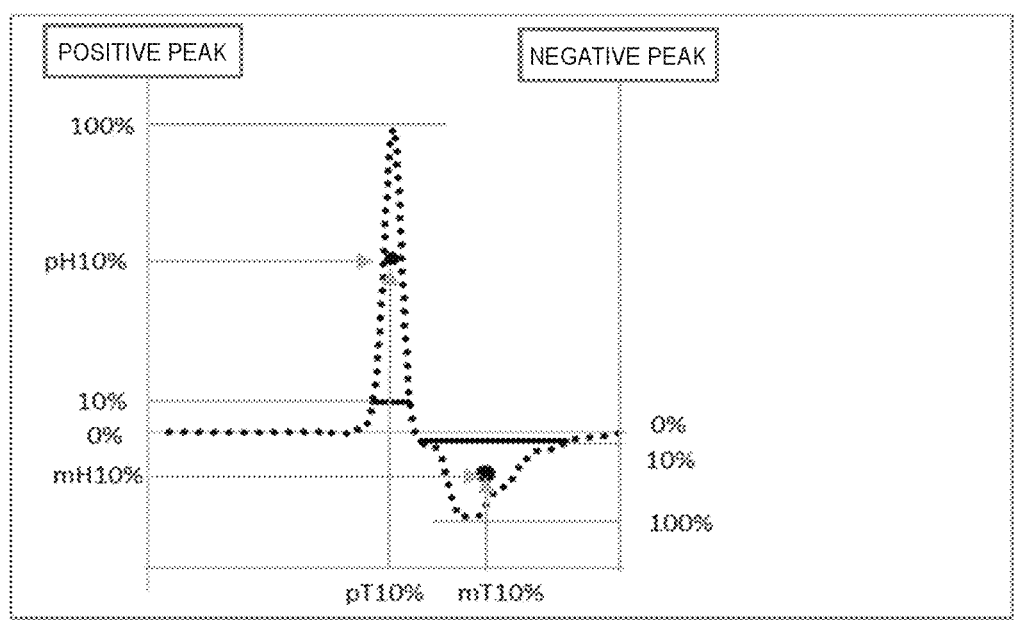
FIG. 10C is a diagram illustrating a center-of-gravity point of a second order curve.

Examples of the parameters used in the present invention further include center-of-gravity peak width vW. As illustrated in FIG. 10B, vW is a peak width satisfying first order curve $F(t) \geq vH$ (a time length satisfying F(t) vH during a period from a minimum time to a maximum time satisfying $F(t) \geq vH$). Examples of the parameters used in the present invention further include vTr. vTr is a width from vTs to vTe. FIG. 10B illustrates a calculation target area (dotted line) of a first order curve when calculation target area value S is 10%. A center-of-gravity point (vT, vH) (black circle), vTs, and vTe are illustrated in the upper drawing of FIG. 10B, and vB and vW are illustrated in the lower drawing of FIG. 10B. Similarly, for the positive peak of the second order curve, a peak width satisfying F'(t)≥pH is defined as center-of-gravity peak width pW. For the negative peak of the second order curve, a width of a coagulation reaction time satisfying F'(t)≤mH is defined as center-of-gravity peak width mW. FIG. 10C illustrates a center-of-gravity point (pT, pH) of the positive peak and a center-of-gravity point (mT, mH) of the negative peak of the second order curve when calculation target area value S is 10%.

Examples of the parameters used in the present invention further include average time vTa, average height vHa, and area center time vTm. FIG. 10D illustrates an average point (vTa, vHa) (white rhombus), a center-of-gravity point (vT, vH) (black circle), vTs, vTe, and vTm of the first order curve when calculation target area value S is 10%. vTa, vHa, and vTm are represented by the following formulas, respectively when n is the number of data points from F(vTs) to F(vTe). Similarly, area center time vTm for the positive and negative peaks of the second order curve can be determined.

[Numerical Formula 9]

$$vTa = \frac{\sum_{i=vTs}^{vTe} i}{n} \quad (10)$$

$$vHa = \frac{\sum_{i=vTs}^{vTe} F(i)}{n} \quad (11)$$

$$vTm = \frac{vTs + vTe}{2} \quad (12)$$

In the present embodiment, flattening ratios vAB and vABa based on a peak width of a first order curve and flattening ratios vAW and vAWa based on a center-of-gravity peak width are defined as the following formulas (8a), (8b), (8c), and (8d) using center-of-gravity height vH, average height vHa, peak width vB, and center-of-gravity peak width vW of the first order curve.

$$vAB = vH/vB \quad (8a)$$

$$vAW = vH/vW \quad (8b)$$

$$vABa = vHa/vB \quad (8c)$$

$$vAWa = vHa/vW \quad (8d)$$

In the present embodiment, time ratio vTB based on a peak width of a first order curve and time ratio vTW based on a center-of-gravity peak width are defined as the following formulas (9a) and (9b) using center-of-gravity time vT, peak width vB, and center-of-gravity peak width vW of the first order curve.

$$vTB = vT/vB \quad (9a)$$

$$vTW = vT/vW \quad (9b)$$

Note that for the flattening ratio, vAB=vB/vH and vAW=vW/vH may be satisfied, or vABa=vB/vHa and vAWa=vW/vHa may be satisfied. That is, the flattening ratio only needs to be a ratio between center-of-gravity height vT or average height vHa and peak width vB or vW. Similarly, for the time ratio, vTB=vB/vT and vTW=vW/vT may be satisfied. That is, the time ratio only needs to be a ratio between center-of-gravity time vT and peak width vB or vW. Each of these ratios may be multiplied by a constant K. That is, for example, for the flattening ratio, vAB=(vH/vB) K, vAB=(vB/vH) K, vAW=(vH/vW) K, or vAW=(vW/vH) K may be satisfied, or vABa=(vHa/vB) K, vABa=(vB/vHa) K, vAWa=(vHa/vW) K, or vAWa=(vW/vHa) K may be satisfied, and for the time ratio, vTB=(vT/vB) K, vTB=(vB/vT) K, vTW=(vT/vW) K, or vTW=(vW/vT) K may be satisfied.

Peak width vB, center-of-gravity peak width vW, average time vTa, average height vHa, area start point time vTs, area end time vTe, area center time vTm, peak width vTr, flattening ratios vAB, vAW, vABa, and vAWa, and time ratios vTB and vTW as described above are also parameters related to a center-of-gravity point, and can be evaluation parameters in the present invention.

The flattening ratio and the time ratio as described above can also be determined for a second order curve. For example, for a positive peak of the second order curve, flattening ratio pAB based on a peak width or flattening ratio pAW based on a center-of-gravity peak width can be determined as a ratio between pH and pB or pW, while time ratio pTB based on a peak width or time ratio pTW based on a center-of-gravity peak width can be determined as a ratio between pT and pB or pW. Similarly, for a negative peak of the second order curve, flattening ratio mAB based on a peak width or flattening ratio mAW based on a center-of-gravity peak width can be determined as a ratio between mH and mB or mW, while time ratio mTB based on a peak width or time ratio mTW based on a center-of-gravity peak width can be determined as a ratio between mT and mB or mW.

Here, in order to distinguish parameters derived from different calculation target areas from each other, each of the parameters may be represented by adding calculation target area value S from which each of the parameters is derived. For example, a parameter related to a center-of-gravity point of a first order curve when S is x (%) may be referred to as vHx, vTx, vBx, or vWx. For example, parameters vH, vT, vB, vW, vTa, vHa, vTs, vTe, vTm, vTr, vAB, vAW, vABa, vAWa, vTB, and vTW related to a center-of-gravity point of a first order curve when S is 10% may be referred to as vH10%, vT10%, vB10%, vW10%, vTa10%, vHa10%, vTs10%, vTe10%, vTm10%, vTr10%, vAB10%, vAW10%, vABa10%, vAWa10%, vTB10%, and vTW10%, respectively. The same applies to a parameter related to a center-of-gravity point of a second order curve.

Figure 12A:
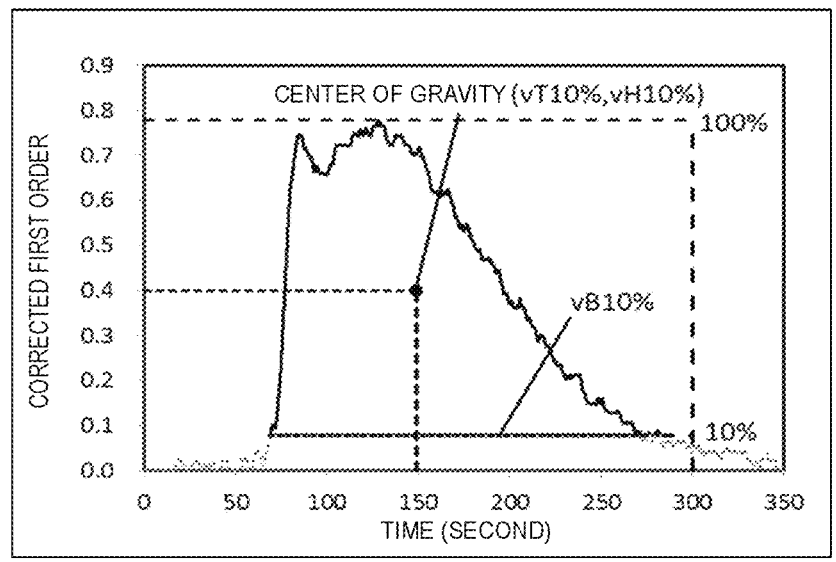
FIG. 12A is a diagram for explaining, for example, a center-of-gravity point when a calculation target area value is set to 10%.
Figure 12B:
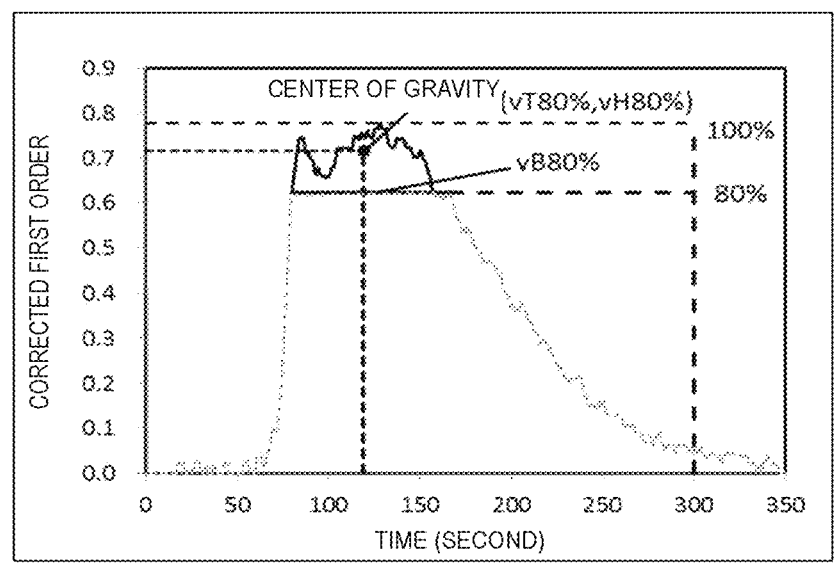
FIG. 12B is a diagram for explaining, for example, a center-of-gravity point when a calculation target area value is set to 80%.

FIGS. 12A and 12B illustrate parameters when different calculation target area values S are set for the same first order curve. FIG. 12A illustrates a case where calculation target area value S is 10%, and FIG. 12B illustrates a case where calculation target area value S is 80%. In the case of FIG. 12A where calculation target area value S is 10%, center-of-gravity height vH10% of the first order curve is 0.4, center-of-gravity time vT10% is 149 seconds, and peak width vB10% is 200 seconds. In contrast, in the case of FIG. 12B where calculation target area value S is 80%, center-of-gravity height vH80% is 0.72, center-of-gravity time vT80% is 119 seconds, and peak width vB80% is 78 seconds.

1.3.3.5. Others

Examples of parameters related to the center-of-gravity point used in the present invention further include an area under a curve (AUC) in a calculation target area of a first order curve or a second order curve. Since the second order curve has a positive peak and a negative peak, an area under a curve (AUC) in a calculation target area in which a maximum peak height of the second order curve is 100% can be AUC in a calculation target area for the positive peak (pAUC) and AUC in a calculation target area of the negative peak (mAUC). Here, in order to distinguish AUCs derived from different calculation target areas from each other, AUC may be referred to as AUCx according to calculation target area value S from which the AUCx is derived. For example, vAUC, pAUC, and mAUC of a calculation target area in which S is 5% are vAUC5%, pAUC5%, and mAUC5%, respectively. Furthermore, additional parameters other than the above-described parameters related to the center-of-gravity point can be included in the parameters used in the present invention. Examples of the parameters include the above-described coagulation time Tc, maximum first order differential value Vmax, maximum second order differential value Amax, minimum second order differential value Amin, and VmaxT, AmaxT, and AminT representing time required for reaching these values. These parameters can also be used as evaluation parameters.

The above-described series of parameters can include parameters derived from a corrected coagulation reaction curve (corrected 0th to second order curves) and parameters derived from an uncorrected coagulation reaction curve (uncorrected 0th to second order curves).

1.4. Evaluation

An example of evaluation performed in step S104 will be described.

Parameters illustrated in Table 1 below, that is, coagulation time Tc, maximum first order differential value Vmax, maximum second order differential value Amax, minimum second order differential value Amin, VmaxT, AmaxT, and AminT representing time required for reaching these values, parameters related to a center-of-gravity point of a first order curve (center-of-gravity time vT, center-of-gravity height vH, average time vTa, average height vHa, peak width vB, center-of-gravity peak width vW, flattening ratio vAB, vAW, vABa, or vAWa and time ratio vTB or vTW determined from these values, vAUC vTs, vTe, vTr, and vTm), parameters related to a center-of-gravity point of a second order curve (center-of-gravity time pT or mT, center-of-gravity height pH or mH, peak width pB or mB, center-of-gravity peak width pW or mW, flattening ratio pAB, pAW, mAB, or mAW and time ratio pTB, pTW, mTB, or mTW determined from these values, pAUC, mAUC, pTs, pTe, pTm, mTs, mTe, and mTm) reflect characteristics related to blood coagulation. At this time, the center-of-gravity time, the center-of-gravity height, the peak width, the average time, the average height, the flattening ratio, the time ratio, and AUC of the first order curve and the second order curve can change a reflection result of the characteristics related to blood coagulation also depending on setting of calculation target area value S. A combination of the above parameters can also reflect the characteristics related to blood coagulation. For example, results of a four arithmetic operation and other various operations between these parameters may also more significantly reflect the characteristics related to blood coagulation. For example, based on coagulation time Tc, center-of-gravity time vT, center-of-gravity height vH, peak width vB, center-of-gravity peak width vW, average time vTa, average height vHa, flattening ratio vAB, vAW, vABa, or vAWa, time ratio vTB or vTW, vAUC, or a combination thereof, characteristics related to blood coagulation, such as presence or absence of abnormal blood coagulation including a deficiency status of a coagulation factor, presence of an antiphospholipid antibody such as a lupus anticoagulant or an anticardiolipin antibody, presence of a coagulation factor inhibitor, and reduction of a von Willebrand factor, and the concentration of each component, can be determined.

Evaluation parameters illustrated in Table 1 below, such as coagulation time Tc, center-of-gravity time vT, center-of-gravity height vH, peak width vB, center-of-gravity peak width vW, average time vTa, average height vHa, flattening ratio vAB, vAW, vABa, or vAWa, time ratio vTB or vTW, vTm, and vAUC, may correlate with the concentration of a component such as a coagulation factor. Therefore, a calibration curve can be created by acquiring an evaluation parameter of a sample in which the concentration of a component such as a coagulation factor is known. Using this calibration curve, the concentration of a component such as a coagulation factor can be calculated based on an evaluation parameter of a patient specimen measured and analyzed.

A ratio or a difference between the above parameters may correlate with the concentration of a component such as a coagulation factor. Examples of the ratio between the evaluation parameters include the above-described flattening ratio vAB, vAW, vABa, or vAWa, time ratio vTB or vTW, and area center time vTm. Examples of the differences between the evaluation parameters include a difference between coagulation time Tc and center-of-gravity time vT, a difference between a peak width and a center-of-gravity peak width, and a difference between vTs at different S's. A calibration curve can be created by acquiring the ratio or the difference between these parameters. Using this calibration curve, the concentration of a component such as a coagulation factor can be calculated based on an evaluation parameter of a patient specimen measured and analyzed.

For example, when calculation target area value S is set to 0% or more and 70% or less, preferably 5% or more and 70% or less, time ratio vTB has a high correlation with a factor VIII concentration. When calculation target area value S is set to 0% or more and 80% or less, preferably 5% or more and 80% or less, flattening ratio vAB has a high correlation with the factor VIII concentration. In particular, for example, when calculation target area value S is set to 70%, flattening ratio vAB has a high correlation with the factor VIII concentration in a case where the concentration is relatively high, and when calculation target area value S is set to 80%, flattening ratio vAB has a high correlation with the factor VIII concentration in a case where the concentration is relatively low.

Evaluation parameters such as maximum first order differential value Vmax, maximum second order differential value Amax, and time VmaxT and AmaxT required for reaching these values may exhibit a correlation with the concentration of a component such as a coagulation factor. Therefore, a calibration curve can be created by acquiring an evaluation parameter of a sample in which the concentration of a component such as a coagulation factor is known. Using this calibration curve, the concentration of a component such as a coagulation factor can be calculated based on an evaluation parameter of a patient specimen measured and analyzed.

In addition, behavior of coagulation time Tc and behavior of center-of-gravity time vT may differ depending on the shape of the first order curve. In particular, the first order curve of an abnormal coagulation specimen may have a bimodal shape with two peaks or a shoulder-like shape in which one of the bimodal peaks is an incomplete peak instead of having a monomodal shape. Due to such a shape of the first order curve, in an abnormal coagulation specimen, for example, a difference d between coagulation time Tc and center-of-gravity time vT illustrated in FIG. 10A is large. Therefore, based on this difference d, characteristics related to blood coagulation, such as presence or absence of abnormal blood coagulation, can be determined. Depending on the shape of the first order curve, a relationship between center-of-gravity height vH or center-of-gravity time vT and maximum first order differential value Vmax or time indicating Vmax can change in various ways. Therefore, based on the relationship between center-of-gravity height vH or center-of-gravity time vT and maximum first order differential value Vmax or time VmaxT indicating Vmax, characteristics related to blood coagulation, such as presence or absence of abnormal blood coagulation or the degree of abnormal blood coagulation, can be determined.

Evaluation parameters such as center-of-gravity height vHx or center-of-gravity time vTx determined by changing calculation target area value S (=x (%)) in various ways, and flattening ratio vABx or time ratio vTBx determined using these values may exhibit characteristics of, for example, a coagulation factor or another coagulation function-related component. Therefore, characteristics related to blood coagulation, such as presence or absence of abnormal blood coagulation or the degree of abnormal blood coagulation, can be determined based on behavior of the evaluation parameters determined by changing calculation target area value x in various ways.

The various characteristics described above can also differ depending on the type of, for example, a coagulation factor or a coagulation function-related component. Therefore, based on the above-described evaluation parameters, it is possible to identify, for example, which coagulation factor causes abnormality.

For example, in a case where factor VIII is deficient, the amount of change in center-of-gravity time vTx is more significant when calculation target area value S (=x (%)) is changed than, for example, in a case where factor IX is deficient. Therefore, it is possible to identify a deficient blood coagulation factor from a change ratio of center-of-gravity time vTx when calculation target area value S (=x (%)) is changed.

For example, in a case where the factor VIII concentration is low, time ratio vTB80% determined when calculation target area value x is set to 80% is significantly lower than in a case where another coagulation factor is deficient. Therefore, time ratio vTB80% determined when calculation target area value x is set to 80% can be used to determine deficiency of factor VIII.

Specific examples of identification items related to a coagulation factor and parameters used for the identification include the following (the subscript x of calculation target area value x added to the end is omitted):

For the factor VIII concentration, T50, vH, vT, vTe, vTr, vTa, vHa, vTm, vB, vW, vAB, vTB, vAW, pH, pAB, pAW, pAUC, VmaxT, Amax, AmaxT, mAUC, or a combination of two or more out of these values. Calculation target area S at this time is preferably 0.5% to 99%, more preferably 1% to 95%, still more preferably 5% to 80%, further still more preferably 30% to 80%, and further still more preferably 30% to 70% or 50% to 80% when Vmax is 100%.

For the factor IX concentration, T50, vT, vTs, vTa, vTm, pT, or a combination of two or more out of these values. Calculation target area S at this time is 0.5% to 99%, more preferably 10% to 95%, and still more preferably 10% to 80% when Vmax is 100%.

The above evaluation parameters may be determined from corrected 0th to second order curves, or may be determined from uncorrected 0th to second order curves. For example, the corrected 0th order curve represents a coagulation rate as a relative value, and a certain blood coagulation abnormality is reflected in the magnitude of the coagulation rate. Therefore, some evaluation parameters, preferably parameters related to the coagulation rate, such as center-of-gravity height, average height, flattening ratio, and AUC, determined from uncorrected 0th to second order curves may reflect blood coagulation characteristics in a better manner than those determined from corrected 0th to second order curves.

1.5. Regarding Center-of-Gravity Point

The peak shape of the first order curve is often monomodal in a normal specimen, however may be bimodal or a shoulder-shaped curve depending on, for example, the type of a reagent or a difference in effect of a coagulation function-related component contained in a specimen. For example, in a case where a maximum coagulation rate is used as an evaluation parameter as in the techniques disclosed in Patent Literatures 1 to 3, even when a coagulation rate curve is not actually monomodal, a monomodal coagulation rate curve may be obtained by a powerful smoothing process, and a maximum coagulation rate may be specified. However, such a smoothing process may result in loss of useful information included in measurement data. Various factors act in a complex manner in a blood coagulation reaction. The first order curve and the second order curve having various shapes may include information related to such various factors. The analysis method according to the present embodiment does not need to perform, for example, an excessive smoothing process to the extent that necessary information is lost by using an evaluation parameter related to a center-of-gravity point. Therefore, the analysis method according to the present embodiment makes it possible to obtain an analysis result reflecting the states of various factors in detail.

Calculation of a center-of-gravity point according to the present embodiment includes calculation related to an average. Therefore, an influence of random noise included in measurement data can be reduced by calculation. Therefore, it is not necessary to excessively perform the smoothing process for noise removal, and a lot of information is maintained. This method is an analysis method with a good S/N ratio. In particular, data related to the first order curve or the second order curve tends to include a lot of noise. However, according to this method using a center-of-gravity point, useful information can be obtained also from the data of the first order curve or the second order curve.

In the calculation of a center-of-gravity point according to the present embodiment, calculation target area value S can be set in various ways, and different center-of-gravity points can be calculated depending on setting of calculation target area value S. For example, if calculation target area value S changes from 0% to 99% at intervals of 1%, 100 center-of-gravity points can be obtained, and various evaluation parameters such as center-of-gravity height vH can be obtained for each of the center-of-gravity points. In addition, as described above, a combination of these evaluation parameters can also be useful information. Therefore, a lot of information can be obtained by using a center-of-gravity point.

The coagulation reaction curve, which is data from which a center-of-gravity point is determined in the present embodiment, is measured on a daily basis in clinical practice, such as measurement of APTT. Therefore, the analysis according to the present embodiment can be easily used in clinical practice only by introducing a data analysis method.

For example, a parameter such as a maximum value (Vmax) of a first order curve is a parameter representing a certain point out of first order differential values, whereas a center-of-gravity point is a parameter reflecting a wide range of data with respect to a time axis. Therefore, for example, data that is asymmetric about the time axis can be a parameter indicating asymmetry.

In the analysis method according to the present embodiment, the correction process illustrated as step S203 is performed. This correction process cancels a difference in the magnitude of the fibrinogen concentration between specimens, and makes it possible to quantitatively compare a difference in the shape of a coagulation reaction curve between the specimens.

In the present embodiment, the intra-section average slope represented by the above formula (4) is used in a differential process for determining a first order curve or a second order curve from a coagulation reaction curve (0th order curve). According to this method, more detailed information can be obtained than in a case where the difference method indicated in the above formula (2) is used. In particular, a good S/N ratio can be obtained even when the amount of change in a value on the coagulation reaction curve is small.

2. Identification of Cause of Prolongation of Coagulation Time

Another aspect of the present invention relates to a method for analyzing a coagulation characteristic of a blood specimen, the method including:
preparing a mixed plasma obtained by mixing a test plasma and a normal plasma;
measuring coagulation time of the mixed plasma without heating treatment;
measuring coagulation time of the mixed plasma after heating treatment;
calculating a first parameter related to a coagulation reaction state based on the coagulation time measurement data of the mixed plasma without heating treatment;
calculating a second parameter related to a coagulation reaction state based on the coagulation time measurement data of the mixed plasma after heating treatment; and
identifying a cause of prolongation of coagulation time based on a ratio or a difference between the first parameter and the second parameter.

The present embodiment will be described with reference to the drawings. The present embodiment relates to analyzing characteristics of a specimen related to blood coagulation. In particular, measurement of APTT used for a test of an intrinsic coagulation function is performed, the data obtained is analyzed, and a cause of extending APTT is identified.

2.1. Outline of Analysis Method

An outline of an analysis method according to the present embodiment will be described with reference to the flowchart illustrated in FIG. 1.

First, a sample used for a test is prepared (step S101). As the sample, a plasma of a specimen (test plasma), a normal plasma, and at least one mixed plasma in which a mixing ratio between the test plasma and the normal plasma is changed are used. Next, measurement of APTT of the mixed plasma without heating treatment and measurement of APTT of the mixed plasma after heating treatment are executed on the prepared samples (step S102).

Next, a predetermined analysis is performed on the data obtained by the measurement of APTT (step S103). Here, a first parameter is calculated from the result of the measurement of APTT of the mixed plasma without heating treatment, and a second parameter is calculated from the result of the measurement of APTT of the mixed plasma after heating treatment.

Finally, based on the analysis results, the specimen is evaluated for a blood coagulation function (step S104). Here, a cause of extending APTT is identified based on a ratio or a difference between the calculated first parameter and the calculated second parameter, and for example, presence or absence of an inhibitor is identified. For example, when the ratio between the first parameter and the second parameter does not fall within a predetermined range including 1, the cause of extending APTT is determined to be an effect of an inhibitor such as presence of the inhibitor. When the ratio between the first parameter and the second parameter falls within a predetermined range including 1, the cause of extending APTT is determined to be not an effect of an inhibitor but an effect of LA such as presence of LA. For example, when the difference between the first parameter and the second parameter does not fall within a predetermined range including 0, the cause of extending APTT is determined to be an effect of an inhibitor. When the difference between the first parameter and the second parameter falls within a predetermined range including 0, the cause of extending APTT is determined to be not an effect of an inhibitor but an effect of, for example, LA. Note that the effect of an inhibitor or LA can change not only depending on presence or absence of the inhibitor or LA, but also depending on the amount of the inhibitor or LA.

2.2. Sample Preparation and Measurement of APTT

Sample preparation performed in step S101 and measurement of APTT performed in step S102 will be described. A specimen to be examined is as described in 1.2. above. In sample preparation, a test plasma and a separately prepared normal plasma are mixed at a predetermined volume ratio. The mixing ratio between the test plasma and the normal plasma is a volume ratio in which the total amount is defined as 10 volumes, and only needs to be within a range of test plasma:normal plasma=1:9 to 9:1, preferably within a range of from 4:6 to 6:4, and more preferably 5:5. For example, the mixing ratio is 1:1, 1:4, or 4:1.

Measurement of APTT is performed promptly on a part of the prepared mixed plasma, and measurement of APTT is performed on another part of the prepared mixed plasma after the mixed plasma is subjected to heating treatment for a predetermined time. The temperature when the mixed plasma is heated is, for example, 30° C. or higher and 40° C. or lower, preferably 35° C. or higher and 39° C. or lower, and more preferably 37° C. The heating time only needs to be, for example, within a range of from 2 to 30 minutes, and is preferably from 5 to 30 minutes. For example, the heating time is about 2 to 10 minutes. The heating time may be longer, such as 30 minutes or one hour, however is preferably within one hour and at most two hours. In the following, the basic procedure for measurement of APTT of an unheated or heated mixed plasma is as described in 1.2. above. Here, the mixed plasma obtained by the above heating treatment is also referred to as "heated plasma". Meanwhile, the mixed plasma that has not been subjected to the above heating treatment is also referred to as "unheated plasma". However, the "unheated plasma" may be subjected to specimen heating treatment in normal coagulation reaction measurement, for example, heating at 30° C. or higher and 40° C. or lower for one minute or less.

2.3. Data Analysis

According to the procedure described in 1.3. above, data on the unheated mixed plasma and the heated mixed plasma, which are analysis targets, is acquired. According to the procedure described in 1.3.1. and 1.3.2. above, a smoothing process and zero point adjustment can be performed on coagulation reaction curves of the unheated mixed plasma and the heated mixed plasma, or a corrected coagulation reaction curve can be obtained. Furthermore, a first order curve or a second order curve can be acquired from the corrected coagulation reaction curve thus obtained and the uncorrected coagulation reaction curve (0th order curve). Various evaluation parameters are calculated from the obtained curves. The details of the acquired evaluation parameters are as described in 1.3.3. above.

2.4. Evaluation

An example of evaluation performed in step S104 will be described. In the present embodiment, when an antiphospholipid antibody such as LA is an extension cause, a change in APTT is not observed so much depending on presence or absence of heating treatment. Meanwhile, when an inhibitor is a cause, extension of APTT after heating treatment is detected with high sensitivity.

For example, for each of the above-described evaluation parameters, evaluation is performed based on a ratio (Pb/Pa) or a difference (Pb−Pa) between a value obtained with an unheated plasma (first parameter, Pa) and a value obtained with a heated plasma (second parameter, Pb).

For example, for the coagulation time, the ratio (Pb/Pa) is approximately 1 in a mixed plasma of a LA-positive plasma and a normal plasma, whereas the ratio (Pb/Pa) is clearly more than 1 in a mixed plasma of a factor VIII inhibitor-positive plasma and a normal plasma.

For example, for maximum value Vmax of corrected first order differentiation, the ratio (Pb/Pa) is approximately 1 in a mixed plasma of a LA-positive plasma and a normal plasma, whereas the ratio (Pb/Pa) is clearly less than 1 in a mixed plasma of a factor VIII inhibitor-positive plasma and a normal plasma.

For example, for peak width vB, the ratio (Pb/Pa) is approximately 1 in a mixed plasma of a LA-positive plasma and a normal plasma, whereas the ratio (Pb/Pa) is clearly more than 1 in a mixed plasma of a factor VIII inhibitor-positive plasma and a normal plasma.

For example, for flattening ratio vAW, the ratio (Pb/Pa) is approximately 1 in a mixed plasma of a LA-positive plasma and a normal plasma, whereas the ratio (Pb/Pa) is clearly less than 1 in a mixed plasma of a factor VIII inhibitor-positive plasma and a normal plasma.

For example, for center-of-gravity time vT, the ratio (Pb/Pa) is approximately 1 in a mixed plasma of a LA-positive plasma and a normal plasma, whereas the ratio (Pb/Pa) is clearly more than 1 in a mixed plasma of a factor VIII inhibitor-positive plasma and a normal plasma.

For example, for center-of-gravity height vH, the ratio (Pb/Pa) is approximately 1 in a mixed plasma of a LA-positive plasma and a normal plasma, whereas the ratio (Pb/Pa) is clearly less than 1 in a mixed plasma of a factor VIII inhibitor-positive plasma and a normal plasma.

For example, for time ratio vTW, the ratio (Pb/Pa) is approximately 1 in a mixed plasma of a LA-positive plasma and a normal plasma, whereas the ratio (Pb/Pa) is less than 1 in a mixed plasma of a factor VIII inhibitor-positive plasma and a normal plasma.

The same applies not only to the ratio (Pb/Pa) but also to the difference (Pb−Pa). For example, for center-of-gravity time vT, the difference (Pb−Pa) is approximately 0 in a mixed plasma of a LA-positive plasma and a normal plasma, whereas the difference (Pb−Pa) is clearly more than 0 in a mixed plasma of a factor VIII inhibitor-positive plasma and a normal plasma.

By using these tendencies, for example, it can be identified whether a specimen of a subject is LA-positive or factor VIII inhibitor-positive based on the ratio (Pb/Pa) or the difference (Pb−Pa). For this identification, any of the above-described evaluation parameters may be used, any combination of these parameters may be used, or a combination of any of these parameters and another evaluation parameter may be used. For example, results of a four arithmetic operation and other various operations between the above-described evaluation parameters may also reflect whether a specimen of a subject is LA-positive or factor VIII inhibitor-positive.

When coagulation factor deficiency is a cause, extension of APTT is also corrected regardless of presence or absence of heating treatment, and therefore the ratio (Pb/Pa) is about 1. Therefore, it can be said that this method can determine whether a cause of extending APTT is an inhibitor, LA, or factor deficiency.

Calculation target area value S set in analysis can be set to various values. The heating treatment time can be set to various values. The heating time is preferably 2 minutes or longer and 30 minutes or shorter within two hours, and more preferably about 10 minutes. The mixing ratio of the mixed plasma is not limited to 1:1 but may be any other ratio.

According to the present embodiment, the test time of a delayed type cross-mixing test can be shortened. For example, in identifying presence or absence of an inhibitor, the heating time of a specimen can be shortened. In addition, in identifying presence or absence of an inhibitor, quantitative determination can be made using an indicator such as a ratio or a difference between evaluation parameters.

3. Automatic Analysis Apparatus

The data analysis and evaluation described above can be performed automatically using a computer. In addition, the series of analyses described above including sample preparation and measurement of coagulation time can be performed automatically by an automatic analysis apparatus. An automatic analysis apparatus that performs such analyses will be described.

3.1. Apparatus Configuration

Figure 13:
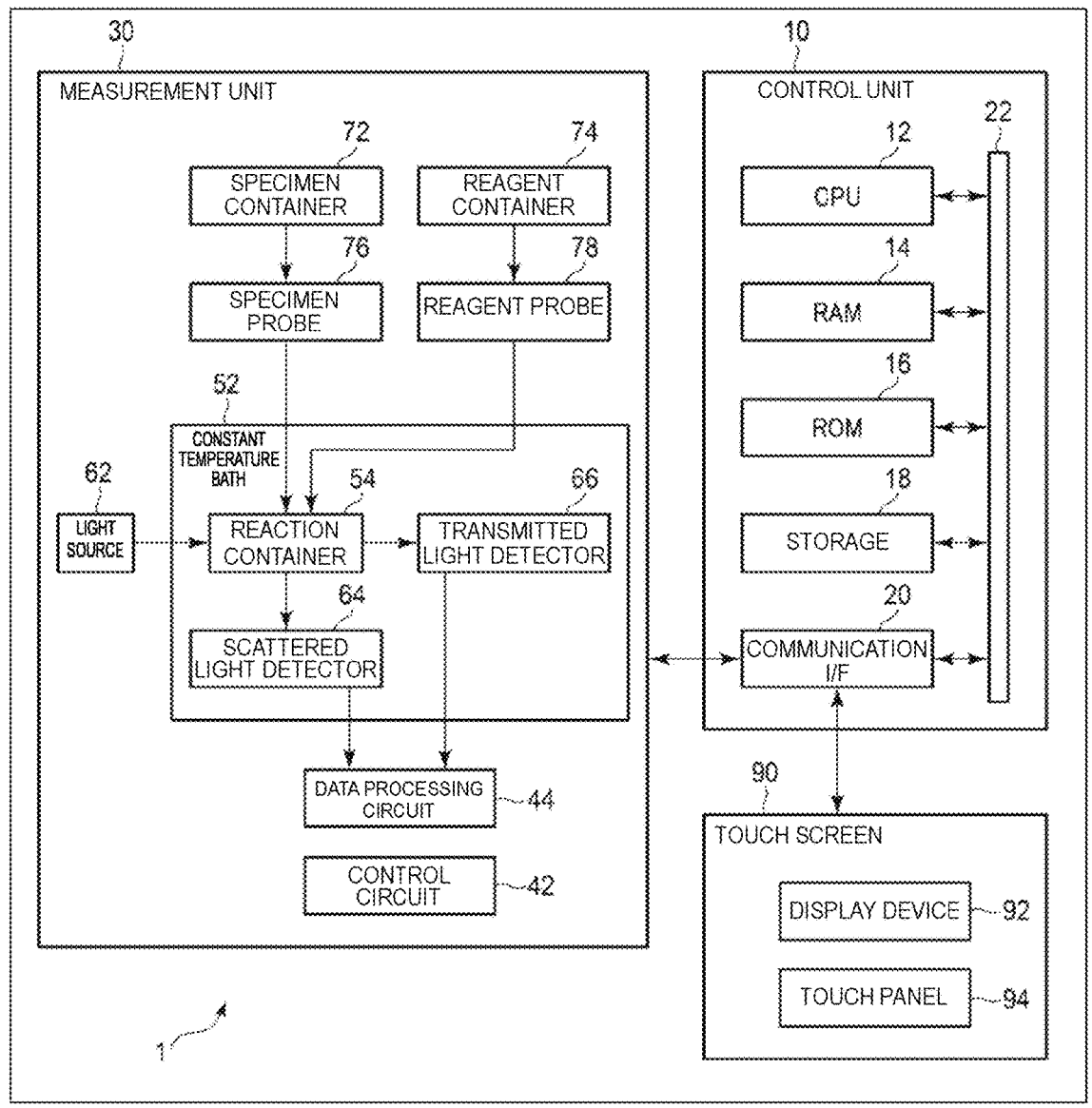
FIG. 13 is a block diagram illustrating an outline of a configuration example of an automatic analysis apparatus according to an embodiment.

FIG. 13 is a block diagram illustrating an outline of a configuration example of an automatic analysis apparatus 1 according to the present embodiment. The automatic analysis apparatus 1 includes a control unit 10, a measurement unit 30, and a touch screen 90.

The control unit 10 controls an overall operation of the automatic analysis apparatus 1. The control unit 10 is constituted by, for example, a personal computer (PC). The control unit 10 includes a central processing unit (CPU) 12, a random access memory (RAM) 14, a read only memory (ROM) 16, a storage 18, and a communication interface (I/F) 20 connected to each other via a bus line 22. The CPU 12 performs, for example, various signal processes. The RAM 14 functions as a main storage device of the CPU 12. For the RAM 14, for example, dynamic RAM (DRAM) or static RAM (SRAM) can be used. The ROM 16 records, for example, various boot programs. For the storage 18, for example, a hard disk drive (HDD) or a solid state drive (SSD) can be used. Various types of information such as programs and parameters used by the CPU 12 are recorded in the storage 18. Data acquired by the measurement unit 30 is recorded in the storage 18. The RAM 14 and the storage 18 are not limited to these, and can be replaced with various storage devices. The control unit 10 communicates with an external device such as the measurement unit 30 or the touch screen 90 via the communication I/F 20.

The touch screen 90 includes a display device 92 and a touch panel 94. The display device 92 can include, for example, a liquid crystal display (LCD) or an organic EL display. The display device 92 displays various screens under control of the control unit 10. The various screens can include various screens such as an operation screen of the automatic analysis apparatus 1, a screen displaying a measurement result, and a screen displaying an analysis result. The touch panel 94 is disposed on the display device 92. The touch panel 94 acquires an input from a user and transmits the obtained input information to the control unit 10.

The control unit 10 may be connected to another device such as a printer, a handy code reader, or a host computer via the communication I/F 20.

The measurement unit 30 includes a control circuit 42, a data processing circuit 44, a constant temperature bath 52, a reaction container 54, a light source 62, a scattered light detector 64, a transmitted light detector 66, a specimen container 72, a reagent container 74, a specimen probe 76, and a reagent probe 78.

The control circuit 42 controls an operation of each of the units of the measurement unit 30 based on a command from the control unit 10. Although not illustrated, the control circuit 42 is connected to, for example, the data processing circuit 44, the constant temperature bath 52, the light source 62, the scattered light detector 64, the transmitted light detector 66, the specimen probe 76, and the reagent probe 78, and controls an operation of each of the units.

The data processing circuit 44 is connected to the scattered light detector 64 and the transmitted light detector 66, and acquires detection results from the scattered light detector 64 and the transmitted light detector 66. The data processing circuit 44 performs various processes on the acquired detection results and outputs the processing results. The process performed by the data processing circuit 44 includes, for example, an A/D conversion process for changing the format of data output from the scattered light detector 64 and the transmitted light detector 66 to a format that can be processed by the control unit 10.

The control circuit 42 and the data processing circuit 44 can each include, for example, a CPU, an application specific integrated circuit (ASIC), or a field programmable gate array (FPGA). The control circuit 42 and the data processing circuit 44 may be each constituted by, for example, one integrated circuit or a combination of a plurality of integrated circuits. In addition, the control circuit 42 and the data processing circuit 44 may be constituted by, for example, one integrated circuit. Operations of the control circuit 42 and the data processing circuit 44 can be performed according to, for example, a program recorded in a storage device or recording areas in the circuits.

The specimen container 72 contains a specimen such as blood of a patient. The reagent container 74 contains various reagents used for measurement. Any number of the specimen containers 72 and any number of the reagent containers 74 may be disposed. Usually, a plurality of types of reagents is used in a test, and therefore there is generally a plurality of reagent containers 74. The specimen probe 76 dispenses a specimen contained in the specimen container 72 into the reaction container 54 under control of the control circuit 42. The reagent probe 78 dispenses a reagent contained in the reagent container 74 into the reaction container 54 under control of the control circuit 42. Any number of the specimen probes 76 and any number of the reagent probes 78 may be disposed.

The constant temperature bath 52 maintains the temperature of the reaction container 54 at a predetermined temperature under control of the control circuit 42. In the reaction container 54, a mixed solution obtained by mixing the specimen dispensed by the specimen probe 76 and the reagent dispensed by the reagent probe 78 reacts. Note that any number of the reaction containers 54 may be disposed.

The light source 62 emits light having a predetermined wavelength under control of the control circuit 42. The light source 62 may emit light the wavelength of which differs depending on a measurement condition. Therefore, the light source 62 may include a plurality of light source elements. The light emitted from the light source 62 is guided by, for example, an optical fiber, and the reaction container 54 is irradiated with the light. The light with which the reaction container 54 is irradiated is partially scattered and partially passes through the reaction container 54 depending on components of a mixed solution in the reaction container 54 and a distribution state of the components. The scattered light detector 64 detects light scattered in the reaction container 54, and for example, detects the amount of the light. The transmitted light detector 66 detects light that has passed through the reaction container 54, and for example, detects the amount of the light. The data processing circuit 44 processes information regarding the amount of scattered light detected by the scattered light detector 64, and processes information regarding the amount of transmitted light detected by the transmitted light detector 66. Either one of the scattered light detector 64 and the transmitted light detector 66 may operate depending on a measurement condition. Therefore, the data processing circuit 44 may process either information regarding the amount of scattered light detected by the scattered light detector 64 or information regarding the amount of transmitted light detected by the transmitted light detector 66 depending on a measurement condition. The data processing circuit 44 transmits processed data to the control unit 10. Note that the measurement unit 30 illustrated in FIG. 13 includes both the scattered light detector 64 and the transmitted light detector 66, but may include only one of these.

The control unit 10 performs various analyses based on the data acquired from the measurement unit 30. The various analyses include, for example, calculation of the evaluation parameters described above and evaluation of a test object based on the evaluation parameters. The data processing circuit 44 may perform some or all of the analyses.

Note that the case where the PC that controls the operation of the measurement unit 30 and the PC that performs data analysis and evaluation are the same control unit 10 has been described here, however these may be separate units. In other words, a PC into which a measurement result is input and which performs data analysis and evaluation can exist as a single unit.

3.2. Operation of Analysis Apparatus 3.2.1. Outline of Operation

Figure 14:
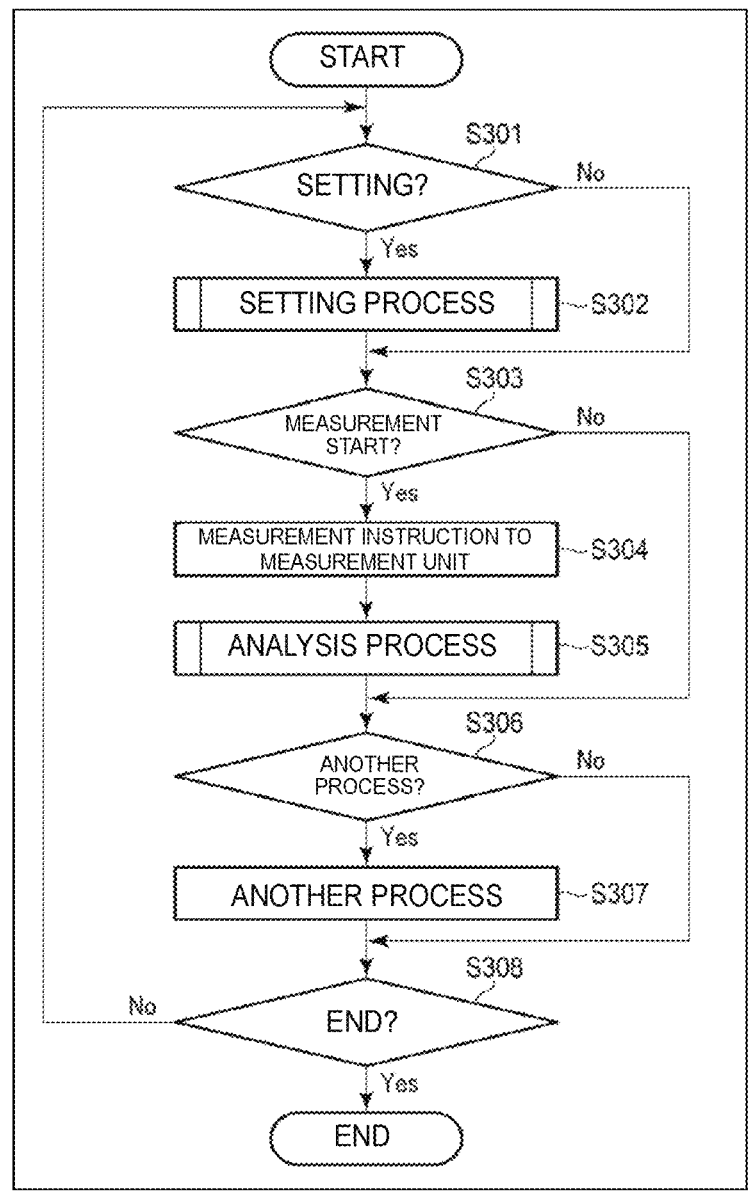
FIG. 14 is a flowchart illustrating an outline of an operation example of an automatic analysis apparatus according to an embodiment.

An operation of the automatic analysis d apparatus 1 according to the present embodiment will be described. FIG. 14 is a diagram illustrating an outline of an operation of the control unit 10.

In step S301, the control unit 10 determines whether or not a setting mode has been selected by a user. The control unit 10 detects, as a user's selection, that a setting mode has been selected, for example, on a menu screen displayed on the display device 92 of the touch screen 90 using the touch panel 94. If the setting mode has not been selected, the process proceeds to step S303. If the setting mode has been selected, the process proceeds to step S302.

In step S302, the control unit 10 performs a setting process. In the setting process, the control unit 10 executes various settings based on an input by a user. For example, a measurement condition, information regarding a test object, information regarding a reagent, a measurement parameter, and an analysis parameter are set. After the setting process, the process proceeds to step S303.

In step S303, the control unit 10 determines whether or not a measurement start instruction has been input. When the measurement start instruction has not been input, the process proceeds to step S306. When the measurement start instruction has been input, the process proceeds to step S304.

In step S304, the control unit 10 outputs a measurement start instruction to the measurement unit 30. Based on this instruction, the measurement unit 30 executes an operation related to a measurement process described later. By this operation, measurement using the measurement unit 30 is performed. Thereafter, the process proceeds to step S305. In step S305, the control unit 10 executes an analysis process described later. In the analysis process, the control unit 10 analyzes the data obtained by the measurement based on the setting. Thereafter, the process proceeds to step S306.

In step S306, the control unit 10 determines whether or not another process has been selected. If no other process has been selected, the process proceeds to step S308. If another process has been selected, the process proceeds to step S307. In step S307, the control unit 10 performs the selected process. For example, the control unit 10 may perform analysis again based on data stored in the storage 18. The control unit 10 may output an instruction for maintenance of the measurement unit 30. Thereafter, the process proceeds to step S308.

In step S308, the control unit 10 determines whether or not to end the process. For example, if an input of an end of the process is made, the control unit 10 determines to end the process. If the process is not ended, the process returns to step S301. As a result, the above processes are repeated. If the control unit 10 determines that the process is ended, the present process is ended.

3.2.2. Measurement Operation

Figure 15:
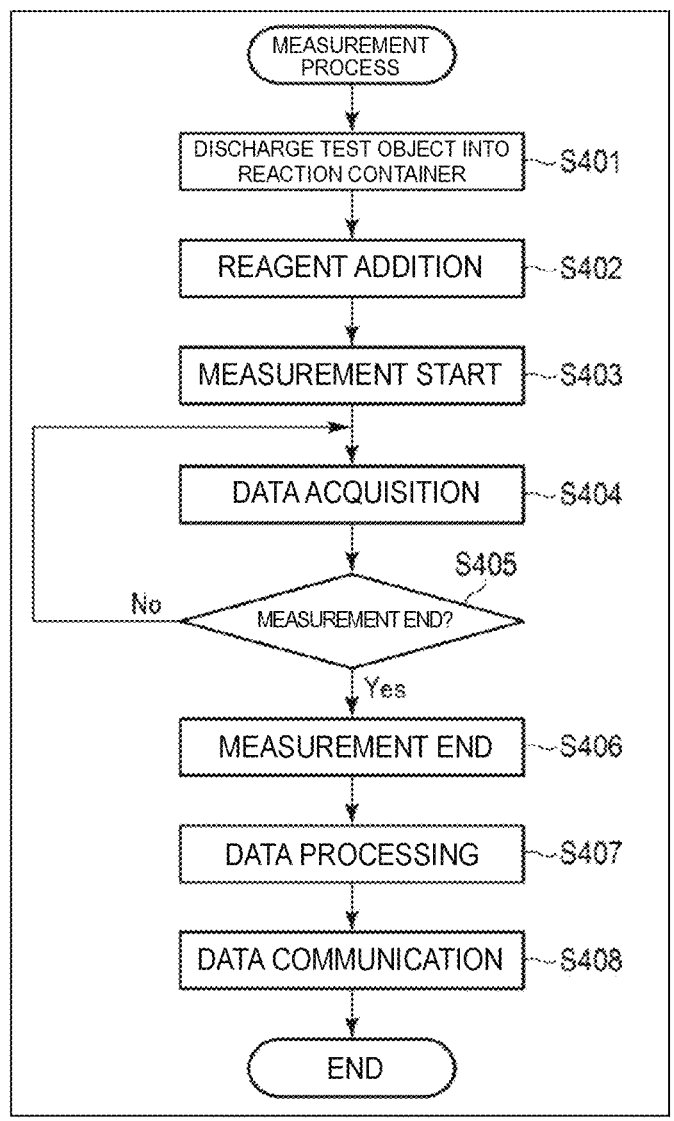
FIG. 15 is a flowchart illustrating an outline of an example of a measurement process according to an embodiment.

FIG. 15 is a flowchart illustrating an outline of an operation related to measurement performed by the measurement unit 30.

In step S401, the control circuit 42 causes the specimen probe 76 to suck a predetermined amount of a test object in the specimen container 72 and then to discharge the test object into the reaction container 54. Before or after discharge of the test object into the reaction container 54, the temperature of the reaction container 54 is adjusted to a temperature according to a measurement condition by the constant temperature bath 52.

In step S402, the control circuit 42 causes the reagent probe 78 to suck a predetermined amount of a reagent in the reagent container 74 and then to discharge the reagent into the reaction container 54, and prepares a mixed solution with the test object. A plurality of reagents may be discharged, and various types of reagents may be discharged depending on, for example, the type of test. A coagulation reaction of the mixed solution is started by discharge of a reagent that starts the reaction.

In step S403, the control circuit 42 causes each unit to start detecting a reaction amount (photometry). That is, the control circuit 42 causes the light source 62 to start emitting light having an appropriate wavelength according to a measurement condition. The control circuit 42 causes one or both of the scattered light detector 64 and the transmitted light detector 66 to start light detection according to a measurement condition. The scattered light detector 64 starts detecting scattered light in the reaction container 54. The transmitted light detector 66 starts detecting transmitted light in the reaction container 54.

In step S404, the control circuit 42 acquires detection data from a required one out of the scattered light detector 64 and the transmitted light detector 66. In step S405, the control circuit 42 determines whether or not to end the measurement. For example, if a predetermined end condition is satisfied, the control circuit 42 determines that the measurement is ended. The end condition may be, for example, that time elapsed from addition of a reagent is a predetermined time. If the control circuit 42 determines that the measurement is not ended, the process returns to step S404. In this way, for example, data is continuously acquired at predetermined intervals.

If the control circuit 42 determines in step S405 that the measurement is ended, the process proceeds to step S406. In step S406, the control circuit 42 ends the measurement. For example, the control circuit 42 causes the light source 62 to stop emitting light. The control circuit 42 causes the scattered light detector 64 and the transmitted light detector 66 to stop light detection.

In step S407, the control circuit 42 causes the data processing circuit 44 to perform data processing on the acquired data. In step S408, the control circuit 42 transmits the processed data to the control unit 10. This completes the measurement process.

3.2.3. Analysis Process

Figure 16:
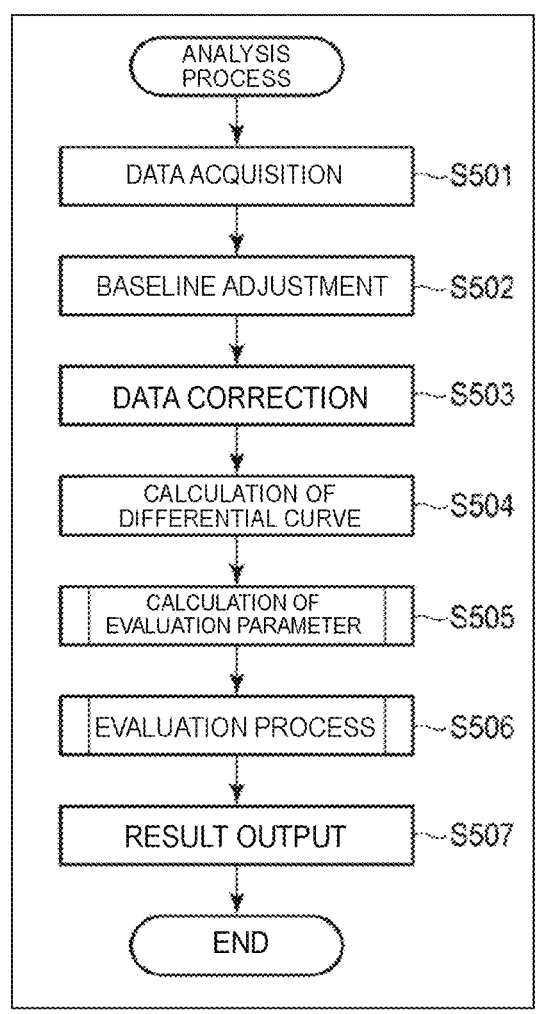
FIG. 16 is a flowchart illustrating an outline of an example of an analysis process according to an embodiment.

An example of the analysis process performed in step S305 will be described with reference to the flowchart illustrated in FIG. 16. The analysis process described here is a process for analyzing measurement data of the above-described coagulation time such as APTT for an analysis target, calculating various evaluation parameters, and analyzing characteristics related to blood coagulation such as presence or absence of abnormal blood coagulation based on the obtained evaluation parameters. Here, the analysis target may be the test plasma as described in 1.2. above or the mixed plasma (heated plasma and unheated plasma) as described in 2.2. above.

In step S501, the control unit 10 acquires measurement data of the coagulation time of the analysis target. Data can be acquired, for example, from the measurement unit 30. The control unit 10 may acquire measurement data from another device, for example, via a network or a medium, or may acquire data stored in a storage device.

In step S502, the control unit 10 performs baseline adjustment. In this baseline adjustment, the control unit 10 performs the above-described process in step S202. In step S503, the control unit 10 performs a data correction process. In this data correction process, the control unit 10 performs the above-described process in step S203. In step S504, the control unit 10 performs a process for calculating a differential curve such as a first order curve or a second order curve. In this differential curve calculation process, the control unit 10 performs the above-described process in step S204.

In step S505, the control unit 10 performs an evaluation parameter calculation process. In this evaluation parameter calculation process, the control unit 10 performs the above-described process in step S205. Here, when analyzing a mixed plasma (heated plasma and unheated plasma), the control unit 10 calculates a ratio or a difference between a first parameter from an unheated plasma of and a second parameter from a heated plasma based on the calculated various evaluation parameters for each of the heated plasma and the unheated plasma. In step S506, the control unit 10 performs an evaluation process. In this evaluation process, the control unit 10 performs the above-described process in step S104 to derive an evaluation result.

In step S507, the control unit 10 causes the evaluation result to be recorded in the storage 18, to be output to the display device 92, or to be transmitted to a host computer.

As described above, the analysis according to the present embodiment can be automatically performed by the automatic analysis apparatus 1.

EXAMPLES

Examples related to an analysis method for blood coagulation using the above-described method will be described.

Parameters used in the following Examples represent parameters derived from corrected 0th to second order curves unless otherwise specified. Meanwhile, parameters derived from uncorrected 0th to second order curves are represented by adding R to the beginning of the name of each of the parameters. For example, when the center-of-gravity height of the corrected first order curve is vH, the center-of-gravity height of the uncorrected first order curve is represented by RvH, and when the center-of-gravity time of the corrected first order curve is vT, the center-of-gravity time of the uncorrected first order curve is represented by RvT. Table 1 below illustrates a list of parameters. In the following description, B flattening ratio, W flattening ratio, B time ratio, and W time ratio, which are combined waveform parameters, may be expressed such that calculation contents of the parameters with a coefficient k omitted can be understood.

TABLE 1

| Waveform parameter of coagulation reaction curve (0th order curve) | | |
|---|---|---|
| Reaction time | Tc | Time required for reaching c % height when maximum height of 0th order curve is 100% |

| | First order curve | Second order curve (Positive peak) | Second order curve (Negative peak) |
|---|---|---|---|
| Waveform parameters of first order curve and second order curve | | | |
| Peak width (time) Bx | vBx | pBx | mBx |
| Center-of-gravity height Hx | vHx | pHx | mHx |
| Center-of-gravity time Tx | vTx | pTx | mTx |
| Center-of-gravity peak width Wx | vWx | pWx | mWx |
| Average height Hax | vHax | — | — |
| Average time Tax | vTax | — | — |
| Area under curve AUCx | vAUCx | pAUCx | mAUCx |
| Area start time Tax | vTsx | pTsx | mTsx |
| Area end time Tex | vTex | pTex | mTex |
| Area center time Tmx | vTmx | pTmx | mTmx |
| Peak width (time) Trx | vTrx | — | — |
| Maximum first order differential value | Vmax (vH100%) | — | — |
| Maximum first order differential value time | VmaxT (vT100%) | — | — |
| Maximum/minimun second order differential value | — | Amax (pH100%) | Amin (mH100%) |
| Maximum/minimun second order differential value time | — | AmaxT (pT100%) | AminT (mT100%) |
| Combined waveform parameters | | | |
| B flattening ratio (Hx/Bx)*k | vABx | pABx | mABx |
| W flattening ratio (Hx/Wx)*k | vAWx | pAWx | mAWx |
| B flattening ratio (Hax/Bx)*k | vABax | | |
| W flattening ratio (Hax/Wx)*k | vAWax | | |
| B flattening ratio (Tx/Bx)*k | vTBx | pTBx | mTBx |
| W flattening ratio (Tx/Wx)*k | vTWx | pTWx | mTWx | x: calculation target area value k: constant

A parameter derived from an uncorrected coagulation reaction curve is represented by adding R to the beginning of the name of the parameter

4. First Example

4.1. Method
4.1.1. Method for Measuring Coagulation Reaction of Blood Specimen An analysis according to the present embodiment was performed on a plurality of mixed samples each obtained by mixing a blood specimen derived from a subject having an abnormality due to a blood coagulation factor and a normal blood specimen (normal plasma) at a specific ratio. That is, a measurement target sample was prepared by mixing each of the plurality of mixed samples with a coagulation time measuring reagent. Photometric data of the amount of scattered light was acquired as coagulation reaction data of the measurement target sample. An analysis according to the present embodiment was performed on the acquired photometric data.

In the present Example, as a specimen, a mixed solution of Factor VIII Deficient Plasma (manufactured by George King Bio-Medical, Inc.) or Factor IX Deficient Plasma (manufactured by George King Bio-Medical, Inc.) with a normal pool plasma (hereinafter, referred to as a normal plasma) which could be regarded as having a factor VIII concentration and a factor IX concentration of 100% was used. By changing a mixing ratio between Factor VIII Deficient Plasma having a factor VIII concentration of 0.1% or less or Factor IX Deficient Plasma having a factor IX concentration of 0.1% or less and a normal plasma, mixed plasmas were prepared such that the factor VIII concentration and the factor IX concentration were each 50%, 25%, 10%, 5%, 2.5%, 1%, 0.75%, 0.5%, 0.25%, and 0.1% or less.

In the present Example, as the measurement reagents, Coagpia APTT-N(manufactured by Sekisui Medical Co., Ltd.) and 50 µL of Coagpia APTT-N calcium chloride solution (manufactured by Sekisui Medical Co., Ltd.), which are reagents for measurement of APTT, were used.

In the present Example, the coagulation reaction was measured using a blood coagulation automatic analysis apparatus CP3000 (manufactured by Sekisui Medical Co., Ltd.). In the present Example, to 50 µL of a sample discharged into a cuvette (reaction container) and heated at 37° C. for 45 seconds, 50 µL of an APTT reagent heated to about 37° C. was added (discharged), and 50 µL of a 25 mM calcium chloride solution was further added thereto after an elapse of 171 seconds to start a coagulation reaction. The reaction was performed while the temperature was maintained at 37° C. Detection (photometry) of the coagulation reaction was performed by emitting light from an LED light with a wavelength of 660 nm as a light source and detecting the amount of 90-degree laterally scattered light at 0.1 second intervals. Detection time was 360 seconds.

4.1.2. Method for Analyzing Photometric Data

Using the chronological photometric data of the coagulation reaction acquired as described above, a coagulation reaction curve was formed. This coagulation reaction curve was analyzed. First, baseline adjustment was performed for the coagulation reaction curve. That is, a smoothing process including noise removal was performed on the coagulation reaction curve, and adjustment was performed such that the amount of scattered light at a measurement start time point was zero. Subsequently, correction was performed such that a maximum height of the coagulation reaction curve (uncorrected 0th order curve) was 100 to obtain a corrected coagulation reaction curve (corrected 0th order curve). The corrected 0th order curve was subjected to first order differentiation to obtain a corrected first order curve. The intra-section average slope according to the above formula (4) was used to calculate the corrected first order curve.

For the obtained corrected first order curve, maximum first order differential value Vmax and time VmaxT at which the first order differential value was a maximum value were determined. In addition, the above-described peak width vB was specified based on the corrected first order curve. Furthermore, center-of-gravity time vT and center-of-gravity height vH were calculated using the corrected first order curve and the above formulas (5), (6), and (7).

Figure 17A:
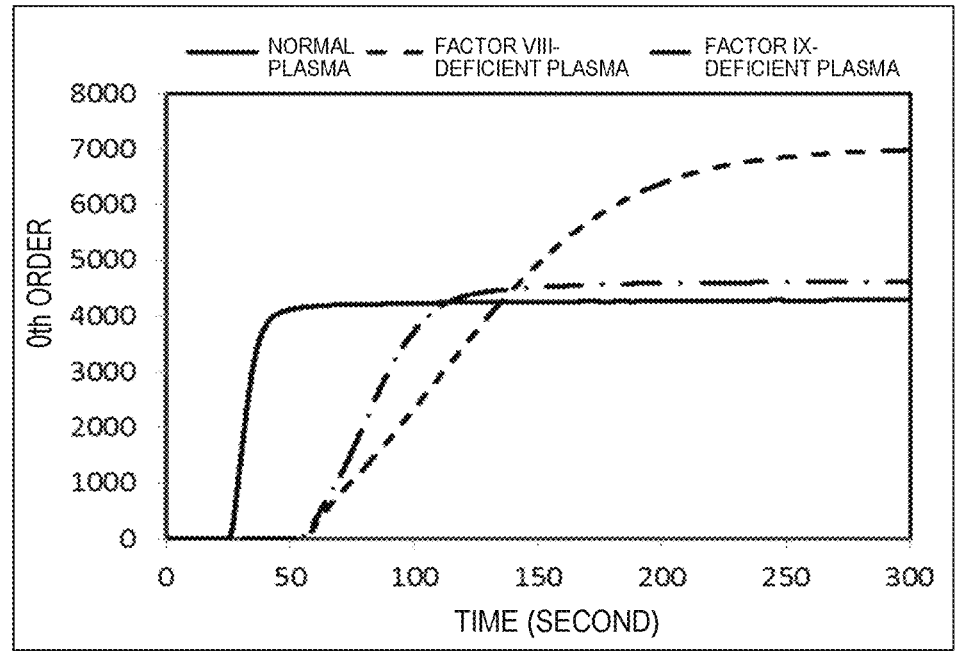
FIG. 17A is a diagram illustrating examples of uncorrected 0th order curves of a normal plasma and a coagulation factor-deficient plasma.
Figure 17B:
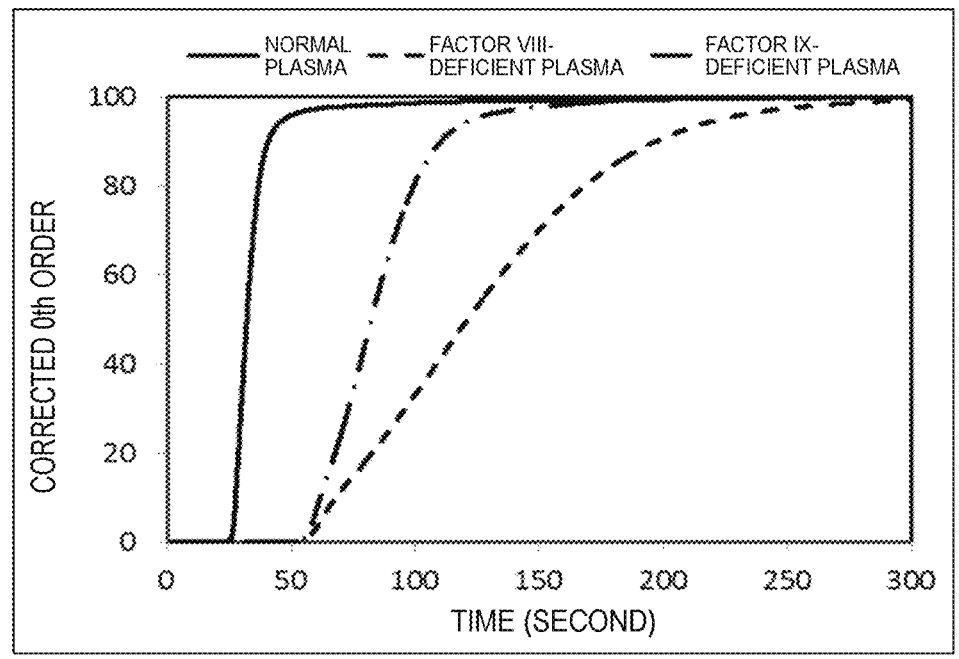
FIG. 17B is a diagram illustrating examples of corrected 0th order curves of a normal plasma and a coagulation factor-deficient plasma.

4.2. Analysis Result and Discussion
4.2.1. 0th Order Curve and First Order Curve FIG. 17A illustrates an example of the obtained coagulation reaction curve (uncorrected 0th order curve). The solid line indicates an uncorrected 0th order curve of a normal plasma, the broken line indicates an uncorrected 0th order curve of a plasma having a factor VIII concentration of 0.1% or less, and the alternate long and short dash line indicates an uncorrected 0th order curve of a plasma having a factor IX concentration of 0.1% or less. FIG. 17B illustrates corrected 0th order curves obtained by correcting the uncorrected 0th order curves of the specimens illustrated in FIG. 17A such that a maximum value of the amount of scattered light amount was 100.

In the factor VIII-deficient plasma and the factor IX-deficient plasma, each coagulation factor is deficient, and therefore prolongation of coagulation time is observed. That is, in each of these coagulation factor-deficient plasmas, the time at which the amount of scattered light starts to increase and the time at which the increase in the amount of scattered light ends are later than those in the case of the normal plasma. In addition, the slope when the amount of scattered light increases is smaller than that in the case of the normal plasma.

Figure 18A:
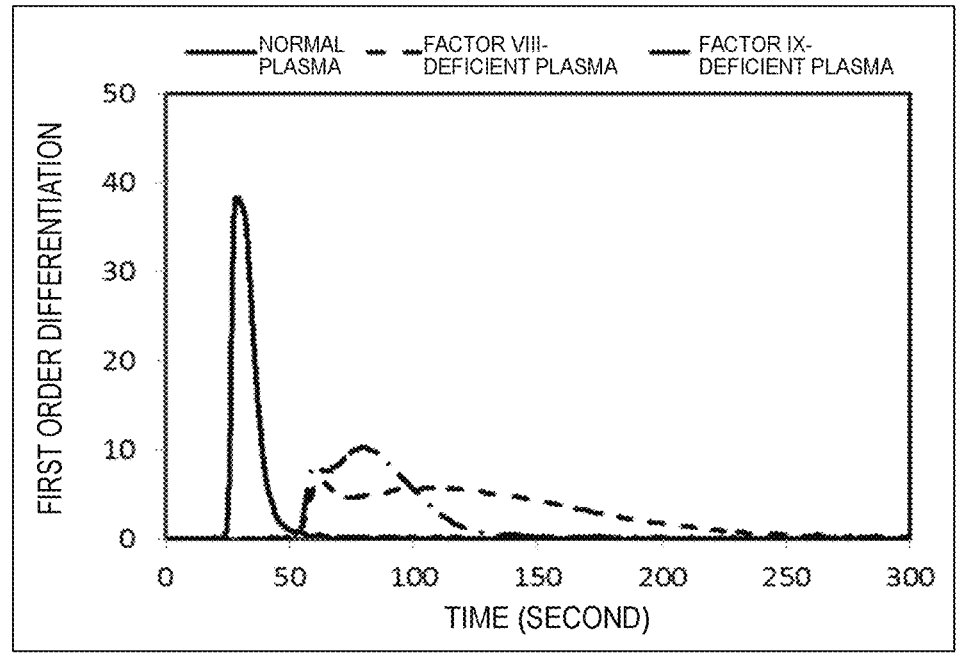
FIG. 18A is a diagram illustrating examples of uncorrected first order curves of a normal plasma and a coagulation factor-deficient plasma.
Figure 18B:
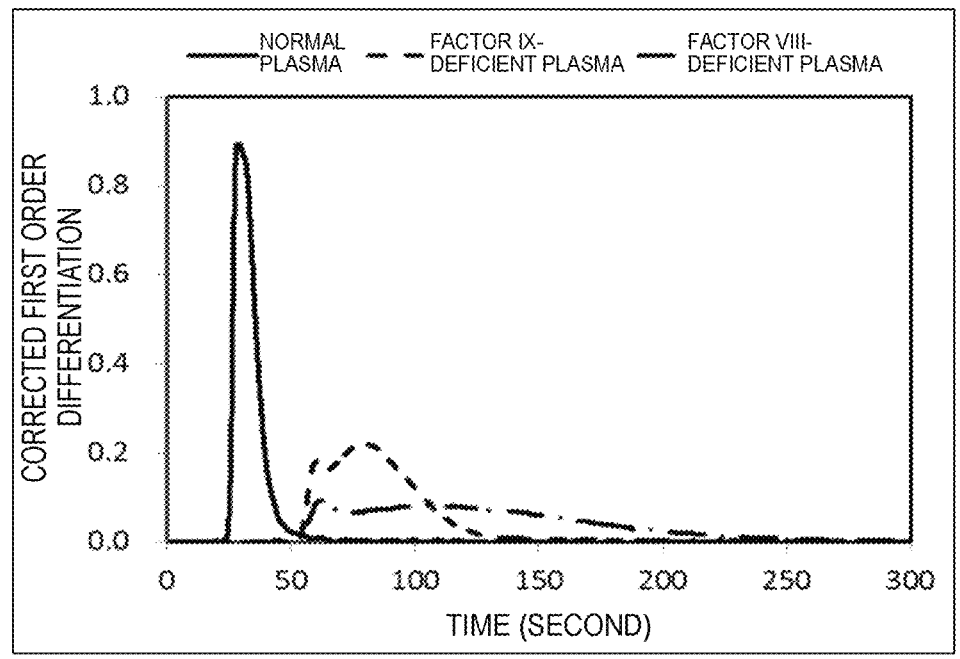
FIG. 18B is a diagram illustrating examples of corrected first order curves of a normal plasma and a coagulation factor-deficient plasma.

FIG. 18A illustrates uncorrected first order curves obtained by differentiating the 0th order curves of the normal plasma and the coagulation factor-deficient plasmas illustrated in FIG. 17A. FIG. 18B illustrates corrected first order curves obtained by differentiating the corrected 0th order curves of the normal plasma and the coagulation factor-deficient plasmas illustrated in FIG. 17B.

In each of the factor VIII-deficient plasma and the factor IX-deficient plasma, the maximum first order differential value is smaller and the time at which the first order differential value is a maximum value is later than those in the case of the normal plasma.

Figure 19A:
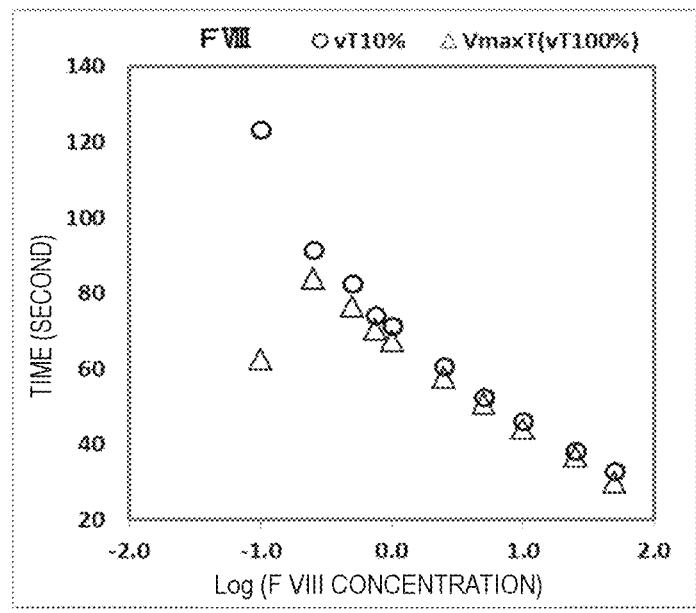
FIG. 19A is a diagram illustrating an example of a relationship between a logarithm of a factor VIII concentration and each of time VmaxT indicating a maximum first order differential value and center-of-gravity time vT10%.
Figure 19B:
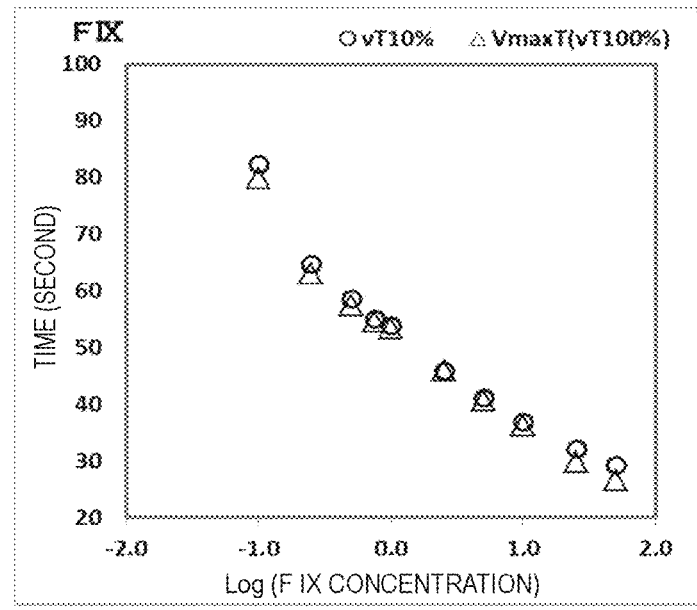
FIG. 19B is a diagram illustrating an example of a relationship between a logarithm of a factor IX concentration and each of time VmaxT indicating a maximum first order differential value and center-of-gravity time vT10%.

4.2.2. Relationship Between Coagulation Factor Concentration and Evaluation Parameter FIG. 19A illustrates a relationship of coagulation time to a logarithm of a factor VIII concentration. Note that when logarithmic conversion was performed for a concentration of 0.1% or less, calculation was performed by assuming that the concentration was 0.1%. The same applies to other drawings. In this drawing, the triangle (Δ) indicates time (VmaxT) at which the first order differential value is a maximum value, and the circle (○) indicates center-of-gravity time vT. For determining center-of-gravity time vT, calculation target area value S was set to 10%. FIG. 19B illustrates a relationship of coagulation time to a logarithm of a factor IX concentration. In this drawing, the triangle (Δ) indicates time (VmaxT) at which the first order differential value is a maximum value, and the circle (○) indicates center-of-gravity time vT. For determining center-of-gravity time vT, calculation target area value S was set to 10%.

Figure 19C:
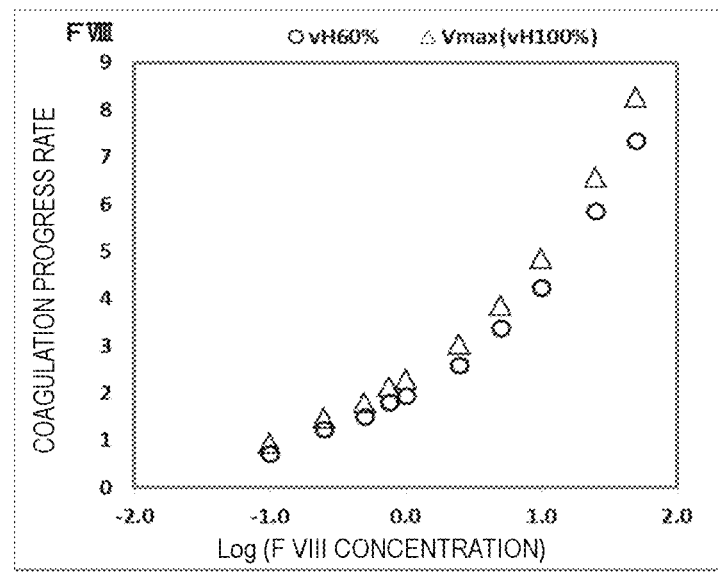
FIG. 19C is a diagram illustrating an example of a relationship between a logarithm of a factor VIII concentration and each of a maximum first order differential value Vmax and center-of-gravity height vH60%.
Figure 19D:
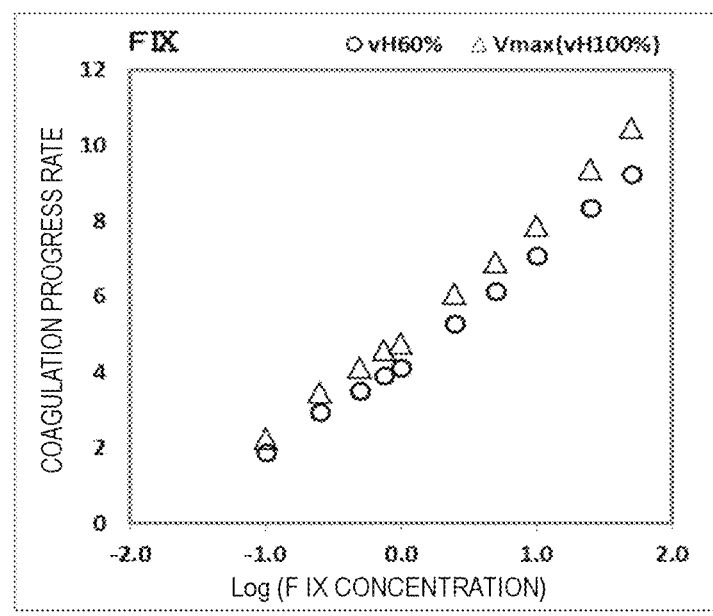
FIG. 19D is a diagram illustrating an example of a relationship between a logarithm of a factor IX concentration and each of a maximum first order differential value Vmax and center-of-gravity height vH60%.

FIG. 19C illustrates a relationship of a first order differential value to a logarithm of a factor VIII concentration. FIG. 19D illustrates a relationship of a first order differential value to a logarithm of a factor IX concentration. In these drawings, the triangle (Δ) indicates maximum value Vmax of the first order differential value, and the circle (○) indicates center-of-gravity height vH. For determining center-of-gravity height vH, calculation target area value S was set to 60%.

As is clear from FIGS. 19A and 19B, center-of-gravity time vT exhibits a high correlation with the factor VIII concentration and the factor IX concentration. As is clear from FIGS. 19C and 19D, center-of-gravity height vH also exhibits a high correlation with the factor VIII concentration and the factor IX concentration.

The above description indicates that the factor VIII concentration or the factor IX concentration of a patient specimen can be calculated by determining center-of-gravity time vT or center-of-gravity height vH of a patient specimen, and using a calibration curve indicating the relationship determined as illustrated in FIGS. 19A, 19B, 19C, and 19D.

As described above, since the center-of-gravity point is calculated from the calculation related to an average, an influence of random noise included in measurement data is reduced by the calculation. Therefore, this method using the center-of-gravity point is not easily affected by noise, and it is expected that the coagulation factor concentration can be acquired with high accuracy according to this method. In addition, the examples illustrated in FIGS. 19A and 19B are the cases where calculation target area value S is set to 10%, and the examples illustrated in FIGS. 19C and 19D are the cases where calculation target area value S is set to 60%. However, calculation target area value S can be set to various values without being limited to these values. Therefore, various parameters can be obtained, and various types of information can be obtained.

Figure 20A:
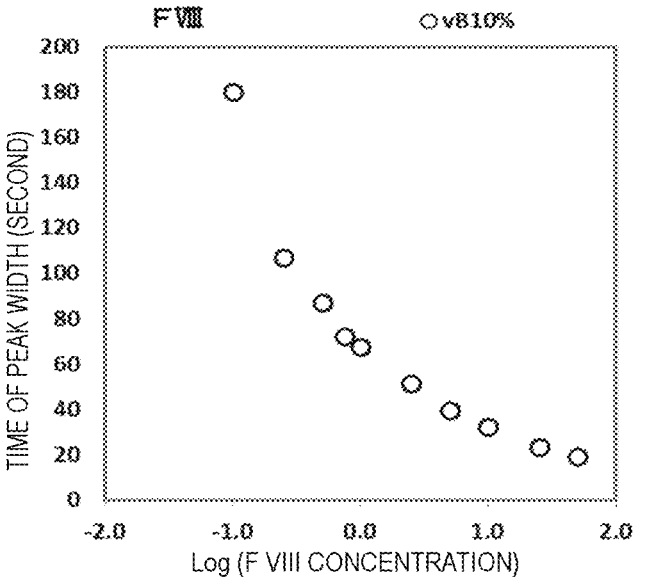
FIG. 20A is a diagram illustrating an example of a relationship between a logarithm of a factor VIII concentration and peak width vB10%.
Figure 20B:
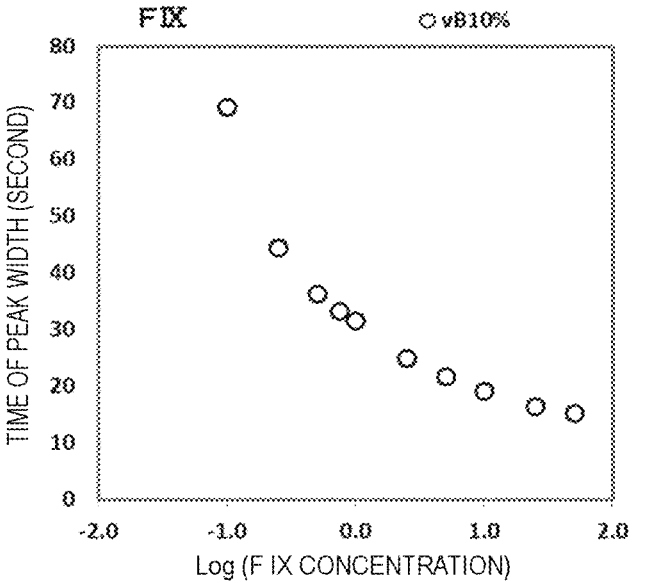
FIG. 20B is a diagram illustrating an example of a relationship between a logarithm of a factor IX concentration and peak width vB10%.

FIG. 20A illustrates a relationship of peak width vB to a logarithm of a factor VIII concentration. For determining peak width vB, calculation target area value S was set to 10%. FIG. 20B illustrates a relationship of peak width vB to a logarithm of a factor IX concentration. For determining peak width vB, calculation target area value S was set to 10%.

As illustrated in FIGS. 20A and 20B, peak width vB exhibited a high correlation with the factor VIII concentration and the factor IX concentration. Therefore, based on the calibration curve determined from these, the factor VIII concentration and the factor IX concentration contained in a patient specimen can be calculated by measuring peak width vB of the patient specimen. It has been indicated that a deficiency status of a coagulation factor can be determined based on these calculated concentrations.

Figure 21A:
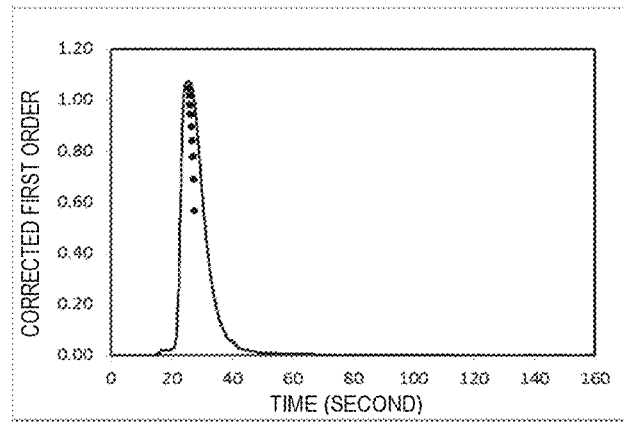
FIG. 21A is a diagram illustrating the position of a center-of-gravity point according to a calculation target area value in an example of a corrected first order curve of a normal plasma.
Figure 21B:
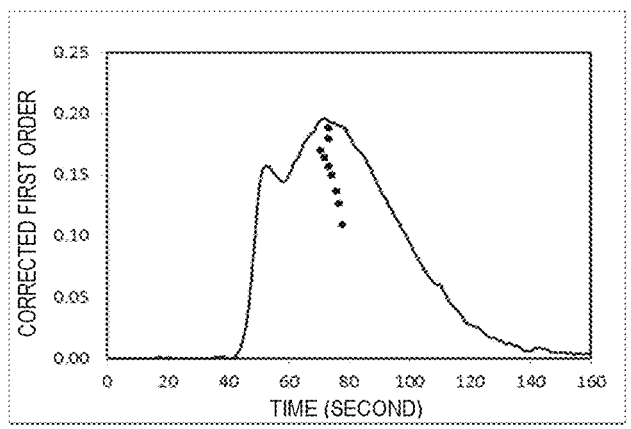
FIG. 21B is a diagram illustrating the position of a center-of-gravity point according to a calculation target area value in an example of a corrected first order curve of a factor VIII-deficient plasma.
Figure 21C:
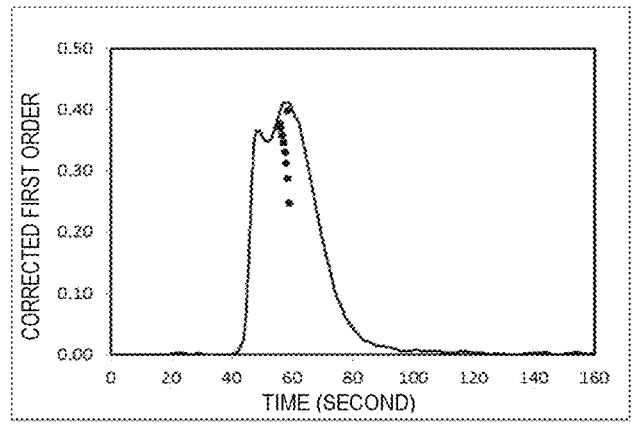
FIG. 21C is a diagram illustrating the position of a center-of-gravity point according to a calculation target area value in an example of a corrected first order curve of a factor IX-deficient plasma.

4.2.3. Relationship Between Calculation Target Area Value and Center-of-Gravity Point FIG. 21A illustrates a corrected first order curve of the normal plasma. FIG. 21B illustrates a corrected first order curve of the factor VIII-deficient plasma (Factor VIII Deficient Plasma). FIG. 21C illustrates a corrected first order curve of the factor IX-deficient plasma (Factor IX Deficient Plasma). In each of the drawings, the black circles indicate center-of-gravity points when calculation target area values S are set to 10%, 20%, 30%, 40%, 50%, 60%, 70%, 80%, and 90%, respectively, in order from bottom to top.

The corrected first order curve in FIG. 21A has a monomodal shape with one peak. In this case, center-of-gravity time vT is monotonically and slightly shortened as calculation target area value S increases. In contrast, the corrected first order curves in FIGS. 21B and 21C each have a bimodal shape with two peaks. Therefore, under an influence of the first small peak, center-of-gravity time vT is shortened at a relatively large ratio up to the middle as calculation target area value S increases. When calculation target area value S exceeds the maximal value of the first small peak, center-of-gravity time vT is extended at a relatively large ratio. In this way, for example, those values, change contents, a ratio, and a difference obtained by determining a plurality of center-of-gravity points having different calculation target area values S can also be evaluation parameters.

As in the examples illustrated in FIGS. 21B and 21C, the corrected first order curve may have two maximal values. The relatively wide maximal value on the right side, which is observed at about 80 seconds in the example illustrated in FIG. 21B and at about 60 seconds in the example illustrated in FIG. 21C, is referred to as a main peak, and the relatively narrow maximal value on the left side, which is observed at about 50 seconds in the example illustrated in FIG. 21B and at about 50 seconds in the example illustrated in FIG. 21C, is referred to as a side peak. It has been found that when calculation target area value S is less than 10%, an influence of the shape of the main peak of the corrected first order curve is largely reflected on the analysis result, and an influence of the shape of the side peak is not reflected thereon so much. In addition, it has been found that when calculation target area value S is 60% to 70%, an influence of the shape of the side peak of the corrected first order curve appears in the analysis result.

How to set calculation target area value S has an important meaning. In measurement of the factor VIII-deficient plasma, it has been found that when calculation target area value S is set to 50% to 70%, the side peak appearing in the corrected first order curve is closely related to the factor VIII concentration. Therefore, for analyzing the factor VIII-deficient plasma, it is one preferable setting to set calculation target area value S to 50% to 70%.

By analyzing peaks appearing in the first order curves of plasmas deficient in various coagulation factors, it is possible to estimate effects of various factors involved in coagulation.

Figure 22A:
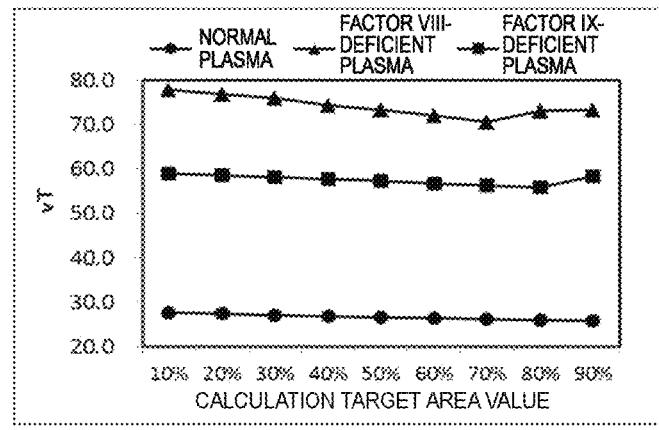
FIG. 22A is a diagram illustrating an example of center-of-gravity time according to a calculation target area value.
Figure 22B:
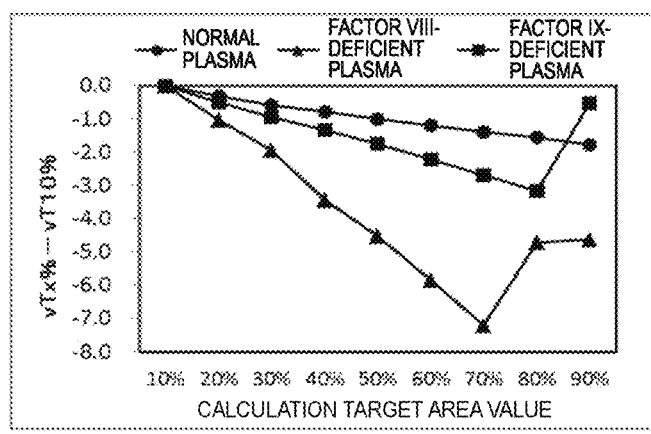
FIG. 22B is a diagram illustrating an example of a relative difference in center-of-gravity time according to a calculation target area value.
Figure 22C:
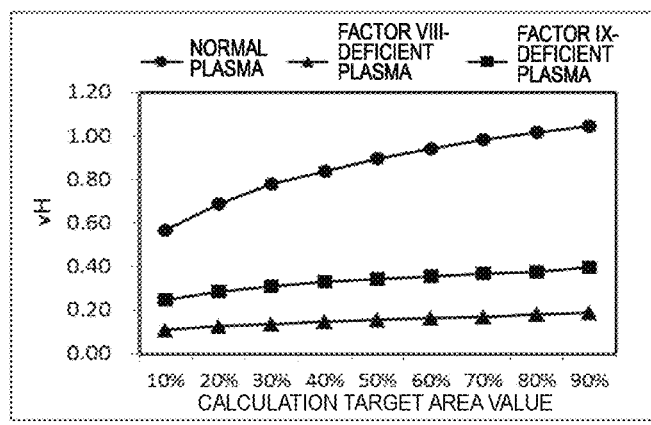
FIG. 22C is a diagram illustrating an example of center-of-gravity height according to a calculation target area value.

FIG. 22A illustrates a relationship between a set value (10% to 90%) of calculation target area value S and center-of-gravity time vT. FIG. 22B illustrates a difference between center-of-gravity time vT obtained when calculation target area value S is 10% and center-of-gravity time vT obtained when a set value of calculation target area value S is each of 20% to 90%. FIG. 22C illustrates a relationship between the set value (10% to 90%) of calculation target area value S and center-of-gravity height vH.

As illustrated in FIGS. 22A and 22B, it has been revealed that center-of-gravity time vT of the normal plasma is significantly different from center-of-gravity time vT of each of the coagulation factor-deficient plasmas. That is, it has been revealed that, for example, by comparing center-of-gravity time vT of the normal plasma with center-of-gravity time vT of a patient specimen, a deficiency status of a coagulation factor can be detected.

In addition, as illustrated in FIG. 22B, it has been revealed that in particular, in the factor VIII-deficient plasma, center-of-gravity time vT is more dependent on calculation target area value S than that in the other plasmas. That is, it has been revealed that a deficiency status of factor VIII can be detected by examining dependence of center-of-gravity time vT of a patient specimen on calculation target area value S.

As illustrated in FIG. 22C, it has been revealed that center-of-gravity height vH of the normal plasma is significantly different from center-of-gravity height vH of each of the coagulation factor-deficient plasmas. That is, it has been revealed that, for example, by comparing center-of-gravity height vH of the normal plasma with center-of-gravity height vH of a patient specimen, a deficiency status of a coagulation factor can be detected.

Figure 23:
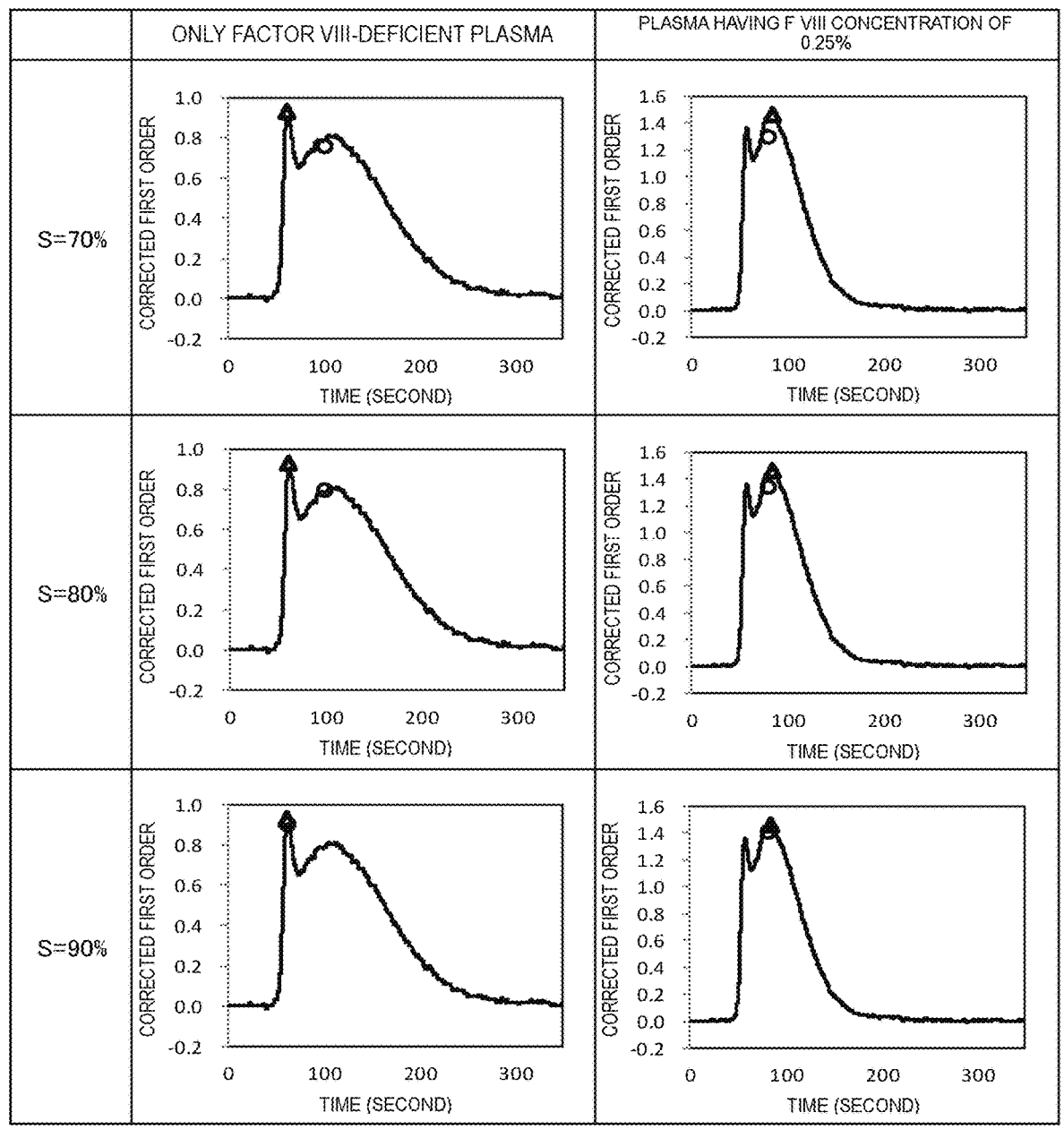
FIG. 23 is a diagram for explaining an example of behavior of a center-of-gravity point according to a calculation target area value that differs depending on a sample.

Another example illustrating usefulness of center-of-gravity height vH will be described with reference to FIG. 23. The left column of FIG. 23 illustrates corrected first order curves obtained for a test plasma containing only the factor VIII-deficient plasma. The right column of FIG. 23 illustrates corrected first order curves obtained for a test plasma having a factor VIII concentration of 0.25%. Maximum first order differential value Vmax is indicated by a triangle (Δ) on each of the curves. The upper row illustrates a case where calculation target area value S is set to 70%, the middle row illustrates a case where calculation target area value S is set to 80%, and the lower row illustrates a case where calculation target area value S is set to 90%, in which a center-of-gravity point is indicated by a circle (○). In the corrected first order curves obtained in the case where only the factor VIII-deficient plasma is contained, illustrated in the left column, maximum first order differential value Vmax is located at the narrow side peak on the left side. When calculation target area value S is set to 70% or 80%, the center-of-gravity point is located in the wide main peak on the right side. Meanwhile, when calculation target area value S is set to 90%, the center-of-gravity point is located in the side peak indicating maximum first order differential value Vmax. In contrast, in the corrected first order curves obtained in the case of the test plasma having a factor VIII concentration of 0.25%, illustrated in the right column, maximum first order differential value Vmax is located in the main peak on the right side. When calculation target area value S is set to any one of 70%, 80%, and 90%, the center-of-gravity point is located in the wide main peak on the right side, and is close to the time indicating maximum first order differential value Vmax. As described above, according to the method of the present embodiment, it is possible to identify factor VIII even in a plasma having a factor VIII concentration of 0.25%.

4.2.4. Regarding Intra-Section Average Slope

Figure 24A:
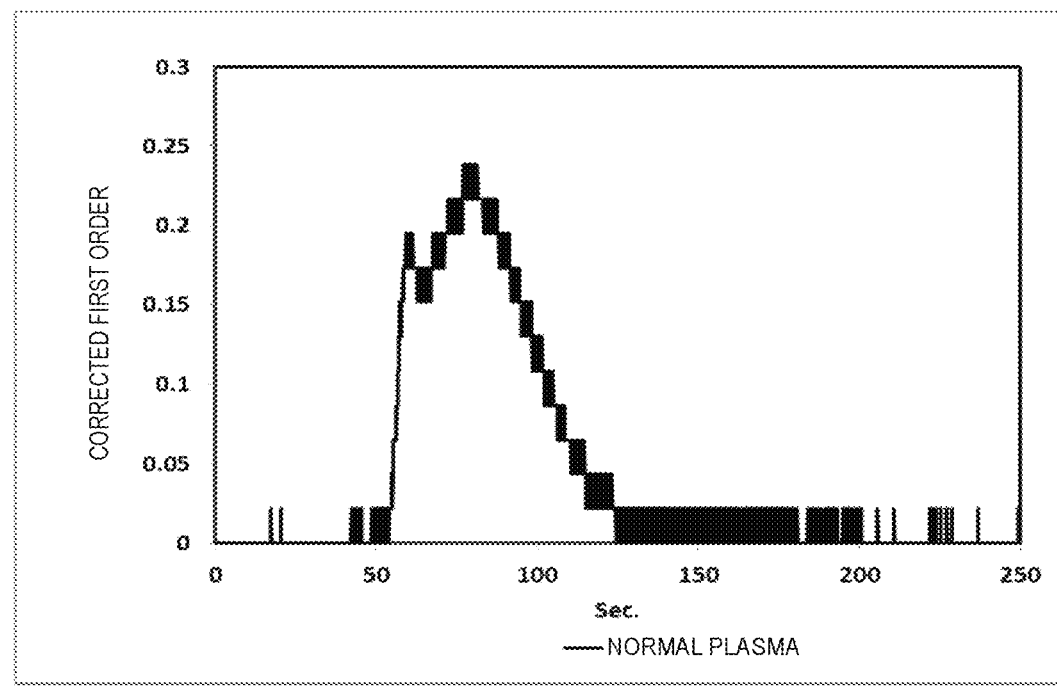
FIG. 24A is a diagram illustrating an example of a corrected first order curve calculated based on a difference method.
Figure 24B:
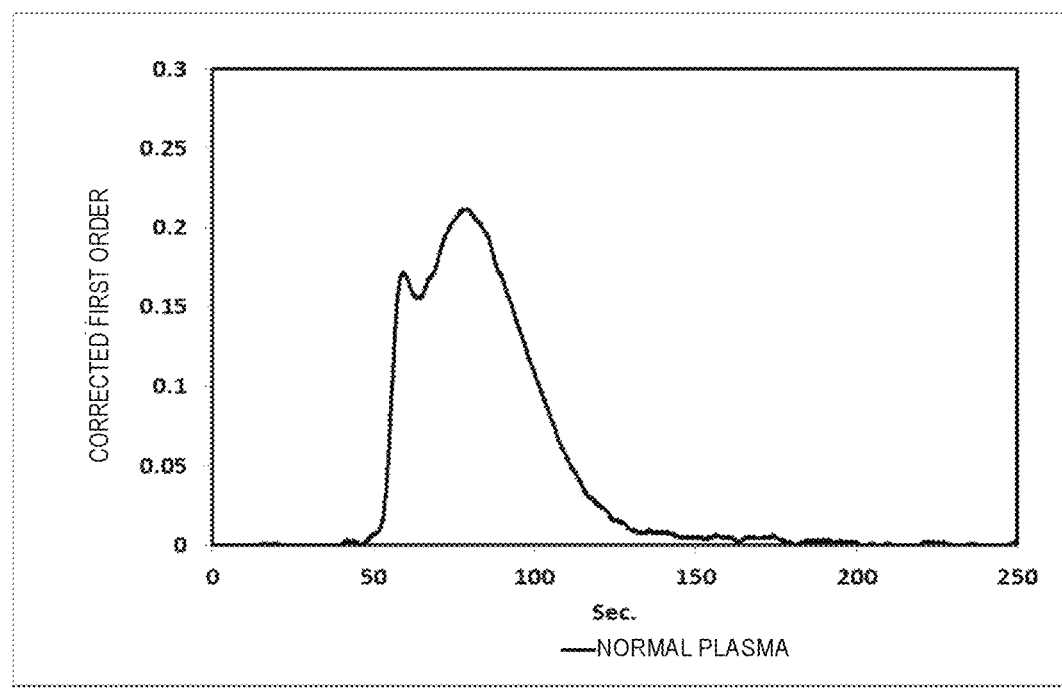
FIG. 24B is a diagram illustrating an example of a corrected first order curve calculated based on an intra-section average slope.

FIG. 24A illustrates an example of a corrected first order curve of the factor IX-deficient plasma calculated using the above formula (2). FIG. 24B illustrates an example of a corrected first order curve of the factor IX-deficient plasma calculated using the above formula (4). As is clear from a comparison between FIGS. 24A and 243, the first order differential value can be grasped in more detail in the example based on the above formula (4) in FIG. 24B. For example, in FIG. 24B, information regarding the side peak around the time 45 seconds can be grasped in detail. In this way, it has been revealed that more detailed information can be obtained by the above-described analysis by using the corrected first order curve based on the intra-section average slope.

The corrected first order curve based on the intra-section average slope can be calculated from a series of pieces of measurement data. The calculation of the intra-section average slope value is suitable for analysis in an analysis apparatus that uses an optical detector to reduce a change in photometric quantity, for example, a blood coagulation analysis apparatus.

5. Second Example 5.1. Method 5.1.1. Method for Measuring Coagulation Reaction of Blood Specimen As a test plasma, a mixture of a factor VIII-deficient plasma and a normal plasma was used. For the factor VIII-deficient plasma, Factor VIII Deficient Plasma (manufactured by George King Bio-Medical, Inc.) was used. For the normal plasma, a normal pool plasma which could be regarded as having a factor VIII concentration and a factor IX concentration of 100% was used. As test plasmas, a sample obtained by mixing the factor VIII-deficient plasma (manufactured by George King Bio-Medical, Inc.) and the normal plasma and adjusting a factor VIII concentration to 50%, 25%, 10%, 5%, 2.5%, 1%, 0.75%, 0.5%, or 0.25%, and a factor VIII-deficient plasma (having a factor VIII concentration of 0.1% or less) were used.

Similarly, a sample obtained by mixing a plasma deficient in another coagulation factor (having a concentration of 0.1% or less) and the normal plasma, and adjusting each factor concentration to 50%, 25%, 10%, 5%, 2.5%, 1%, 0.75%, 0.5%, or 0.25% was also prepared as a test plasma. As the other coagulation factor-deficient plasma, a factor V-deficient plasma, a factor IX-deficient plasma, a factor X-deficient plasma, a factor XI-deficient plasma, a factor XII-deficient plasma, and a prekallikrein-deficient plasma were used. Note that when logarithmic conversion was performed for the case containing only a plasma deficient in a factor, calculation was performed by assuming that the concentration was 0.1%.

For the factor V-deficient plasma, Factor V Deficient Plasma (manufactured by George King Bio-Medical, Inc.) was used. For the factor IX-deficient plasma, Factor IX Deficient Plasma (manufactured by George King Bio-Medical, Inc.) was used. For the factor X-deficient plasma, Factor X Deficient Plasma (manufactured by George King Bio-Medical, Inc.) was used. For the factor XI-deficient plasma, Factor XI Deficient Plasma (manufactured by George King Bio-Medical, Inc.) was used. For the factor XII-deficient plasma, Factor XII Deficient Plasma (manufactured by George King Bio-Medical, Inc.) was used. For the prekallikrein-deficient plasma, Prekallikrein Deficient Plasma (manufactured by George King Bio-Medical, Inc.) was used. Note that measurement of factor V, factor XI, and factor XII has the following clinical significance, and it is expected that factor V, factor XI, and factor XII can be measured using a waveform analysis technique. Congenital coagulation factor V deficiency is a hemorrhagic disease caused by quantitative deficiency of coagulation factor V caused by mutation of a coagulation factor V gene or dysfunction, and measurement of coagulation factor V is necessary for diagnosis of congenital coagulation factor V deficiency. When factor XI deficiency is suspected, measurement of coagulation factor XI is required. Furthermore, congenital factor XII deficiency that has been recently reported to be associated with recurrent miscarriage is examined by measurement of coagulation factor XII.

As APTT measurement reagents, Coagpia APTT-N (manufactured by Sekisui Medical Co., Ltd.) and Coagpia APTT-N calcium chloride solution (manufactured by Sekisui Medical Co., Ltd.) were used.

The measurement of APTT for each of the above test plasmas was performed using a blood coagulation automatic analysis apparatus CP3000 (manufactured by Sekisui Medical Co., Ltd.). The procedure for measuring APTT with CP3000 was the same as that in the first Example.

4.1.2. Method for Analyzing Photometric Data

The procedure for obtaining the corrected first order curve based on the photometric data was the same as that in the first Example.

When a curve indicating obtained first order differential value V is expressed by V=F(t) and a maximum value of first order differential value V is represented by Vmax, by setting calculation target area value S (%) and using data satisfying F(t)≥Vmax×S×0.01, center-of-gravity time vT and center-of-gravity height vH were calculated based on the above formulas (5), (6), and (7). Peak width vB was also calculated. Using these parameters, flattening ratio vAB and time ratio vTB were calculated based on the above formulas (8) and (9).

5.2. Analysis Result and Discussion

5.2.1. Regarding Effectiveness of Correction Process

Figure 25A:
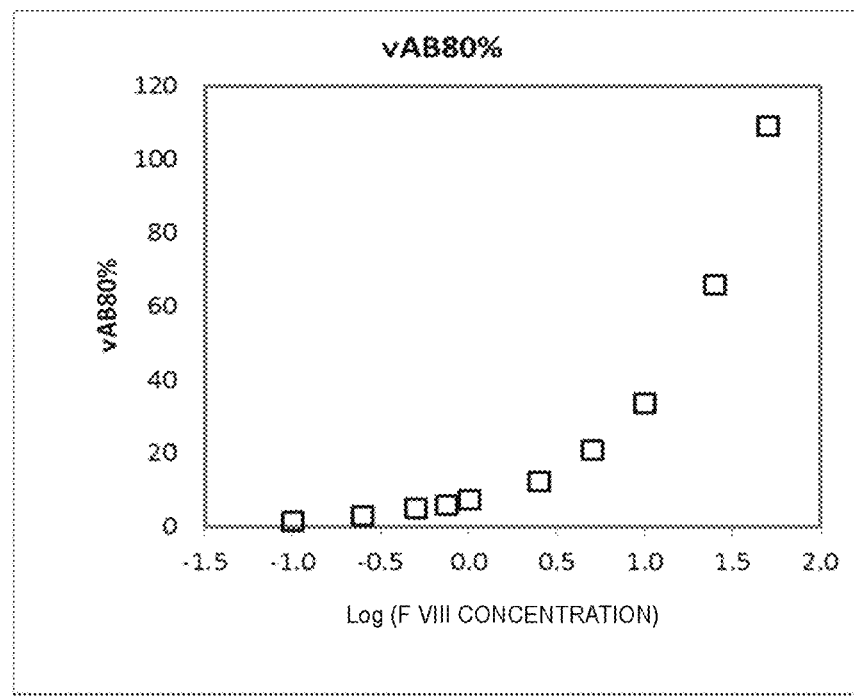
FIG. 25A is a diagram illustrating an example of flattening ratio vAB80% obtained by performing a correction process on a logarithm of a factor VIII concentration.
Figure 25B:
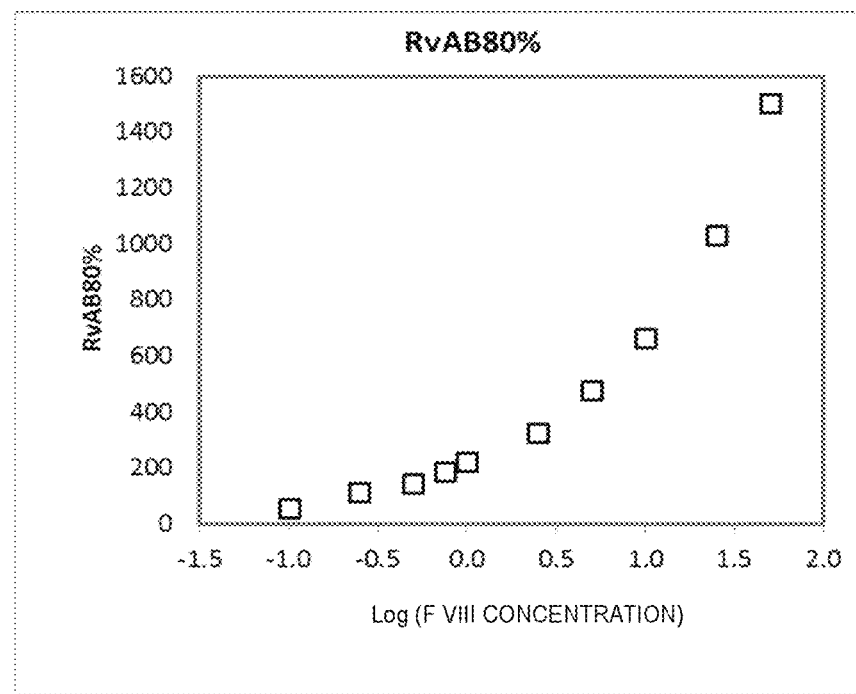
FIG. 25B is a diagram illustrating an example of flattening ratio RvAB80% obtained without performing a correction process on a logarithm of a factor VIII concentration.

An effect of the correction process in step S203 was examined. Measurement of APTT was performed on test plasmas having different factor VIII concentrations, and flattening ratio vAB80% when the calculation target area value was 80% was calculated based on a corrected first order curve obtained from a corrected 0th order curve. Note that flattening ratio vAB at this time was calculated by being multiplied by a constant 100 such that the value was 1 or more. In addition, based on an uncorrected first order curve obtained from an uncorrected 0th order curve, flattening ratio RvAB80% when the calculation target area value was 80% was calculated. FIG. 25A illustrates a relationship between a factor VIII concentration and vAB80% based on the corrected first order curve. FIG. 25B illustrates a relationship between a factor VIII concentration and RvAB80% based on the uncorrected first order curve. In each of the graphs, the horizontal axis indicates a logarithm of a factor VIII concentration. The corrected first order curve illustrated in FIG. 25A was slightly more consistent with a regression curve than the uncorrected first order curve illustrated in FIG. 25B.

Figure 25C:
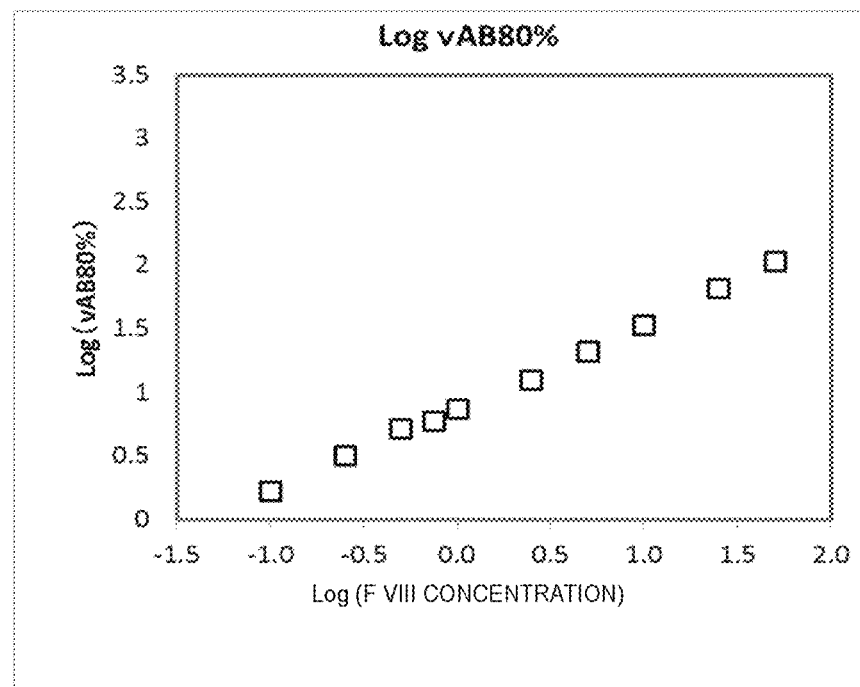
FIG. 25C is a diagram illustrating an example of a logarithm of flattening ratio vAB80% obtained by performing a correction process on a logarithm of a factor VIII concentration.
Figure 25D:
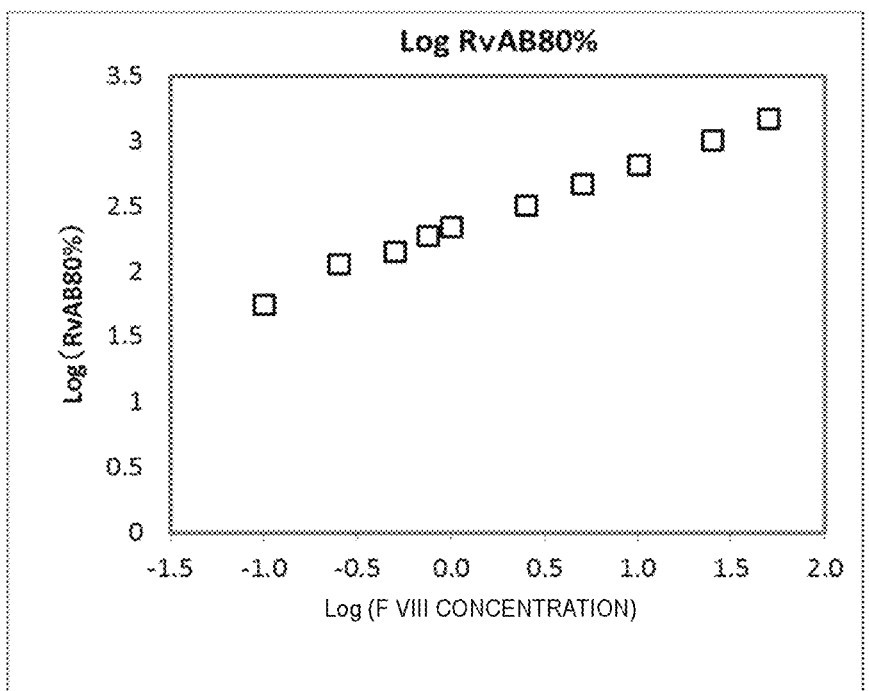
FIG. 25D is a diagram illustrating an example of a logarithm of flattening ratio RvAB80% obtained without performing a correction process on a logarithm of a factor VIII concentration.

FIGS. 25C and 25D illustrate examples in which logarithmic conversion was also performed on the vertical axis in FIGS. 25A and 25B, respectively. It has been found that the corrected first order curve illustrated in FIG. 25C has a larger slope of a linear regression formula and an intercept closer to 0 than the uncorrected first order curve illustrated in FIG. 25D. Normally, in a linear calibration curve with a concentration as the horizontal axis, reproducibility is better when the slope is larger, and restriction of a measurement concentration area is smaller when the intercept is closer to 0. From these results, if it is considered that the factor VIII concentration is calculated from the calibration curve based on vAB80%, the slope is preferably larger, and the intercept is preferably closer to 0 as illustrated in FIG. 25C.

From the above, it has been revealed that the correction process is useful. Therefore, in the analysis described below, a corrected first order curve obtained from a corrected coagulation reaction curve was used. Also in the following analysis result, evaluation parameters are displayed with a log-log graph.

5.2.2. Regarding Corrected First Order Curve

Figure 26:
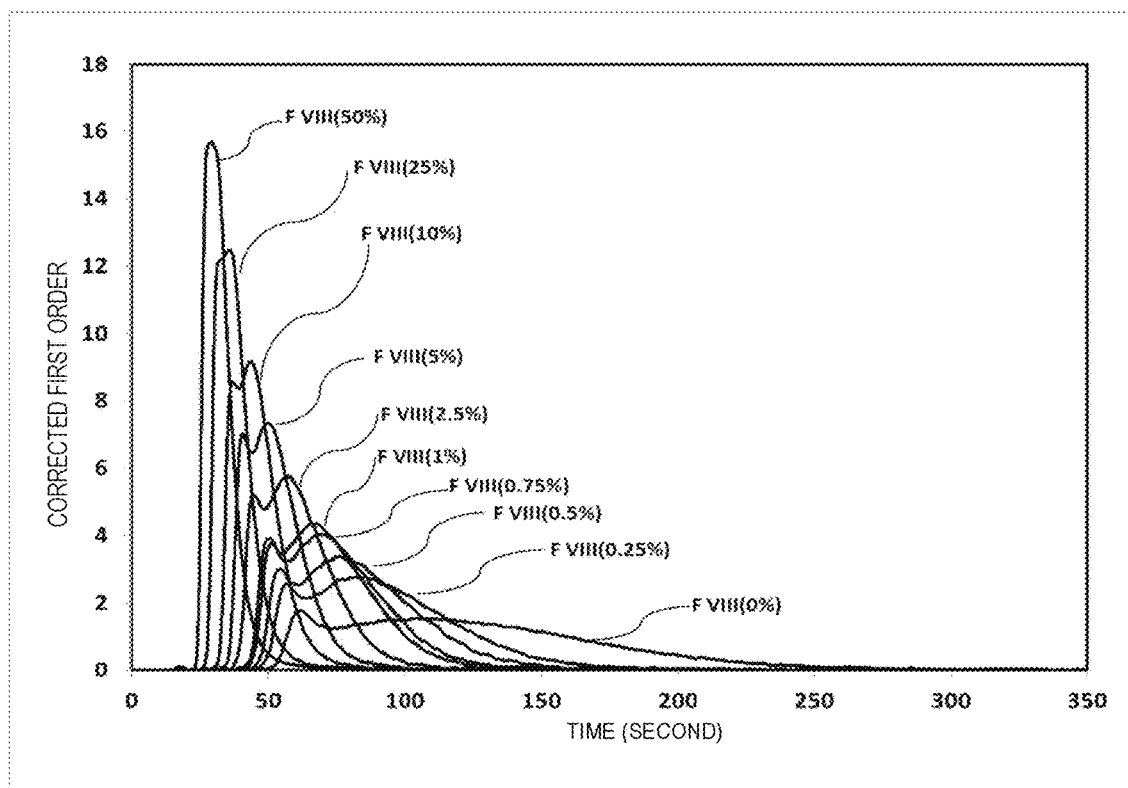
FIG. 26 is a diagram illustrating an example of a corrected first order curve for each factor VIII concentration.

As test plasmas, factor VIII-deficient plasmas having factor VIII concentrations of 50%, 25%, 10%, 5%, 2.5%, 1%, 0.75%, 0.5%, 0.25%, and 0%, respectively (hereinafter, referred to as FVIII (50%), FVIII (25%), FVIII (10%), FVIII (5%), FVIII (2.5%), FVIII (1%), FVIII (0.75%), FVIII (0.5%), FVIII (0.25%), and FVIII (0%)) were prepared, and measurement of APTT was performed on the test plasmas to obtain a corrected first order curve, which is illustrated in FIG. 26. As illustrated in FIG. 26, the shape of the corrected first order curve is as follows. As the factor VIII concentration decreased, the maximum peak height decreased, and the peak shape became flattened. In addition, as the factor VIII concentration decreased, a bimodal peak appeared.

Figure 27:
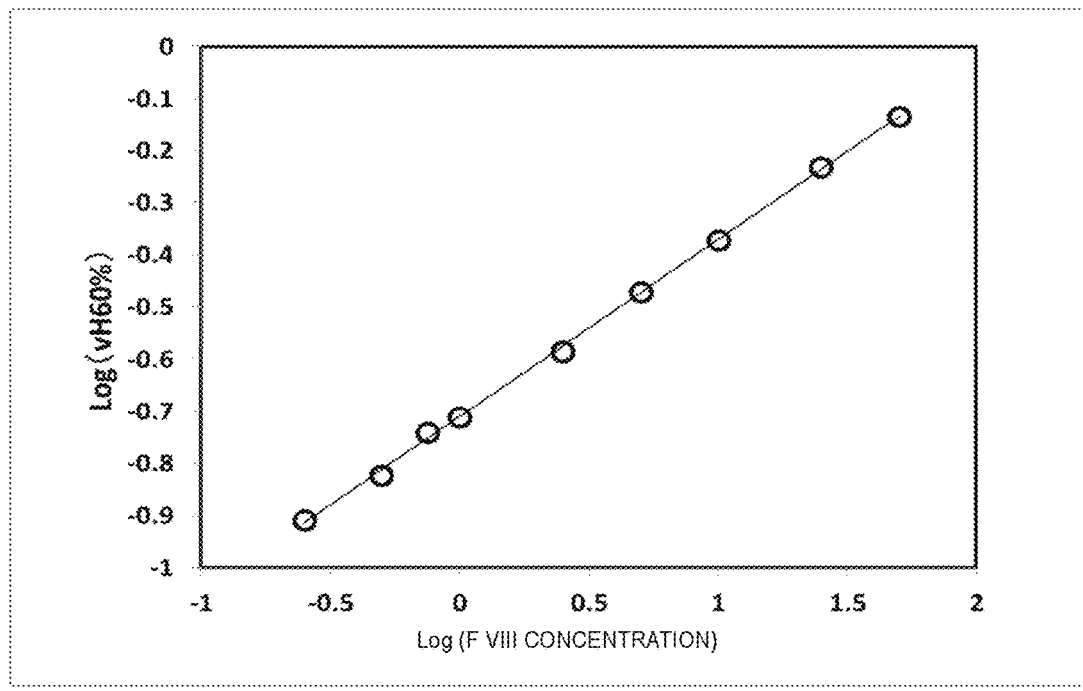
FIG. 27 is a diagram illustrating an example of a relationship between a logarithm of a factor VIII concentration and a logarithm of center-of-gravity height vH60%.

A center-of-gravity point (vT, vH) was determined by setting calculation target area value S to 60%. FIG. 27 is a graph illustrating a relationship between a logarithmic conversion value of a factor VIII concentration (%) and a logarithmic conversion value of center-of-gravity height vH60%. It has been revealed that there is a good linear relationship between a logarithmic conversion value of a factor VIII concentration (%) and a logarithmic conversion value of center-of-gravity height vH60%. From this, it has been revealed that the factor VIII concentration can be calculated, that is, a factor VIII deficiency level can be determined by using an evaluation parameter related to a center-of-gravity point such as center-of-gravity height vH.

5.2.3. Regarding Time Ratio vTB

A time ratio vTB was analyzed for various coagulation factor-deficient plasmas. As evaluation parameters obtained when the calculation target area value is set to x %, center-of-gravity time vT of a center-of-gravity point is represented by vTx %, peak width vB is represented by vBx %, and time ratio vTB is represented by vTBx %. Time ratio vTB is represented by vTBx %=(vTx %/vBx %)×100.

Regarding various factor-deficient plasmas, for cases where the concentrations of various factors are 0%, 0.25%, 0.5%, 0.75%, 1%, 2.5%, 5%, 10%, 25%, and 50%, when calculation target area value S is set to 5%, 10%, 20%, 30%, 40%, 50%, 60%, 70%, 80%, 90%, and 95%, a relationship between the concentrations of the various deficient factors and time ratio vTB are illustrated in FIGS. 28A, 28B, 28C, 28D, 28E, 28F, 28G, 28H, 28I, 28J, and FIG. 28K, respectively. In each of the drawings, the horizontal axis indicates a logarithm of the concentration (%) of a coagulation factor. In each of the drawings, the vertical axis indicates a logarithm of time ratio vTB. In each of the drawings, data related to a factor V-deficient plasma (FV), a factor VIII-deficient plasma (FVIII), a factor IX-deficient plasma (FIX), a factor X-deficient plasma (FX), a factor XI-deficient plasma (FXI), a factor XII-deficient plasma (FXII), and a prekallikrein-deficient plasma (PK) are illustrated. Note that in the measurement of APTT in which the factor XII concentration of the factor XII-deficient plasma was 0% and 0.25%, data thereof was not plotted because the coagulation reaction was not ended within the measurement time.

Figure 32:
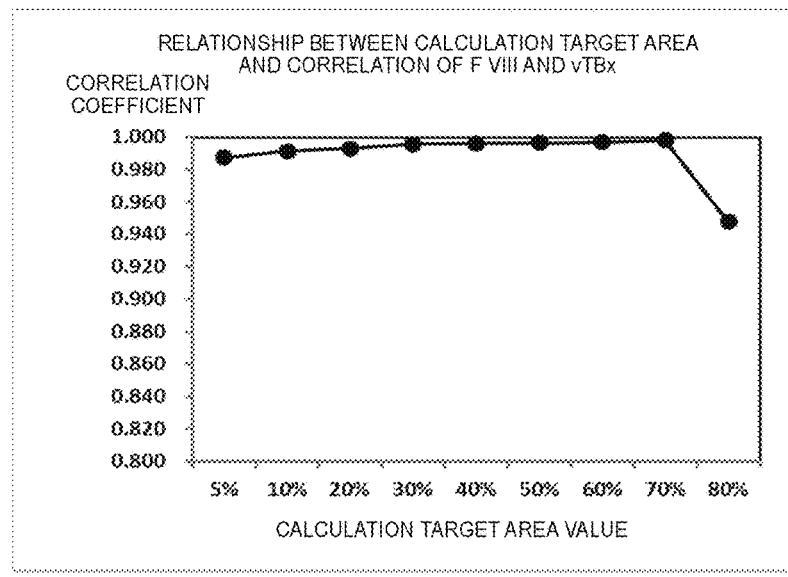
FIG. 32 is a diagram illustrating an example of a relationship of a correlation coefficient between a logarithm of a factor VIII concentration and a logarithm of a time ratio, obtained for each calculation target area value.

FIG. 29 illustrates, for each factor VIII concentration, a value of time ratio vTBx % when calculation target area value S is set to each value. FIG. 30 illustrates, for each factor VIII concentration, the order of a value of each time ratio vTBx % when being counted from the lowest among time ratios vTBx % for all the coagulation factor-deficient plasmas illustrated in a corresponding drawing out of FIGS. 28A to 28K. For example, in the result illustrated in FIG. 28A, when time ratios vTB are arranged in ascending order, FVIII (0%), FVIII (0.25%), FVIII (0.5%), FVIII (0.75%), FVIII (1%), FVIII (2.5%), FIX (0%), FVIII (5%), FXI (0%), FXI (0.25%), FVIII (10%), . . . , and therefore the orders of FVIII (0%), FVIII (0.25%), FVIII (0.5%), FVIII (0.75%), FVIII (1%), FVIII (2.5%), FVIII (5%), and FVIII (10%), are 1, 2, 3, 4, 5, 6, 8, and 11, respectively. FIG. 31 illustrates, for the factor VIII-deficient plasma, a correlation coefficient between Log (vTB) and Log (factor VIII concentration), and a slope and an intercept of a linear regression formula, obtained based on FIGS. 28A to 28K and FIG. 29. FIG. 32 illustrates a graph indicating the correlation coefficients illustrated in FIG. 31.

Figure 28A:
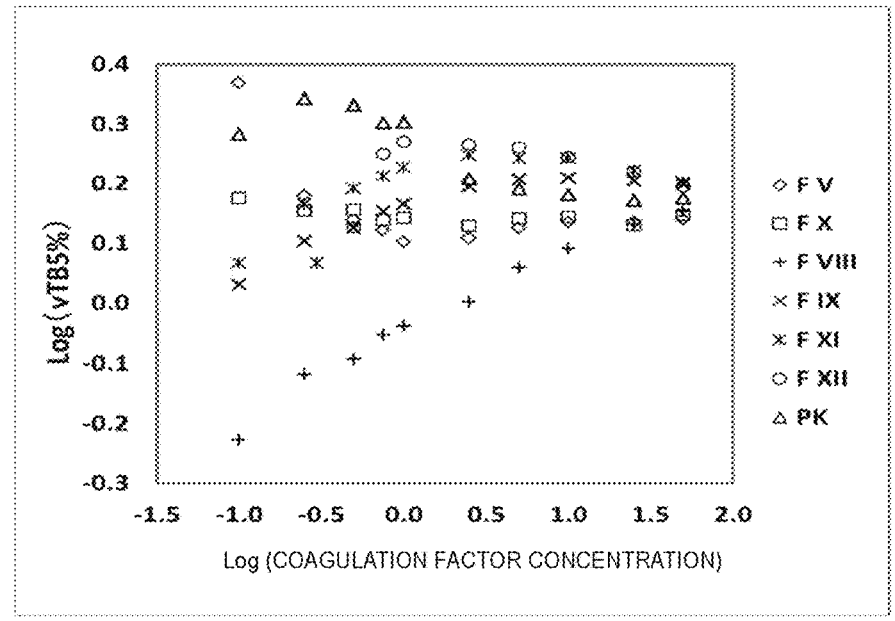
FIG. 28A is a diagram illustrating an example of a relationship between a logarithm of each of the concentrations of various coagulation factors and a logarithm of time ratio vTB5%.
Figure 28B:
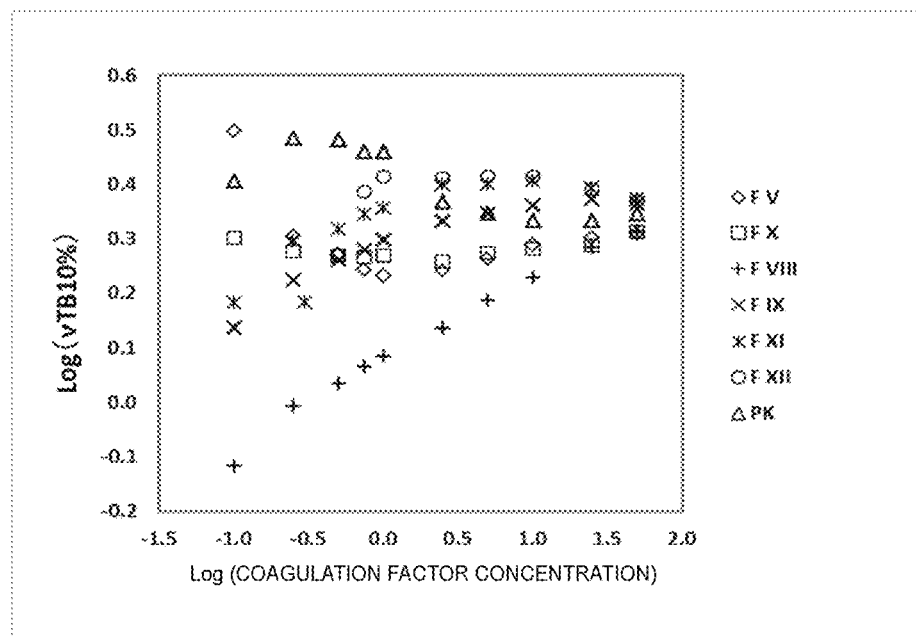
FIG. 28B is a diagram illustrating an example of a relationship between a logarithm of each of the concentrations of various coagulation factors and a logarithm of time ratio vTB10%.
Figure 28C:
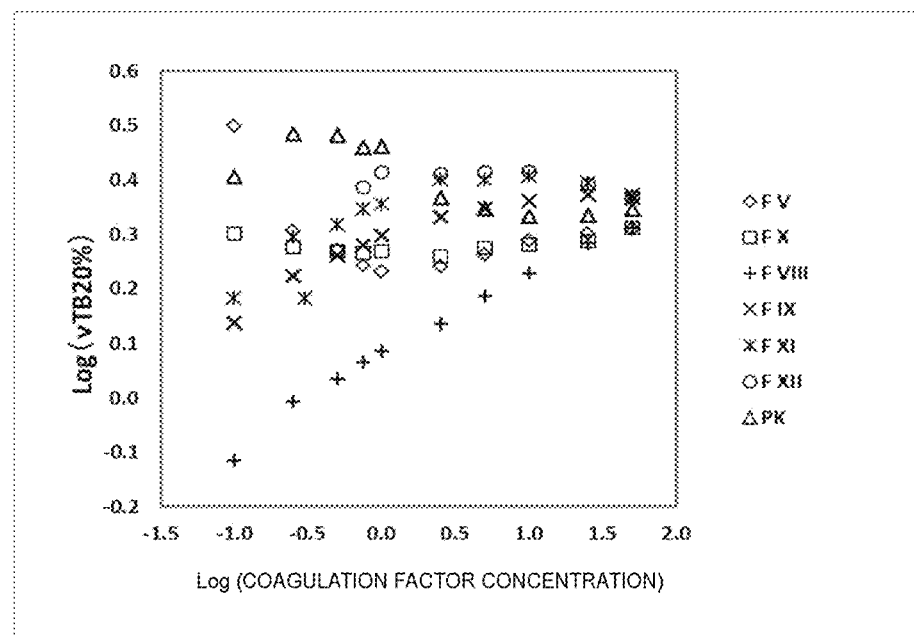
FIG. 28D is a diagram illustrating an example of a relationship between a logarithm of each of the concentrations of various coagulation factors and a logarithm of time ratio vTB30%.
FIG. 28E is a diagram illustrating an example of a relationship between a logarithm of each of the concentrations of various coagulation factors and a logarithm of time ratio vTB40%.
FIG. 28F is a diagram illustrating an example of a relationship between a logarithm of each of the concentrations of various coagulation factors and a logarithm of time ratio vTB50%.
FIG. 28G is a diagram illustrating an example of a relationship between a logarithm of each of the concentrations of various coagulation factors and a logarithm of time ratio vTB60%.
FIG. 28H is a diagram illustrating an example of a relationship between a logarithm of each of the concentrations of various coagulation factors and a logarithm of time ratio vTB70%.
FIG. 28I is a diagram illustrating an example of a relationship between a logarithm of each of the concentrations of various coagulation factors and a logarithm of time ratio vTB80%.
FIG. 28J is a diagram illustrating an example of a relationship between a logarithm of each of the concentrations of various coagulation factors and a logarithm of time ratio vTB90%.
FIG. 28K is a diagram illustrating an example of a relationship between a logarithm of each of the concentrations of various coagulation factors and a logarithm of time ratio vTB95%.
Figure 28D:
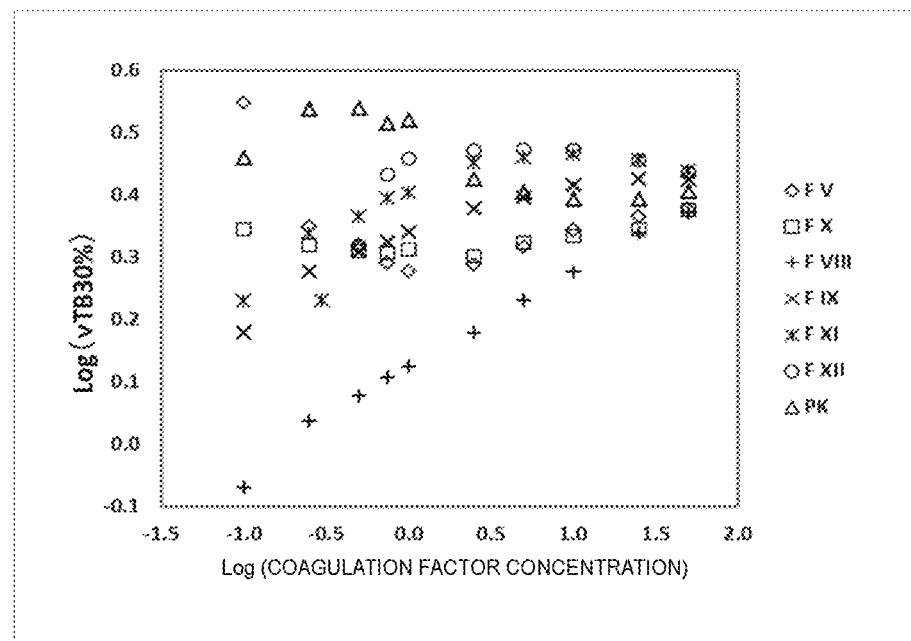
Figure 28E:
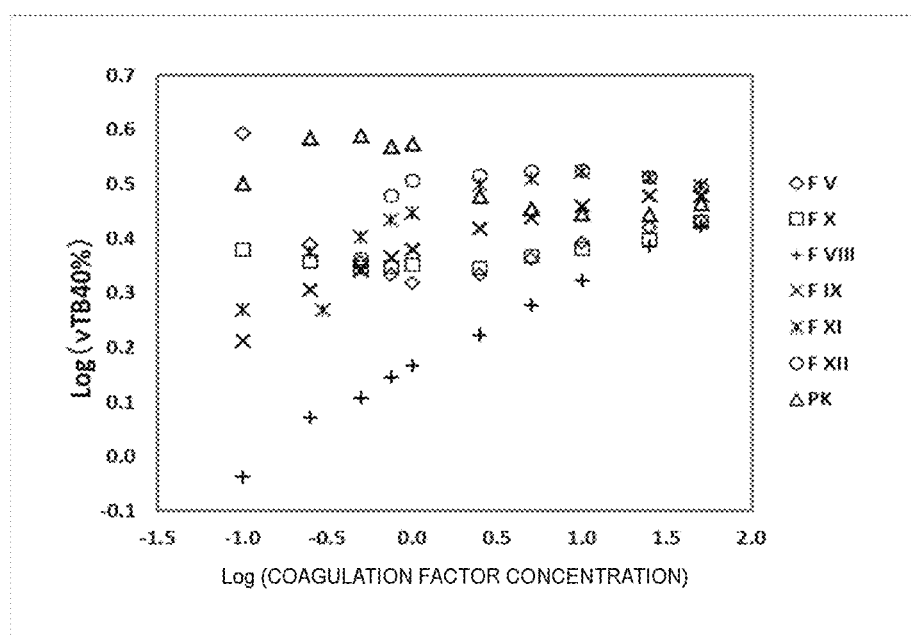
Figure 28F:
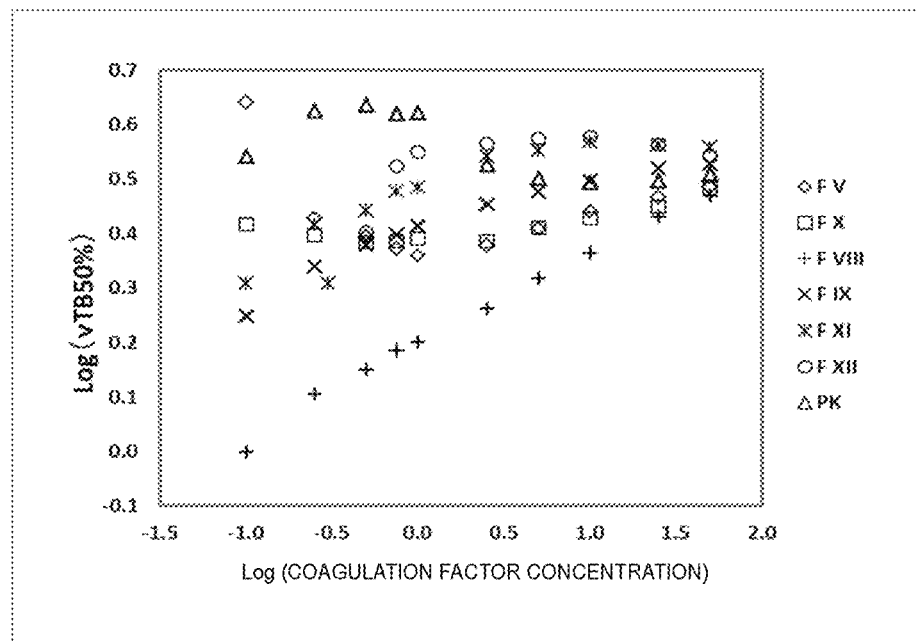
Figure 28G:
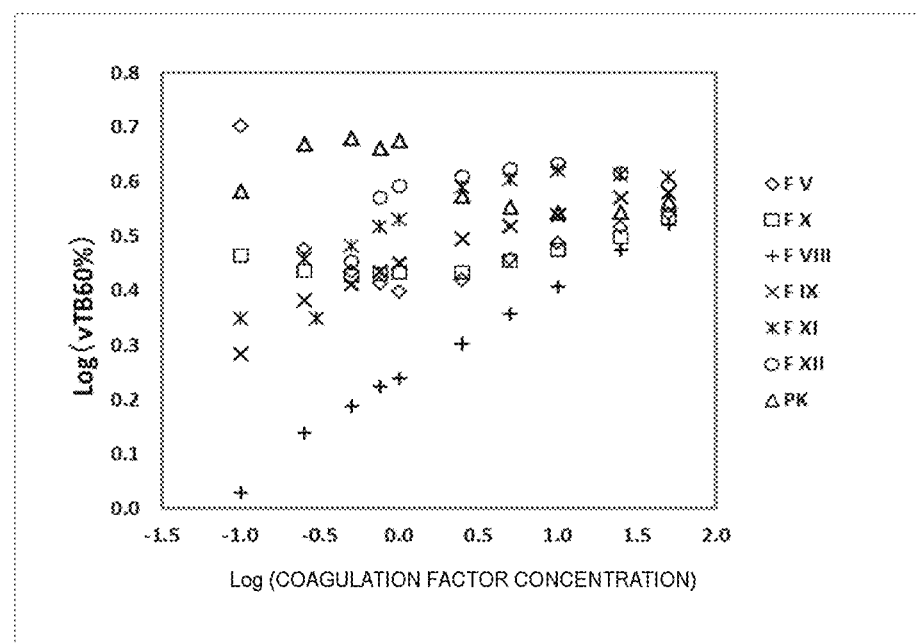
Figure 28H:
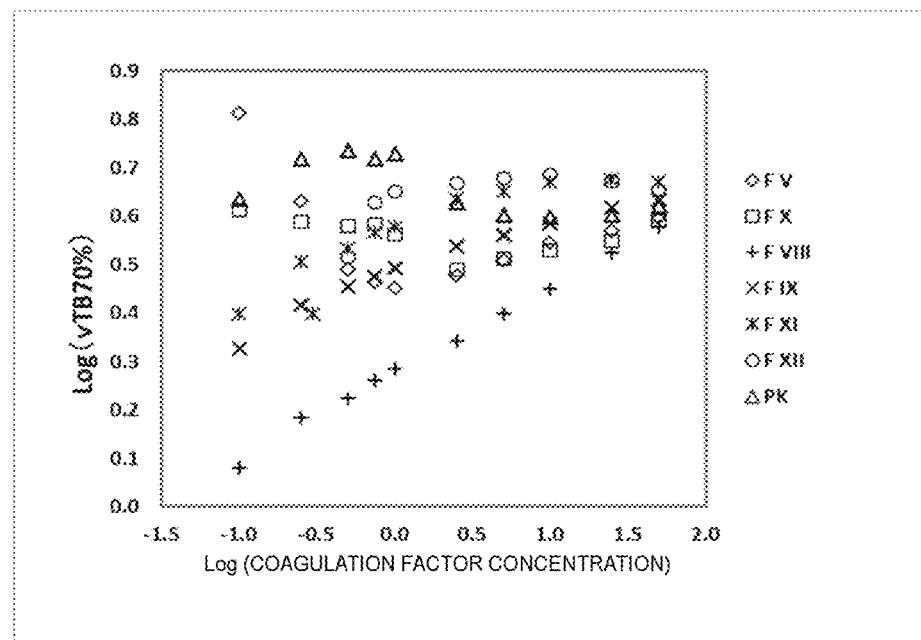
Figure 28I:
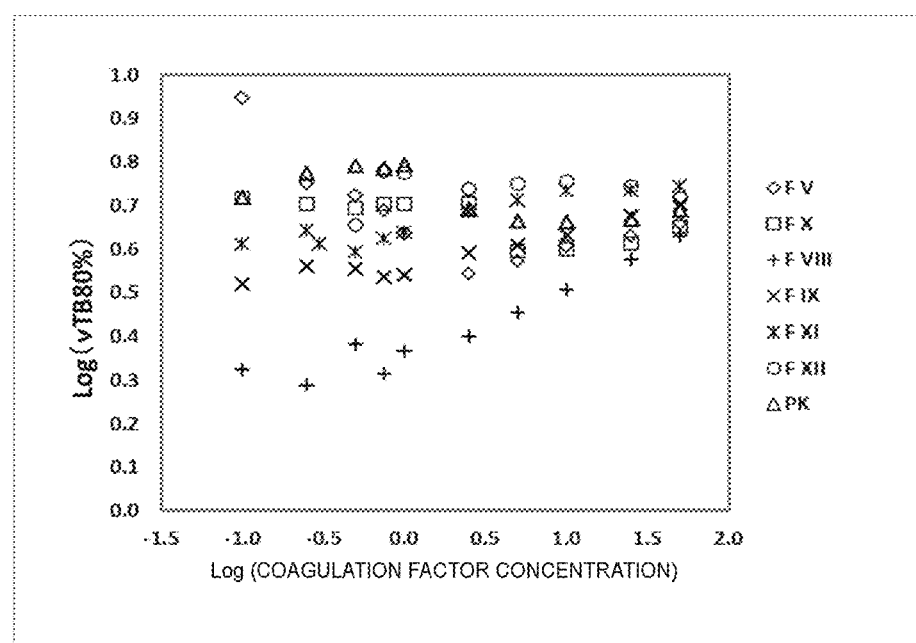
Figure 28J:
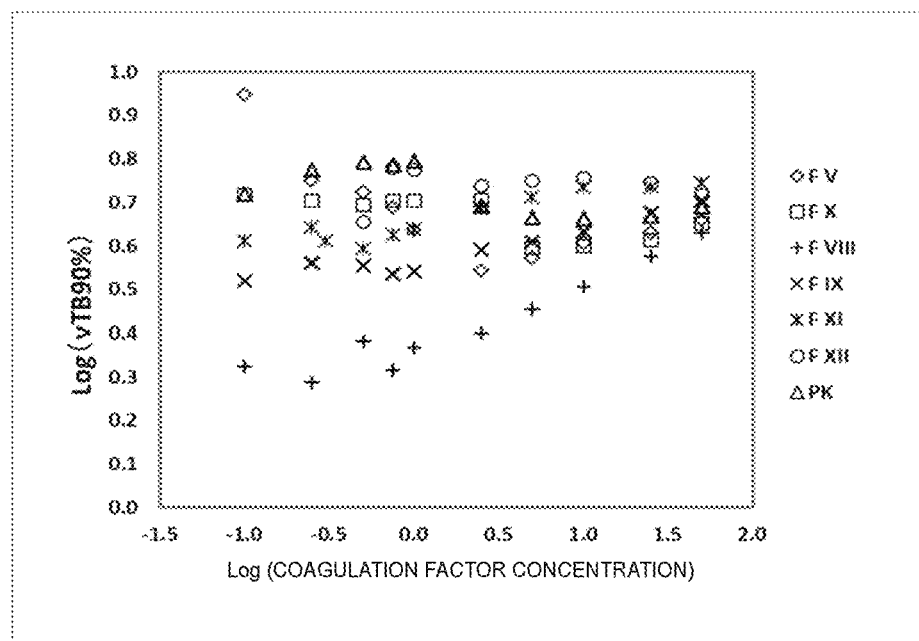
Figure 28K:
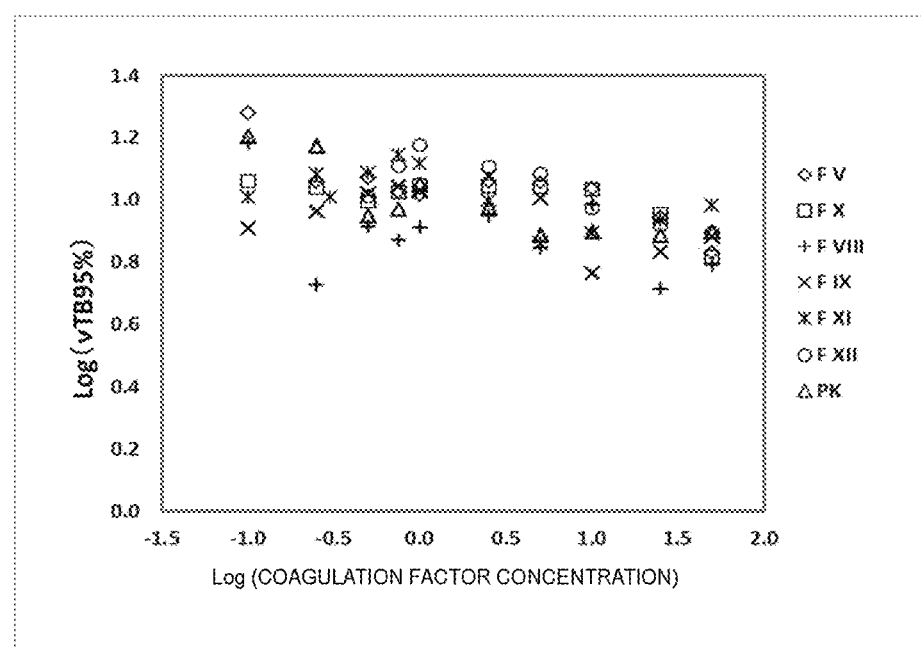

Based on FIGS. 28A and 30, the following can be said. For example, when calculation target area value S is set to 5%, Log (vTB5%)≤0 is satisfied only when factor VIII is deficient, and only when the factor VIII concentration is 2.5% or less. That is, at a factor VIII concentration of 2.5% or less, data of the factor VIII-deficient plasma can be distinguished from data of another coagulation factor-deficient plasma. That is, it can be identified that a cause of prolongation of coagulation time is factor VIII deficiency. There are some unclear points other than the factors examined here, but it can be seen that among the various factors examined here, at least factor VIII deficiency can be identified. Even if other factors cannot be identified by this method, this method is effective because other factors can be identified by another method.

When calculation target area value S is set from 5% to 30%, similarly, at a factor VIII concentration of 2.5% or less, data of the factor VIII-deficient plasma can be distinguished from data of another coagulation factor-deficient plasma. That is, it can be identified that a cause of prolongation of coagulation time is factor VIII deficiency. This corresponds to the fact that in FIGS. 28A to 28D, time ratio vTB obtained for the factor VIII-deficient plasma is clearly lower than time ratio vTB obtained for another coagulation factor-deficient plasma. As illustrated in FIG. 31, when calculation target area value S is set from 5% to 30%, a high correlation coefficient is obtained. Therefore, it can be seen that the factor VIII concentration can be calculated by using a regression line obtained by a least squares method as a calibration curve.

When calculation target area value S is set from 40% to 70%, at a factor VIII concentration of 1% or less, data of the factor VIII-deficient plasma can be distinguished from data of another coagulation factor-deficient plasma. That is, it can be identified that a cause of prolongation of coagulation time is factor VIII deficiency. This corresponds to the fact that in FIGS. 28E to 28H, at a factor VIII concentration of 1% or less, time ratio vTB obtained for the factor VIII-deficient plasma is lower than time ratio vTB obtained for another coagulation factor-deficient plasma. As illustrated in FIG. 31, when calculation target area value S is set from 40% to 70%, a high correlation coefficient is obtained. Therefore, it can be seen that the factor VIII concentration can be calculated by using a regression line obtained by a least squares method as a calibration curve. Note that as illustrated in FIGS. 31 and 32, a maximum correlation coefficient was obtained when calculation target area value S was 70%.

When calculation target area value S is set to 80%, at a factor VIII concentration of 10% or less, data of the factor VIII-deficient plasma can be distinguished from data of another coagulation factor-deficient plasma. That is, it can be identified that a cause of prolongation of coagulation time is factor VIII deficiency. However, as illustrated in FIG. 31, the correlation coefficient is relatively low, which is not suitable for calculating the factor VIII concentration.

Note that when calculation target area value S is set to 90% or more, data of the factor VIII-deficient plasma cannot be distinguished from data of another coagulation factor-deficient plasma. That is, a cause of prolongation of coagulation time cannot be identified.

From the above, it has been revealed that by setting calculation target area value S to 80% or less and determining time ratio vTB, it is possible to identify whether or not APTT is extended by a low factor VIII concentration. In addition, it has been revealed that the factor VIII concentration can be calculated based on time ratio vTB obtained by setting calculation target area value S to 70% or less. In particular, it has been revealed that by setting calculation target area value S to 80% and performing analysis, it is possible to identify whether or not a cause of extending APTT is factor VIII deficiency even at a factor VIII concentration of 10% or less, which is relatively high. In addition, it has been found that by setting calculation target area value S to 70% and performing analysis, the factor VIII concentration can be calculated with high accuracy.

In addition, by referring to FIGS. 28A to 28K, dependence of time ratio vTB on the concentration is observed for factor IX. Therefore, it has been found that when factor IX deficiency can be identified by some method, the concentration of factor IX can also be calculated based on time ratio vTB.

5.2.4. Regarding Flattening Ratio vAB

Flattening ratio vAB was analyzed for various coagulation factor-deficient plasmas. As evaluation parameters obtained when calculation target area value S is set to x %, center-of-gravity height vH of center-of-gravity point W is represented by vHx %, peak width vB is represented by vBx %, and flattening ratio vAB is represented by vABx %. Flattening ratio vAB is represented by vABx %=vHx %/vBx %, multiplied by a constant 100.

Figure 33:
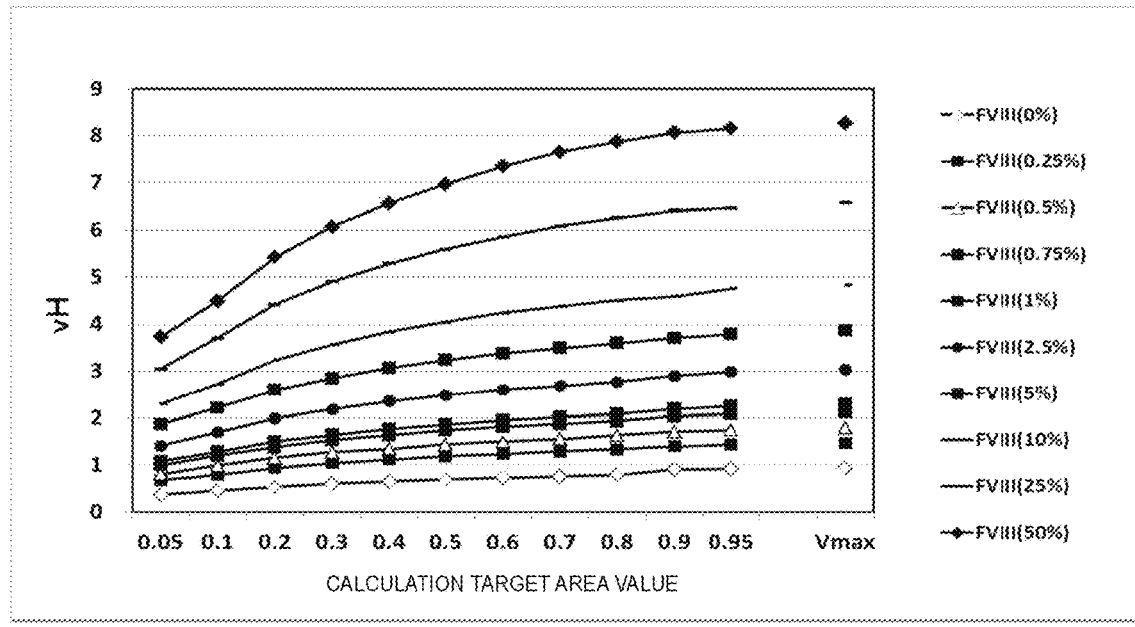
FIG. 33 is a diagram illustrating an example of a relationship between a calculation target area value obtained for each factor VIII concentration and each of center-of-gravity height vH and maximum first order differential value Vmax.
Figure 34:
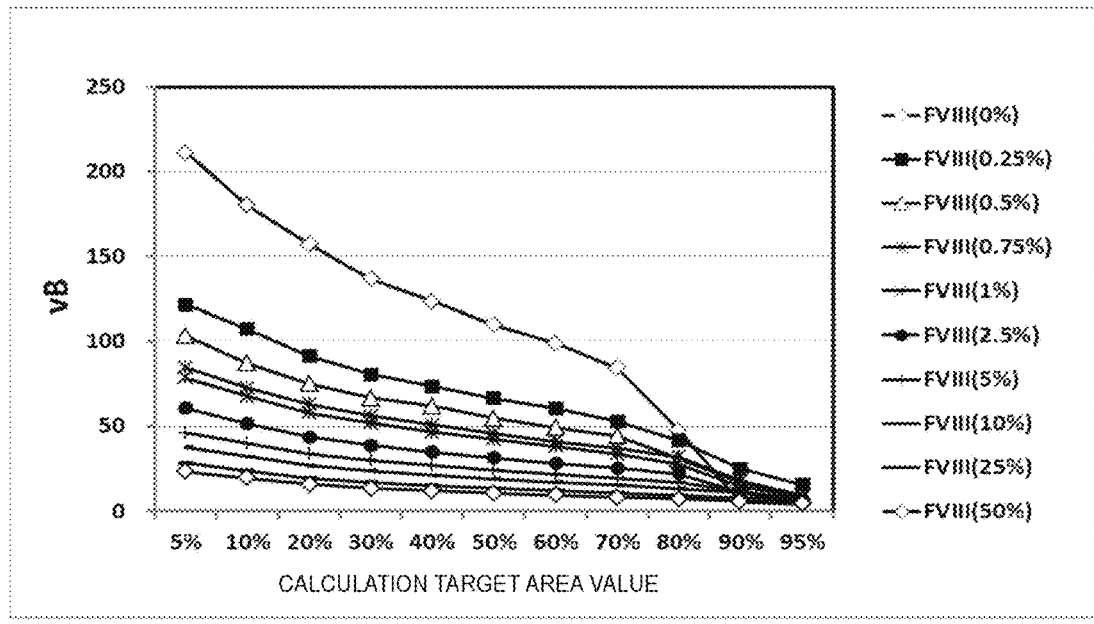
FIG. 34 is a diagram illustrating an example of a relationship between a calculation target area value obtained for each factor VIII concentration and peak width vB.
Figure 35A:
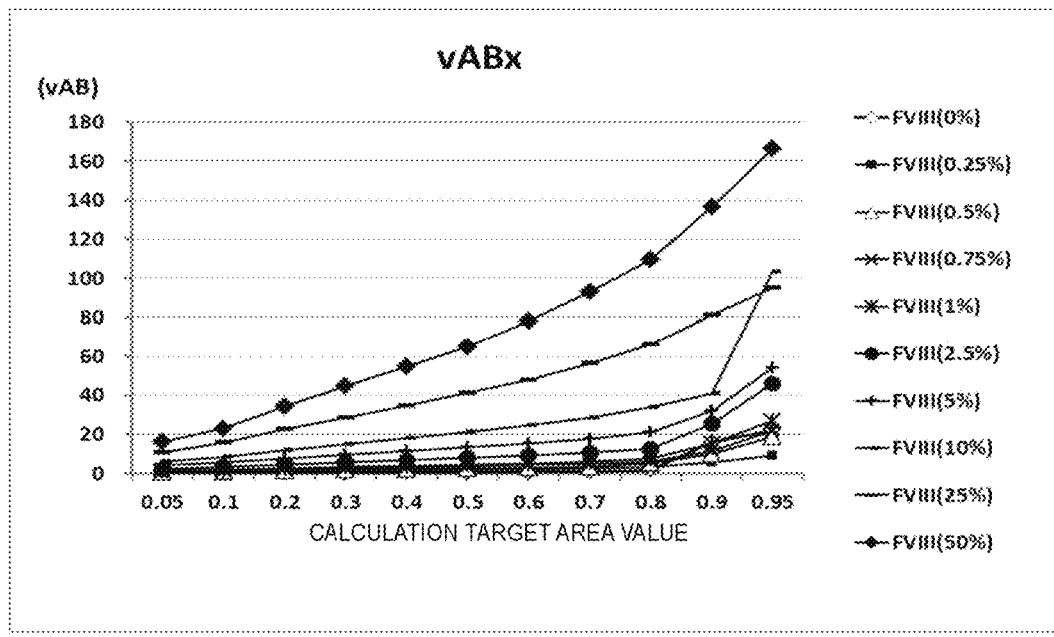
FIG. 35A is a diagram illustrating an example of a relationship between a calculation target area value obtained for each factor VIII concentration and flattening ratio vAB.
Figure 35B:
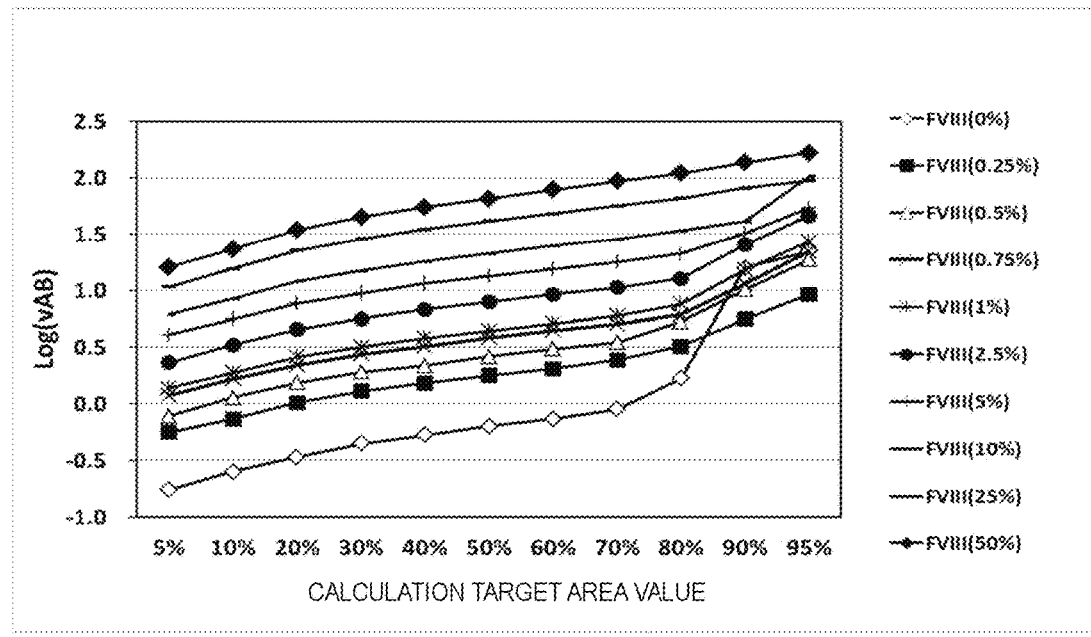
FIG. 35B is a diagram illustrating an example of a relationship between a calculation target area value obtained for each factor VIII concentration and a logarithm of flattening ratio vAB.
Figure 36A:
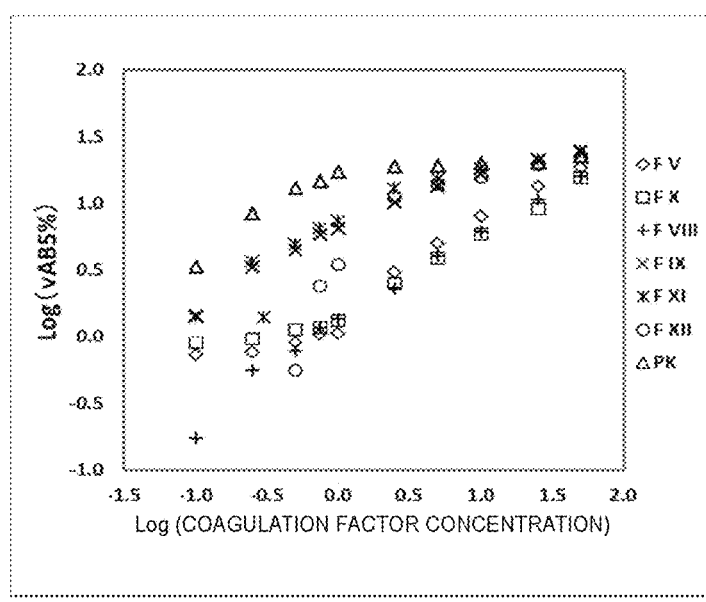
FIG. 36A is a diagram illustrating an example of a relationship between a logarithm of each of the concentrations of various coagulation factors and a logarithm of flattening ratio vAB5%.
Figure 36B:
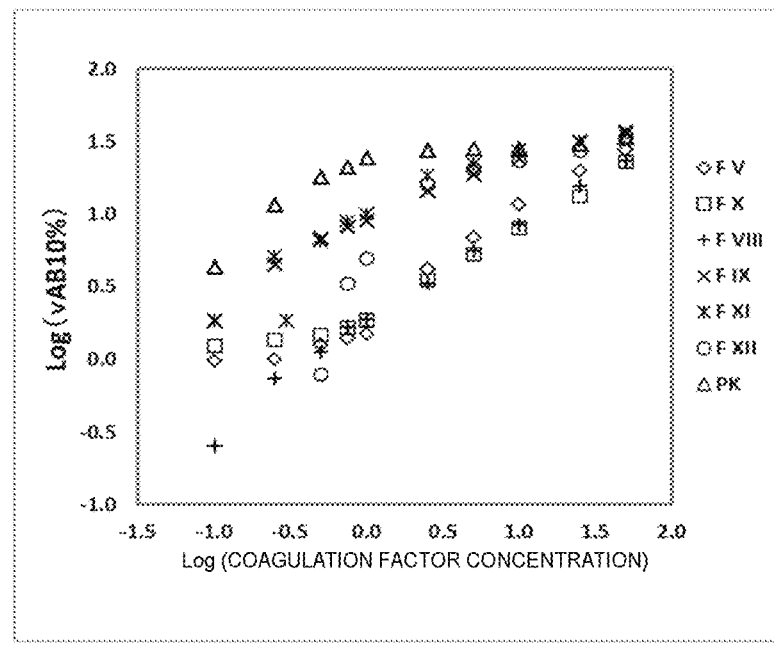
FIG. 36B is a diagram illustrating an example of a relationship between a logarithm of each of the concentrations of various coagulation factors and a logarithm of flattening ratio vAB10%.
Figure 36C:
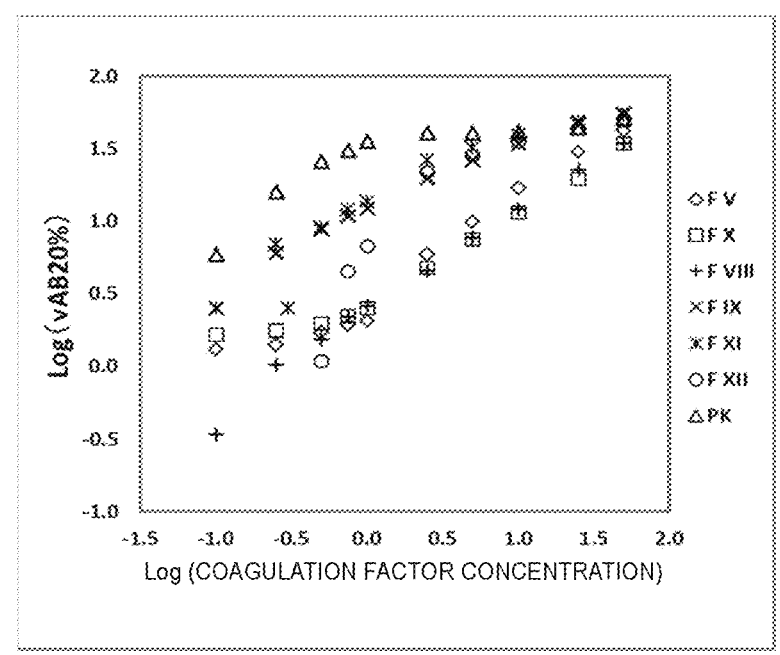
FIG. 36C is a diagram illustrating an example of a relationship between a logarithm of each of the concentrations of various coagulation factors and a logarithm of flattening ratio vAB20%.
Figure 36D:
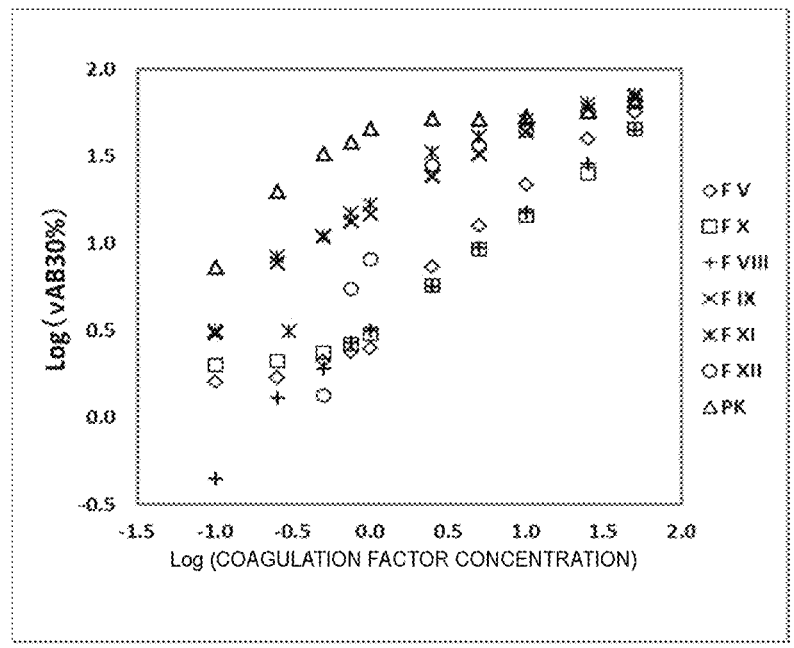
FIG. 36D is a diagram illustrating an example of a relationship between a logarithm of each of the concentrations of various coagulation factors and a logarithm of flattening ratio vAB30%.
Figure 36E:
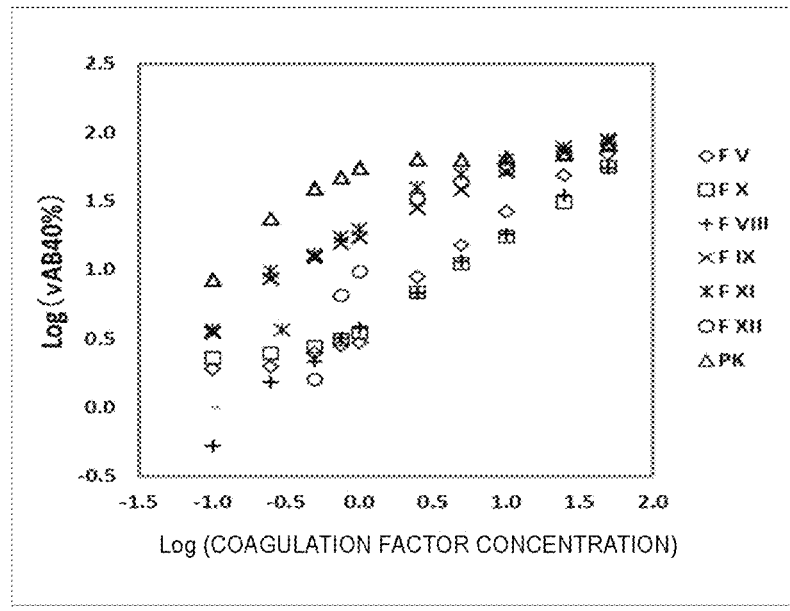
FIG. 36E is a diagram illustrating an example of a relationship between a logarithm of each of the concentrations of various coagulation factors and a logarithm of flattening ratio vAB40%.
Figure 36F:
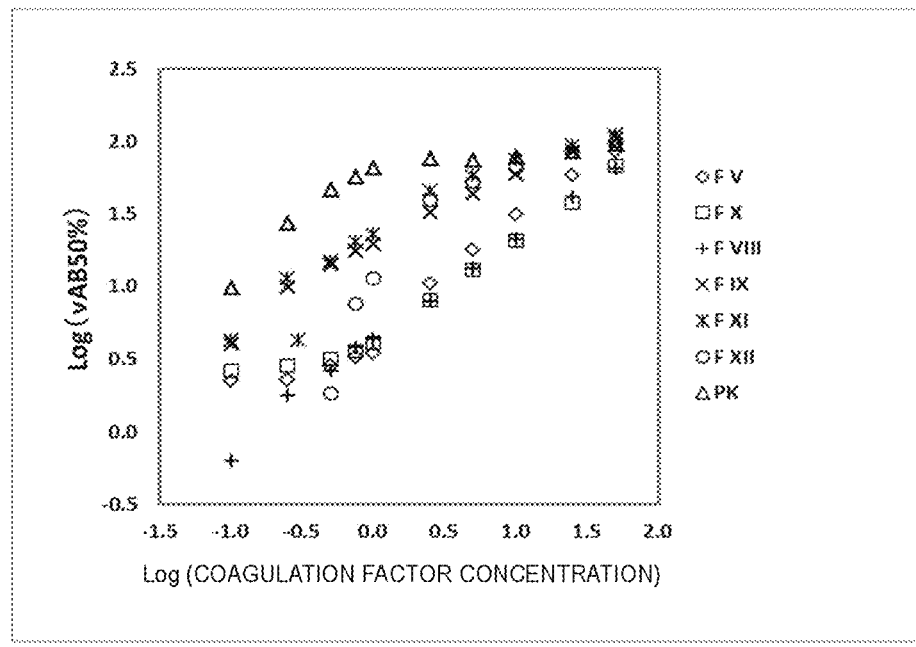
FIG. 36F is a diagram illustrating an example of a relationship between a logarithm of each of the concentrations of various coagulation factors and a logarithm of flattening ratio vAB50%.
Figure 36G:
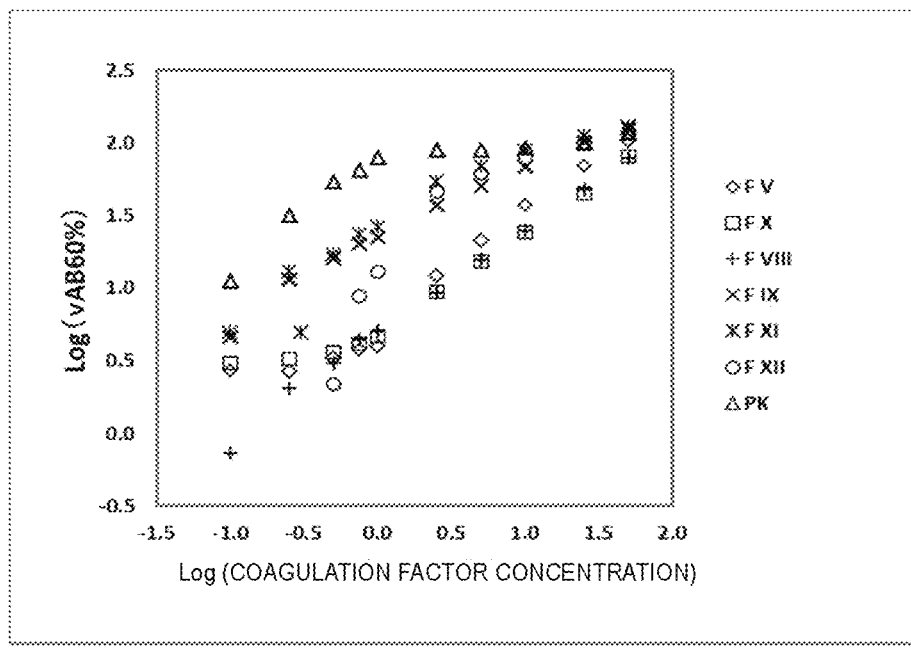
FIG. 36G is a diagram illustrating an example of a relationship between a logarithm of each of the concentrations of various coagulation factors and a logarithm of flattening ratio vAB60%.
Figure 36H:
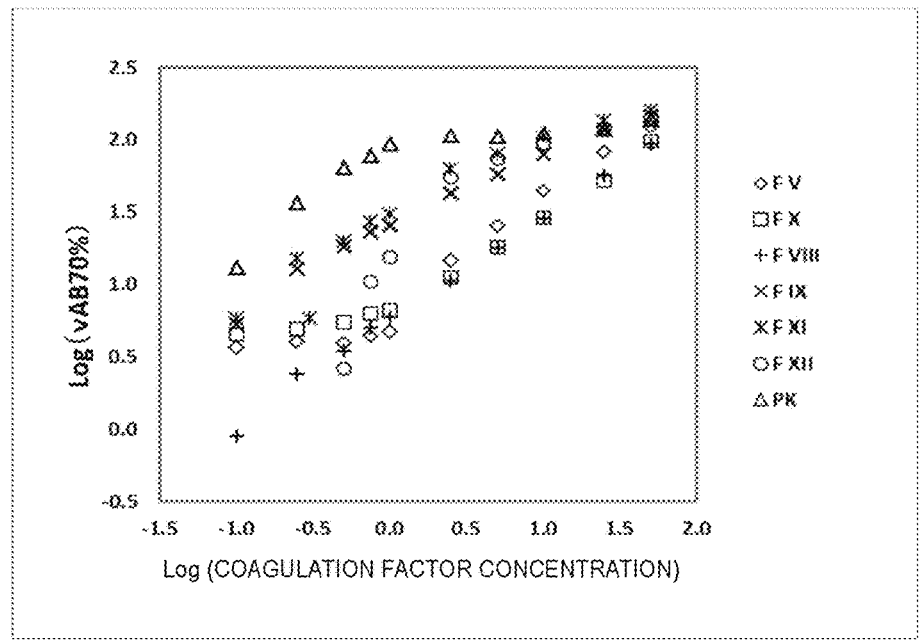
FIG. 36H is a diagram illustrating an example of a relationship between a logarithm of each of the concentrations of various coagulation factors and a logarithm of flattening ratio vAB70%.
Figure 36I:
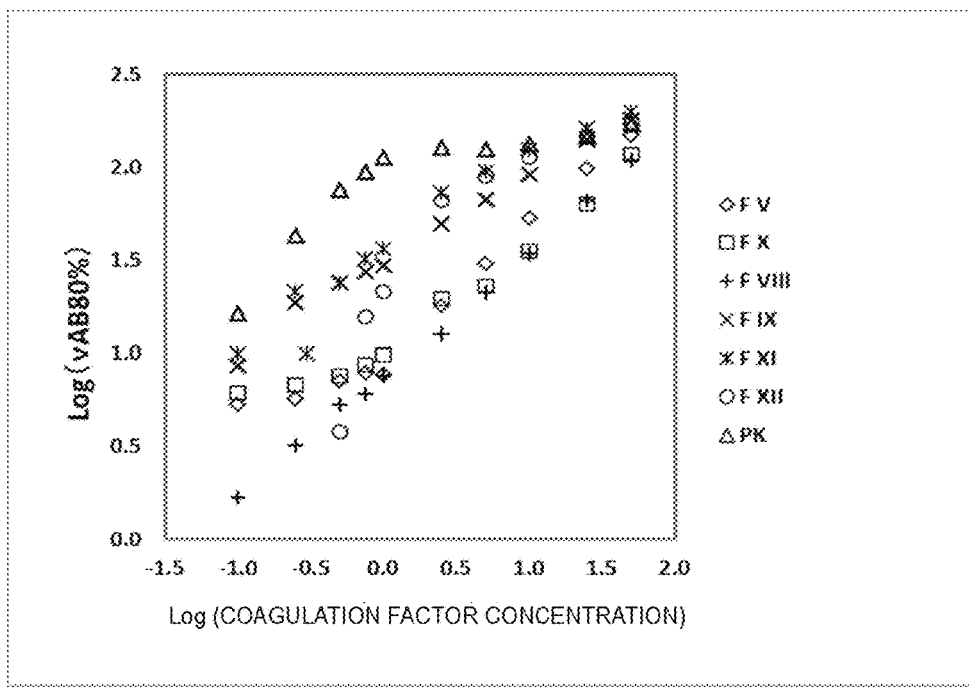
FIG. 36I is a diagram illustrating an example of a relationship between a logarithm of each of the concentrations of various coagulation factors and a logarithm of flattening ratio vAB80%.
Figure 36J:
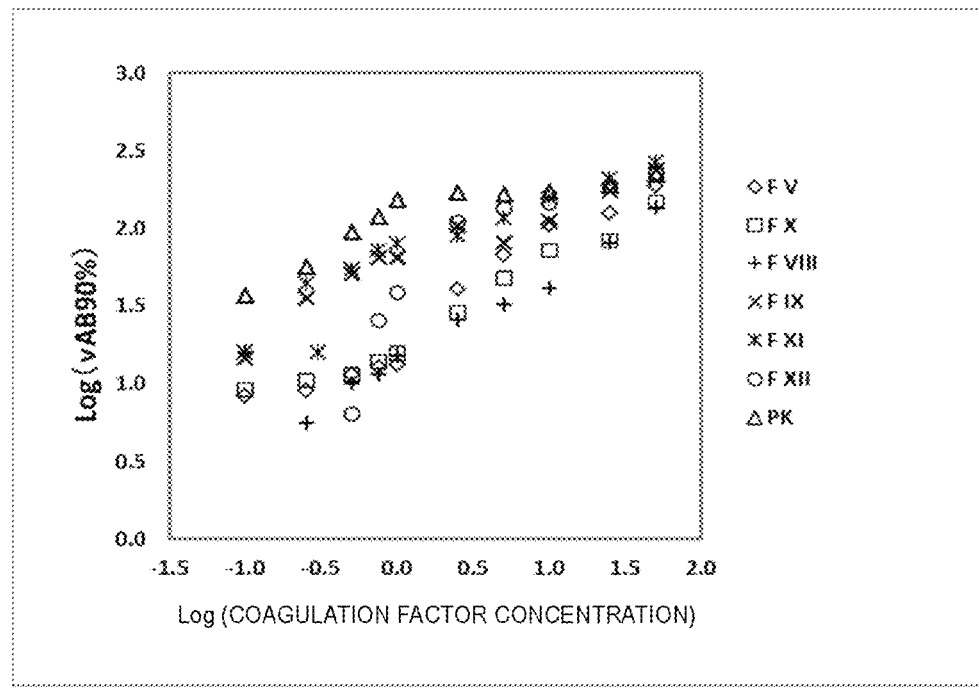
FIG. 36J is a diagram illustrating an example of a relationship between a logarithm of each of the concentrations of various coagulation factors and a logarithm of flattening ratio vAB90%.
Figure 36K:
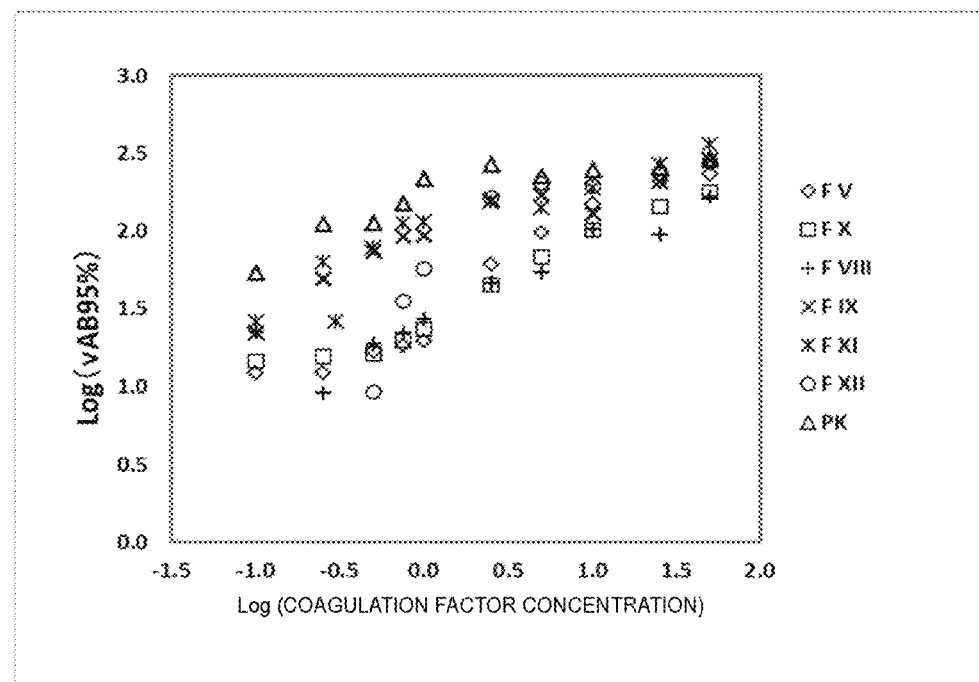
FIG. 36K is a diagram illustrating an example of a relationship between a logarithm of each of the concentrations of various coagulation factors and a logarithm of flattening ratio vAB95%.

Regarding the factor VIII-deficient plasma, for cases where the factor VIII concentrations are 0%, 0.25%, 0.5%, 0.75%, 1%, 2.5%, 5%, 10%, 25%, and 50%, when calculation target area value S is set to 5%, 10%, 20%, 30%, 40%, 50%, 60%, 70%, 80%, 90%, and 95%, a relationship between the various concentrations of the deficient factor and the center-of-gravity height vH are illustrated in FIG. 33. FIG. 33 also illustrates maximum first order differential value Vmax of each factor VIII concentration. FIG. 34 illustrates a relationship between the various concentrations of the deficient factor and peak width vB when calculation target area value S is set under the same conditions. FIG. 35A illustrates flattening ratio vAB obtained based on center-of-gravity height vH and peak width vB. FIG. 35B illustrates a logarithm of flattening ratio vAB.

Relationships between the concentrations of various deficient factors and flattening ratio vAB when calculation target area value S is set under the same conditions are illustrated in FIGS. 36A, 36B, 36C, 36D, 36E, 36F, 36G, 36H, 36I, 36J, and 36K, respectively. In each of the drawings, the horizontal axis indicates a logarithm of the concentration (%) of a coagulation factor, and the vertical axis indicates a logarithm of flattening ratio vAB. In each of the drawings, data related to a factor V-deficient plasma (FV), a factor VIII-deficient plasma (FVIII), a factor IX-deficient plasma (FIX), a factor X-deficient plasma (FX), a factor XI-deficient plasma (FXI), a factor XII-deficient plasma (FXII), and a prekallikrein-deficient plasma (PK) are illustrated. Note that in the measurement of APTT in which the factor XII concentration of the factor XII-deficient plasma was 0% and 0.25%, data thereof was not plotted because the coagulation reaction was not ended within the measurement time.

Figure 37A:
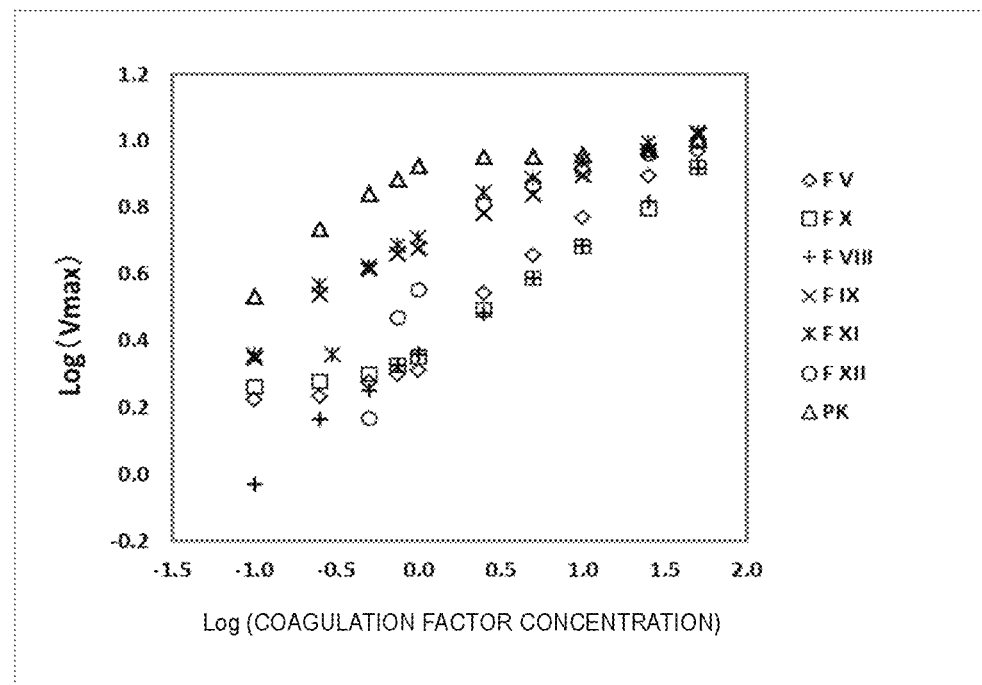
FIG. 37A is a diagram illustrating an example of a relationship between a logarithm of each of the concentrations of various coagulation factors and a logarithm of maximum first order differential value Vmax.
Figure 37B:
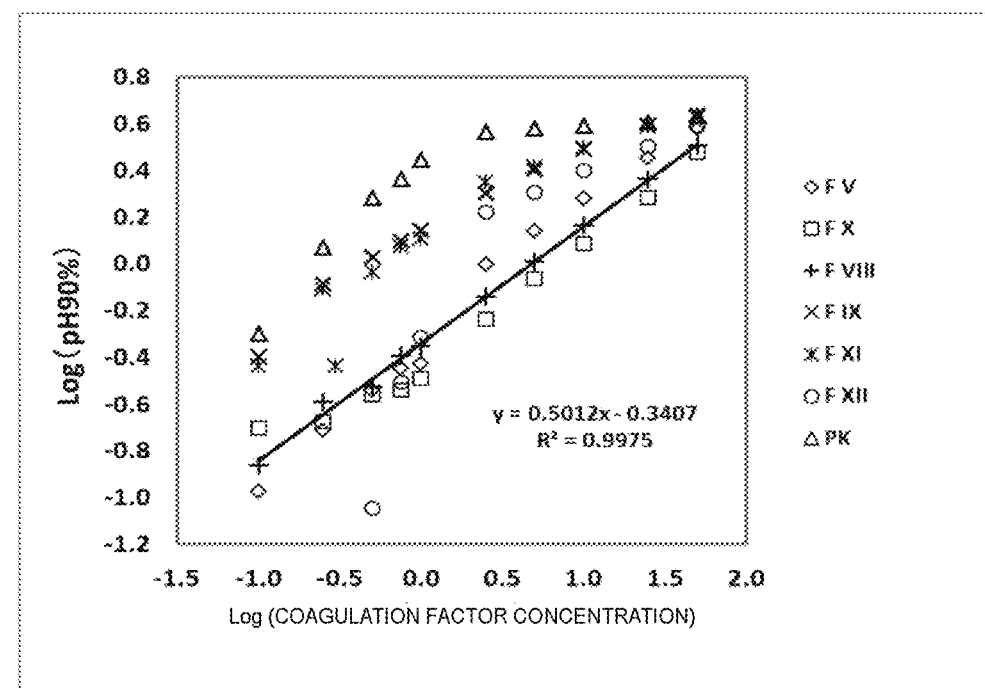
FIG. 37B is a diagram illustrating an example of a relationship between a logarithm of each of the concentrations of various coagulation factors and a logarithm of center-of-gravity height pH90% of a positive peak of a corrected second order curve.

Maximum first order differential value Vmax is illustrated in FIG. 37A similarly. Note that Vmax corresponds to center-of-gravity height vH100% when calculation target area value S is set to 100%. Furthermore, regarding a corrected second order curve obtained by subjecting a corrected first order curve to first order differentiation, center-of-gravity height pH90% of a positive peak obtained when calculation target area value S is set to 90% is illustrated in FIG. 37B similarly.

FIG. 38 illustrates, for each factor VIII concentration, a value of flattening ratio vABx % and maximum first order differential value Vmax (vH100%) when calculation target area value S is set to each value. FIG. 39 illustrates, for the factor VIII-deficient plasma, values related to correlation between Log (factor VIII concentration) and Log (vAB) and correlation between Log (factor VIII concentration) and Log (Vmax), obtained based on FIGS. 36A to 36K and FIG. 38.

As illustrated in FIG. 39, in particular, when calculation target area value S was set to 80% or less, a high correlation coefficient was obtained between Log (factor VIII concentration) and Log (vAB). That is, it has been revealed that the factor VIII concentration can be quantified by using flattening ratio vAB. In addition, it has been revealed that the calibration curve using flattening ratio vAB has a larger slope than the calibration curve using maximum first order differential value Vmax illustrated in FIG. 37A and is highly quantitative. It has been revealed that the calibration curve using flattening ratio vAB has a larger slope than center-of-gravity height pH90% of the positive peak of the corrected second order curve illustrated in FIG. 37B and is highly quantitative.

FIG. 40 illustrates a ratio (recovery ratio) between a factor VIII concentration and a calculated concentration determined from the calibration curve using the values illustrated in FIG. 39. In this drawing, the shaded values indicate values whose calculated concentrations are within ±10% of the factor VIII concentration. By referring to FIG. 40, the recovery ratio of maximum first order differential value Vmax deteriorates at a factor VIII concentration of 0.25% or less. In contrast, vAB80% has a good recovery ratio at a factor VIII concentration of 0.25% or less, however decreases the recovery ratio at a factor VIII concentration of 0.5%, 2.5%, and 50% when the factor VIII concentration is 0.5% or more. Meanwhile, vAB70% has a good recovery ratio at a factor VIII concentration of 0.5% or more excluding 0.75%. That is, by using vAB70% and vAB80%, the factor VIII concentration can be quantified with a high recovery ratio within a range in which the factor VIII concentration is from 0% to 50%.

As described above, it has been revealed that far flattening ratio vAB, an appropriate calibration curve can be selected for each concentration area by changing calculation target area value S. By selecting an appropriate calibration curve, the factor VIII concentration can be accurately determined.

Note that a distribution range of flattening ratio vAB for the factor VIII-deficient plasma could not be distinguished from a distribution range of flattening ratio vAB for another factor-deficient plasma. That is, it has been revealed that it is difficult to identify that a cause of prolongation of coagulation time is factor VIII deficiency based on flattening ratio vAB.

In addition, by referring to FIGS. 36A to 36K, dependence of flattening ratio vAB on the concentration is observed for many coagulation factors. Therefore, it has been found that the concentrations of these coagulation factors can also be calculated based on flattening ratio vAB. In particular, for factor V and factor X, flattening ratio vAB exhibited a good correlation with the factor concentrations regardless of calculation target area value S. For factor IX, flattening ratio vAB exhibited a good correlation with the factor concentration when calculation target area value S was set to a value other than 95%. For factor XI, flattening ratio vAB exhibited a good correlation with the factor concentration when calculation target area value x was set to a value of 50% or more and 80% or less.

By referring to FIG. 37B, center-of-gravity height pH (after logarithmic conversion) of the corrected second order curve with respect to the coagulation factor concentration (after logarithmic conversion) exhibited a very high correlation at all the concentrations in the case of factor VIII, and a good correlation was observed in order of factor V, factor X, factor IX, and factor XI also in the cases of other factors. Therefore, it has been revealed that the concentrations of these factors can also be calculated by using center-of-gravity height pH of the corrected second order curve.

6. Third Example 6.1. Method 6.1.1. Method for Measuring Coagulation Reaction of Blood Specimen As a test plasma, a mixed plasma of a coagulation factor-deficient plasma and a normal plasma was prepared in a similar manner to the second Example. As the coagulation factor-deficient plasma, the factor V-deficient plasma (V), the factor VIII-deficient plasma (VIII), the factor IX-deficient plasma (IX), the factor X-deficient plasma (X), the factor XI-deficient plasma (XI), and the factor XII-deficient plasma (XII) used in the second Example were used. A normal plasma (PNP) was used for comparison. When logarithmic conversion was performed on a coagulation factor concentration in a test plasma (having a concentration of 0%) containing only the coagulation factor-deficient plasma, calculation was performed by assuming that the concentration was 0.1%. Measurement of APTT of each test plasma was performed in the same procedure as in the first Example.

6.1.2. Method for Analyzing Photometric Data

An uncorrected 0th order curve and a corrected 0th order curve were obtained from photometric data in the same procedure as in the first Example. By determining the intra-section average slope according to the above formula (4) in a similar procedure to the first Example from the obtained uncorrected 0th order curve and corrected 0th order curve, an uncorrected first order curve and a corrected first order curve were calculated, respectively. The same calculation was further repeated for the obtained first order curves to calculate an uncorrected second order curve and a corrected second order curve, respectively. Parameters were calculated from the corrected 0th order curve, the corrected first order curve, and the corrected second order curve.

Figure 41A:
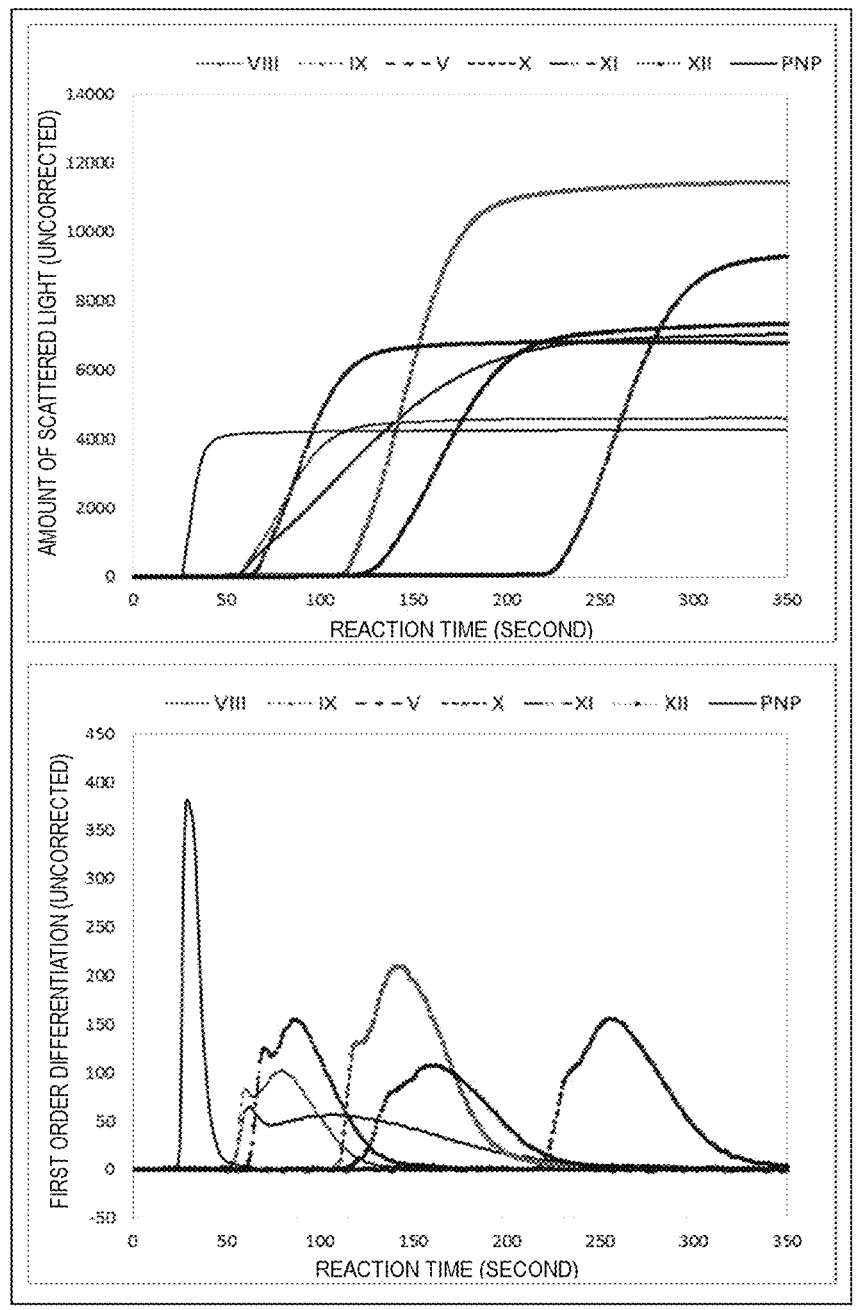
FIG. 41A is a diagram illustrating examples of uncorrected 0th order curves (uncorrected amounts of scattered light) of a normal plasma and various coagulation factor-deficient plasmas and uncorrected first order curves thereof.
Figure 41B:
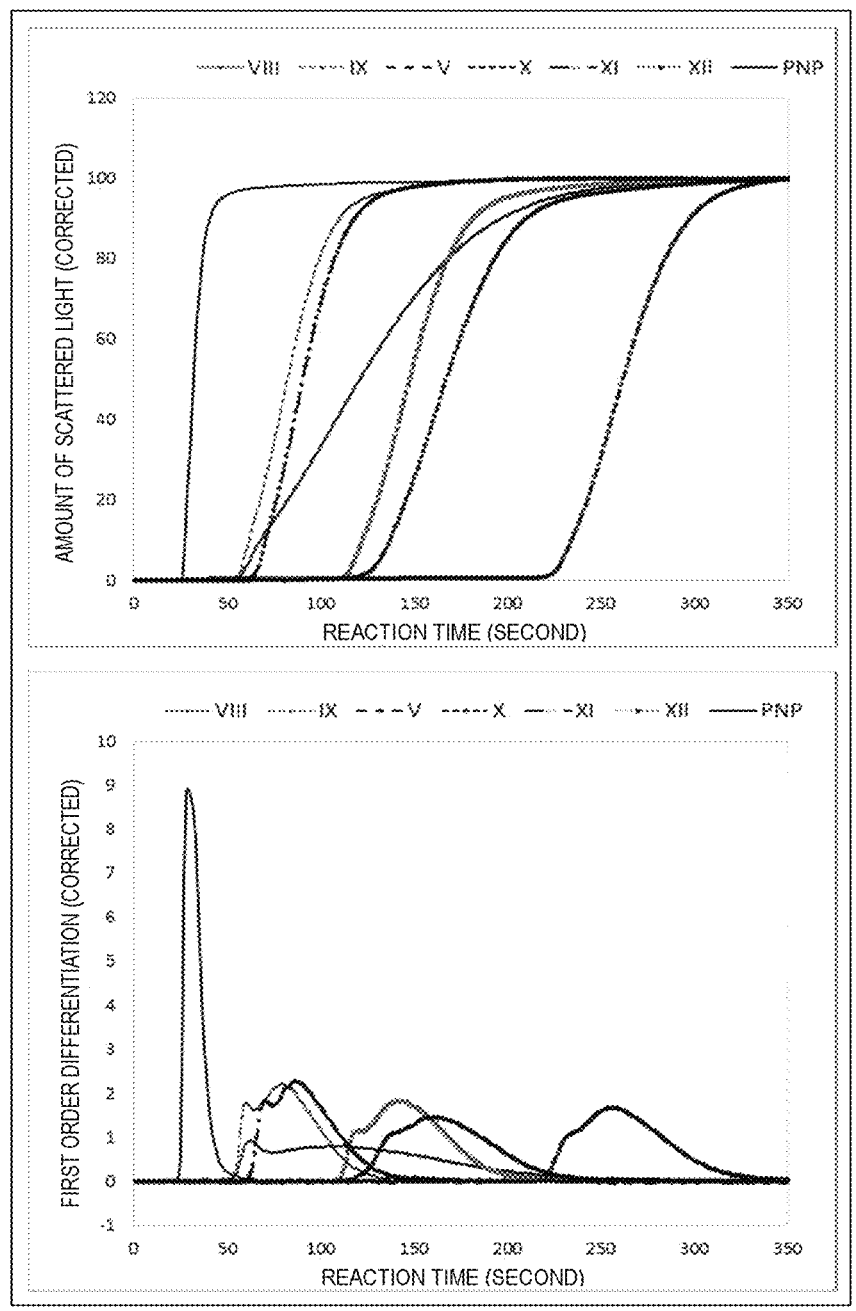
FIG. 41B is a diagram illustrating examples of uncorrected 0th order curves of a normal plasma and various coagulation factor-deficient plasmas and corrected first order curves thereof.
Figure 42A:
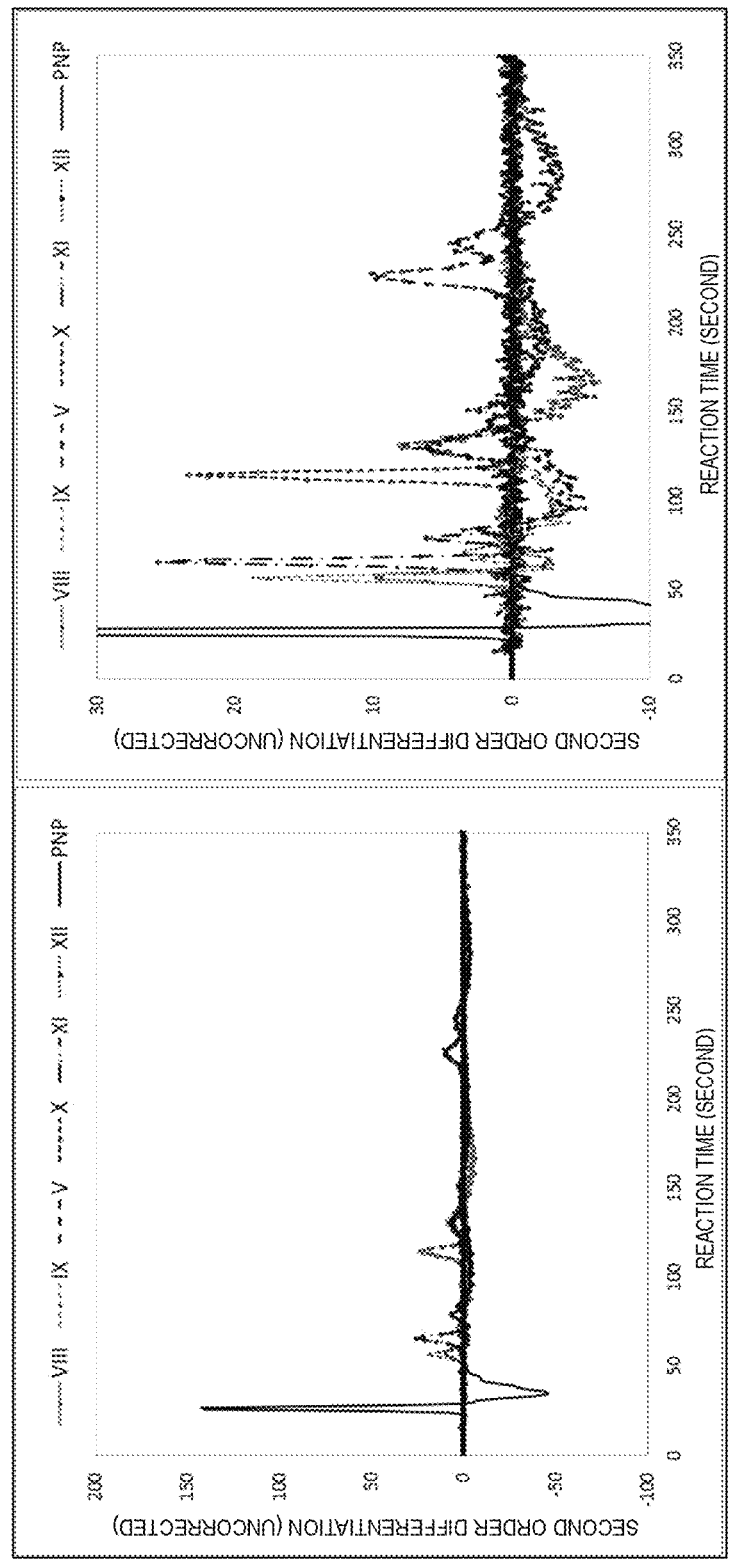
FIG. 42A is a diagram illustrating examples of uncorrected second order curves of a normal plasma and various coagulation factor-deficient plasmas. The right diagram is a diagram obtained by changing the scale of the left diagram in the y-axis direction.
Figure 42B:
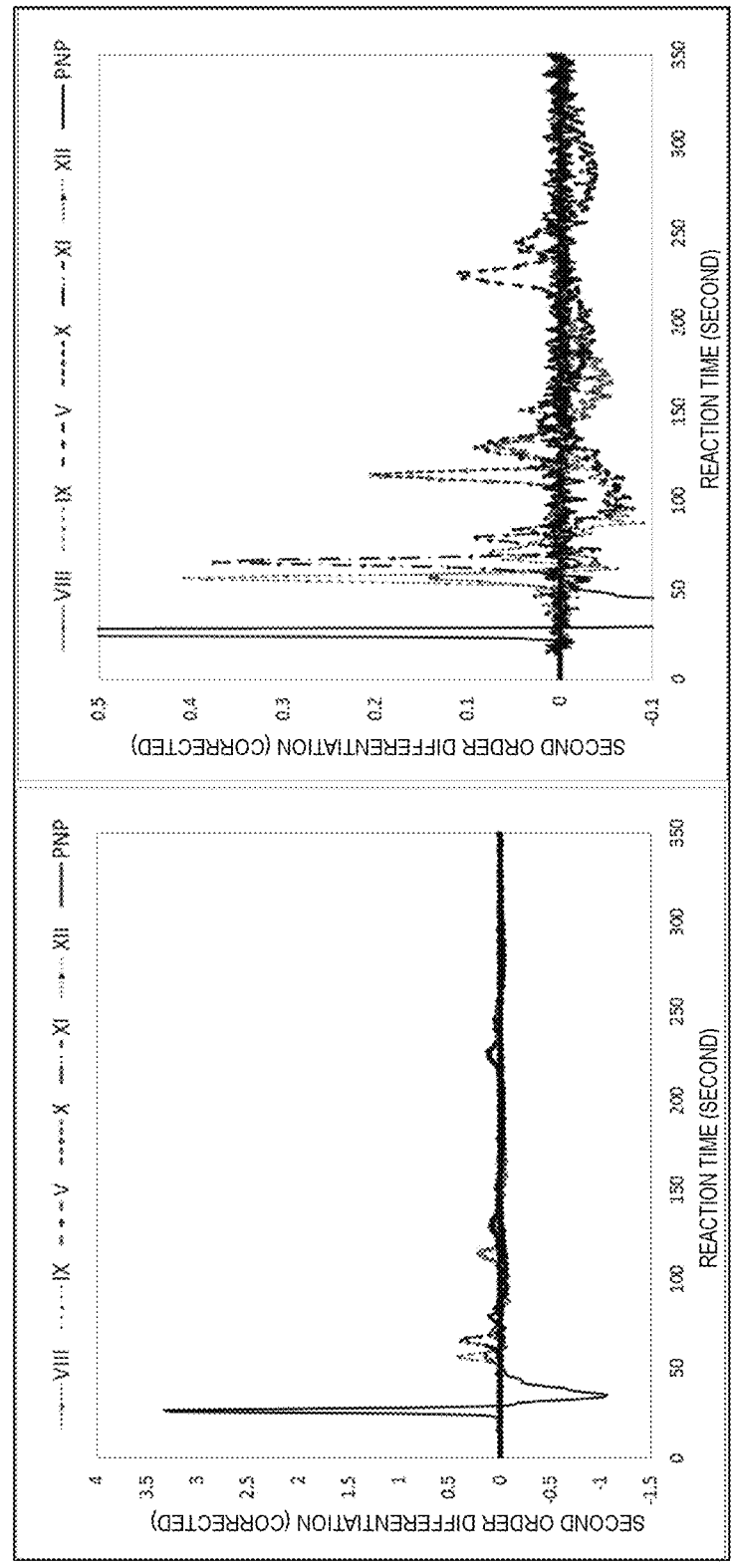
FIG. 42B is a diagram illustrating examples of corrected second order curves of a normal plasma and various coagulation factor-deficient plasmas. The right diagram is a diagram obtained by changing the scale of the left diagram in the y-axis direction.

6.2. Analysis Result and Discussion 6.2.1. Change in Curve Shape Depending on Coagulation Factor FIG. 41A illustrates examples of an uncorrected 0th order curve and an uncorrected first order curve obtained by using coagulation factor deficient plasma (in Example, it was assumed that the factor concentration was 0.1%) as a test plasma. FIG. 41B illustrates examples of a corrected 0th order curve and a corrected first order curve obtained from the same test plasma. FIG. 42A illustrates an example of an uncorrected second order curve obtained from the same test plasma. The right drawing in FIG. 42A is a diagram in which the scale in the y-axis direction of the left drawing in FIG. 42A is changed. FIG. 42B illustrates an example of a corrected second order curve obtained from the same test plasma. The right drawing in FIG. 42B is a diagram in which the scale in the y-axis direction of the left drawing in FIG. 42B is changed. As can be seen from FIGS. 41 and 42, the coagulation time and the height and time of the maximum peak on each of the first order curve and the second order curve differed depending on the type of deficient coagulation factor.

6.2.2. Relationship Between Coagulation Factor Concentration and Evaluation Parameter Table 2 illustrates parameters calculated from corrected 0th to second order curves. Calculation target area value x was set to 0% to 99% when the maximum peak value (Vmax, Amax, Amin) was set to 100%. Note that APTT represents T50 (time required for the 0th order curve to reach 50% of the maximum height). In FIGS. 43A to 43V, the upper drawing illustrates a relationship between a logarithm of each of various coagulation factor concentrations and a logarithm of a parameter value. A calibration curve was created from this relationship. A calculated concentration was calculated from a parameter value based on the calibration curve. In the middle left drawing, correlations of various coagulation factors were plotted such that the X-axis indicates a measured concentration, and the Y-axis indicates a calculated concentration. In the middle right drawing, plot was performed with both axes in logarithmic display such that a correlation at a low concentration could be confirmed. The formulas described below the middle figures are a linear regression formula of a calculated concentration and a correlation coefficient for each coagulation factor concentration.

TABLE 2

| Curve | Drawing | Parameter | Other notation of parameter |
|---|---|---|---|
| 0th order | 43A | APTT | |
| | 43B | T5 | |
| | 43C | T95-T5 | |
| First order | 43D | VmaxT | |
| | 43E | Vmax | |
| Second order | 43F | AmaxT | |
| | 43G | Amax | |
| First order | 43H | vAUC | |
| | 43I | vH | |
| | 43J | vT | |
| | 43K | vTs | |
| | 43L | vTe | |
| | 43M | vTr | |
| | | vB | |
| | | vW | |

TABLE 2-continued

| Curve | Drawing | Parameter | Other notation of parameter |
|---|---|---|---|
| | | vW/vB | |
| | | vB-vW | |
| | 43N | vH/vB | vAB |
| | | vH/vW | vAW |
| | | vT/vB | vTB |
| | | vT/vW | vTW |
| Second order (Positive peak) | 43O | pH | |
| | 43P | pT | |
| | 43Q | pB | |
| | | pW | |
| | | pB-pW | |
| | 43R | pH/pB | pAB |
| | | pT/pB | pTB |
| | | pH/pW | pAW |
| | | pT/pW | pTW |
| | 43S | pAUC | |
| Second order (Negative peak) | 43T | mH | |
| | | mT | |
| | | mB | |
| | | mW | |
| | | mB-mW | |
| | 43U | mH/mB | mAB |
| | | mH/mW | mAW |
| | | mT/mW | mTW |
| | 43V | mAUC | |
| First order | 43W | vHa | |
| | 43X | vTm | |
| Uncorrected first order | 43Y | RvH/RvB | RvAB |

For factor VIII, factor IX, factor V, factor X, factor XI, and factor XII, a parameter in which a linear regression formula of a calculated concentration (Y-axis) with respect to a coagulation factor concentration (X-axis) has a slope of 1±0.1 and a y-intercept of ±1 and a correlation coefficient (R) is 0.9 or more is indicated by "+" in Tables 3 to 8. Table 9 illustrates the number of S values for which a linear regression formula with a "+" condition was obtained for each coagulation factor for each parameter. The parameter for which the linear regression formula of the "+" condition was obtained can be used for measuring the concentration of a coagulation factor or determining deficiency.

TABLE 3

Factor VIII

| Curve | Parameter | | | | | | | | | | | | | |
|---|---|---|---|---|---|---|---|---|---|---|---|---|---|---|
| 0th order | APTT | + | | | | | | | | | | | | |
| First order | Vmax | + | | | | | | | | | | | | |
| Second order | Amax | + | | | | | | | | | | | | |

| | | x value | | | | | | | | | | | | |
|---|---|---|---|---|---|---|---|---|---|---|---|---|---|---|
| Curve | Parameter | 0.5% | 1% | 5% | 10% | 20% | 30% | 40% | 50% | 60% | 70% | 80% | 90% | 95% | 99% |
| First order | vAUC | | | | | | | | | | | | | | + |
| | vH | | | | | | | | + | + | + | + | + | + | + |
| | vT | + | + | + | + | + | + | + | + | + | + | | | | |
| | vTe | | + | | | + | + | + | + | + | + | | | | |
| | vTr | | + | | | + | + | + | + | + | + | | | | |
| | vB | | | | | | + | + | + | + | + | | | | |
| | vW | | | | + | + | + | + | | | | | | | |
| | vB-vW | | | | | | + | | | + | | | | | |
| | vH/vB | | | | | | + | + | + | + | + | | | | |
| | vH/vW | | | | + | + | + | + | + | + | + | | | + | |
| | vT/vB | | | | | | | | + | | | | | | |

TABLE 3-continued

| | | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| | vT/vW | | | | | + | | | | | | | | | |
| | vHa | | | | | + | + | + | + | + | + | + | + | + | + |
| | vTa | + | | + | + | + | + | + | + | + | | + | | | |
| | vTm | | | + | + | + | + | + | + | + | | | | | |
| Second order | pH | | | + | | + | + | + | + | + | + | + | + | + | + |
| | pB | | | | | | | | | + | + | | | | |
| | pW | | | | | | | | | | + | + | | | |
| | pB-pW | | | | + | + | | | | | | | | | |
| | pH/pB | | | + | | + | + | + | + | + | + | + | + | + | |
| | pH/pW | | | + | | + | + | + | + | + | + | + | + | | |
| | pAUC | + | + | + | + | + | + | + | + | + | + | | + | + | |
| | mH | | | | + | + | | | | | | | | | |
| | mT | | | | + | + | | | | | | | | | |
| | mB | | | | + | + | | | | | | | | | |
| | mW | + | | | | | | | | | | | | | |
| | mB-mW | | | | + | | | | | | | | | | |
| | mH/mB | | | | | + | | | | | | | | | |
| | mH/mW | | | | | + | | | | | | | | | |
| | mT/mW | | | + | | | | | | | | | | | |
| | mAUC | + | + | + | + | | | | | | | | | | |

TABLE 3-1

Factor VIII

| | | x value | | | | | | | | | | | | | |
|---|---|---|---|---|---|---|---|---|---|---|---|---|---|---|---|
| Curve | Parameter | 0.5% | 1% | 5% | 10% | 20% | 30% | 40% | 50% | 60% | 70% | 80% | 90% | 95% | 99% |
| First order | RVH | | | | | | | | | | + | + | + | + | + |
| | RvH/RvB | | | | | | + | + | + | + | + | | | | |
| | RvH/RvW | | | | | | + | + | + | + | + | | | | |
| | RvHa | | | | | | | | | | + | + | + | + | + |
| First order | RpH | | | + | | + | + | + | + | + | + | + | + | + | + |
| | RpAUC | + | + | + | + | + | + | + | + | + | + | + | + | + | |
| | RmH | | | | + | + | + | | | | | | | | |
| | RmAUC | + | | | + | + | | | | | | | | | |

TABLE 4

Factor IX

| Curve | Parameter | | | | | | | | | | | | | | |
|---|---|---|---|---|---|---|---|---|---|---|---|---|---|---|---|
| 0th order | T5 | + | | | | | | | | | | | | | |
| Second order | AmaxT | + | | | | | | | | | | | | | |

| | | x value | | | | | | | | | | | | | |
|---|---|---|---|---|---|---|---|---|---|---|---|---|---|---|---|
| Curve | Parameter | 0.5% | 1% | 5% | 10% | 20% | 30% | 40% | 50% | 60% | 70% | 80% | 90% | 95% | 99% |
| First order | vT | | | | | | | | + | + | + | | + | + | + |
| | vTs | | | | + | + | + | + | + | + | + | + | | + | + |
| | vTe | | | | | | | | | | | + | + | + | + |
| | vH/vB | | | | | | | | | | | + | | | |
| | vTa | | | | | | | | + | + | + | | + | + | + |
| | vTm | | | | | | | | + | + | + | + | + | + | + |
| Second order | pT | + | | + | + | + | + | + | + | + | + | + | + | + | + |
| | pAUC | | | | | | | | | | | | | | + |
| | mT | + | | | | | | | | | | + | + | | + |
| | mH/mg | | | | | | | | | | | + | | | |

TABLE 4-continued

| | | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| | vT/PT | | | | | | | | | | | | | | + |
| | pB/mB | | | | | | | | + | | | | | | |

| Factor IX | | | | | | | | | | | | | | | | |
|---|---|---|---|---|---|---|---|---|---|---|---|---|---|---|---|---|
| | | | | | | | | x value | | | | | | | | |
| Curve | Parameter | 0.5% | 1% | 5% | 10% | 20% | 30% | 40% | 50% | 60% | 70% | 80% | 90% | 95% | 99% |
| First order | RvH | | | | | | + | + | + | + | + | + | + | + | + |
| | RvHa | | | | | + | + | + | + | + | + | + | + | + | + |
| | RvH/RvB | | | | | | | | | | | + | | + | |
| | RvH/RvW | | | | | | | | + | + | + | + | | | |
| Second order | RpAUC | | | | | + | + | + | + | + | + | + | + | | |
| | RmAUC | | | | | | + | + | | | | | | | |

TABLE 5

| Factor V | | | | | | | | | | | | | | | | |
|---|---|---|---|---|---|---|---|---|---|---|---|---|---|---|---|---|
| | | | | | | | | x value | | | | | | | | |
| Curve | Parameter | 0.5% | 1% | 5% | 10% | 20% | 30% | 40% | 50% | 60% | 70% | 80% | 90% | 95% | 99% |
| First order | vAUC | | | | | + | | | | | | | | | |
| | vH | | | + | | | | | | | | | | | |
| | vTr | | | + | + | + | | | | | | | | | |
| | vB | | + | + | + | + | | | | | | | | | |
| | vW | | | | | | | | | + | | | | | |
| | vB-vW | | + | + | + | + | | | | | | | | | |
| | vH/vB | | | + | + | | | | | | | | | | |
| | vH/vW | | | | | | | | | | + | | | | |
| | vHa | | | + | + | + | + | | | | | | | | |
| | vTa | + | | | | | | | | | | | | | |
| | vTm | | | + | | | | | | | | | | | |
| Second order | pH | | | + | + | + | | | | | | | | | |
| | pW | | | | | | | | | | | | | + | |
| | pH-PW | | | + | | | | | | | | | | | |
| | pH/PH | | | + | + | | | | | | | | | | |
| | pH/pW | | | | | | | | | | | | | | + |
| | pT/pW | | | | | | | | | | | + | | | |
| | pAUC | | | | | | | | + | + | + | + | + | | |
| | mH | | | | + | + | | | | | | | | | |
| | mT | + | + | | | | | | | | | | | | |
| | mH/mB | | | + | | + | | | | | | | | | |
| | mH/mW | | | | + | | | | | | | | | | |
| | mAUC | + | | | | | | + | + | + | | | | | |

| Factor V | | | | | | | | | | | | | | | | |
|---|---|---|---|---|---|---|---|---|---|---|---|---|---|---|---|---|
| | | | | | | | | x value | | | | | | | | |
| Curve | Parameter | 0.5% | 1% | 5% | 10% | 20% | 30% | 40% | 50% | 60% | 70% | 80% | 90% | 95% | 99% |
| First order | RvH/RvB | | | | | | | + | + | + | + | | | | |
| | RvH/RvW | | | | + | + | + | + | + | + | + | | | | |
| Second order | RpH | | | + | | | | | | | | | | | |
| | RpAUC | | | | | | | + | | | | | | | |
| | RmH | | | | | | | | | | + | + | + | + | + |

TABLE 6

| | Factor X | | | | | | | | | | | | | | |
|---|---|---|---|---|---|---|---|---|---|---|---|---|---|---|---|
| | | | | | | | x value | | | | | | | | |
| Curve | Parameter | 0.5% | 1% | 5% | 10% | 20% | 30% | 40% | 50% | 60% | 70% | 80% | 90% | 95% | 99% |
| First order | vw | | | | | | | | | | | + | | | |
| | vH/vB | | | | | | | | | | | | | + | |
| | vH/vW | | | | | | | | | | | | + | | |
| Second order | pB | | + | | | | | | | | | + | + | | |
| | pW | | | + | | + | | + | | + | | | | | |
| | pB-pW | | | | | + | | | | | | | | | |
| | pH/pB | | | | | | + | | | | | | | | |
| | pH/pW | | | | | | + | | | | | | | | |
| | mB | | | + | | | | | | | | | | | |
| | mB-mW | | | | + | | | | | | | | | | |
| | mT/mw | + | | | | | | | | | | | | | |

| | Factor X | | | | | | | | | | | | | | |
|---|---|---|---|---|---|---|---|---|---|---|---|---|---|---|---|
| | | | | | | | x value | | | | | | | | |
| Curve | Parameter | 0.5% | 1% | 5% | 10% | 20% | 30% | 40% | 50% | 60% | 70% | 80% | 90% | 95% | 99% |
| First order | RvH/RvB | | + | | | | | | | | | | + | | |
| | RvH/RvW | | | | | | | | | | | + | | | |
| | RvH | | | + | | | | | | | | | | | |
| | RvHa | | + | + | + | | | | | | | | | | |
| Second order | RpH | | | | | | + | | | | | | | | |
| | RmAUC | | | | | | + | + | + | + | | | | | |

TABLE 7

| | Factor XI | |
|---|---|---|
| Curve | | Parameter |
| 0th order | T5 | + |
| First order | VmaxT | + |
| Second order | AmaxT | + |

| | | | | | | | | x value | | | | | | | |
|---|---|---|---|---|---|---|---|---|---|---|---|---|---|---|---|
| Curve | Parameter | 0.5% | 1% | 5% | 10% | 20% | 30% | 40% | 50% | 60% | 70% | 80% | 90% | 95% | 99% |
| First order | vAUC | | | | | | + | | | | | | | | |
| | vTs | | | + | + | + | + | + | + | + | + | + | | | |
| | vTe | | | | | | | | | | | | | | + |
| | vW | | | | | | | | | | | + | | | |
| | vW/vB | | | | | | + | | | | | | | | |
| Second order | pT | | | + | + | + | + | + | + | + | + | + | + | + | + |
| | pW | | | | | | | | | | | | + | | |
| | pB-pW | | | | | | | | | | | + | | | |
| | pT/pB | | | | | | | | | | | | | + | |
| | pT/pW | | | | | | | | | | | | + | | |
| | mT/mW | | | | | | | | | | | | | | + |

TABLE 7-continued

Factor XI

| Curve | Parameter | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| | | | | | | | | | x value | | | | | | |
| First order | RvAUC | | | | | | | | + | + | | | | | |
| | RvH/RvB | | | | | | | | | | | | | + | + |
| | RvH/RvW | | | | | | | | | | | | | + | |

TABLE 8

Factor XII

| Curve | Parameter |
|---|---|
| 0th order | T95-T5  + |

| Curve | Parameter | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| | | | | | | | | | x value | | | | | | |
| Second order | pW | | | | | | | | | | | | | + | |

TABLE 9

Number of x values for which linear regression formula with "+" condition was obtained

| Curve | Parameter | Coagulation factor VIII | IX | V | X | XI | XII |
|---|---|---|---|---|---|---|---|
| 0th order | APTT | 1 | | | | | |
| | T5 | | 1 | | | 1 | |
| | T95-15 | | | | | | 1 |
| First order | VmaxT | | | | | 1 | |
| | Vmax | 1 | | | | | |
| Second order | AmaxT | | 1 | | | 1 | |
| | Amax | 1 | | | | | |
| First order | vAUC | 1 | | 1 | | 1 | |
| | vH | 7 | | 1 | | | |
| | vT | 10 | 6 | | | | |
| | vTs | | 10 | | | 9 | |
| | vTe | 8 | 4 | | | 1 | |
| | vTr | 7 | | 3 | | | |
| | vB | 5 | | 4 | | | |
| | vW | 4 | | 1 | 1 | 1 | |
| | vHa | 9 | 4 | | | | |
| | vTa | 9 | 6 | 1 | | | |
| | vTm | 7 | 7 | 1 | | | |
| | vW/vB | | | | | 1 | |
| | vB-vW | 2 | | 4 | | | |
| | vH/vB | 5 | 1 | 2 | 1 | | |
| | vH/vW | 8 | | 1 | 1 | | |
| | vT/vB | 1 | | | | | |
| | vT/vW | 1 | | | | | |
| Second order (Positive peak) | pH | 11 | | 3 | | | |
| | pT | | 13 | | | 12 | |
| | pB | 2 | | | 3 | | |
| | pW | 2 | | 1 | 4 | 1 | 1 |
| | pB-pW | 2 | | 1 | 1 | 1 | |
| | pH/pB | 10 | | 2 | 1 | | |
| | pT/pB | | | | | 1 | |
| | pH/pW | 9 | | 1 | 1 | | |
| | pT/pW | | | 1 | | 1 | |

TABLE 9-continued

Number of x values for which linear regression formula with
"+" condition was obtained

| Curve | Parameter | Coagulation factor VIII | IX | V | X | XI | XII |
|---|---|---|---|---|---|---|---|
| | pAUC | 12 | 1 | 5 | | | |
| | vT/pT | | 1 | | | | |
| Second order | mH | 2 | | 2 | | | |
| (Negative peak) | mT | 2 | 4 | 2 | | | |
| | mB | 2 | | | 1 | | |
| | mW | 1 | | | | | |
| | mB-mW | 1 | | | 1 | | |
| | mH/mB | 1 | 1 | 2 | | | |
| | mH/mW | 1 | | 1 | | | |
| | mT/mW | 1 | | | 1 | 1 | |
| | mAUC | 4 | | 4 | | | |
| | pB/mB | | 1 | | | | |
| First order | RvH | 5 | 9 | | 1 | | |
| | RvH/RvB | 5 | 2 | 4 | 2 | 2 | |
| | RvH/RvW | 5 | 4 | 6 | 1 | 1 | |
| | RvAUC | | | | | 2 | |
| | RvHa | 5 | 10 | | 3 | | |
| Second | RpH | 11 | 1 | 1 | | | |
| (Positive peak) | RpAUC | 13 | 9 | 1 | | | |
| Second | RmH | 3 | | 5 | | | |
| (Negative peak) | RmAUC | 3 | 2 | — | | | |

7. Fourth Example

The embodiment of the present invention described in the present Example is a method for determining a cause of extending APTT using the above-described parameters related to the 0th order curve to the second order curve when the test plasma exhibits abnormal coagulation (APTT extension), or identifying the type of a coagulation factor inhibitor (anticoagulant factor antibody) when the cause of extending APTT is the coagulation factor inhibitor.

In the present embodiment, a mixed plasma of a test plasma having abnormal coagulation and a normal plasma is used. In preparing the mixed plasma, the test plasma and the separately prepared normal plasma are mixed at a predetermined ratio. A mixing ratio between the test plasma and the normal plasma is a volume ratio in which the total amount is defined as 10 volumes, and only needs to be within a range of test plasma:normal plasma=from 1:9 to 9:1, preferably within a range of from 4:6 to 6:4, and more preferably 5:5.

A part of the prepared mixed plasma is heated. The heating temperature only needs to be, for example, 30° C. or higher and 40° C. or lower, and is preferably 35° C. or higher and 39° C. or lower, and more preferably 37° C. The heating time only needs to be, for example, within a range of from 2 to 30 minutes, and is preferably from 5 to 30 minutes. The heating time may be longer, however is preferably within one hour and at most two hours.

In the present embodiment, measurement of APTT is performed on the heated plasma and the unheated plasma, and photometric data is acquired. Therefore, in the present embodiment, a part of the prepared mixed plasma can be subjected to measurement of APTT after the above heating treatment, and another part of the prepared mixed plasma can be subjected to measurement of APTT without the heating treatment.

From the obtained photometric data, uncorrected and corrected 0th order curves to second order curves can be obtained for the heated plasma and the unheated plasma. The data correction process and differentiation can be performed in a similar procedure to the first Example. The parameters illustrated in Table 1 can be calculated from the uncorrected and corrected 0th order curves to second order curves for each of the obtained heated plasma and unheated plasma. In the present Example, a parameter acquired from the unheated plasma is referred to as a first parameter, and a parameter acquired from the heated plasma is referred to as a second parameter. Based on a ratio or a difference between the first and second parameters, or a combination thereof, a cause of extending APTT can be identified, or when the cause of extending APTT is a coagulation factor inhibitor, the type of the coagulation factor inhibitor can be identified.

7.1. Method
7.1.1. Test Plasma

The test plasma used in the present Example is described below. As the normal plasma (NP), a citric acid-added plasma obtained from a healthy person was used. For a LA plasma (LA), Positive Lupus Anticoagulant Plasma manufactured by George King Biomedical, Inc. was used. For a factor VIII-deficient plasma (HA) and a factor IX-deficient plasma (HB), Factor VIII Deficient and Factor IX Deficient manufactured by George King Biomedical were used. For a factor VIII inhibitor plasma (InL, InM, and InH), Factor VIII Deficient with Inhibitor manufactured by George King Biomedical, Inc. was used.

| Group No. | Type of specimen | Number of specimens |
|---|---|---|
| 1 | Normal plasma (NP) | 23 |
| 2 | LA plasma (LA) | 6 |
| 3 | Hemophilia A (HA) | 14 |
| 4 | Hemophilia B (HB) | 12 |
| 5 | Factor VIII Inhibitor low titer plasma (InL) | 12 |
| 6 | Factor VIII Inhibitor medium titer plasma (InM) | 35 |
| 7 | Factor VIII Inhibitor high titer plasma (InH) | 8 |

Note that "low", "medium", and "high" of the inhibitor titer mean the following:
Medium: 2 to 40 (BU/mL) (BU/mL: Bethesda unit)
Low: Lower titer than medium
High: Higher titer than medium

7.1.2. Preparation of Mixed Plasma

A mixed plasma was prepared by mixing each test plasma and the normal plasma (mixture of NP) at a volume ratio of 1:1.

7.1.3. Measurement of APTT

As APTT measurement reagents, Coagpia APTT-N (manufactured by Sekisui Medical Co., Ltd.) was used, and as a calcium chloride solution, Coagpia APTT-N calcium chloride solution (manufactured by Sekisui Medical Co., Ltd.) was used. For the measurement of APTT, a blood coagulation automatic analysis apparatus CP3000 (manufactured by Sekisui Medical Co., Ltd.) was used. 50 μL of the mixed plasma was discharged into a cuvette (reaction container) of the device and treated in a normal (unheating) mode or a heating mode according to the following procedure:

(Normal mode) Heating at 37° C. for 45 seconds
(Heating mode) Heating at 37° C. for 600 to 720 seconds Thereafter, 50 μL of APTT reagent heated to about 37° C. was added to the cuvette, and 50 μL of 25 mM calcium chloride solution was added after an elapse of 171 seconds to start a coagulation reaction. The coagulation reaction was performed with the cuvette maintained at about 37° C. Detection of the coagulation reaction was performed by emitting light from an LED with a wavelength of 660 nm as a light source and measuring the amount of 90-degree laterally scattered light at 0.1 second intervals. Photometric time was 360 seconds. For the same mixed plasma, measurement of APTT was performed under an unheating (normal mode) and heating (heating mode) conditions, respectively, and photometric data was obtained.

7.1.4. Analysis of Photometric Data

For the photometric data obtained for each of the unheated plasma and the heated plasma, corrected 0th to second order curves were obtained in a similar procedure to the first Example. From the obtained curves, the parameters illustrated in Table 1 were calculated. A parameter ratio Pb/Pa was determined by representing a parameter for the unheated plasma by Pa and representing the same parameter for the heated plasma by Pb.

7.2. Analysis Result and Discussion

FIG. 44A illustrates corrected first order curves of the LA plasma (LA) with and without heating. In LA, there was almost no change in the curve shape due to heating.

FIG. 44B illustrates corrected first order differential curves of the factor VIII inhibitor plasma (IN) with and without heating. In IN, there was almost no change in the curve shape due to heating as in LA.

FIG. 45A illustrates corrected first order differential curves of a 1:1 mixed plasma (LA-NP) of the LA plasma and the normal plasma with and without heating. By mixing the LA plasma with the normal plasma, a peak appears earlier (coagulation time is shortened), and the shape is sharper than in FIG. 45A. In LA-NP, there was almost no change in the curve shape due to heating as in LA.

FIG. 45B illustrates corrected first order differential curves of 1:1 mixed plasma (IN-NP) of the factor VIII inhibitor plasma (IN) and the normal plasma with and without heating. In the unheated mixed plasma, by mixing the factor VIII inhibitor plasma with the normal plasma, a peak appears earlier, and the shape is sharper than in FIG. 44B as in LA-NP. Meanwhile, in the heated mixed plasma, a peak appears later, the peak height is lower, and the peak width is wider. It has been determined that this change in shape is caused by the fact that an antigen-antibody reaction of the inhibitor (anti-factor VIII antibody) contained in IN with factor VIII contained in the normal plasma proceeded during the heating treatment, and the coagulation reaction of the mixed plasma was thereby inhibited. It has been confirmed that IN can be distinguished from LA by expressing the change in shape between the unheated plasma and the heated plasma with an indicator as a change in parameter.

Table 10 illustrates various parameter values obtained from the unheated plasma and the heated plasma (heated for 10 minutes) and ratios (Pb/Pa) therebetween. The Pb/Pa of the mixed plasma (IN-NP) of the factor VIII inhibitor plasma largely deviates from 1, which is clearly different from the normal plasma (NP), the LA plasma (LA), and the LA mixed plasma (LA-NP). Therefore, it has been indicated that a factor VIII inhibitor-positive plasma can be identified based on Pb/Pa for various parameters.

TABLE 10

| Parameter | Unheated (Pa) | | | | | Heated (Pb) | | | | |
| --- | --- | --- | --- | --- | --- | --- | --- | --- | --- | --- |
| | NP | LA | LA-NP (mix) | InM | IN-NP (mix) | NP | LA | LA-NP (mix) | InM | IN-NP (mix) |
| APTT (T50) | 26.1 | 62.9 | 51.8 | 151.9 | 49.3 | 26.2 | 67.0 | 51.1 | 145.9 | 80.1 |
| Vmax | 11.4 | 2.9 | 3.8 | 0.7 | 4.3 | 11.1 | 2.7 | 4.0 | 0.8 | 1.9 |
| VmaxT | 23.6 | 58.1 | 49.8 | 120.6 | 47.4 | 23.7 | 63.5 | 49.6 | 81.2 | 75.3 |
| vH: 10% | 5.9 | 1.6 | 2.2 | 0.3 | 2.4 | 5.9 | 1.5 | 2.2 | 0.4 | 1.1 |
| vT: 10% | 26.3 | 63.5 | 52.2 | 158.2 | 49.7 | 26.4 | 67.6 | 51.5 | 150.8 | 80.7 |
| v8: 10% | 14.6 | 55.2 | 40.8 | 241.1 | 35.6 | 14.7 | 57.9 | 39.1 | 217.6 | 80.8 |
| vH: 10%/v8: 10% | 40.6 | 2.9 | 5.3 | 0.1 | 6.9 | 40.1 | 2.6 | 5.7 | 0.2 | 1.3 |
| vT: 10%/vB: 10% | 1.8 | 1.2 | 1.3 | 0.7 | 1.4 | 1.8 | 1.2 | 1.3 | 0.7 | 1.0 |

| Parameter | (Pb/Pa) | | | | |
| --- | --- | --- | --- | --- | --- |
| | NP | LA | LA-NP (mix) | InM | IN-NP (mix) |
| APTT (T50) | 1.00 | 1.07 | 0.99 | 0.96 | 1.62 |
| Vmax | 0.98 | 0.93 | 1.04 | 1.22 | 0.44 |
| VmaxT | 1.00 | 1.09 | 1.00 | 0.67 | 1.59 |
| vH: 10% | 0.99 | 0.96 | 1.04 | 1.11 | 0.43 |
| vT: 10% | 1.00 | 1.06 | 0.99 | 0.95 | 1.63 |
| vB: 10% | 1.01 | 1.05 | 0.96 | 0.90 | 2.27 |
| vH: 10%/vB: 10% | 0.99 | 0.91 | 1.09 | 1.23 | 0.19 |
| vT: 10%/vB: 10% | 1.00 | 1.01 | 1.03 | 1.06 | 0.72 |

FIGS. 46A to 46G each illustrate a parameter Pa for various parameters under an unheated condition, a parameter Pb for various parameters under a heated condition, a ratio Pa/Pb therebetween, and a difference Pb−Pa therebetween in a case of using a plasma of a healthy person (NP) and a mixed plasma obtained by mixing each of a LA plasma, a HA plasma, a HB plasma, a factor VIII inhibitor low titer plasma (InL), a factor VIII inhibitor medium titer plasma (InL), and a factor VIII inhibitor high titer plasma (InH) with a normal plasma at a volume ratio of 1:1. The factor VIII inhibitor medium titer plasma (InM) tended to have Pa/Pb more than or less than 1. The factor VIII inhibitor low titer plasma (InL) tended to have a distribution similar to HA for both Pa/Pb and Pb−Pa, however had a wider distribution than HA for some parameters. Meanwhile, the factor VIII inhibitor high titer plasma (InH) tended to have Pa/Pb more than or less than 1 overall, or tended to have Pb−Pa deviating from 0, however had Pa/Pb close to 1 for some parameters (APTT, vT). However, for APTT of InH, Pb−Pa was not 0 even when Pa/Pb was about 1, and extended for at least 5 seconds. Therefore, it has been indicated that InH can be identified using APTT by using a ratio and a difference between Pa and Pb in combination.

More specifically, the present Example indicates the following results for APTT (seconds). Note that "extension" of APTT means that APTT is longer than that of a normal plasma, and "shortening" of APTT means that APTT is the same as or close to that of the normal plasma.

A mixed plasma containing LA extends both Pa and Pb, in which Pb/Pa is about 1.

A mixed plasma containing HA and a mixed plasma containing HB shorten both Pa and Pb, in which Pb/Pa is about 1.

A mixed plasma containing InL shortens both Pa and Pb, in which Pb/Pa is about 1.

A mixed plasma containing InM slightly extends Pa, and extends Pb more than Pa, in which Pb/Pa is more than 1.

A mixed plasma containing InH extends Pa, and extends Pb to the same extent as PA or more than Pa, in which Pb/Pa is about 1 or more than 1.

The above results are summarized in Table 11. It is indicated that the test plasma contained in the mixed plasma can be identified as follows based on APTT with and without heating.

(1) When both Pa and Pb are extended and Pb/Pa is about 1, the test plasma is LA or InH.

(2) When both Pa and Pb are shortened and Pb/Pa is about 1, the test plasma is HAB (HA or HB) or InL.

(3) When both Pa and Pb are extended and Pb/Pa is more than 1, the test plasma is InM or InH.

TABLE 11

| Symbol | Type of specimen | Nonheated (Pa) | Heated (Pb) | Change ratio (Pb/Pa) |
|---|---|---|---|---|
| LA | LA | Extended | Extended | About 1 |
| HAB | Hemophilia A, Hemophilia B | Shortened | Shortened | About 1 |
| InL | Inhibitor titer: low | Shortened | Shortened | About 1 |
| InM | Inhibitor titer: medium | Slightly extended | Further extended than unheated case | More than 1 |
| InH | Inhibitor titer: high | Extended | Extended | About 1 or more than 1 |

As can be seen from FIG. 46B, Pb/Pa for Vmax is about 1 in LA, HA, HB, InL, and some InH-containing plasmas like Pb/Pa for APTT, while Pb/Pa for Vmax is less than 1 in InM and InH-containing plasmas excluding the some InH-containing plasmas. When the coagulation reaction is inhibited by an inhibitor, APTT is extended and the coagulation rate is reduced according to an inhibitor titer, and as a result, parameter ratios Pb/Pa thereof deviate from 1. Therefore, in 1 nM and InH-containing plasmas excluding some InH-containing plasmas, Pb/Pa for APTT is more than 1, and Pb/Pa for Vmax is less than 1. Some InH-containing plasmas correspond to a high titer specimen (ultrahigh titer specimen) in a high titer group. As illustrated in FIG. 44B, Vmax drops to around 1 under an unheated condition (Pa), and does not almost change under a heated condition (Pb). Therefore, a parameter ratio Pb/Pa is around 1. In order to identify an ultrahigh titer specimen among InH-containing plasmas, as an example, the ultrahigh titer specimen only needs to be defined as a specimen having Vmax of 2 or less under an unheated condition (Pa).

As illustrated in FIGS. 46C to 46G, Amax exhibited a similar tendency to Vmax, vB and vT exhibited a similar tendency to APTT, and vAB and vTB exhibited a similar tendency to Vmax and Amax.

From the above results, it is indicated that a specimen in which a cause of extending APTT is a coagulation factor inhibitor can be identified based on a ratio or a difference between Pa and Pb for various parameters, or a combination thereof.

8. Fifth Example 8.1. Method 8.1.1. Blood Specimen

The following five types of measurement target samples were prepared using a blood specimen derived from a subject having an abnormality in a blood coagulation factor and a normal blood specimen (normal plasma).

(1) Normal Plasma

As the normal plasma, CRYOcheck Pooled Normal Plasma (Precision BioLogic Incorporated) was used.

(2) LA-Positive Plasma

As a LA-positive plasma, Positive Lupus Anticoagulant Plasma (George King Biomedical, Inc.) was used.

(3) Factor VIII Inhibitor-Positive Plasma

As a factor VIII inhibitor-positive plasma, Factor VIII Deficient with Inhibitor (George King Biomedical, Inc.) was used.

(4) Equal Volume Mixed Plasma of a LA-Positive Plasma and a Normal Plasma

A mixed plasma was prepared by mixing "(2) LA-positive plasma" and "(1) normal plasma" described above at a volume ratio of 1:1.

(5) Equal Volume Mixed Plasma of a Factor VIII Inhibitor-Positive Plasma and a Normal Plasma A mixed plasma was prepared by mixing "(3) factor VIII inhibitor-positive plasma" and "(1) normal plasma" described above at a volume ratio of 1:1.

8.1.2. Method for Measuring Coagulation Reaction of Blood Specimen

For each of the above five types of samples, measurement of APTT without heating treatment, measurement of APTT after heating treatment at 37° C. for 10 minutes, measurement of APTT after heating treatment at 37° C. for 30 minutes, and measurement of APTT after heating treatment at 37° C. for 120 minutes were performed.

In the present Example, each of the APTT measurements was performed using a blood coagulation automatic analysis apparatus CP3000 (manufactured by Sekisui Medical Co., Ltd.). In the present Example, to 50 μL of a sample discharged into a cuvette (reaction container) and heated at 37° C. for 45 seconds, 50 μL of an APTT reagent heated to about 37° C. was added (discharged), and 50 μL of a 25 mM calcium chloride solution was further added (discharged) thereto after an elapse of 171 seconds to start a coagulation reaction. The reaction was performed while the temperature was maintained at 37° C. Detection (photometry) of the coagulation reaction was performed by emitting light from an LED light with a wavelength of 660 nm as a light source and detecting the amount of 90-degree laterally scattered light at 0.1 second intervals. Detection time was 360 seconds.

8.1.3. Method for Analyzing Photometric Data

Chronological optical information, that is, photometric data indicating the result of measurement of APTT without heating treatment, the result of measurement of APTT after heating treatment for 10 minutes, the result of measurement of APTT after heating treatment for 30 minutes, and the result of measurement of APTT after heating treatment for 120 minutes, performed for each of the above five types of samples, was acquired to obtain a coagulation reaction curve.

Baseline adjustment was performed on the coagulation reaction curve. That is, a smoothing process including noise removal was performed on the coagulation reaction curve, and adjustment was performed such that the amount of scattered light at a measurement start time point was zero. Subsequently, correction was made such that the maximum height of the coagulation reaction curve was 100 to obtain a corrected 0th order curve. The corrected 0th order curve was subjected to first order differentiation to obtain a corrected first order curve. The intra-section average slope according to the above formula (4) was used to calculate the corrected first order curve.

Coagulation time was calculated based on the coagulation reaction curve after baseline adjustment.

Maximum value Vmax of the corrected first order curve and time VmaxT at which the first order differential value was a maximum value were calculated. A corrected second order curve was determined, and maximum value Amax of the corrected second order curve and time AmaxT at which the second order differential value was a maximum value were calculated.

Peak width vB10% when calculation target area value S was set to 10% was calculated based on the corrected first order curve. Center-of-gravity time vT60% and center-of-gravity height vH60% when calculation target area value S was set to 60% were calculated. Flattening ratio vAB10% when calculation target area value S was set to 10% was calculated. Time ratio vTB5% when calculation target area value S was set to 5% was calculated.

8.2. Analysis Result and Discussion

FIGS. 47A to 47E illustrate representative corrected first order curves of the above-described five types of samples, respectively. The four curves M0, M10, M30, and M120 in each of the drawings indicate a corrected first order curve of a mixed plasma without heating treatment, a corrected first order curve of the mixed plasma after heating treatment for 10 minutes, a corrected first order curve of the mixed plasma after heating treatment for 30 minutes, and a corrected first order curve of the mixed plasma after heating treatment for 120 minutes, respectively.

FIG. 47A illustrates the corrected first order curves of "(1) normal plasma". These curves each have a higher peak height and a narrower peak width than those of other samples. These curves each have a monomodal shape. As for an influence of a difference in heating treatment time, there is almost no change in the shape of the curve among the curves M0, M10, M30, and M120.

FIG. 47B illustrates the corrected first order curves of "(2) LA-positive plasma". These curves each have more extension observed, a lower peak height, and a wider peak width than those of the normal plasma. These curves each have a shoulder-like shape in which one of bimodal peaks is an incomplete peak or a bimodal shape. As for an influence of a difference in heating treatment time, there is a slight change in the shape of the curve among the curves M0, M10, M30, and M120, however there is no particular large change.

FIG. 47C illustrates the corrected first order curves of "(3) factor VIII inhibitor-positive plasma". These curves each have more extension observed, a higher peak height, and a wider peak width than those of the normal plasma, and each have a significant bimodal shape. These curves each have a lower peak height and a wider peak width than those of the LA-positive plasma. As for an influence of a difference in heating treatment time, there is a small change in shape, for example, at a top among the curves M0, M10, M30, and M120, however there is no particular large change.

FIG. 47D illustrates the corrected first order curves of "(4) equal volume mixed plasma of a LA-positive plasma and a normal plasma". These curves each have a higher peak height and a narrower peak width than "(2) LA-positive plasma" illustrated in FIG. 47B. As for an influence of a difference in heating treatment time, there is a slight change in the shape of the waveform among the curves M0, M10, M30, and M120, however there is no particular large change.

FIG. 47E illustrates the corrected first order curves of "(5) equal volume mixed plasma of a factor VIII inhibitor-positive plasma and a normal plasma". In these curves, particularly the curve of M0 without heating treatment has a significantly higher peak height and a narrower peak width than those of "(3) factor VIII inhibitor-positive plasma" illustrated in FIG. 47C. Meanwhile, these curves each have a lower peak height and a wider peak width as the heating treatment time is longer. In particular, there is a large change in shape between the curves M0 and M10. For example, in the curve after heating treatment for 10 minutes (M10), the peak height is equal to or less than half of that of the curve without heating treatment (M0), and a bimodal peak appears. The curve after heating treatment for 10 minutes (M10) is flattened, and there is a large change in shape. A change in shape could be confirmed up to the time after heating treatment for 30 minutes (M30), but no change in shape was observed thereafter.

There is a large change in shape between the curves M0 and M10 in this way. Therefore, in "(5) equal volume mixed plasma of a factor VIII inhibitor-positive plasma and a normal plasma", it has been found that factor VIII inhibitor positive can be identified by analyzing the corrected first order curve even after heating treatment for 10 minutes, which is shorter than two hours. As illustrated in FIG. 47E, the shape of the curve without heating treatment (M0) is clearly different from the shape of the curve after heating treatment for 10 minutes (M10). There can be various evaluation parameters indicating this difference in shape. For identifying factor VIII inhibitor positive, it is desirable to find and use an evaluation parameter that is effective as an indicator for the identification from each corrected first order curve.

FIG. 48 illustrates an example of a table illustrating, for each of the above-described five types of samples, various evaluation parameters obtained from measurement of APTT of a mixed plasma after heating treatment for 10 minutes, various evaluation parameters obtained from measurement of APTT of the mixed plasma without heating treatment, and results of calculating ratios between both the various evaluation parameters.

Note that in FIG. 48, "NP" represents "normal plasma", "LA" represents "LA-positive plasma", "LA M" represents an equal volume mixed plasma of a LA-positive plasma and a normal plasma", "IN" represents "factor VIII inhibitor-positive plasma", and "IN M" represents "equal volume mixed plasma of a factor VIII inhibitor-positive plasma and a normal plasma". "10 min" represents "heating treatment at 37° C. for 10 minutes", and "0 min" represents "without heating treatment".

The various evaluation parameters illustrated in FIG. 48 are as follows. The coagulation time indicates reaction elapsed time at which the amount of scattered light of the coagulation reaction curve after baseline adjustment reaches 50%. Vmax indicates a maximum value of a corrected first order curve. VmaxT indicates time from start of photometry until reaching Vmax. Amax indicates a maximum value of a corrected second order curve. AmaxT indicates time from start of photometry until reaching Amax. vB10% indicates a peak width when calculation target area value S is set to 10%. vAB10% indicates a flattening ratio when calculation target area value S is set to 10%, and a value obtained by dividing center-of-gravity height vH10% when calculation target area value S is set to 10% by peak width vB10% (vH10%/vB10%). vTB5% indicates a time ratio when calculation target area value S is set to 5%, and a value obtained by dividing center-of-gravity time vT5% when calculation target area value S is set to 5% by peak width vB5% (vT5%/vB5%). vT60% indicates center-of-gravity time when calculation target area value S is set to 60%. vH60% indicates center-of-gravity height when calculation target area value S is set to 60%.

Since it is known that there is no difference between an immediate reaction and a delayed reaction in the LA-positive plasma, a ratio (Pb/Pa) was expected to be close to 1 in the equal volume mixed plasma of a LA-positive plasma and a normal plasma (LA M). As illustrated in FIG. 48, the analysis result indicated that the ratio (Pb/Pa) was close to 1 excluding the ratio (Pb/Pa) for Amax. It is presumed that a reason why the ratio (Pb/Pa) for Amax largely deviates from 1.0 is an influence of deterioration of an S/N ratio due to a decrease in the values of Pb and Pa by the second differentiation. For the other evaluation parameters, a ratio (Pb/Pa) of "equal volume mixed plasma of a LA-positive plasma and a normal plasma (LA M)" and a ratio (Pb/Pa) of "equal volume mixed plasma of a factor VIII inhibitor-positive plasma and a normal plasma (IN M)" was examined As for the coagulation time, the ratio (Pb/Pa) in LA M is 0.988, whereas the ratio (Pb/Pa) in IN M is 1.596, which is clearly more than that in LA M. The ratio (Pb/Pa) in IN M of 1.596 indicates that action of the coagulation inhibitory reaction of the factor VIII inhibitor is strengthened by the heating treatment for 10 minutes in this specimen. The ratio (Pb/Pa) in LA M of 0.988 indicates that the coagulation reaction of LA is not affected by the heating treatment for 10 minutes.

As for a difference between Vmax without heating treatment and Vmax after heating treatment for 10 minutes, Vmax does not almost change in LA M as illustrated in FIG. 47D, whereas Vmax is clearly reduced by heating treatment for 10 minutes in IN M as illustrated in FIG. 47E. Reflecting this, the ratio (Pb/Pa) for Vmax is 1.038 in LA M, whereas the ratio (Pb/Pa) for Vmax is 0.435 in IN M, which is clearly less than that in LA M. As described above, Vmax is considered to be one preferable example as an evaluation parameter for determining an effect of the factor VIII inhibitor such as presence of the factor VIII inhibitor.

As for a difference between VmaxT without heating treatment and VmaxT after heating treatment for 10 minutes, VmaxT does not almost change in LA M as illustrated in FIG. 47D, whereas VmaxT is clearly extended by heating treatment for 10 minutes in IN M as illustrated in FIG. 47E. Reflecting this, the ratio (Pb/Pa) for VmaxT is 0.998 in LA M, whereas the ratio (Pb/Pa) for VmaxT is 1.589 in IN M. However, as illustrated in FIG. 47E, the bimodality of the corrected first order curve is significant after the heating treatment, and a value of VmaxT largely depends on which of the first peak and the second peak has a maximum value. Therefore, VmaxT is considered to be unfavorable as an evaluation parameter for determining an effect of the factor VIII inhibitor such as presence of the factor VIII inhibitor.

Examples of a parameter indicating a progress rate of the coagulation reaction include center-of-gravity height vH. The ratio (Pb/Pa) for center-of-gravity height vH60% is 1.052 in LA M, whereas the ratio (Pb/Pa) for center-of-gravity height vH60% is 0.427 in IN M, which is clearly less than that in LA M. As described above, center-of-gravity height vH is considered to be one preferable example as an evaluation parameter for determining an effect of the factor VIII inhibitor such as presence of the factor VIII inhibitor.

Examples of a parameter reflecting a temporal change in progress state of the coagulation reaction include center-of-gravity time vT. The ratio (Pb/Pa) for center-of-gravity time vT60% is 0.988 in LA M, whereas the ratio (Pb/Pa) for center-of-gravity time vT60% is 1.592 in IN M, which is clearly more than that in LA M. As described above, center-of-gravity time vT is considered to be one preferable example as an evaluation parameter for determining an effect of the factor VIII inhibitor such as presence of the factor VIII inhibitor. VmaxT is easily affected by a bimodal peak, whereas center-of-gravity time vT is a parameter reflecting the averaged shape of the entire corrected first order curve, and therefore can be a better evaluation parameter than VmaxT.

As illustrated in FIG. 47D, the curve shape is hardly changed even after heating treatment for 10 minutes in LA M, whereas as illustrated in FIG. 47E, the curve is flattened by heating treatment for 10 minutes in IN M. Reflecting this, the ratio (Pb/Pa) for peak width vB10% is 0.956 in LA M, whereas the ratio (Pb/Pa) for peak width vB10% is 2.270 in IN M, which is clearly more than that in LA M. As described above, peak width vB is considered to be one preferable example as an evaluation parameter for determining an effect of the factor VIII inhibitor such as presence of the factor VIII inhibitor.

Similarly, the ratio (Pb/Pa) for flattening ratio vAB10% is 1.087 in LA M, whereas the ratio (Pb/Pa) for flattening ratio vAB10% is 0.191 in IN M, which is clearly less than that in LA M. As described above, flattening ratio vAB is considered to be one preferable example as an evaluation parameter for determining an effect of the factor VIII inhibitor such as presence of the factor VIII inhibitor.

The ratio (Pb/Pa) for time ratio vTB5% is 1.019 in LA M, whereas the ratio (Pb/Pa) for time ratio vTB5% is 0.718 in IN M, which is less than that in LA M. In IN M, center-of-gravity time vTx is extended and peak width vB is increased by the heating treatment, and therefore these changes cancel each other out and the ratio (Pb/Pa) does not deviate so much from 1.0 as compared with the ratios (Pb/Pa) for the other parameters.

Also regarding a difference (Pb−Pa) for each parameter, when Pb and Pa are close to each other, the difference is a value around 0, and when Pb and Pa are not close to each other, the difference is a value deviating from 0. Therefore, it can be seen that the difference can also be used as a determination indicator.

From these results, it has been found that it can be identified whether a specimen of a subject is factor VIII inhibitor-positive or LA-positive based on parameters related to a coagulation reaction state, particularly such as maximum first order differential value Vmax, peak width vB, flattening ratio vAB, center-of-gravity time VT, center-of-gravity height vH, and time ratio vTB.

In identifying whether a specimen of a subject is factor VIII inhibitor-positive or LA-positive, in order to confirm that the parameters related to the corrected first order curve are effective, a cross-mixing test and analysis according to this method were performed on a plurality of specimens. Here, heating treatment time at 37° C. was set to 10 minutes unlike a usual delayed type cross-mixing test. In an immediate type test, heating treatment is not performed like a conventional immediate type test.

FIGS. 49A to 49L illustrate results of cross-mixing tests of different LA-positive specimens. FIGS. 49A to 49L illustrate results of samples A, B, C, D, H, I, J, K, O, P, Q, and R, respectively. The horizontal axis of each graph indicates a mixing ratio between a LA-positive plasma and a normal plasma, and indicates that the ratio of the LA-positive plasma is 0%, 50%, or 100%. The vertical axis indicates measured APTT coagulation time. In each of the drawings, m0 illustrated by the solid line indicates an APTT measurement result without heating treatment, and m10 illustrated by the broken line indicates an APTT measurement result in a case where a mixed plasma is subjected to heating treatment for 10 minutes.

The LA-positive plasma is known to exhibit no difference between an immediate reaction and a delayed reaction. As described in this finding, in any of the cases illustrated in FIGS. 49A to 49L, there was almost no difference in measurement result depending on presence or absence of heating treatment. The graphs each illustrate a "convex upward curve" pattern regardless of presence or absence of heating treatment except for the cases of sample O illustrated in FIG. 49I and sample R illustrated in FIG. 49L. Sample O exhibits a "convex downward curve" pattern in m0 and m10. Sample R slightly exhibits a convex downward curve pattern in m0, however exhibits a "linear" pattern in m10.

FIGS. 50A to 50I illustrate results of cross-mixing tests of different factor VIII inhibitor-positive specimens. FIGS. 50A to 50I illustrate results of samples E, F, G, L, M, N, S, T, and U, respectively. The horizontal axis of each graph indicates a mixing ratio between a factor VIII inhibitor-positive plasma and a normal plasma, and indicates that the ratio of the factor VIII inhibitor-positive plasma is 0%, 50%, or 100%. The vertical axis indicates measured APTT coagulation time. In each of the drawings, m0 illustrated by the solid line indicates an APTT measurement result without heating treatment, and m10 illustrated by the broken line indicates a measurement result in a case where a mixed plasma is subjected to heating treatment for 10 minutes.

The factor VIII inhibitor-positive plasma is known to exhibit a "convex upward curve" pattern in a delayed reaction. As described in this finding, in any of the cases illustrated in FIGS. 50A to 50I, in a mixed plasma of the factor VIII inhibitor-positive plasma and the normal plasma, the coagulation time after heating treatment was prolonged, and a "convex upward curve" pattern was exhibited in m10 except for sample T illustrated in FIG. 50H. In the case of sample T illustrated in FIG. 50H, although prolongation of coagulation time was observed in m10 as compared with that in m0, a "convex downward curve" pattern was exhibited in m10.

FIG. 51A illustrates, for each of the samples, an APTT measurement result without heating treatment and an APTT measurement result with heating treatment at 37° C. for 10 minutes in a 100% test plasma.

In any of the LA-positive plasma samples A, B, C, D, H, I, J, K, O, P, Q, and R and the factor VIII inhibitor-positive plasma samples E, F, G, L, M, N, S, T, and U, a change in APTT measurement result by the heating treatment was within 5%, and it has been confirmed that an influence of the heating treatment is slight.

FIG. 51B illustrates, for each of the samples, an APTT measurement result without heating treatment and an APTT measurement result with heating treatment at 37° C. for 10 minutes in an equal volume mixed plasma of a test plasma and a normal plasma.

In FIG. 51B, in the LA-positive plasma samples A, B, C, D, H, I, J, K, O, P, Q, and R, a change in APTT measurement result by the heating treatment was within 5%, and it has been confirmed that an influence of the heating treatment is slight. Meanwhile, in the factor VIII inhibitor-positive plasma samples E, F, G, L, M, N, S, T, and U, changes in APTT measurement results due to the heating treatment differed depending on a sample, however all of the changes exceeded 10%. Therefore, it has been confirmed that there is an influence of the heating treatment.

In a conventional cross-mixing test, heating treatment conditions are set such that prolongation of coagulation time is observed in a factor VIII inhibitor-positive specimen by subjecting a sample to heating treatment at 37° C. for two hours. In contrast, the method of the present application tries to detect a factor VIII inhibitor even with heating treatment for only 10 minutes in the factor VIII inhibitor-positive specimen (sample T) exhibiting a "convex downward curve" pattern after heating treatment for 10 minutes.

For each of the above-described plurality of LA-positive plasmas and factor VIII inhibitor-positive plasmas, a corrected first order curve was calculated based on APTT measurement data regarding an equal volume mixed plasma with a normal plasma without heating treatment and with heating treatment at 37° C. for 10 minutes.

FIGS. 52A to 52L illustrate corrected first order curves of the above-described 12 examples of mixed plasmas in each of which a LA-positive plasma and a normal plasma are mixed at a volume ratio of 1:1, that is, samples A, B, C, D, H, I, J, K, O, P, Q, and R without heating treatment and with heating treatment at 37° C. for 10 minutes. In each of the curves, the solid line M0 illustrates the case without heating treatment, and the broken line m10 illustrates the case of heating treatment at 37° C. for 10 minutes.

In any of the samples, there is almost no change in shape between curves M0 and M10, and it has been confirmed that no influence on the curve shape due to the heating treatment is observed.

FIGS. 53A to 53I illustrate corrected first order curves of the above-described 9 examples of mixed plasmas in each of which a factor VIII inhibitor-positive plasma and a normal plasma are mixed at a volume ratio of 1:1, that is, samples E, F, G, L, M, N, S, T, and U without heating treatment and with heating treatment at 37° C. for 10 minutes. In each of the curves, the solid line M0 illustrates the case without heating treatment, and the broken line M10 illustrates the case of heating treatment at 37° C. for 10 minutes.

In all the samples, there is a large change in shape between curves M0 and M10, and it has been confirmed that a significant influence on the curve shape due to the heating treatment is observed. In particular, the heating treatment lowered the peak height and widened the peak width in all the samples. Such a change in shape has been confirmed as illustrated in FIG. 53H even in sample T exhibiting a "convex downward curve" pattern in the cross-mixing test with heating treatment for 10 minutes.

Based on each of the data without heating treatment and the data with heating treatment for 10 minutes, illustrated in FIGS. 52A to 52L, "flattening ratio vAB10% when calculation target area value S is set to 10%" related to "equal volume mixed plasma of a LA-positive plasma and a normal plasma" was calculated. Then, a ratio between flattening ratio vAB10% without heating treatment and flattening ratio vAB10% with heating treatment for 10 minutes (vAB10% 10/0 ratio) was calculated. Similarly, based on each of the data without heating treatment and the data with heating treatment for 10 minutes, illustrated in FIGS. 53A to 53I, "flattening ratio vAB10% when calculation target area value S is set to 10%" related to "equal volume mixed plasma of a factor VIII inhibitor-positive plasma and a normal plasma" was calculated. Then, a ratio between flattening ratio vAB10% without heating treatment and flattening ratio vAB10% with heating treatment for 10 minutes (vAB10% 10/0 ratio) was calculated. Calculation results thereof are illustrated in FIG. 54A.

As illustrated in FIG. 54A, in the data (LA) of "equal volume mixed plasma of a LA-positive plasma and a normal plasma", it has been found that the values of "vAB10% 10/0 ratio" are distributed within a certain range including 1.0. Meanwhile, in the data (Inhibitor) of "equal volume mixed plasma of a factor VIII inhibitor-positive plasma and a normal plasma", it has been found that the values of "vAB10% 10/0 ratio" are distributed within a range of less than 0.6. Therefore, it has been revealed that it can be identified whether a specimen of a subject is LA-positive or factor VIII inhibitor-positive by setting a threshold between both distributions. For example, it has been confirmed that even a specimen such as sample T can be correctly identified by this method.

As described above, it has been confirmed that the ratio between flattening ratio vAB determined from the data obtained by measurement of APTT without heating treatment and flattening ratio vAB determined from the data obtained by measurement of APTT after heating treatment for 10 minutes (vAB 10/0 ratio) can be an effective indicator for identifying whether a specimen of a subject is LA-positive or factor VIII inhibitor-positive.

Based on each of the data without heating treatment and the data with heating treatment for 10 minutes, illustrated in FIGS. 52A to 52L, "center-of-gravity height vH60% when calculation target area value S is set to 60%" related to "equal volume mixed plasma of a LA-positive plasma and a normal plasma" was calculated. Then, the ratio between center-of-gravity height vH60% without heating treatment and center-of-gravity height vH60% with heating treatment for 10 minutes (vH60% 10/0 ratio) was calculated. Similarly, based on each of the data without heating treatment and the data with heating treatment for 10 minutes, illustrated in FIGS. 53A to 53I, "center-of-gravity height vH60% when calculation target area value S is set to 60%" related to "equal volume mixed plasma of a factor VIII inhibitor-positive plasma and a normal plasma" was calculated. Then, the ratio between center-of-gravity height vH60% without heating and center-of-gravity height vH60% with heating treatment for 10 minutes (vH60% 10/0 ratio) was calculated. Calculation results thereof are illustrated in FIG. 54B.

As illustrated in this drawing, in the data (LA) of "equal volume mixed plasma of a LA-positive plasma and a normal plasma", it has been found that the values of "vH60% 10/0 ratio" are distributed within a certain range including 1.0. Meanwhile, in the data (Inhibitor) of "equal volume mixed plasma of a factor VIII inhibitor-positive plasma and a normal plasma", it has been found that the values of "vH60% 10/0 ratio" are distributed within a range of less than 0.8. Therefore, it has been revealed that it can be identified whether a specimen of a subject is LA-positive or factor VIII inhibitor-positive by setting a threshold between both distributions. For example, it has been confirmed that even a specimen such as sample T can be correctly identified by this method.

As described above, it has been confirmed that the ratio between center-of-gravity height vH determined from the data obtained by measurement of APTT without heating treatment and center-of-gravity height vH determined from the data obtained by measurement of APTT after heating treatment for 10 minutes (vH 10/0 ratio) can be an effective indicator for identifying whether a specimen of a subject is LA-positive or factor VIII inhibitor-positive.

Based on each of the data without heating treatment and the data with heating treatment for 10 minutes, illustrated in FIGS. 52A to 52L, "flattening ratio vAB10% when calculation target area value S is set to 10%" related to "equal volume mixed plasma of a LA-positive plasma and a normal plasma" was calculated. Then, a difference between flattening ratio vAB10% without heating treatment and flattening ratio vAB10% with heating treatment for 10 minutes (vAB10% 10/0 difference) was calculated. Similarly, based on each of the data without heating treatment and the data with heating treatment for 10 minutes, illustrated in FIGS. 53A to 53I, "flattening ratio vAB10% when calculation target area value S is set to 10%" related to "equal volume mixed plasma of a factor VIII inhibitor-positive plasma and a normal plasma" was calculated. Then, a difference between flattening ratio vAB10% without heating treatment and flattening ratio vAB10% with heating treatment for 10 minutes (vAB10% 10/0 difference) was calculated. Calculation results thereof are illustrated in FIG. 55A.

As illustrated in FIG. 55A, in the data (LA) of "equal volume mixed plasma of a LA-positive plasma and a normal plasma", it has been found that the values of "vAB10% 10/0 difference" are distributed within a range of from −0.2 to 0.2. Meanwhile, in the data (Inhibitor) of "equal volume mixed plasma of a factor VIII inhibitor-positive plasma and a normal plasma", it has been found that the values of "vAB10% 10/0 difference" are distributed within a wide range of from −1.2 to 0.0. A threshold cannot be provided between the two distributions, and it has been revealed that it cannot be identified whether a specimen of a subject is LA-positive or factor VIII inhibitor-positive with "vAB10% 10/0 difference".

Based on each of the data without heating treatment and the data with heating treatment for 10 minutes, illustrated in FIGS. 52A to 52L, "center-of-gravity height vH60% when calculation target area value S is set to 60%" related to "equal volume mixed plasma of a LA-positive plasma and a normal plasma" was calculated. Then, the difference between center-of-gravity height vH60% without heating treatment and center-of-gravity height vH60% with heating treatment for 10 minutes (vH60% 10/0 difference) was calculated. Similarly, based on each of the data without heating treatment and the data with heating treatment for 10 minutes, illustrated in FIGS. 53A to 53I, "center-of-gravity height vH60% when calculation target area value S is set to 60%" related to "equal volume mixed plasma of a factor VIII inhibitor-positive plasma and a normal plasma" was calculated. Then, the difference between center-of-gravity height vH60% without heating and center-of-gravity height vH60% with heating treatment for 10 minutes (vH60% 10/0 difference) was calculated. Calculation results thereof are illustrated in FIG. 55B.

As illustrated in this drawing, in the data (LA) of "equal volume mixed plasma of a LA-positive plasma and a normal plasma", it has been found that the values of "vH60% 10/0 difference" are distributed within a range of from −0.05 to 0.05. Meanwhile, in the data (Inhibitor) of "equal volume mixed plasma of a factor VIII inhibitor-positive plasma and a normal plasma", it has been found that the values of "vH60% 10/0 difference" are distributed within a wide range of from −0.30 to 0.00. Therefore, a threshold cannot be provided between the two distributions, and it has been revealed that it cannot be identified whether a specimen of a subject is LA-positive or factor VIII inhibitor-positive with "vH60% 10/0 difference".

Based on each of the data without heating treatment and the data with heating treatment for 10 minutes, illustrated in FIGS. 52A to 52L, "center-of-gravity time vT60% when calculation target area value S is set to 60%" related to "equal volume mixed plasma of a LA-positive plasma and a normal plasma" was calculated. Then, the difference between center-of-gravity time vT60% without heating treatment and center-of-gravity time vT60% with heating treatment for 10 minutes (vT60% 10/0 difference) was calculated. Similarly, based on each of the data without heating treatment and the data with heating treatment for 10 minutes, illustrated in FIGS. 53A to 53I, "center-of-gravity time vT60% when calculation target area value S is set to 60%" related to "equal volume mixed plasma of a factor VIII inhibitor-positive plasma and a normal plasma" was calculated. Then, the difference between center-of-gravity time vT60% without heating and center-of-gravity time vT60% with heating treatment for 10 minutes (vT60% 10/0 difference) was calculated. Calculation results thereof are illustrated in FIG. 55C.

As illustrated in this drawing, in the data (LA) of "equal volume mixed plasma of a LA-positive plasma and a normal plasma", it has been found that the values of "vT60% 10/0 difference" are distributed within a certain range including 0.0. Meanwhile, in the data (Inhibitor) of "equal volume mixed plasma of a factor VIII inhibitor-positive plasma and a normal plasma", it has been found that the values of "vT60% 10/0 difference" are distributed within a range of more than 10. Therefore, it has been revealed that it can be identified whether a specimen of a subject is LA-positive or factor VIII inhibitor-positive by setting a threshold between both distributions. For example, it has been confirmed that even a specimen such as sample T can be correctly identified by this method.

As described above, it has been confirmed that the ratio between center-of-gravity time vT determined from the data obtained by measurement of APTT without heating treatment and center-of-gravity time vT determined from the data obtained by measurement of APTT after heating treatment for 10 minutes (vT 10/0 difference) can be an effective indicator for identifying whether a specimen of a subject is LA-positive or factor VIII inhibitor-positive.

9. Sixth Example 9.1. Method

In the fifth Example, the experimental results when the heating treatment time of the mixed plasma was set to 10 minutes have been described. However, in the sixth Example, experimental results when the heating treatment time of a mixed plasma was set to 2 minutes will be described. Conditions different from those in the fifth Example are test plasmas and the number thereof, and heating treatment time of a mixed plasma, and the other conditions are the same.

9.2. Analysis Result and Discussion

FIG. 56 illustrates results of a cross-mixing test of a LA-positive specimen. In the drawing, m0 illustrated by the solid line indicates an APTT measurement result without heating treatment, and m2 illustrated by the broken line indicates an APTT measurement result in a case where a mixed plasma is subjected to heating treatment for 2 minutes. In FIG. 56, there is almost no difference between the measurement result in which mixed plasma heating treatment time is 0 minutes (unheated) and the measurement result in which mixed plasma heating treatment time is 2 minutes, and the graph exhibits a "convex upward curve" pattern.

FIG. 57 also illustrates results of a cross-mixing test of a LA-positive specimen. In the drawing, m10 illustrated by the solid line indicates an APTT measurement result in a case where a mixed plasma is subjected to heating treatment for 10 minutes, and m2 illustrated by the broken line indicates an APTT measurement result in a case where a mixed plasma is subjected to heating treatment for 2 minutes. In FIG. 57, there is almost no difference between the measurement result in which mixed plasma heating treatment time is 10 minutes and the measurement result in which mixed plasma heating treatment time is 2 minutes. That is, there is almost no difference among the measurement result in which mixed plasma heating treatment time is 0 minutes (unheated), the measurement result in which mixed plasma heating treatment time is 2 minutes, and the measurement result in which mixed plasma heating treatment time is 10 minutes.

FIG. 5B illustrates results of a cross-mixing test of a factor VIII inhibitor-positive specimen. In the drawing, m0 illustrated by the solid line indicates an APTT measurement result without heating treatment, and m2 illustrated by the broken line indicates an APTT measurement result in a case where a mixed plasma is subjected to heating treatment for 2 minutes. In FIG. 58, both the measurement result in which mixed plasma heating treatment time is 0 minutes (unheated) and the measurement result in which mixed plasma heating treatment time is 2 minutes exhibit "convex upward curve" patterns, and the coagulation time after heating treatment for 2 minutes is prolonged as compared with that of the unheated plasma to make the "convex upward curve" pattern stronger.

FIG. 59 also illustrates results of a cross-mixing test of a factor VIII inhibitor-positive specimen. In the drawing, m10 illustrated by the solid line indicates an APTT measurement result in a case where a mixed plasma is subjected to heating treatment for 10 minutes, and m2 illustrated by the broken line indicates an APTT measurement result in a case where a mixed plasma is subjected to heating treatment for 2 minutes. In FIG. 59, there is almost no difference between the measurement result in which mixed plasma heating treatment time is 10 minutes and the measurement result in which mixed plasma heating treatment time is 2 minutes.

FIG. 60 illustrates corrected first order curves of a mixed plasma of a LA-positive plasma and a normal plasma at a volume ratio of 1:1 without heating treatment and after heating treatment at 37° C. for 2 minutes. The solid line LA_0 illustrates the case without heating treatment, and the broken line LA_2 illustrates the case of heating treatment at 37° C. for 2 minutes. There is almost no change in shape between curves LA_0 and LA_2, and it has been confirmed that no influence on the curve shape due to the heating treatment is observed.

FIG. 61 illustrates corrected first order curves of a mixed plasma of a factor VIII inhibitor-positive plasma and a normal plasma at a volume ratio of 1:1 without heating treatment and after heating treatment at 37° C. for 2 minutes. The meaning of each curve is the same as that in FIG. 60. There is a large change in shape between curves 8M_0 and 8M_2, and it has been confirmed that a significant influence on the curve shape due to the heating treatment is observed. The heating treatment for 2 minutes also lowered the peak height and widened the peak width like the heating treatment for 10 minutes in the fifth Example.

FIG. 62 illustrates an example of a table illustrating, for each of five types of samples as in the fifth Example, various evaluation parameters obtained from measurement of APTT of a mixed plasma after heating treatment for 2 minutes, various evaluation parameters obtained from measurement of APTT of the mixed plasma without heating, and results of calculating ratios between both the various evaluation parameters.

Note that in FIG. 62, "2 min" represents "heating treatment at 37° C. for 2 minutes", and the others have the same meaning as in FIG. 48.

As for the coagulation time, the ratio (Pb/Pa) in LA M is 1.045, whereas the ratio (Pb/Pa) in IN M is 1.082, and there is no difference therebetween. This result indicates that the coagulation reaction of the LA-positive specimen is not affected by the heating treatment for 2 minutes, and that a coagulation-inhibiting reaction of the factor VIII inhibitor-positive specimen does not have a strong effect.

As for a difference between Vmax without heating treatment and Vmax after heating treatment for 2 minutes, Vmax does not almost change in LA M, whereas Vmax is clearly reduced in IN M, as illustrated in FIG. 62. Reflecting this, the ratio (Pb/Pa) for Vmax is 0.953 in LA M, whereas the ratio (Pb/Pa) for Vmax is 0.731 in IN M, which is clearly less than that in LA M.

As for a difference between VmaxT without heating treatment and VmaxT after heating treatment for 2 minutes, VmaxT does not almost change in LA M, whereas VmaxT is clearly extended in IN M, as illustrated in FIG. 62. Reflecting this, the ratio (Pb/Pa) for VmaxT is 1.020 in LA M, whereas the ratio (Pb/Pa) for VmaxT is 1.182 in IN M. As illustrated in FIG. 61, even by the heating treatment for 2 minutes, the bimodality of the corrected first order curve is significant after the heating treatment as in the heating treatment for 10 minutes in the fifth Example.

The ratio (Pb/Pa) for center-of-gravity height vH60% is 0.947 in LA M, whereas the ratio (Pb/Pa) for center-of-gravity height vH60% is 0.737 in IN M, which is clearly less than that in LA M.

The ratio (Pb/Pa) for center-of-gravity time vT60% is 1.044 in LA M, whereas the ratio (Pb/Pa) for center-of-gravity time vT60% is 1.146 in IN M, which is more than that in LA M.

As illustrated in FIG. 60, the curve shape is hardly changed even after heating treatment for 2 minutes in LA M, whereas as illustrated in FIG. 61, the curve is flattened in IN M. As illustrated in FIG. 62, reflecting this, the ratio (Pb/Pa) for peak width vB10% is 1.076 in LA M, whereas the ratio (Pb/Pa) for peak width vB10% is 1.405 in IN M, which is clearly more than that in LA M.

Similarly, the ratio (Pb/Pa) for flattening ratio vAB10% is 0.864 in LA M, whereas the ratio (Pb/Pa) for flattening ratio vAB10% is 0.490 in IN M, which is clearly less than that in LA M.

The ratio (Pb/Pa) for time ratio vTB is 0.975 in LA M, whereas the ratio (Pb/Pa) for time ratio vTB is 0.840 in IN M, which is less than that in LA M.

From these results, also by the heating treatment for 2 minutes, in a similar manner to the heating treatment for 10 minutes in the fifth Example, it has been found that it can be identified whether a specimen of a subject is factor VIII inhibitor-positive or LA-positive based on parameters related to a coagulation reaction state, particularly such as maximum first order differential value Vmax, peak width vB, flattening ratio vAB, center-of-gravity time vT, center-of-gravity height vH, and time ratio vTB.

Note that here, "vAB10% 10/0 ratio", "vH60% 10/0 ratio", and "vT60% 10/0 difference" have been mentioned as evaluation parameters that can be effective indicators. However, without being limited thereto, evaluation parameters other than these parameters can also be effective indicators for identifying whether a specimen of a subject is LA-positive or factor VIII inhibitor-positive. For example, calculation target area value S set for calculating flattening ratio vABx is not limited to 10%, and may be another value. Similarly, calculation target area value S set for calculating center-of-gravity height vHx is not limited to 60%, and may be another value. Calculation target area value S set for calculating center-of-gravity time vTx is not limited to 60%, and may be another value. Similarly, it can be identified whether a specimen of a subject is LA-positive or factor VIII inhibitor-positive not only based on flattening ratio vABx, center-of-gravity height vHx, and center-of-gravity time vTx but also based on, for example, maximum first order differential value Vmax, peak width vBx, and time ratio vTBx. The heating time is not limited to 10 minutes. According to the corrected first order curve in FIG. 47E, it is considered that the heating treatment time does not need to be longer than 30 minutes. Meanwhile, since time for the inhibitor to react is necessary, heating is preferably performed for 2 minutes or longer. Therefore, the heating time may be appropriately changed within a range of 2 minutes or longer and 30 minutes or shorter. In any case, the test time is sufficiently shortened as compared with the conventional test time of two hours.

10. Seventh Example 10.1. Method

A mixed plasma (12 specimens for a LA-positive plasma and 9 specimens for a factor VIII inhibitor-positive plasma) was prepared in the same procedure as that in the fifth Example, and measurement of APTT was performed without heating treatment and after heating treatment at 37° C. for 10 minutes. Various evaluation parameters were calculated from the acquired photometric data, and a ratio (Pb/Pa)

and a difference (Pb−Pa) between each of the parameters of an unheated plasma (Pa) and each of the parameters of a heated plasma (Pb) were determined. A significant difference in an average value of each of distributions of the ratio (Pb/Pa) and the difference (Pb−Pa) was evaluated between an equal volume mixed plasma of a LA-positive plasma and a normal plasma (LA) and an equal volume mixed plasma of a factor VIII inhibitor-positive plasma and a normal plasma (Inhibitor). For each of the distributions, equal variance and unequal variance were determined by F-test (significance level 1%), and then a P value of a difference between an average value of the LA distribution and an average value of the Inhibitor distribution was calculated by T test (both sides).

10.2. Result

FIGS. 63A to 63E illustrate examples of differences (Pb−Pa) and ratios (Pb/Pa) for various evaluation parameters between an unheated plasma and a heated plasma for LA and Inhibitor. FIG. 63A illustrates results of APTT time (T50) and Vmax, FIG. 63B illustrates results of vAB40% and vABa40%, FIG. 63C illustrates results of vH40% and vHa40%, FIG. 63D illustrates results of vAUC90% and vW10%/vB10%, and FIG. 63E illustrates results of pAUC80% and mAUC20%.

Tables 12 to 15 illustrate a difference (P value) in each of the distributions of Pb/Pa and Pb−Pa for various parameters between LA and Inhibitor. The values in Tables indicate −: P value≥1%, 1: 0.1%≤P value<1%, 2: 0.01%≤P value<0.1%, 3: 0.001%≤P value<0.01%, 4: 0.0001%≤P value<0.001%, and 5: P value<0.0001%. As illustrated in Tables 13 to 15, overall, the ratio (Pb/Pa) had a larger distribution difference between LA and Inhibitor than the difference (Pb−Pa). The distributions of the ratio (Pb/Pa) for many parameters were different between LA and Inhibitor at the level of P value<0.01%. Meanwhile, a parameter was also found in which the distribution of the difference (Pb−Pa) was different between LA and Inhibitor at the level of P value<0.1%.

TABLE 12

| Curve | Parameter | P value Pb/Pa | P value Pb−Pa |
|---|---|---|---|
| 0th order | APTT (T50) | 2 | 3 |
|  | T5 | 2 | 2 |
|  | T95 | 2 | 2 |
|  | T95−T5 | 2 | 2 |
| First order | Vmax | 3 | 2 |
|  | VmaxT | — | — |
| Second order (+peak) | Amax | 2 | 1 |
|  | AmaxT | 2 | 2 |
| Second order (−peak) | Amin | — | — |
|  | AminT | — | — |

TABLE 13

P value: Pb/Pa

| Curve | Parameter | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| First order | vH | 2 | 1 | 3 | 3 | 4 | 4 | 4 | 4 | 4 | 4 | 3 | 3 | 3 | 3 |
|  | vHa | 2 | 2 | 3 | 3 | 4 | 4 | 4 | 4 | 4 | 4 | 3 | 3 | 3 | 3 |
|  | vAB | 2 | 3 | 5 | 5 | 5 | 5 | 5 | 5 | 4 | 4 | — | — | — | — |
|  | vABa | 3 | 4 | 5 | 5 | 5 | 5 | 5 | 5 | 4 | 4 | — | — | — | — |
|  | vAW | 4 | 4 | 5 | 5 | 5 | 5 | 5 | 5 | 3 | 2 | — | — | — | — |
|  | vAWa | 5 | 5 | 5 | 5 | 5 | 5 | 5 | 5 | 3 | 2 | — | — | — | — |
|  | vAUC | — | — | 2 | — | — | — | — | — | — | — | 1 | 4 | 3 | 2 |
|  | vW/vB | — | — | 5 | 5 | 4 | 2 | 2 | — | 4 | — | — | — | — | — |
| Second order (+peak) | pH | 1 | 1 | 4 | 4 | 2 | 2 | 3 | 3 | 5 | 3 | 2 | 2 | 2 | 2 |
|  | pH | 1 | 1 | 1 | 1 | 2 | 1 | 2 | 2 | 4 | 1 | 1 | 1 | 1 | 1 |
|  | pAB | — | — | 2 | 3 | 1 | 1 | 3 | 2 | 5 | 3 | — | — | — | — |
|  | pAW | — | — | 2 | 4 | 4 | 2 | 3 | 1 | 3 | 2 | — | — | — | — |
|  | pAUC | 3 | 3 | 3 | 3 | 4 | 3 | 3 | 2 | 2 | 4 | 5 | 5 | 5 | 5 |
| Second order (−peak) | mH | 4 | 4 | 3 | 2 | 1 | — | — | — | — | — | — | — | — | — |
|  | mAW | 4 | 4 | 2 | — | — | — | — | — | — | — | — | — | — | — |
|  | mAUC | 3 | 3 | 4 | 5 | 5 | 4 | 3 | 1 | 2 | 3 | 2 | 1 | 1 | — |

TABLE 14

P value: Pb−Pa

| Curve | Parameter | 0.5% | 1% | 5% | 10% | 20% | 30% | 40% | 50% | 60% | 70% | 80% | 90% | 95% | 99% |
|---|---|---|---|---|---|---|---|---|---|---|---|---|---|---|---|
| First order | vAUC | — | — | 2 | — | — | — | — | — | — | — | 1 | 5 | 3 | 1 |
|  | vW/vB | — | — | 5 | 5 | 4 | 4 | 2 | — | 2 | — | — | — | — | — |
| Second order (+peak) | pB | 3 | 2 | 1 | 1 | 1 | 1 | 1 | 1 | 5 | 1 | 1 | 1 | 1 | 1 |

TABLE 15

| | | P value: Pb/Pa | | | | | | | | | | | | | |
|---|---|---|---|---|---|---|---|---|---|---|---|---|---|---|---|
| | | x value | | | | | | | | | | | | | |
| Curve | Parameter | 0.5% | 1% | 5% | 10% | 20% | 30% | 40% | 50% | 60% | 70% | 80% | 90% | 95% | 99% |
| First order | RvH | 2 | 1 | 3 | 3 | 4 | 4 | 4 | 4 | 4 | 4 | 3 | 3 | 3 | 3 |
| | RvHa | 2 | 2 | 4 | 4 | 4 | 4 | 4 | 4 | 4 | 4 | 3 | 3 | 3 | 3 |
| | RvAB | 2 | 3 | 5 | 5 | 5 | 5 | 5 | 5 | 5 | 4 | — | — | — | — |
| | RvABa | 4 | 4 | 5 | 5 | 5 | 5 | 5 | 5 | 5 | 4 | — | — | — | — |
| | RvAW | 4 | 4 | 5 | 5 | 5 | 5 | 5 | 5 | 3 | 2 | — | — | — | — |
| | RvAWa | 5 | 5 | 5 | 5 | 5 | 5 | 5 | 5 | 3 | 2 | — | — | — | — |
| Second order (+peak) | RpH | 1 | 1 | 4 | 4 | 2 | 2 | 3 | 3 | 5 | 3 | 3 | 2 | 2 | 2 |
| | RpAUC | 3 | 4 | 3 | 3 | 5 | 4 | 3 | 3 | 2 | 5 | 5 | 5 | 5 | 5 |
| Second order (−peak) | RmH | 4 | 5 | 3 | 2 | 1 | — | — | — | — | — | — | — | — | — |
| | RmAUC | 3 | 3 | 4 | 5 | 5 | 4 | 3 | 1 | 2 | 3 | 2 | 1 | 1 | — |

| | | P value: Pb−Pa | | | | | | | | | | | | | |
|---|---|---|---|---|---|---|---|---|---|---|---|---|---|---|---|
| | | x value | | | | | | | | | | | | | |
| Curve | Parameter | 0.5% | 1% | 5% | 10% | 20% | 30% | 40% | 50% | 60% | 70% | 80% | 90% | 95% | 99% |
| First order | RvH | 1 | 1 | 1 | 1 | — | — | — | — | — | — | — | 4 | 2 | — |

In the above-described embodiments and Examples, measurement of APTT has been described as an example, but the present invention is not limited thereto. The technique described above can be similarly applied to other coagulation time measurements such as measurement of prothrombin time, measurement of diluted prothrombin time, measurement of diluted partial thromboplastin time, measurement of kaolin clotting time, and measurement of diluted Russell's viper venom time.

In addition, in the above-described embodiments and Examples, the factor VIII inhibitor has been described as an example of the coagulation factor inhibitor. However, the above-described technique can be similarly applied to inhibitors of factors other than factor VIII.

The embodiments of the present invention have been illustrated above. However, the above embodiments are merely examples and are not intended to limit the scope of the invention. The above-described embodiments can be performed in various other forms, and various omissions, substitutions, and changes can be made without departing from the gist of the invention. In addition, the above-described embodiments can be performed by appropriately changing, for example, each component, shape, size, length, width, thickness, height, and number. Furthermore, the Examples can be combined with each other into a new embodiment.

REFERENCE SIGNS LIST

1 Automatic analysis apparatus
10 Control unit
12 Central Processing Unit (CPU)
14 Random Access Memory (RAM)
16 Read Only Memory (ROM)
18 Storage
20 Communication interface (I/F)
22 Bus line
30 Measurement unit
42 Control circuit
44 Data processing circuit
52 Constant temperature bath
54 Reaction container
62 Light source
64 Scattered light detector
66 Transmitted light detector
72 Specimen container
74 Reagent container
76 Specimen probe
78 Reagent probe
90 Touch screen
92 Display device
94 Touch panel

The invention claimed is:

1. A method for analyzing a coagulation characteristic of a blood specimen, comprising:
   (1) acquiring data for a coagulation reaction curve indicating a coagulation reaction amount of a mixed solution containing a blood sample and a reagent with respect to reaction time;
   (2) calculating data for a differential curve obtained by differentiating the coagulation reaction curve;
   (3) calculating information related to a center-of-gravity point of the differential curve; and
   (4) evaluating the coagulation characteristic of the blood sample using the information related to the center-of-gravity point wherein the differential curve is at least one selected from the group consisting of a first order differential curve related to the coagulation reaction curve and a second order differential curve related to the coagulation reaction curve, wherein the center-of-gravity point of the differential curve is a center-of-gravity point of the first order differential curve represented by coordinates (vT, vH) defined by center-of-gravity time vT and center-of-gravity height vH, and the vT and the vH are represented by the following formulas when the first order differential curve is represented by F (t) (t: time) and time when F(t) is a predetermined value x is represented by t1 or t2 (t1<t2);

Numerical Formula 1

$$vT = \frac{M}{\sum_{i=t1}^{t2} F(i)} \quad (6)$$

$$vH = \frac{M}{\sum_{i=t1}^{t2} i} \quad (7)$$

in which $$M = \sum_{i=t1}^{t2} (i \times F(i)), \quad (5)$$

or
wherein the center-of-gravity point of the differential curve is a center-of-gravity point of a positive peak of the second order differential curve represented by coordinates (pT, pH) defined by center-of-gravity time pT and center-of-gravity height pH, and the pT and the pH are represented by the following formulas when the second order differential curve is represented by F'(t) (t: time) and time when F'(t) is a predetermined value x is represented by t1 or t2 (t1<t2):

Numerical Formula 3

$$pT = \frac{M}{\sum_{i=t1}^{t2} F'(i)} \quad (6)'$$

$$pH = \frac{M}{\sum_{i=t1}^{t2} i} \quad (7)'$$

in which $$M = \sum_{i=t1}^{t2} (i \times F'(i)), \quad (5)'$$

or
wherein the center-of-gravity point of the differential curve is a center-of-gravity point of a negative peak of the second order differential curve represented by coordinates (mT, mH) defined by center-of-gravity time mT and center-of-gravity height mH, and the mT and the mH are represented by the following formulas when the second order differential curve is represented by F'.(t) (t: time) and time when F'(t) is a predetermined value x is represented by t1 or t2 (t1<t2):

Numerical Formula 4

$$mT = \frac{M}{\sum_{i=t1}^{t2} F'(i)} \quad (6)''$$

$$mH = \frac{M}{\sum_{i=t1}^{t2} i} \quad (7)''$$

in which $$M = \sum_{i=t1}^{t2} (i \times F'(i)), \quad (5)''$$

2. The analysis method according to claim 1, wherein:
the information related to the center-of-gravity point includes one or more parameters selected from the group consisting of the vT, the vH, peak width vB, center-of-gravity peak width vW, B flattening ratio vAB, B time ratio vTB, W flattening ratio vAW, W time ratio vTW, average time vTa, average height vHa, vTm, vABa, and vAWa,
the peak width vB is a length of time where F(t)≥x within a period from the t1 to the t2,
the center-of-gravity peak width vW is a length of time where F (t) >vH within a period from the t1 to the t2,
the vAB represents a ratio between the vH and the vB,
the vTB represents a ratio between the vT and the vB,
the vAW represents a ratio between the vH and the vW,
the vTW represents a ratio between the vT and the vW,
the vTa, the vHa, and the vTm are represented by the following formulas, respectively, when F(t), t1, and t2 have the same definitions as those described above, and the number of data points from F(t1) to F(t2) is n,

[Numerical Formula 2]

$$vTa = \frac{\sum_{i=t1}^{t2} i}{n} \quad (10)$$

$$vHa = \frac{\sum_{i=t1}^{t2} F(i)}{n} \quad (11)$$

$$vTm = \frac{t1 + t2}{2} \quad (12)$$

the vABa represents a ratio between the vHa and the vB, and
the vAWa represents a ratio between the vHa and the vW.

3. The analysis method according to claim 1, wherein:
the information related to the center-of-gravity point includes one or more parameters selected from the group consisting of the pT, the pH, peak width pB, center-of-gravity peak width pW, B flattening ratio pAB, B time ratio pTB, W flattening ratio pAW, and W time ratio pTW,
the peak width pB is a length of time where F'(t) >x within a period from the t1 to the t2,
the center-of-gravity peak width pW is a length of time where F'(t)≥pH within a period from the t1 to the t2,
the pAB represents a ratio between the pH and the pB,
the pTB represents a ratio between the pT and the pB,
the pAW represents a ratio between the pH and the pW, and
the pTW represents a ratio between the pT and the pW.

4. The analysis method according to claim 1, wherein:
the information related to the center-of-gravity point includes one or more parameters selected from the group consisting of the mT, the mH, peak width mB, center-of-gravity peak width mW, B flattening ratio mAB, B time ratio mTB, W flattening ratio mAW, and W time ratio mTW,
the peak width mB is a length of time where F'(t)≤x within a period from the t1 to the the center-of-gravity peak width mW is a length of time where F'(t)≤ mH within a period from the t1 to the t2,
the mAB represents a ratio between the mH and the mB, the mTB represents a ratio between the mT and the mB,
the mAW represents a ratio between the mH and the mW, and
the mTW represents a ratio between the mT and the mW.

5. The analysis method according to claim 1, wherein the predetermined value x is a value that is 0.5% to 99% of a maximum value of the first order differential curve F(t) or the second order differential curve F'(t).

6. The analysis method according to claim 1, wherein the coagulation characteristic is a coagulation factor concentration, and the coagulation factor is at least one selected from the group consisting of coagulation factor V, coagulation factor VIII, coagulation factor IX, coagulation factor X, coagulation factor XI, and coagulation factor XII.

7. The analysis method according to claim 2, wherein step (4) includes, qualifying an analysis target component and quantifying a concentration of the analysis target component based on a relationship between a concentration of the analysis target component and a flattening ratio, and on the flattening ratio obtained from the blood specimen,
wherein the flattening ratio is the B flattening ratio vAB or the W flattening ratio vAW.

8. The analysis method according to claim 2, wherein the above step (4) includes an analysis using a ratio between the center-of-gravity time and the peak width (time ratio).

9. The analysis method according to claim 8, wherein the above step (4) includes determining whether or not a cause of prolongation of coagulation time is coagulation factor VIII based on the time ratio.

10. The analysis method according to claim 8, wherein the above step (4) includes, based on a relationship between the concentration of an analysis target component and the time ratio, and on the obtained time ratio, qualifying the analysis target component and quantifying a concentration of the analysis target component.

11. The analysis method according to claim 1, wherein the data of the coagulation reaction curve is obtained by measuring activated partial thromboplastin time.

12. The analysis method according to claim 1, wherein:
the above step (2) further includes performing a correction process based on a maximum value of the acquired data of the coagulation reaction curve to calculate corrected data of the coagulation reaction curve, and
in the above step (2), the corrected data of the coagulation reaction curve is used for calculating the data of the differential curve.

13. The analysis method according to claim 1, wherein:
the above step (1) includes:
preparing a mixed plasma obtained by mixing a test plasma and a normal plasma;
measuring coagulation time of the mixed plasma without heating treatment; and
measuring coagulation time of the mixed plasma after heating treatment,
the above step (3) includes:
calculating a first parameter related to a coagulation reaction state based on the coagulation time measurement data of the mixed plasma without heating treatment; and
calculating a second parameter related to a coagulation reaction state based on the coagulation time measurement data of the mixed plasma after heating treatment, and
the above step (4) includes:
identifying a cause of prolongation of coagulation time based on a ratio or a difference between the first parameter and the second parameter.

14. The analysis method according to claim 13, wherein the identification includes determining whether the cause of prolongation of coagulation time is an effect of a coagulation factor inhibitor or an effect of a lupus anticoagulant.

15. The analysis method according to claim 13, wherein heating time of the mixed plasma is 2 minutes or longer and 30 minutes or shorter.

16. The analysis method according to claim 13, wherein the first parameter and the second parameter each include at least one selected from the group consisting of a maximum value of the first order differential curve, center-of-gravity height vH, center-of-gravity time vT, peak width vB, center-of-gravity peak width vW, B flattening ratio vAB, B time ratio vTB, W flattening ratio vAW, W time ratio vTW, average time vTa, average height vHa, vTm, vABa, and vAWa.

17. The analysis method according to claim 13, wherein the identification includes determining that a cause of prolongation of coagulation time is an effect of a coagulation factor inhibitor when a ratio between the first parameter and the second parameter does not fall within a predetermined range including 1.

18. The analysis method according to claim 13, wherein the identification includes determining that a cause of prolongation of coagulation time is an effect of a lupus anticoagulant when a ratio between the first parameter and the second parameter falls within a predetermined range including 1.

19. The analysis method according to claim 13, wherein a mixing ratio between the test plasma and the normal plasma is 1:1.

20. The analysis method according to claim 3, wherein step (4) includes qualifying an analysis target component and quantifying a concentration of the analysis target component, based on a relationship between a concentration of the analysis target component and a flattening ratio, and on the flattening ratio obtained from the blood specimen, wherein the flattening ratio is the B flattening ratio pAB or the W flattening ratio pAW.

21. The analysis method according to claim 4, wherein step (4) includes qualifying an analysis target component and quantifying a concentration of the analysis target component, based on a relationship between a concentration of the analysis target component and a flattening ratio, and on the flattening ratio obtained from the blood specimen, wherein the flattening ratio is the B flattening ratio mAB or the W flattening ratio mAW.

* * * * *